United States Patent
Do et al.

(10) Patent No.: US 9,434,725 B2
(45) Date of Patent: Sep. 6, 2016

(54) 5-AZAINDAZOLE COMPOUNDS AND METHODS OF USE

(71) Applicant: Genentech, Inc., South San Francisco, CA (US)

(72) Inventors: Steven Do, San Jose, CA (US); Huiyong Hu, San Mateo, CA (US); Aleksandr Kolesnikov, San Francisco, CA (US); Vickie H. Tsui, Burlingame, CA (US); Xiaojing Wang, Foster City, CA (US)

(73) Assignee: F. HOFFMANN-LA ROCHE AG, Basel (CH)

( * ) Notice: Subject to any disclaimer, the term of this patent is extended or adjusted under 35 U.S.C. 154(b) by 16 days.

(21) Appl. No.: 13/927,278

(22) Filed: Jun. 26, 2013

(65) Prior Publication Data

US 2014/0005168 A1    Jan. 2, 2014

Related U.S. Application Data

(60) Provisional application No. 61/664,840, filed on Jun. 27, 2012.

(51) Int. Cl.
| | |
|---|---|
| C07D 471/04 | (2006.01) |
| C07D 471/10 | (2006.01) |
| C07D 487/10 | (2006.01) |
| C07D 491/052 | (2006.01) |
| A61K 31/496 | (2006.01) |
| A61K 31/551 | (2006.01) |
| A61K 31/4545 | (2006.01) |
| A61K 31/497 | (2006.01) |
| A61K 31/513 | (2006.01) |
| A61K 31/444 | (2006.01) |
| A61K 31/55 | (2006.01) |
| A61K 45/06 | (2006.01) |
| A61K 31/501 | (2006.01) |

(52) U.S. Cl.
CPC .......... *C07D 471/04* (2013.01); *A61K 31/444* (2013.01); *A61K 31/4545* (2013.01); *A61K 31/496* (2013.01); *A61K 31/497* (2013.01); *A61K 31/501* (2013.01); *A61K 31/513* (2013.01); *A61K 31/55* (2013.01); *A61K 31/551* (2013.01); *A61K 45/06* (2013.01); *C07D 471/10* (2013.01); *C07D 487/10* (2013.01); *C07D 491/052* (2013.01)

(58) Field of Classification Search
CPC  C07D 471/04; C07D 471/10; C07D 487/10; C07D 491/052
See application file for complete search history.

(56) References Cited

U.S. PATENT DOCUMENTS

| | | |
|---|---|---|
| 5,264,576 A | 11/1993 | Shutske et al. |
| 5,300,478 A | 4/1994 | Michaely et al. |
| 5,604,240 A | 2/1997 | Chambers et al. |
| 6,046,136 A | 4/2000 | James et al. |
| 7,429,609 B2 | 9/2008 | Ohi et al. |
| 7,994,202 B2 | 8/2011 | Atobe et al. |
| 2010/0144705 A1 | 6/2010 | Miller |
| 2011/0195992 A1 | 8/2011 | Savory et al. |
| 2012/0108589 A1 | 5/2012 | Kitade et al. |

FOREIGN PATENT DOCUMENTS

| | | |
|---|---|---|
| EP | 1510516 A1 | 3/2005 |
| WO | 2010/022081 A1 | 2/2010 |
| WO | 2011/101069 A2 | 8/2011 |
| WO | 2012/078777 A1 | 6/2012 |
| WO | 2013/024002 A1 | 2/2013 |

OTHER PUBLICATIONS

Dong et al., "QSAR study of Akt/protein kinase B (PKB) inhibitors using support vector machine" Eur J Med Chem. 44(10):4090-7 ( 2009).
Muddassar et al., "Elucidation of binding mode and three dimensional quantitative structure-activity relationship studies of a novel series of protein kinase B/Akt inhibitors" J Mol Model. 15(2):183-92 (Feb. 2009).
Nishiguchi et al., "Discovery of novel 3,5-disubstituted indole derivatives as potent inhibitors of Pim-1, Pim-2, and Pim-3 protein kinases" Bioorg Med Chem Lett. 21(21):6366-9 ( 2011).
Vilkauskaite et al., "Sonogashira-Type Reactions with 5-Chloro-1-phenyl-1H-pyrazole-4-carbaldehydes: A Straightforward Approach to Pyrazolo[4,3-c]pyridines" European Journ. of Organic Chemistry 2011(26):5123-33.
Wang et al., "Discovery of novel pyrazolo[1,5-a]pyrimidines as potent pan-Pim inhibitors by structure- and property-based drug design" Bioorg Med Chem Lett. 23(11):3149-53 (Jun. 2013).
Zhu et al., "Design and synthesis of pyridine-pyrazolopyridine-based inhibitors of protein kinase B/Akt" Bioorg Med Chem. 15(6):2441-52 ( 2007).

*Primary Examiner* — James D Anderson
(74) *Attorney, Agent, or Firm* — Alston & Bird LLP

(57) ABSTRACT

5-Azaindazole compounds of Formula I, including stereoisomers, geometric isomers, tautomers, and pharmaceutically acceptable salts thereof, are useful for inhibiting Pim kinase, and for treating disorders such as cancer mediated by Pim kinase. Methods of using compounds of Formula I for in vitro, in situ, and in vivo diagnosis, prevention or treatment of such disorders in mammalian cells, or associated pathological conditions, are disclosed.

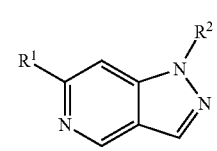

17 Claims, No Drawings

5-AZAINDAZOLE COMPOUNDS AND METHODS OF USE

CROSS REFERENCE TO RELATED APPLICATIONS

This non-provisional application filed under 37 CFR §1.53(b), claims the benefit under 35 USC §119(e) of U.S. Provisional Application Ser. No. 61/664,840 filed on 27 Jun. 2012, which is incorporated by reference in their entirety.

FIELD OF THE INVENTION

The invention relates generally to 5-azaindazole compounds for treating disorders mediated by Pim kinase (Pim-1, Pim-2, and/or Pim-3) inhibitors, thus useful as cancer therapeutics. The invention also relates to compositions, more specifically pharmaceutical compositions comprising these compounds and methods of using the same, either alone or in combination, to treat various forms of cancer and hyperproliferative disorders, as well as methods of using the compounds for in vitro, in situ, and in vivo diagnosis or treatment of mammalian cells, or associated pathological conditions.

BACKGROUND OF THE INVENTION

Pim kinases are a family of three highly-related serine and threonine protein kinases encoded by the genes Pim-1, Pim-2, and Pim-3. The gene names are derived from the phrase Proviral Insertion, Moloney, frequent integration sites for murine moloney virus wherein the insertions lead to overexpression of Pim kinases and either de novo T-cell lymphomas, or dramatic acceleration of tumorigenesis in a transgenic Myc-driven lymphoma model (Cuypers et al. (1984) Cell, vol. 37 (1) pp. 141-50; Selten et al. (1985) EMBO J. vol. 4 (7) pp. 1793-8; van der Lugt et al. (1995) EMBO J. vol. 14 (11) pp. 2536-44; Mikkers et al. (2002) Nature Genetics, vol. 32 (1) pp. 153-9; van Lohuizen et al. (1991) Cell, vol. 65 (5) pp. 737-52). These experiments reveal synergy with the oncogene c-Myc, and suggest that inhibition of the Pim kinases may have therapeutic benefit.

Mouse genetics suggests that antagonizing Pim kinases may have an acceptable safety profile; a Pim 1–/–; Pim-2–/–, Pim-3–/– mouse knockout is viable although slightly smaller than wild type littermates (Mikkers et al. (2004) Mol Cell Biol vol. 24 (13) pp. 6104-154). The three genes give rise to six protein isoforms including a protein kinase domain, and apparently without recognizable regulatory domains. All six isoforms are constitutively active protein kinases that do not require post-translational modification for activity, thus Pim kinases are regulated primarily at the transcriptional level (Qian et al. (2005) J Biol Chem, vol. 280 (7) pp. 6130-7). Pim kinase expression is highly inducible by cytokines and growth factors receptors and Pims are direct transcriptional targets of the Stat proteins, including Stat3 and Stat5. Pim-1, for example, is required for the gp130-mediated Stat3 proliferation signal (Aksoy et al. (2007) Stem Cells, vol. 25 (12) pp. 2996-3004; Hirano et al. (2000) Oncogene vol. 19 (21) pp. 2548-56; Shirogane et al. (1999) Immunity vol. 11 (6) pp. 709-19).

Pim kinases function in cellular proliferation and survival pathways parallel to the PI3k/Akt/mTOR signaling axis (Hammerman et al. (2005) Blood vol. 105 (11) pp. 4477-83). Indeed, several of the phosphorylation targets of the PI3k axis including Bad and eIF4E-BP1 are cell growth and apoptosis regulators and are also phosphorylation targets of the Pim kinases (Fox et al. (2003) Genes Dev vol. 17 (15) pp. 1841-54; Macdonald et al. (2006) Cell Biol vol. 7 pp. 1; Aho et al. (2004) FEBS Letters vol. 571 (1-3) pp. 43-9; Tamburini et al. (2009) Blood vol. 114 (8) pp. 1618-27). Pim kinase may affect cell survival since phosphorylation of Bad increases Bcl-2 activity and therefore promotes cell survival. Likewise, phosphorylation of eIF4E-BP1 by mTOR or Pim kinases causes depression of eIF4E, promoting mRNA translation and cellular growth. In addition, Pim-1 has been recognized to promote cell cycle progression through phosphorylation of CDC25A, p21, and Cdc25C (Mochizuki et al. (1999) J Biol Chemvol. 274 (26) pp. 18659-66; Bachmann et al. (2006) Int J Biochem Cell Biol vol. 38 (3) pp. 430-43; Wang et al. (2002) Biochim Biophys Acta vol. 1593 (1) pp. 45-55.

Pim kinases show synergy in transgenic mouse models with c-Myc-driven and Akt-driven tumors (Verbeek et al. (1991) Mol Cell Biol vol. 11 (2) pp. 1176-9; Allen et al. Oncogene (1997) vol. 15 (10) pp. 1133-41; Hammerman et al. (2005) Blood vol. 105 (11) pp. 4477-83). Pim Kinases are involved in transforming activity of oncogenes identified in acute myeloid leukemia (AML) including Flt3-ITD, BCR-abl, and Tel-Jak2. Expression of these oncogenes in BaF3 cells results in upregulation of Pim-1 and Pim-2 expression, resulting in IL-3 independent growth, and subsequent Pim inhibition results in apoptosis and cell growth arrest (Adam et al. (2006) Cancer Research 66 (7):3828-35). Pim overexpression and dysregulation has also been noted as a frequent event in many hematopoietic cancers, including leukemias and lymphoma (Amson et al. (1989) Proc Natl Acad Sci USA 86 (22):8857-61); Cohen et al. (2004) Leuk Lymphoma 45 (5):951-5; Hüttmann et al. (2006) Leukemia 20 (10):1774-82) as well as multiple myeloma (Claudio et al. (2002) Blood 100 (6):2175-86. Pim 1 has been shown to be overexpressed and correlated to prostate cancer progression (Cibull et al. (2006) J Clin Pathol 59 (3):285-8; Dhanasekaran et al. (2001) Nature vol. 412 (6849):822-6). Pim 1 expression increases in mouse models with disease progression (Kim et al. (2002) Proc Natl Acad Sci USA 99 (5):2884-9). Pim-1 has been reported to be the most highly overexpressed mRNA in the subset of human prostate tumor samples which have a c-Myc-driven gene signature (Ellwood-Yen et al. (2003) Cancer Cell 4(3):223-38). Pim-3 has been also been shown to be overexpressed and to have a functional role in pancreatic cancer and hepatocellular carcinoma (Li et al. (2006) Cancer Research 66 (13):6741-7; Fujii et al. (2005) Int J Cancer 114 (2):209-18.

Beyond oncology therapeutic and diagnostic applications, Pim kinases could play a role in normal immune system function and Pim inhibition could be therapeutic for a number of different immunologic pathologies including inflammation, autoimmune conditions, allergy, and immune suppression for organ transplantation (Aho et al. (2005) Immunology 116 (1):82-8).

SUMMARY OF THE INVENTION

The invention relates to 5-azaindazole compounds for treating disorders mediated by Pim kinase (Pim-1, Pim-2, and/or Pim-3) inhibitors Formula I compounds.

Formula I compounds have the pyrazolo[4,3-c]pyridine (5-azaindazole) structure:

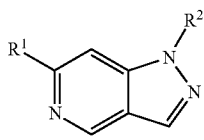

I and stereoisomers, geometric isomers, tautomers, and pharmaceutically acceptable salts thereof. The various substituents, including $R^1$ and $R^2$ are as defined herein.

One aspect of the invention is a pharmaceutical composition comprised of a Formula I compound and a pharmaceutically acceptable carrier, glidant, diluent, or excipient. The pharmaceutical composition may further comprise a chemotherapeutic agent.

The invention includes a method of treating a disease or disorder mediated by Pim kinase, which method comprises administering a therapeutically effective amount of a Formula I compound to a patient with a disease or disorder selected from cancer, immune disorders, cardiovascular disease, viral infection, inflammation, metabolism/endocrine function disorders and neurological disorders. The method includes further administering an additional therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

The invention includes use of a Formula I compound in the manufacture of a medicament for the treatment of cancer, immune disorders, cardiovascular disease, viral infection, inflammation, metabolism/endocrine function disorders and neurological disorders, wherein the medicament mediates Pim kinase.

The invention includes a kit for treating a condition mediated by Pim kinase, comprising: a) a first pharmaceutical composition comprising a Formula I compound; and b) instructions for use.

The invention includes a Formula I compound for use as a medicament, and for use in treating a disease or disorder selected from cancer, immune disorders, cardiovascular disease, viral infection, inflammation, metabolism/endocrine function disorders and neurological disorders, and mediated by Pim kinase.

The invention includes methods of making a Formula I compound.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this application is based on IUPAC systematic nomenclature, unless indicated otherwise.

DEFINITIONS

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen or more than one such as two, three, or four, including replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═$CH_2$), allyl (—$CH_2$CH═$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally substituted substituted independently with one or more substituents described herein, and includes radicals having "cis" and "trans" orientations, or alternatively, "E" and "Z" orientations. Examples include, but are not limited to, ethylenylene or vinylene (—CH═CH—), allyl (—$CH_2$CH═CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (═O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (MEK inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), a rapamycin analog, mTOR inhibitor such as everolimus, a MEK inhibitor (GDC-0973), a Bcl-2 inhibitor such as navitoclax, (ABT-263) or ABT-199), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (CAMPATH®), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), and tositumomab (BEXXAR®, Corixa, GlaxoSmithKline).

Humanized monoclonal antibodies with therapeutic potential as chemotherapeutic agents in combination with the Formula I compounds of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lebrikizumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, de-esterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Tables 1 and 2 structures for illustrative purposes, while stereochemical determination awaits, such as x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099).

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

5-Azaindazole Compounds

The present invention provides 5-azaindazole compounds of Formula I, including Formulas Ia-i, and pharmaceutical formulations thereof, which are potentially useful in the treatment of diseases, conditions and/or disorders modulated by Pim kinases.

Formula I compounds have the structure:

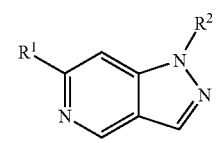

and stereoisomers, geometric isomers, tautomers, and pharmaceutically acceptable salts thereof, wherein:

$R^1$ is a five-membered or six-membered heteroaryl, optionally substituted with one or more groups independently selected from F, Cl, Br, —CN, —NO$_2$, OH, $C_1$-$C_{12}$ alkyl, —NH($C_1$-$C_{12}$ alkyl), —N($C_1$-$C_{12}$ alkyl)$_2$, —O($C_1$-$C_{12}$ alkyl), —S($C_1$-$C_{12}$ alkyl), —S(O)$_2$($C_1$-$C_{12}$ alkyl), —S(O)$_2$N($C_1$-$C_{12}$ alkyl)$_2$, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_2$-$C_8$ alkenylene)-($C_3$-$C_{12}$ carbocyclyl), —($C_2$-$C_8$ alkenylene)-($C_2$-$C_{20}$ heterocyclyl), $C_6$-$C_{20}$ aryl, —($C_6$-$C_{20}$ arylene)-($C_2$-$C_{20}$ heterocyclyl), —($C_6$-$C_{20}$ arylene)-($C_1$-$C_{12}$ alkylene)-($C_2$-$C_{20}$ heterocyclyl), $C_3$-$C_{12}$ carbocyclyl, $C_2$-$C_{20}$ heterocyclyl, and $C_1$-$C_{20}$ heteroaryl, where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$CH$_3$, —CH(CH$_3$)$_2$, —CH$_2$CH(CH$_3$)$_2$, —CH$_2$NH$_2$, —CH$_2$CH$_2$NH$_2$, —CH$_2$CH$_2$CH$_2$NH$_2$, —CH$_2$CH(CH$_3$)NH$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CHF$_2$, —CF$_3$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, =O, —OH, —OCH$_3$, —OCH$_2$CH$_3$, —S(O)$_2$N(CH$_3$)$_2$, —SCH$_3$, —CH$_2$OCH$_3$, —S(O)$_2$CH$_3$, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino; and $R^2$ is phenyl or a six-membered heteroaryl, where the phenyl or the six-membered heteroaryl is optionally substituted with one or more groups independently selected from F, Cl, Br, —CN, —NO$_2$, OH, $C_1$-$C_{12}$ alkyl, —NH($C_1$-$C_{12}$ alkyl), —N(C₁-C₁₂ alkyl)₂, —O(C₁-C₁₂ alkyl), —S(C₁-C₁₂ alkyl), —S(O)₂(C₁-C₁₂ alkyl), —S(O)₂N(C₁-C₁₂ alkyl)₂, —(C₁-C₁₂ alkylene)-(C₃-C₁₂ carbocyclyl), —(C₁-C₁₂ alkylene)-(C₂-C₂₀ heterocyclyl), —O(C₂-C₂₀ heterocyclyl), —NH(C₂-C₂₀ heterocyclyl), —N(C₁-C₁₂ alkyl)(C₂-C₂₀ heterocyclyl), —(C₂-C₈ alkenylene)-(C₃-C₁₂ carbocyclyl), —(C₂-C₈ alkenylene)-(C₂-C₂₀ heterocyclyl), C₆-C₂₀ aryl, —(C₆-C₂₀ arylene)-(C₂-C₂₀ heterocyclyl), —(C₆-C₂₀ arylene)-(C₁-C₁₂ alkylene)-(C₂-C₂₀ heterocyclyl), C₃-C₁₂ carbocyclyl, C₂-C₂₀ heterocyclyl, and C₁-C₂₀ heteroaryl, where alkyl, alkenyl, alkynyl, alkylene, carbocyclyl, heterocyclyl, aryl, and heteroaryl are optionally substituted with one or more groups independently selected from F, Cl, Br, I, —CH₃, —CH₂CH₃, —CH(CH₃)₂, —CH₂CH(CH₃)₂, —CH₂NH₂, —CH₂CH₂NH₂, —CH₂CH₂CH₂NH₂, —CH₂CH(CH₃)NH₂, —CH₂OH, —CH₂CH₂OH, —C(CH₃)₂OH, —CH(OH)CH(CH₃)₂, —C(CH₃)₂CH₂OH, —CH₂CH₂SO₂CH₃, —CN, —CHF₂, —CF₃, —CO₂H, —COCH₃, —CO₂CH₃, —CO₂C(CH₃)₃, —COCH(OH)CH₃, —CONH₂, —CONHCH₃, —CON(CH₃)₂, —C(CH₃)₂CONH₂, —NO₂, —NH₂, —NHCH₃, —N(CH₃)₂, —NHCOCH₃, —N(CH₃)COCH₃, —NHS(O)₂CH₃, —N(CH₃)C(CH₃)₂CONH₂, —N(CH₃)CH₂CH₂S(O)₂CH₃, =O, —OH, —OCH₃, —OCH₂CH₃, —S(O)₂N(CH₃)₂, —SCH₃, —CH₂OCH₃, —S(O)₂CH₃, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino.

Exemplary embodiments of Formula I compounds include wherein $R^1$ is selected from the structures:

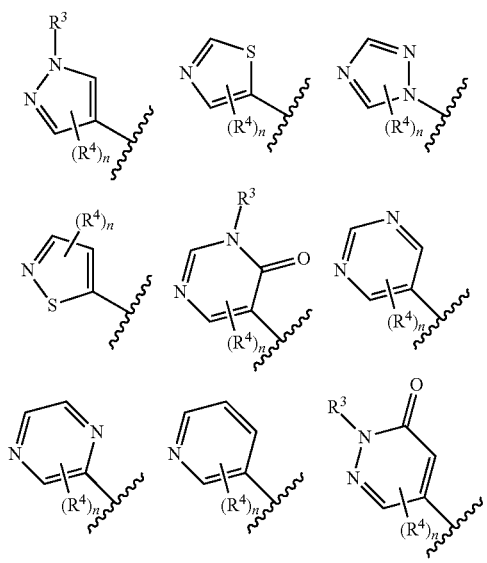

where the wavy line indicates the site of attachment;
$R^3$ is selected from H, —CH₃, —CH₂CH₃, —CH(CH₃)₂, —C(CH₃)₃, —CH₂CH(CH₃)₂, —CH₂NH₂, —CH₂NHCH₃, —CH₂CH₂NH₂, —CH₂CH₂CH₂NH₂, —CH₂CH(CH₃)NH₂, —CH₂OH, —CH₂CH₂OH, —C(CH₃)₂OH, —CH(OH)CH(CH₃)₂, —C(CH₃)₂CH₂OH, —CH₂CH₂SO₂CH₃, —CN, —CF₃, —CO₂H, —COCH₃, —CO₂CH₃, —CO₂C(CH₃)₃, —COCH(OH)CH₃, —CONH₂, —CONHCH₃, —CON(CH₃)₂, —C(CH₃)₂CONH₂, —S(O)₂N(CH₃)₂, —SCH₃, —CH₂OCH₃, —S(O)₂CH₃, cyclopropyl, cyclobutyl, cyclopentyl, cyclohexyl, cycloheptyl, and oxetanyl;

$R^4$ is independently selected from F, Cl, Br, I, —CH₃, —CH₂CH₃, —CH(CH₃)₂, —C(CH₃)₃, —CH₂CH(CH₃)₂, —CH₂NH₂, —CH₂NHCH₃, —CH₂CH₂NH₂, —CH₂CH₂CH₂NH₂, —CH₂CH(CH₃)NH₂, —CH₂OH, —CH₂CH₂OH, —C(CH₃)₂OH, —CH(OH)CH(CH₃)₂, —C(CH₃)₂CH₂OH, —CH₂CH₂SO₂CH₃, —CN, —CF₃, —CO₂H, —COCH₃, —CO₂CH₃, —CO₂C(CH₃)₃, —COCH(OH)CH₃, —CONH₂, —CONHCH₃, —CON(CH₃)₂, —C(CH₃)₂CONH₂, —NO₂, —NH₂, —NHCH₃, —N(CH₃)₂, —NHCH₂CHF₂, —NHCH₂CF₃, —NHCOCH₃, —N(CH₃)COCH₃, —NHC(O)OCH₂CH₃, —NHC(O)OCH₂Cl₃, —NHC(O)OC₆H₅, —NHS(O)₂CH₃, —N(CH₃)C(CH₃)₂CONH₂, —N(CH₃)CH₂CH₂S(O)₂CH₃, =O, —OH, —OCH₃, —S(O)₂N(CH₃)₂, —SCH₃, —CH₂OCH₃, —S(O)₂CH₃, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino;

and n is 0, 1, 2, or 3.

Exemplary embodiments of Formula I compounds include wherein $R^2$ is a six-membered heteroaryl having the structure:

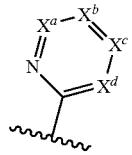

where the wavy line indicates the point of attachment;
$X^a$ is N or $CR^a$;
$X^b$ is N or $CR^b$;
$X^c$ is N or $CR^c$;
$X^d$ is N or $CR^d$;
where 0 or 1 of $X^a$, $X^b$, $X^c$, and $X^d$ is N;
$R^a$, $R^b$, $R^c$, and $R^d$ are independently selected from H, C₂-C₂₀ heterocyclyl, and —NH(C₂-C₂₀ heterocyclyl) where heterocyclyl is optionally substituted with one or more groups selected from F, Cl, Br, I, —CH₃, —CH₂CH₃, —CH(CH₃)₂, —C(CH₃)₃, —CH₂CH(CH₃)₂, —CH₂NH₂, —CH₂NHCH₃, —CH₂CH₂NH₂, —CH₂CH₂CH₂NH₂, —CH₂CH(CH₃)NH₂, —CH₂OH, —CH₂CH₂OH, —C(CH₃)₂OH, —CH(OH)CH(CH₃)₂, —C(CH₃)₂CH₂OH, —CH₂CH₂SO₂CH₃, —CN, —CF₃, —CO₂H, —COCH₃, —CO₂CH₃, —CO₂C(CH₃)₃, —COCH(OH)CH₃, —CONH₂, —CONHCH₃, —CON(CH₃)₂, —C(CH₃)₂CONH₂, —NO₂, —NH₂, —NHCH₃, —N(CH₃)₂, —NHCH₂CHF₂, —NHCH₂CF₃, —NHCOCH₃, —N(CH₃)COCH₃, —NHC(O)OCH₂CH₃, —NHC(O)OCH₂Cl₃, —NHC(O)OC₆H₅, —NHS(O)₂CH₃, —N(CH₃)C(CH₃)₂CONH₂, —N(CH₃)CH₂CH₂S(O)₂CH₃, =O, —OH, —OCH₃, —S(O)₂N(CH₃)₂, —SCH₃, —CH₂OCH₃, —S(O)₂CH₃, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino;

or where $X^a$ is $CR^a$ and $X^b$ is $CR^b$, and $R^a$ and $R^b$ form a six-membered ring.

Exemplary embodiments of Formula I compounds include wherein $R^2$ is selected from the structures:

Exemplary embodiments of Formula I compounds include wherein $R^2$ is selected from the structures:

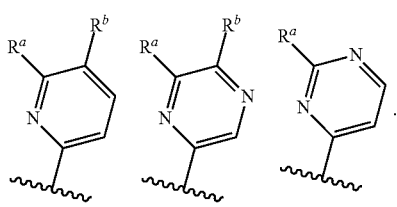

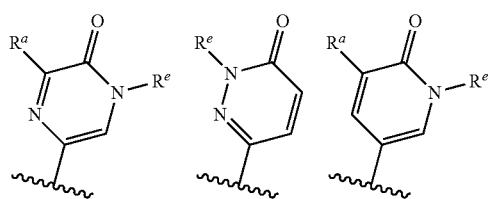

where $R^e$ is selected from H, —CH₃, —CH₂CH₃, —CH(CH₃)₂, —C(CH₃)₃, —CH₂CH(CH₃)₂, —CH₂NH₂, —CH₂NHCH₃, —CH₂CH₂NH₂, —CH₂CH₂CH₂NH₂, —CH₂CH(CH₃)NH₂, —CH₂OH, —CH₂CH₂OH, —C(CH₃)₂OH, —CH(OH)CH(CH₃)₂, —C(CH₃)₂CH₂OH, —CH₂CH₂SO₂CH₃, —CN, —CF₃, —CO₂H, —COCH₃, —CO₂CH₃, —CO₂C(CH₃)₃, —COCH(OH)CH₃, —CONH₂, —CONHCH₃, —CON(CH₃)₂, —C(CH₃)₂CONH₂, —S(O)₂N(CH₃)₂, —SCH₃, —CH₂OCH₃, —S(O)₂CH₃, cyclopropyl, cyclobutyl, cyclopentyl, cyclohexyl, cycloheptyl, and oxetanyl.

Exemplary embodiments of Formula I compounds include wherein $R^a$ is a heterocyclyl selected from the structures:

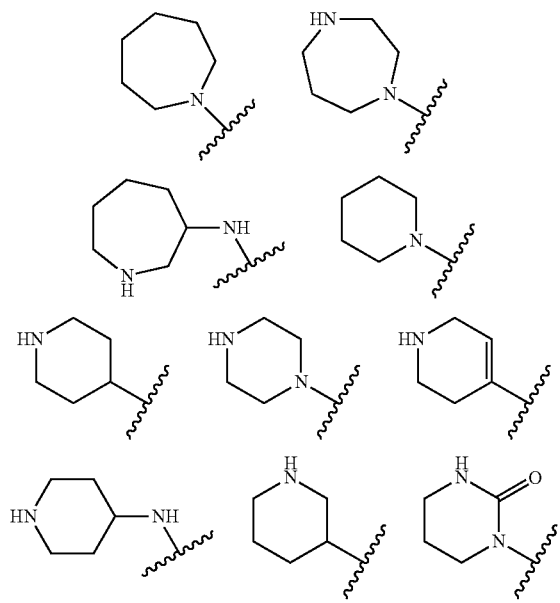

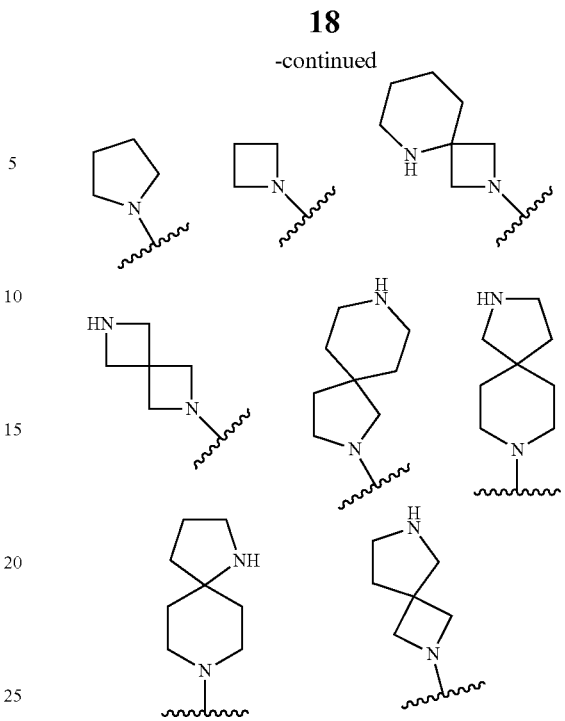

wherein the heterocyclyl is optionally substituted with one or more groups independently selected from F, —OH, —OCH₃, =O, —NH₂, —CH₃, —CH₂CH₃, and oxetan-3-yl.

Exemplary embodiments of Formula I compounds include wherein $R^2$ is phenyl, optionally substituted with one or more groups selected from F, Cl, Br, —CH₃ and —NH₂.

Exemplary embodiments of Formula I compounds include the structure of Formula Ia:

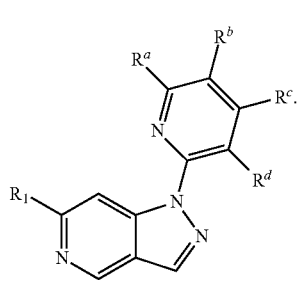

Ia

Exemplary embodiments of Formula I compounds include the structure of Formula Ib:

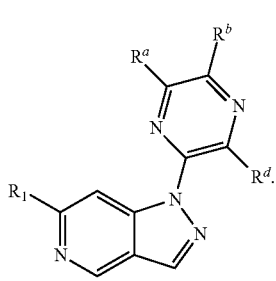

Ib

Exemplary embodiments of Formula I compounds include the structure of Formula Ic:

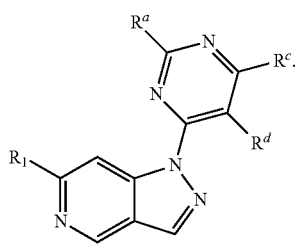

Exemplary embodiments of Formula I compounds include the structure of Formula Id:

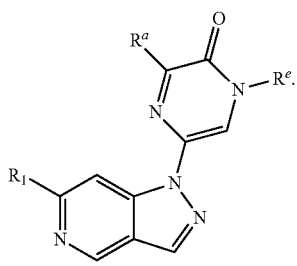

Exemplary embodiments of Formula I compounds include compounds of Tables 1 and 2.

Biological Evaluation

Determination of the Pim kinase activity of a Formula I compound is possible by a number of direct and indirect detection methods. Certain exemplary compounds described herein were assayed for their Pim kinase binding activity, including isoforms Pim-1, Pim-2, and Pim-3, (Example 901) and in vitro activity against tumor cells (Example 902). Certain exemplary compounds of the invention had Pim binding activity $IC_{50}$ values less than about 1 micromolar (μM). Certain compounds of the invention had tumor cell-based activity $EC_{50}$ values less than about 1 micromolar (μM). Formula I compounds having $Ki/IC_{50}/EC_{50}$ of less than 1 μM in assays described in Examples 901 and 902, may be useful therapeutically as Pim kinase inhibitors (Pim-1, Pim-2 and/or Pim-3).

Exemplary Formula I compounds in Tables 1 and 2 were made, characterized, and tested for inhibition of Pim kinase according to the methods of this invention, and have the following structures and corresponding names (ChemBioDraw Ultra, Version 11.0, CambridgeSoft Corp., Cambridge Mass.).

TABLE 1

| No. | Structure | IUPAC Name | MW |
|---|---|---|---|
| 101 | 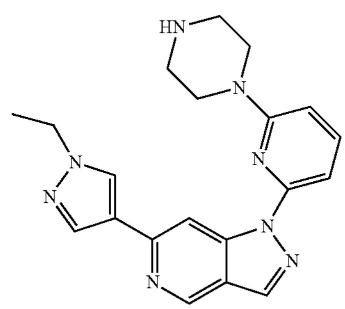 [SMILES: CCn1cc(-c2cc3c(cn2)cnn3-c2cccc(N3CCNCC3)n2)cn1] | 6-(1-ethylpyrazol-4-yl)-1-(6-piperazin-1-yl-2-pyridyl)pyrazolo[4,3-c]pyridine | 374.442 |
| 102 | 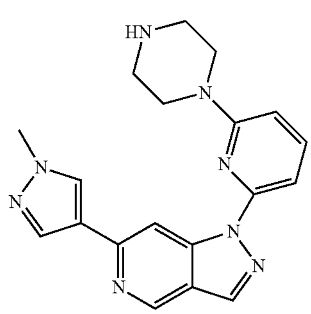 [SMILES: Cn1cc(-c2cc3c(cn2)cnn3-c2cccc(N3CCNCC3)n2)cn1] | 6-(1-methylpyrazol-4-yl)-1-(6-piperazin-1-yl-2-pyridyl)pyrazolo[4,3-c]pyridine | 360.416 |

TABLE 1-continued

| No. | Structure | IUPAC Name | MW |
|---|---|---|---|
| 103 | 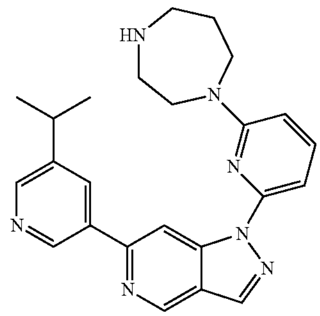 [SMILES: CC(C)c1cncc(-c2cc3c(cn2)cnn3-c2cccc(N3CCCNCC3)n2)c1] | 1-[6-(1,4-diazepan-1-yl)-2-pyridyl]-6-(5-isopropyl-3-pyridyl)pyrazolo[4,3-c]pyridine | 413.518 |
| 104 | 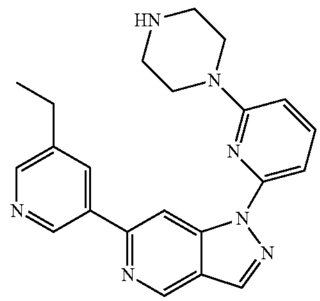 [SMILES: CCc1cncc(-c2cc3c(cn2)cnn3-c2cccc(N3CCNCC3)n2)c1] | 6-(5-ethyl-3-pyridyl)-1-(6-piperazin-1-yl-2-pyridyl)pyrazolo[4,3-c]pyridine | 385.465 |
| 105 | 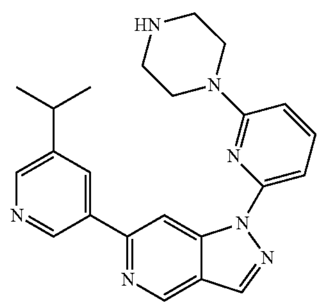 [SMILES: CC(C)c1cncc(-c2cc3c(cn2)cnn3-c2cccc(N3CCNCC3)n2)c1] | 6-(5-isopropyl-3-pyridyl)-1-(6-piperazin-1-yl-2-pyridyl)pyrazolo[4,3-c]pyridine | 399.492 |
| 106 | 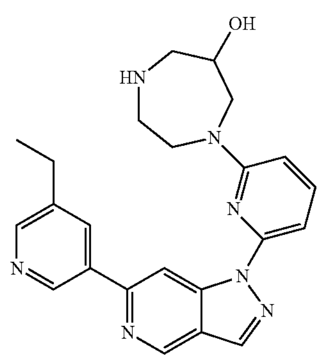 [SMILES: CCc1cncc(-c2cc3c(cn2)cnn3-c2cccc(N3CCNCC(O)C3)n2)c1] | 1-[6-[6-(5-ethyl-3-pyridyl)pyrazolo[4,3-c]pyridin-1-yl]-2-pyridyl]-1,4-diazepan-6-ol | 415.491 |
| 107 | 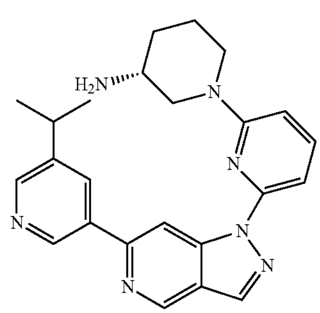 [SMILES: CC(C)c1cncc(-c2cc3c(cn2)cnn3-c2cccc(N3CCC[C@@H](N)C3)n2)c1] | (3R)-1-[6-[6-(5-isopropyl-3-pyridyl)pyrazolo[4,3-c]pyridin-1-yl]-2-pyridyl]piperidin-3-amine | 413.518 |

TABLE 1-continued

| No. | Structure | IUPAC Name | MW |
|---|---|---|---|
| 108 | 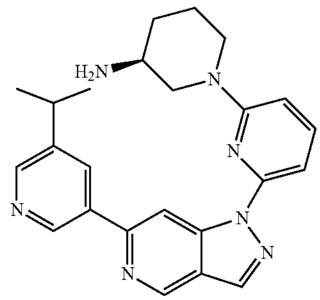 [SMILES: CC(C)c1cncc(-c2cc3c(cn2)cnn3-c2cccc(N3CCC[C@H](N)C3)n2)c1] | (3S)-1-[6-[6-(5-isopropyl-3-pyridyl)pyrazolo[4,3-c]pyridin-1-yl]-2-pyridyl]piperidin-3-amine | 413.518 |
| 109 | 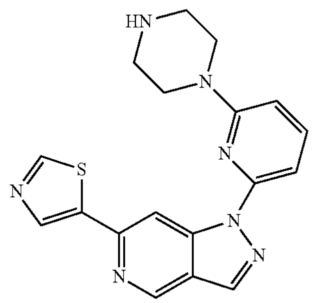 [SMILES: c1cc(N2CCNCC2)nc(-n2ncc3cnc(-c4cncs4)cc32)c1] | 5-[1-(6-piperazin-1-yl-2-pyridyl)pyrazolo[4,3-c]pyridin-6-yl]thiazole | 363.439 |
| 110 | 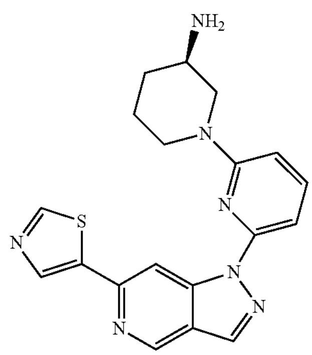 [SMILES: N[C@@H]1CCCN(c2cccc(-n3ncc4cnc(-c5cncs5)cc43)n2)C1] | (3R)-1-[6-(6-thiazol-5-ylpyrazolo[4,3-c]pyridin-1-yl)-2-pyridyl]piperidin-3-amine | 377.466 |
| 111 | 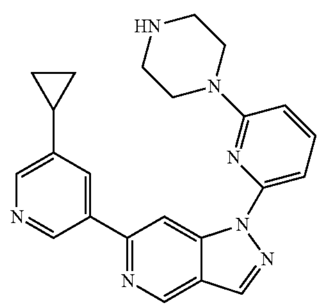 [SMILES: c1cc(N2CCNCC2)nc(-n2ncc3cnc(-c4cncc(C5CC5)c4)cc32)c1] | 6-(5-cyclopropyl-3-pyridyl)-1-(6-piperazin-1-yl-2-pyridyl)pyrazolo[4,3-c]pyridine | 397.476 |
| 112 | 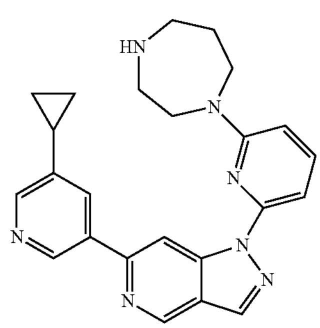 [SMILES: c1cc(N2CCCNCC2)nc(-n2ncc3cnc(-c4cncc(C5CC5)c4)cc32)c1] | 6-(5-cyclopropyl-3-pyridyl)-1-[6-(1,4-diazepan-1-yl)-2-pyridyl]pyrazolo[4,3-c]pyridine | 411.502 |

TABLE 1-continued

| No. | Structure | IUPAC Name | MW |
|---|---|---|---|
| 113 | 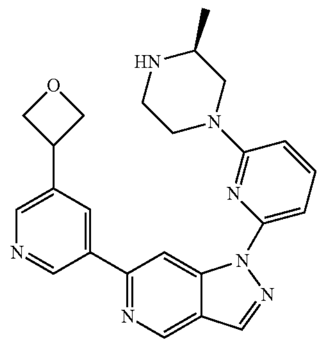 [SMILES: C[C@H]1CN(c2cccc(-n3ncc4cnc(-c5cncc(C6COC6)c5)cc43)n2)CCN1] | 1-[6-[(3S)-3-methylpiperazin-1-yl]-2-pyridyl]-6-[5-(oxetan-3-yl)-3-pyridyl]pyrazolo[4,3-c]pyridine | 427.502 |
| 114 | 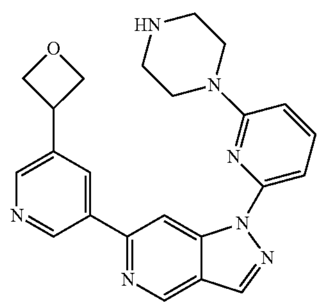 [SMILES: c1cc(N2CCNCC2)nc(-n2ncc3cnc(-c4cncc(C5COC5)c4)cc32)c1] | 6-[5-(oxetan-3-yl)-3-pyridyl]-1-(6-piperazin-1-yl-2-pyridyl)pyrazolo[4,3-c]pyridine | 413.475 |
| 115 | 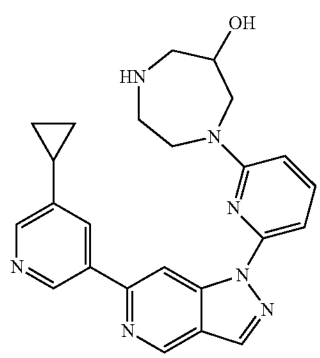 [SMILES: OC1CNCCN(c2cccc(-n3ncc4cnc(-c5cncc(C6CC6)c5)cc43)n2)C1] | 1-[6-[6-(5-cyclopropyl-3-pyridyl)pyrazolo[4,3-c]pyridin-1-yl]-2-pyridyl]-1,4-diazepan-6-ol | 427.502 |
| 116 | 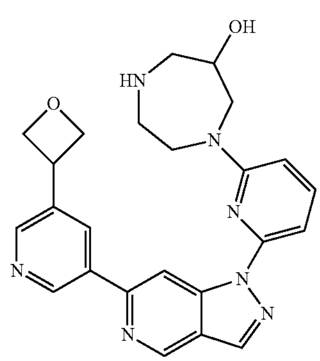 [SMILES: OC1CNCCN(c2cccc(-n3ncc4cnc(-c5cncc(C6COC6)c5)cc43)n2)C1] | 1-[6-[6-[5-(oxetan-3-yl)-3-pyridyl]pyrazolo[4,3-c]pyridin-1-yl]-2-pyridyl]-1,4-diazepan-6-ol | 443.501 |

TABLE 1-continued

| No. | Structure | IUPAC Name | MW |
|---|---|---|---|
| 117 | 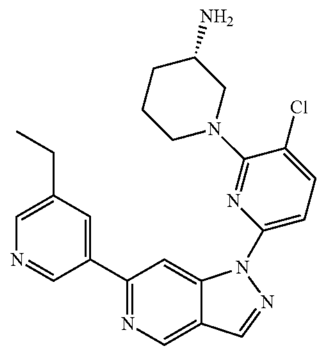 [SMILES: CCc1cncc(-c2cc3c(cn2)cnn3-c2ccc(Cl)c(N3CCC[C@H](N)C3)n2)c1] | (3S)-1-[3-chloro-6-[6-(5-ethyl-3-pyridyl)pyrazolo[4,3-c]pyridin-1-yl]-2-pyridyl]piperidin-3-amine | 433.937 |
| 118 | 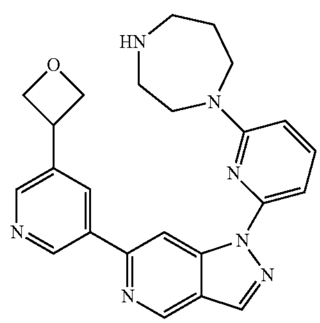 [SMILES: c1cc(N2CCCNCC2)nc(-n2ncc3cnc(-c4cncc(C5COC5)c4)cc32)c1] | 1-[6-(1,4-diazepan-1-yl)-2-pyridyl]-6-[5-(oxetan-3-yl)-3-pyridyl]pyrazolo[4,3-c]pyridine | 427.502 |
| 119 | 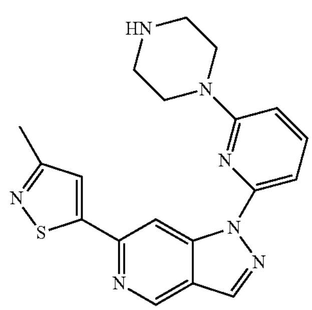 [SMILES: Cc1cc(-c2cc3c(cn2)cnn3-c2cccc(N3CCNCC3)n2)sn1] | 3-methyl-5-[1-(6-piperazin-1-yl-2-pyridyl)pyrazolo[4,3-c]pyridin-6-yl]isothiazole | 377.466 |
| 120 | 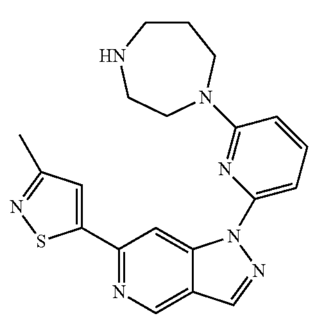 [SMILES: Cc1cc(-c2cc3c(cn2)cnn3-c2cccc(N3CCCNCC3)n2)sn1] | 5-[1-[6-(1,4-diazepan-1-yl)-2-pyridyl]pyrazolo[4,3-c]pyridin-6-yl]-3-methyl-isothiazole | 391.493 |

TABLE 1-continued

| No. | Structure | IUPAC Name | MW |
|---|---|---|---|
| 121 | 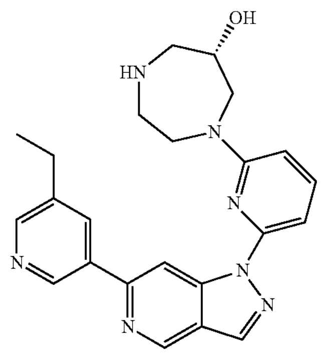 [SMILES: CCc1cncc(-c2cc3c(cn2)cnn3-c2cccc(N3CCNC[C@H](O)C3)n2)c1] | (S)-1-[6-[6-(5-ethyl-3-pyridyl)pyrazolo[4,3-c]pyridin-1-yl]-2-pyridyl]-1,4-diazepan-6-ol | 415.491 |
| 122 | 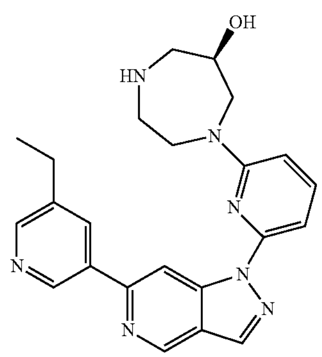 [SMILES: CCc1cncc(-c2cc3c(cn2)cnn3-c2cccc(N3CCNC[C@@H](O)C3)n2)c1] | (R)-1-[6-[6-(5-ethyl-3-pyridyl)pyrazolo[4,3-c]pyridin-1-yl]-2-pyridyl]-1,4-diazepan-6-ol | 415.491 |
| 123 | 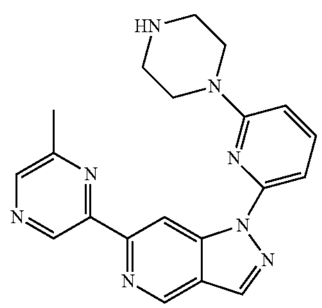 [SMILES: Cc1cncc(-c2cc3c(cn2)cnn3-c2cccc(N3CCNCC3)n2)n1] | 6-(6-methylpyrazin-2-yl)-1-(6-piperazin-1-yl-2-pyridyl)pyrazolo[4,3-c]pyridine | 372.426 |
| 124 | 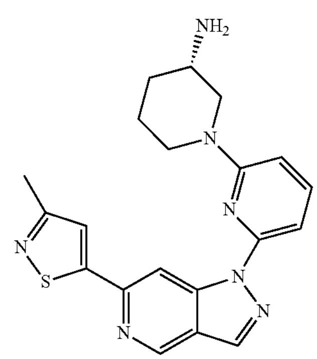 [SMILES: Cc1cc(-c2cc3c(cn2)cnn3-c2cccc(N3CCC[C@H](N)C3)n2)sn1] | (3S)-1-[6-[6-(3-methylisothiazol-5-yl)pyrazolo[4,3-c]pyridin-1-yl]-2-pyridyl]piperidin-3-amine | 391.493 |

TABLE 1-continued

| No. | Structure | IUPAC Name | MW |
|---|---|---|---|
| 125 | 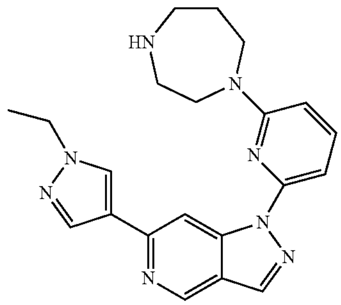 [SMILES: CCn1cc(-c2cc3c(cn2)cnn3-c2cccc(N3CCCNCC3)n2)cn1] | 1-[6-(1,4-diazepan-1-yl)-2-pyridyl]-6-(1-ethylpyrazol-4-yl)pyrazolo[4,3-c]pyridine | 388.469 |
| 126 | 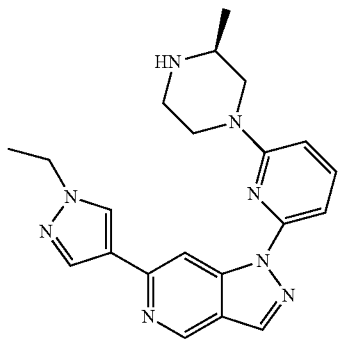 [SMILES: CCn1cc(-c2cc3c(cn2)cnn3-c2cccc(N3CCN[C@@H](C)C3)n2)cn1] | 6-(1-ethylpyrazol-4-yl)-1-[6-[(3S)-3-methylpiperazin-1-yl]-2-pyridyl]pyrazolo[4,3-c]pyridine | 388.469 |
| 127 | 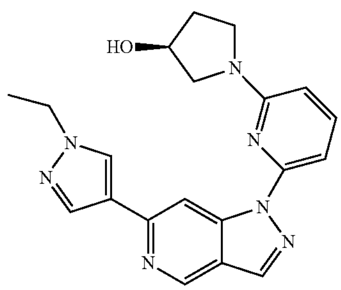 [SMILES: CCn1cc(-c2cc3c(cn2)cnn3-c2cccc(N3CC[C@H](O)C3)n2)cn1] | (3S)-1-[6-[6-(1-ethylpyrazol-4-yl)pyrazolo[4,3-c]pyridin-1-yl]-2-pyridyl]pyrrolidin-3-ol | 375.427 |
| 128 | 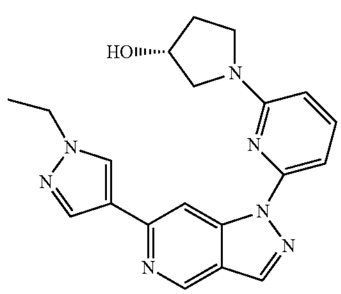 [SMILES: CCn1cc(-c2cc3c(cn2)cnn3-c2cccc(N3CC[C@@H](O)C3)n2)cn1] | (3R)-1-[6-[6-(1-ethylpyrazol-4-yl)pyrazolo[4,3-c]pyridin-1-yl]-2-pyridyl]pyrrolidin-3-ol | 375.427 |
| 129 | 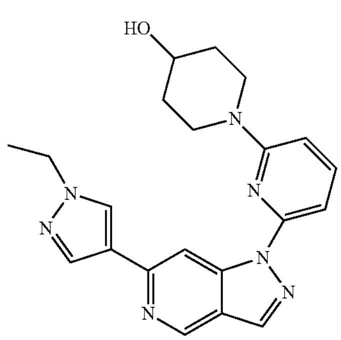 [SMILES: CCn1cc(-c2cc3c(cn2)cnn3-c2cccc(N3CCC(O)CC3)n2)cn1] | 1-[6-[6-(1-ethylpyrazol-4-yl)pyrazolo[4,3-c]pyridin-pyridyl]piperidin-4-ol | 389.454 |

TABLE 1-continued

| No. | Structure | IUPAC Name | MW |
|---|---|---|---|
| 130 | 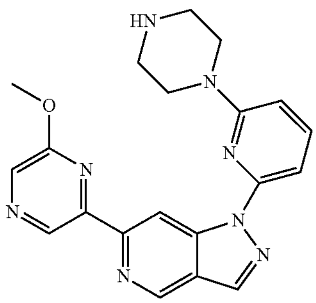 [SMILES: COc1cncc(-c2cc3c(cn2)cnn3-c2cccc(N3CCNCC3)n2)n1] | 6-(6-methoxypyrazin-2-yl)-1-(6-piperazin-1-yl-2-pyridyl)pyrazolo[4,3-c]pyridine | 388.426 |
| 131 | 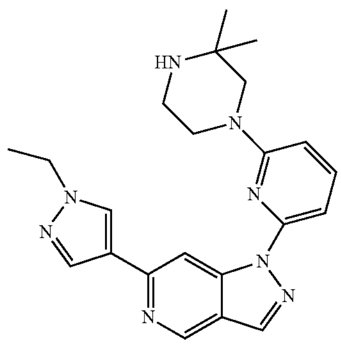 [SMILES: CCn1cc(-c2cc3c(cn2)cnn3-c2cccc(N3CCNC(C)(C)C3)n2)cn1] | 1-[6-(3,3-dimethylpiperazin-1-yl)-2-pyridyl]-6-(1-ethylpyrazol-4-yl)pyrazolo[4,3-c]pyridine | 402.495 |
| 132 | 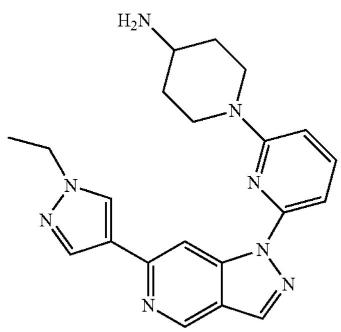 [SMILES: CCn1cc(-c2cc3c(cn2)cnn3-c2cccc(N3CCC(N)CC3)n2)cn1] | 1-[6-[6-(1-ethylpyrazol-4-yl)pyrazolo[4,3-c]pyridin-1-yl]-2-pyridyl]piperidin-4-amine | 388.469 |
| 133 | 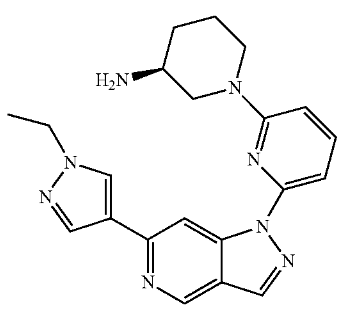 [SMILES: CCn1cc(-c2cc3c(cn2)cnn3-c2cccc(N3CCC[C@H](N)C3)n2)cn1] | (3S)-1-[6-[6-(1-ethylpyrazol-4-yl)pyrazolo[4,3-c]pyridin-1-yl]-2-pyridyl]piperidin-3-amine | 388.469 |
| 134 | 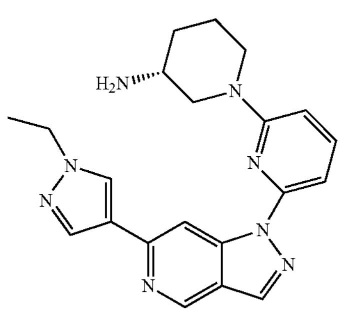 [SMILES: CCn1cc(-c2cc3c(cn2)cnn3-c2cccc(N3CCC[C@@H](N)C3)n2)cn1] | (3R)-1-[6-[6-(1-ethylpyrazol-4-yl)pyrazolo[4,3-c]pyridin-1-yl]-2-pyridyl]piperidin-3-amine | 388.469 |

TABLE 1-continued

| No. | Structure | IUPAC Name | MW |
|---|---|---|---|
| 135 | 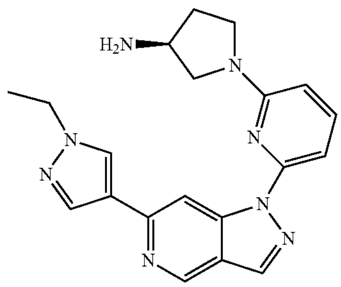 [SMILES: CCn1cc(-c2cc3c(cn2)cnn3-c2cccc(N3CC[C@H](N)C3)n2)cn1] | (3S)-1-[6-[6-(1-ethylpyrazol-4-yl)pyrazolo[4,3-c]pyridin-1-yl]-2-pyridyl]pyrrolidin-3-amine | 374.442 |
| 136 | 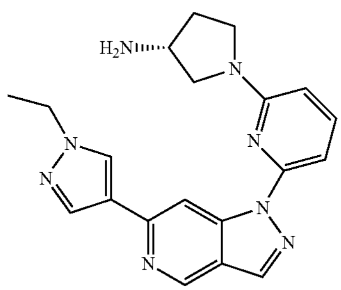 [SMILES: CCn1cc(-c2cc3c(cn2)cnn3-c2cccc(N3CC[C@@H](N)C3)n2)cn1] | (3R)-1-[6-[6-(1-ethylpyrazol-4-yl)pyrazolo[4,3-c]pyridin-1-yl]-2-pyridyl]pyrrolidin-3-amine | 374.442 |
| 137 | 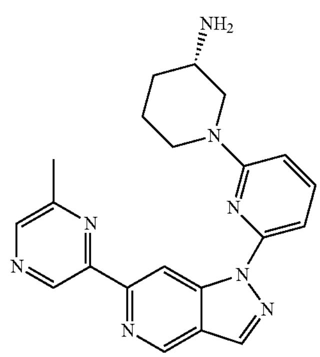 [SMILES: Cc1cncc(-c2cc3c(cn2)cnn3-c2cccc(N3CCC[C@H](N)C3)n2)n1] | (3S)-1-[6-[6-(6-methylpyrazin-2-yl)pyrazolo[4,3-c]pyridin-1-yl]-2-pyridyl]piperidin-3-amine | 386.453 |
| 138 | 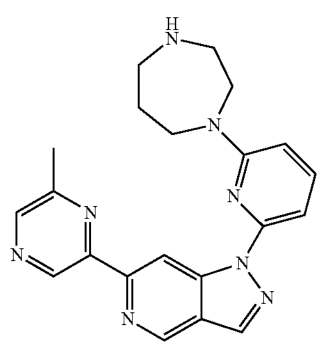 [SMILES: Cc1cncc(-c2cc3c(cn2)cnn3-c2cccc(N3CCCNCC3)n2)n1] | 1-[6-(1,4-diazepan-1-yl)-2-pyridyl]-6-(6-methylpyrazin-2-yl)pyrazolo[4,3-c]pyridine | 386.453 |

TABLE 1-continued

| No. | Structure | IUPAC Name | MW |
|---|---|---|---|
| 139 | 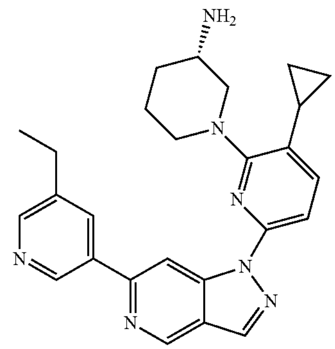 [SMILES: CCc1cncc(-c2cc3c(cn2)cnn3-c2ccc(C3CC3)c(N3CCC[C@H](N)C3)n2)c1] | (3S)-1-[3-cyclopropyl-6-[6-(5-ethyl-3-pyridyl)pyrazolo[4,3-c]pyridin-1-yl]-2-pyridyl]piperidin-3-amine | 439.555 |
| 140 | 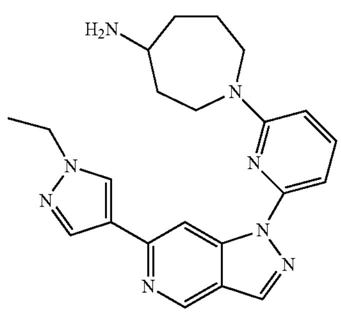 [SMILES: CCn1cc(-c2cc3c(cn2)cnn3-c2cccc(N3CCCC(N)CC3)n2)cn1] | 1-[6-[6-(1-ethylpyrazol-4-yl)pyrazolo[4,3-c]pyridin-1-yl]-2-pyridyl]azepan-4-amine | 402.495 |
| 141 | 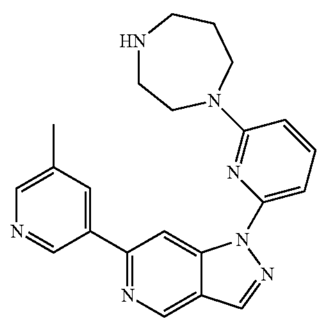 [SMILES: Cc1cncc(-c2cc3c(cn2)cnn3-c2cccc(N3CCCNCC3)n2)c1] | 1-[6-(1,4-diazepan-1-yl)-2-pyridyl]-6-(5-methyl-3-pyridyl)pyrazolo[4,3-c]pyridine | 385.465 |
| 142 | 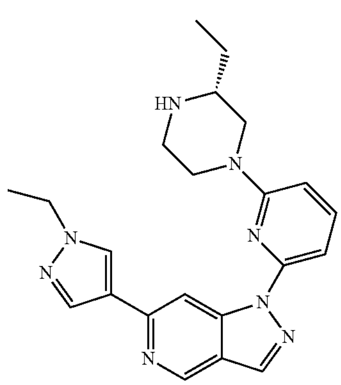 [SMILES: CC[C@@H]1CN(c2cccc(-n3ncc4cnc(-c5cnn(CC)c5)cc43)n2)CCN1] | 1-[6-[(3R)-3-ethylpiperazin-1-yl]-2-pyridyl]-6-(1-ethylpyrazol-4-yl)pyrazolo[4,3-c]pyridine | 402.495 |

TABLE 1-continued

| No. | Structure | IUPAC Name | MW |
|---|---|---|---|
| 143 | 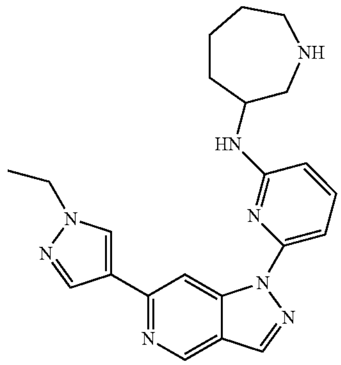 [SMILES: CCn1cc(-c2cc3c(cn2)cnn3-c2cccc(NC3CCCCNC3)n2)cn1] | N-[6-[6-(1-ethylpyrazol-4-yl)pyrazolo[4,3-c]pyridin-1-yl]-2-pyridyl]azepan-3-amine | 402.495 |
| 144 | 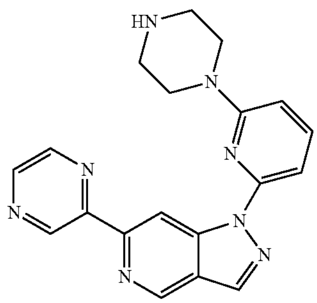 [SMILES: c1cc(N2CCNCC2)nc(-n2ncc3cnc(-c4cnccn4)cc32)c1] | 1-(6-piperazin-1-yl-2-pyridyl)-6-pyrazin-2-yl-pyrazolo[4,3-c]pyridine | 358.4 |
| 145 | 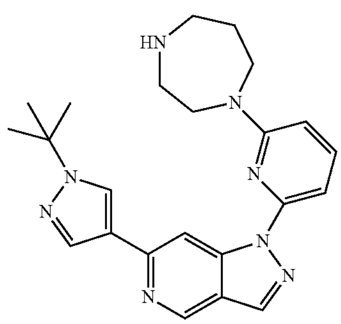 [SMILES: CC(C)(C)n1cc(-c2cc3c(cn2)cnn3-c2cccc(N3CCCNCC3)n2)cn1] | 6-(1-tert-butylpyrazol-4-yl)-1-[6-(1,4-diazepan-1-yl)-2-pyridyl]pyrazolo[4,3-c]pyridine | 416.522 |
| 146 | 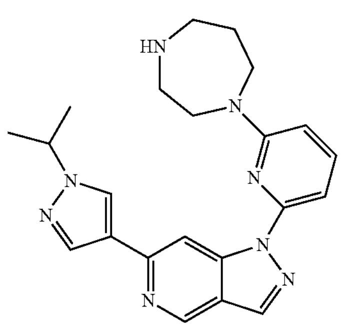 [SMILES: CC(C)n1cc(-c2cc3c(cn2)cnn3-c2cccc(N3CCCNCC3)n2)cn1] | 1-[6-(1,4-diazepan-1-yl)-2-pyridyl]-6-(1-isopropylpyrazol-4-yl)pyrazolo[4,3-c]pyridine | 402.495 |

TABLE 1-continued

| No. | Structure | IUPAC Name | MW |
|---|---|---|---|
| 147 | 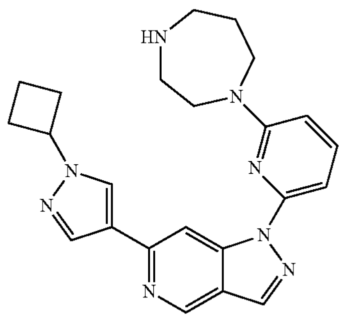 [SMILES: c1cc(N2CCCNCC2)nc(-n2ncc3cnc(-c4cnn(C5CCC5)c4)cc32)c1] | 6-(1-cyclobutylpyrazol-4-yl)-1-[6-(1,4-diazepan-1-yl)-2-pyridyl]pyrazolo[4,3-c]pyridine | 414.506 |
| 148 | 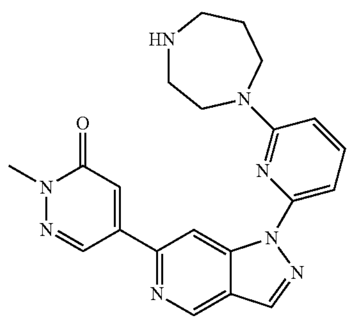 [SMILES: Cn1ncc(-c2cc3c(cn2)cnn3-c2cccc(N3CCCNCC3)n2)cc1=O] | 5-[1-[6-(1,4-diazepan-1-yl)-2-pyridyl]pyrazolo[4,3-c]pyridin-6-yl]-2-methyl-pyridazin-3-one | 402.452 |
| 149 | 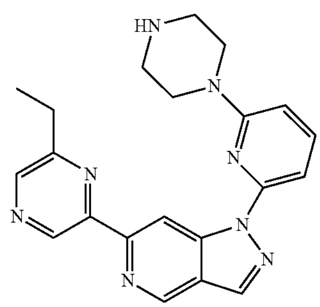 [SMILES: CCc1cncc(-c2cc3c(cn2)cnn3-c2cccc(N3CCNCC3)n2)n1] | 6-(6-ethylpyrazin-2-yl)-1-(6-piperazin-1-yl-2-pyridyl)pyrazolo[4,3-c]pyridine | 386.453 |
| 150 | 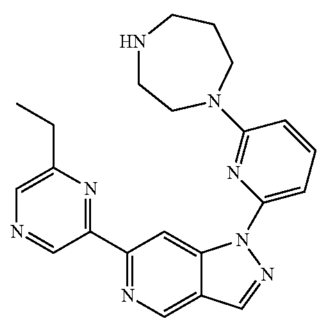 [SMILES: CCc1cncc(-c2cc3c(cn2)cnn3-c2cccc(N3CCCNCC3)n2)n1] | 1-[6-(1,4-diazepan-1-yl)-2-pyridyl]-6-(6-ethylpyrazin-2-yl)pyrazolo[4,3-c]pyridine | 400.48 |
| 151 | 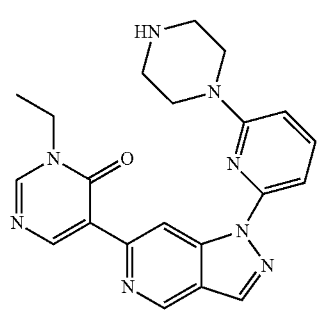 [SMILES: CCn1cncc(-c2cc3c(cn2)cnn3-c2cccc(N3CCNCC3)n2)c1=O] | 3-ethyl-5-[1-(6-piperazin-1-yl-2-pyridyl)pyrazolo[4,3-c]pyridin-6-yl]pyrimidin-4-one | 402.452 |

TABLE 1-continued

| No. | Structure | IUPAC Name | MW |
|---|---|---|---|
| 152 | 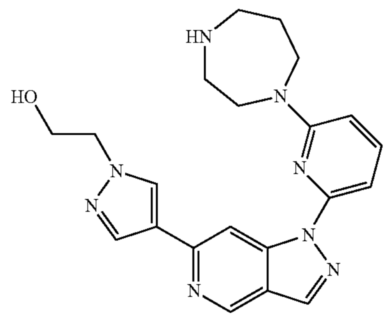 [SMILES: OCCn1cc(-c2cc3c(cn2)cnn3-c2cccc(N3CCCNCC3)n2)cn1] | 2-[4-[1-[6-(1,4-diazepan-1-yl)-2-pyridyl]pyrazolo[4,3-c]pyridin-6-yl]pyrazol-1-yl]ethanol | 404.468 |
| 153 | 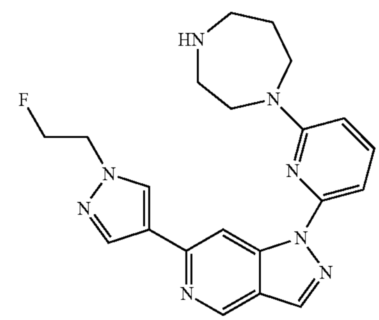 [SMILES: FCCn1cc(-c2cc3c(cn2)cnn3-c2cccc(N3CCCNCC3)n2)cn1] | 1-[6-(1,4-diazepan-1-yl)-2-pyridyl]-6-[1-(2-fluoroethyl)pyrazol-4-yl]pyrazolo[4,3-c]pyridine | 406.459 |
| 154 | 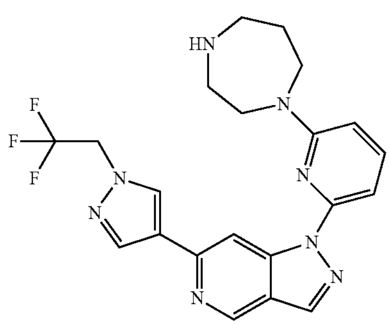 [SMILES: FC(F)(F)Cn1cc(-c2cc3c(cn2)cnn3-c2cccc(N3CCCNCC3)n2)cn1] | 1-[6-(1,4-diazepan-1-yl)-2-pyridyl]-6-[1-(2,2,2-trifluoroethyl)pyrazol-4-yl]pyrazolo[4,3-c]pyridine | 442.44 |
| 155 | 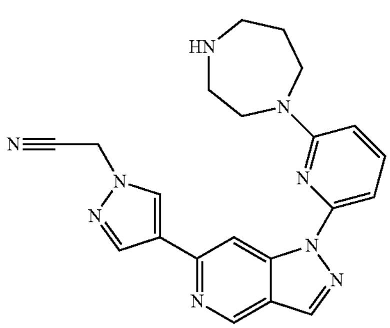 [SMILES: N#CCn1cc(-c2cc3c(cn2)cnn3-c2cccc(N3CCCNCC3)n2)cn1] | 2-[4-[1-[6-(1,4-diazepan-1-yl)-2-pyridyl]pyrazolo[4,3-c]pyridin-6-yl]pyrazol-1-yl]acetonitrile | 399.452 |

TABLE 1-continued

| No. | Structure | IUPAC Name | MW |
|---|---|---|---|
| 156 | 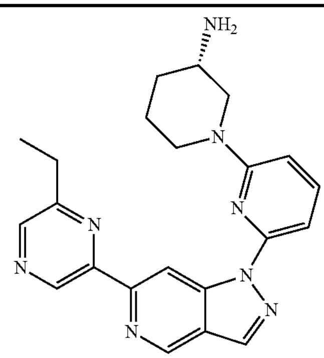 | (3S)-1-[6-[6-(6-ethylpyrazin-2-yl)pyrazolo[4,3-c]pyridin-1-yl]-2-pyridyl]piperidin-3-amine | 400.48 |
| 157 | 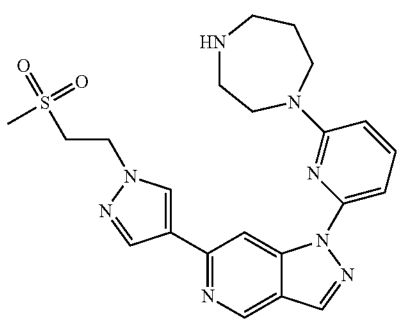 [SMILES: CS(=O)(=O)CCn1cc(-c2cc3c(cn2)cnn3-c2cccc(N3CCCNCC3)n2)cn1] | 1-[6-(1,4-diazepan-1-yl)-2-pyridyl]-6-[1-(2-methylsulfonylethyl)pyrazol-4-yl]pyrazolo[4,3-c]pyridine | 466.559 |
| 158 | 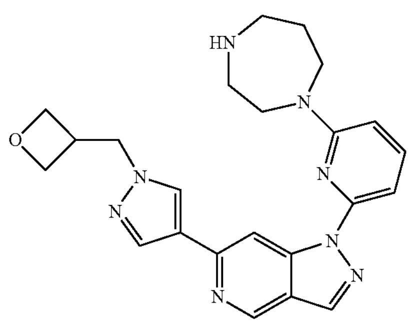 [SMILES: c1cc(N2CCCNCC2)nc(-n2ncc3cnc(-c4cnn(CC5COC5)c4)cc32)c1] | 1-[6-(1,4-diazepan-1-yl)-2-pyridyl]-6-[1-(oxetan-3-ylmethyl)pyrazol-4-yl]pyrazolo[4,3-c]pyridine | 430.506 |
| 159 | 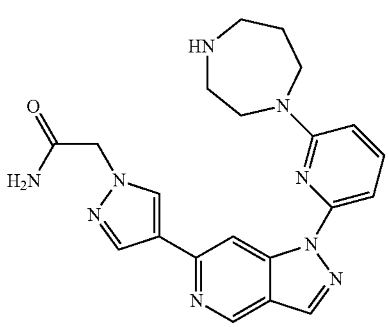 [SMILES: NC(=O)Cn1cc(-c2cc3c(cn2)cnn3-c2cccc(N3CCCNCC3)n2)cn1] | 2-[4-[1-[6-(1,4-diazepan-1-yl)-2-pyridyl]pyrazolo[4,3-c]pyridin-6-yl]pyrazol-1-yl]acetamide | 417.467 |
| 160 | 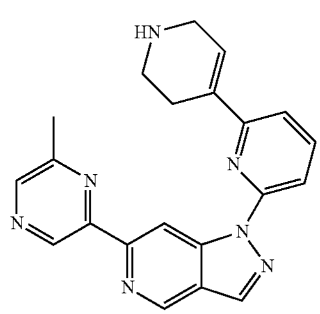 [SMILES: Cc1cncc(-c2cc3c(cn2)cnn3-c2cccc(C3=CCNCC3)n2)n1] | 6-(6-methylpyrazin-2-yl)-1-[6-(1,2,3,6-tetrahydropyridin-4-yl)-2-pyridyl]pyrazolo[4,3-c]pyridine | 369.422 |

TABLE 1-continued

| No. | Structure | IUPAC Name | MW |
|---|---|---|---|
| 161 | 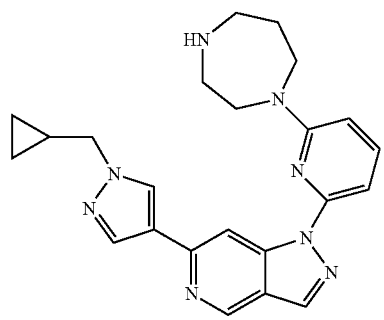 [SMILES: c1cc(N2CCCNCC2)nc(-n2ncc3cnc(-c4cnn(CC5CC5)c4)cc32)c1] | 6-[1-(cyclopropylmethyl)pyrazol-4-yl]-1-[6-(1,4-diazepan-1-yl)-2-pyridyl]pyrazolo[4,3-c]pyridine | 414.506 |
| 162 | 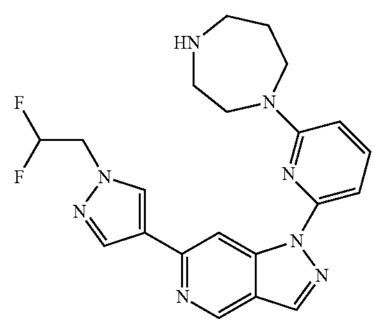 [SMILES: FC(F)Cn1cc(-c2cc3c(cn2)cnn3-c2cccc(N3CCCNCC3)n2)cn1] | 1-[6-(1,4-diazepan-1-yl)-2-pyridyl]-6-[1-(2,2-difluoroethyl)pyrazol-4-yl]pyrazolo[4,3-c]pyridine | 424.45 |
| 163 | 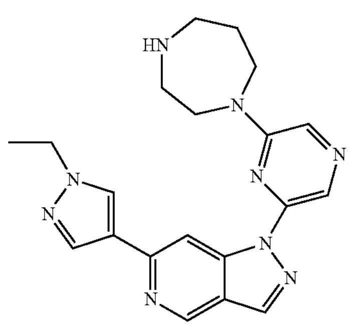 [SMILES: CCn1cc(-c2cc3c(cn2)cnn3-c2cncc(N3CCCNCC3)n2)cn1] | 1-[6-(1,4-diazepan-1-yl)pyrazin-2-yl]-6-(1-ethylpyrazol-4-yl)pyrazolo[4,3-c]pyridine | 389.457 |
| 164 | 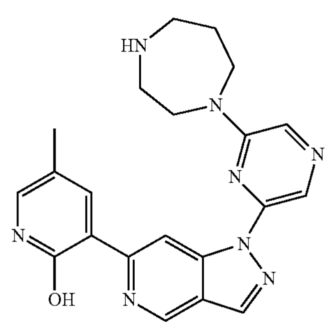 [SMILES: Cc1cnc(O)c(-c2cc3c(cn2)cnn3-c2cncc(N3CCCNCC3)n2)c1] | 3-[1-[6-(1,4-diazepan-1-yl)pyrazin-2-yl]pyrazolo[4,3-c]pyridin-6-yl]-5-methyl-pyridin-2-ol | 402.452 |
| 165 | 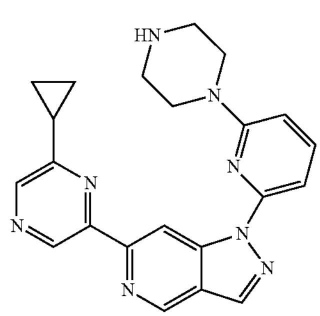 [SMILES: c1cc(N2CCNCC2)nc(-n2ncc3cnc(-c4cncc(C5CC5)n4)cc32)c1] | 6-(6-cyclopropylpyrazin-2-yl)-1-(6-piperazin-1-yl-2-pyridyl)pyrazolo[4,3-c]pyridine | 398.464 |

TABLE 1-continued

| No. | Structure | IUPAC Name | MW |
| --- | --- | --- | --- |
| 166 | 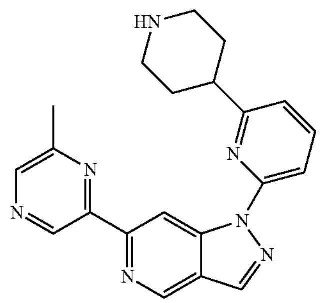 [SMILES: Cc1cncc(-c2cc3c(cn2)cnn3-c2cccc(C3CCNCC3)n2)n1] | 6-(6-methylpyrazin-2-yl)-1-[6-(4-piperidyl)-2-pyridyl]pyrazolo[4,3-c]pyridine | 371.438 |
| 167 | 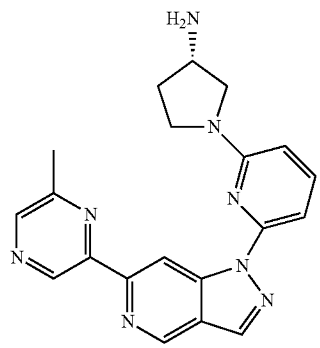 [SMILES: Cc1cncc(-c2cc3c(cn2)cnn3-c2cccc(N3CC[C@H](N)C3)n2)n1] | (3S)-1-[6-[6-(6-methylpyrazin-2-yl)pyrazolo[4,3-c]pyridin-1-yl]-2-pyridyl]pyrrolidin-3-amine | 372.426 |
| 168 | 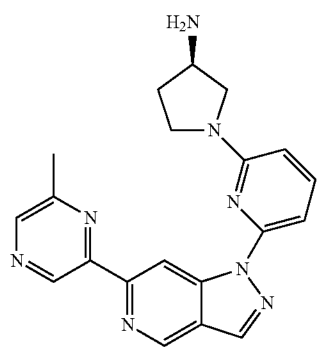 [SMILES: Cc1cncc(-c2cc3c(cn2)cnn3-c2cccc(N3CC[C@@H](N)C3)n2)n1] | (3R)-1-[6-[6-(6-methylpyrazin-2-yl)pyrazolo[4,3-c]pyridin-1-yl]-2-pyridyl]pyrrolidin-3-amine | 372.426 |
| 169 | 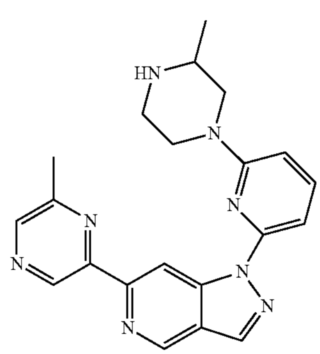 [SMILES: Cc1cncc(-c2cc3c(cn2)cnn3-c2cccc(N3CCNC(C)C3)n2)n1] | 1-[6-(3-methylpiperazin-1-yl)-2-pyridyl]-6-(6-methylpyrazin-2-yl)pyrazolo[4,3-c]pyridine | 386.453 |

TABLE 1-continued

| No. | Structure | IUPAC Name | MW |
|---|---|---|---|
| 170 | 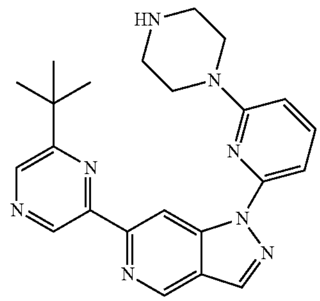 [SMILES: CC(C)(C)c1cncc(-c2cc3c(cn2)cnn3-c2cccc(N3CCNCC3)n2)n1] | 6-(6-tert-butylpyrazin-2-yl)-1-(6-piperazin-1-yl-2-pyridyl)pyrazolo[4,3-c]pyridine | 414.506 |
| 171 | 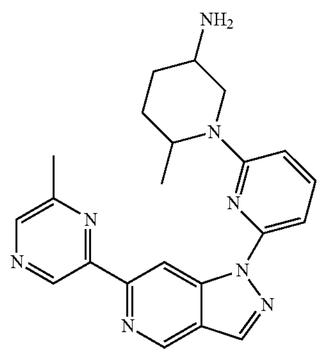 [SMILES: Cc1cncc(-c2cc3c(cn2)cnn3-c2cccc(N3CC(N)CCC3C)n2)n1] | 6-methyl-1-[6-[6-(6-methylpyrazin-2-yl)pyrazolo[4,3-c]pyridin-1-yl]-2-pyridyl]piperidin-3-amine | 400.48 |
| 172 | 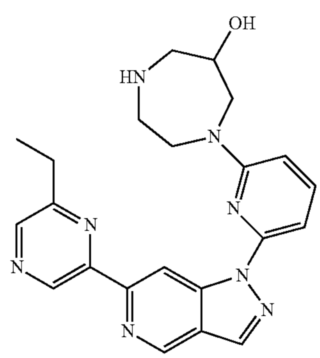 [SMILES: CCc1cncc(-c2cc3c(cn2)cnn3-c2cccc(N3CCNCC(O)C3)n2)n1] | 1-[6-[6-(6-ethylpyrazin-2-yl)pyrazolo[4,3-c]pyridin-1-yl]-2-pyridyl]-1,4-diazepan-6-ol | 416.479 |
| 173 | 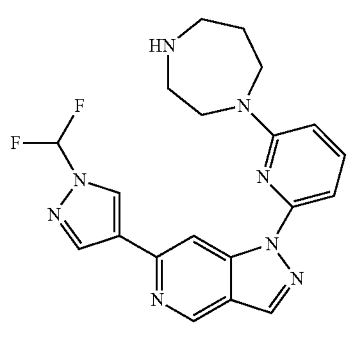 [SMILES: FC(F)n1cc(-c2cc3c(cn2)cnn3-c2cccc(N3CCCNCC3)n2)cn1] | 1-[6-(1,4-diazepan-1-yl)-2-pyridyl]-6-[1-(difluoromethyl)pyrazol-4-yl]pyrazolo[4,3-c]pyridine | 410.423 |

TABLE 1-continued

| No. | Structure | IUPAC Name | MW |
|---|---|---|---|
| 174 | 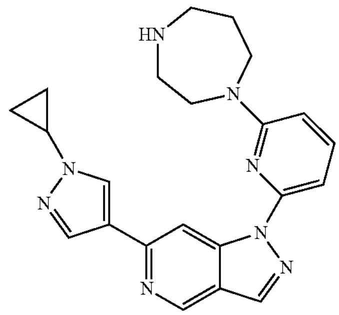 [SMILES: c1cc(N2CCCNCC2)nc(-n2ncc3cnc(-c4cnn(C5CC5)c4)cc32)c1] | 6-(1-cyclopropylpyrazol-4-yl)-1-[6-(1,4-diazepan-1-yl)-2-pyridyl]pyrazolo[4,3-c]pyridine | 400.48 |
| 175 | 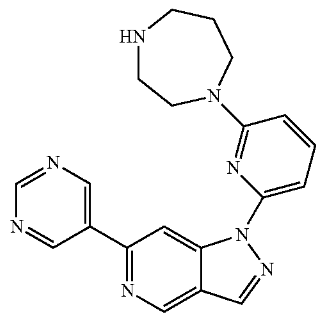 [SMILES: c1cc(N2CCCNCC2)nc(-n2ncc3cnc(-c4cncnc4)cc32)c1] | 1-[6-(1,4-diazepan-1-yl)-2-pyridyl]-6-pyrimidin-5-yl-pyrdzolo[4,3-c]pyridine | 372.426 |
| 176 | 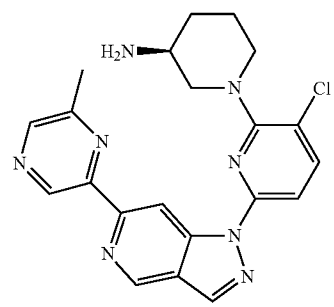 [SMILES: Cc1cncc(-c2cc3c(cn2)cnn3-c2ccc(Cl)c(N3CCC[C@H](N)C3)n2)n1] | (3S)-1-[3-chloro-6-[6-(6-methylpyrazin-2-yl)pyrazolo[4,3-c]pyridin-1-yl]-2-pyridyl]piperidin-3-amine | 420.898 |
| 177 | 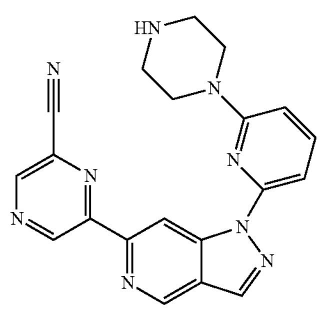 [SMILES: N#Cc1cncc(-c2cc3c(cn2)cnn3-c2cccc(N3CCNCC3)n2)n1] | 6-[1-(6-piperazin-1-yl-2-pyridyl)pyrazolo[4,3-c]pyridin-6-yl]pyrazine-2-carbonitrile | 383.409 |
| 178 | 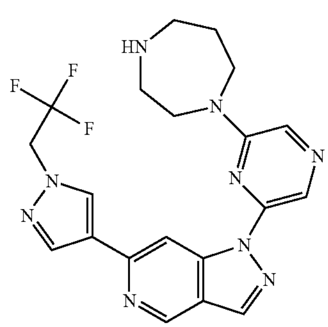 [SMILES: FC(F)(F)Cn1cc(-c2cc3c(cn2)cnn3-c2cncc(N3CCCNCC3)n2)cn1] | 1-[6-(1,4-diazepan-1-yl)pyrazin-2-yl]-6-[1-(2,2,2-trifluoroethyl)pyrazol-4-yl]pyrazolo[4,3-c]pyridine | 443.428 |

TABLE 1-continued

| No. | Structure | IUPAC Name | MW |
|---|---|---|---|
| 179 | 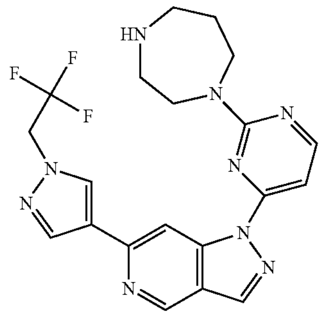 [SMILES: FC(F)(F)Cn1cc(-c2cc3c(cn2)cnn3-c2ccnc(N3CCCNCC3)n2)cn1] | 1-[2-(1,4-diazepan-1-yl)pyrimidin-4-yl]-6-[1-(2,2,2-trifluoroethyl)pyrazol-4-yl]pyrazolo[4,3-c]pyridine | 443.428 |
| 180 | 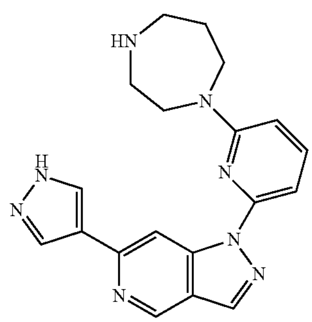 [SMILES: c1cc(N2CCCNCC2)nc(-n2ncc3cnc(-c4cn[nH]c4)cc32)c1] | 1-[6-(1,4-diazepan-1-yl)-2-pyridyl]-6-(1H-pyrazol-4-yl)pyrazolo[4,3-c]pyridine | 360.416 |
| 181 | 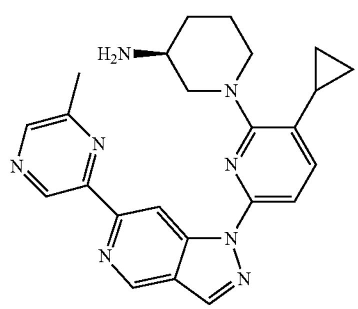 [SMILES: Cc1cncc(-c2cc3c(cn2)cnn3-c2ccc(C3CC3)c(N3CCC[C@H](N)C3)n2)n1] | (3S)-1-[3-cyclopropyl-6-[6-(6-methylpyrazin-2-yl)pyrazolo[4,3-c]pyridin-1-yl]-2-pyridyl]piperidin-3-amine | 426.517 |
| 182 | 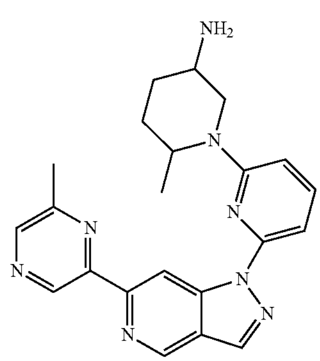 [SMILES: Cc1cncc(-c2cc3c(cn2)cnn3-c2cccc(N3CC(N)CCC3C)n2)n1] | 6-methyl-1-[6-[6-(6-methylpyrazin-2-yl)pyrazolo[4,3-c]pyridin-1-yl]-2-pyridyl]piperidin-3-amine | 400.48 |

TABLE 1-continued

| No. | Structure | IUPAC Name | MW |
|---|---|---|---|
| 183 | 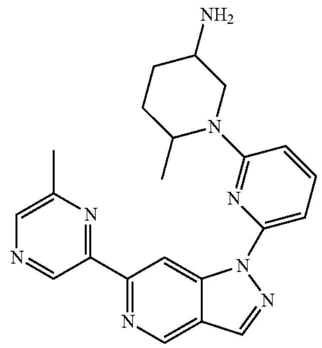 [SMILES: Cc1cncc(-c2cc3c(cn2)cnn3-c2cccc(N3CC(N)CCC3C)n2)n1] | 6-methyl-1-[6-[6-(6-methylpyrazin-2-yl)pyrazolo[4,3-c]pyridin-1-yl]-2-pyridyl]piperidin-3-amine | 400.48 |
| 184 | 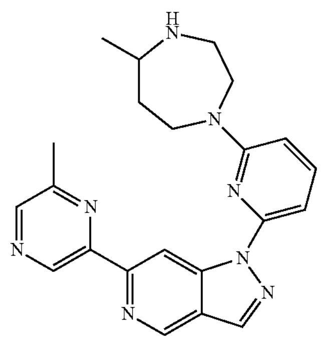 [SMILES: Cc1cncc(-c2cc3c(cn2)cnn3-c2cccc(N3CCNC(C)CC3)n2)n1] | 1-[6-(5-methyl-1,4-diazepan-1-yl)-2-pyridyl]-6-(6-methylpyrazin-2-yl)pyrazolo[4,3-c]pyridine | 400.48 |
| 185 | 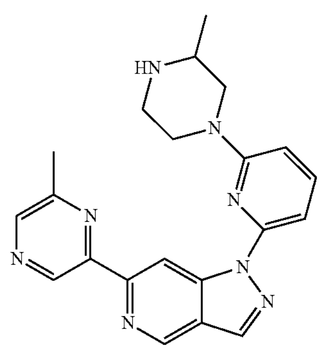 [SMILES: Cc1cncc(-c2cc3c(cn2)cnn3-c2cccc(N3CCNC(C)C3)n2)n1] | 1-[6-(3-methylpiperazin-1-yl)-2-pyridyl]-6-(6-methylpyrazin-2-yl)pyrazolo[4,3-c]pyridine | 386.453 |
| 186 | 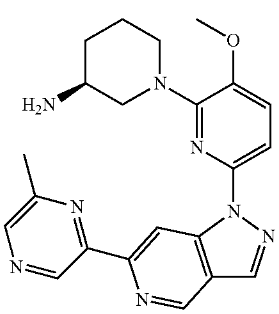 [SMILES: COc1ccc(-n2ncc3cnc(-c4cncc(C)n4)cc32)nc1N1CCC[C@H](N)C1] | (3S)-1-[3-methoxy-6-[6-(6-methylpyrazin-2-yl)pyrazolo[4,3-c]pyridin-1-yl]-2-pyridyl]piperidin-3-amine | 416.479 |

TABLE 1-continued
| No. | Structure | IUPAC Name | MW |
|---|---|---|---|
| 187 | 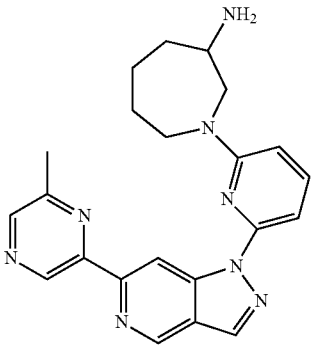 [SMILES: Cc1cncc(-c2cc3c(cn2)cnn3-c2cccc(N3CCCCC(N)C3)n2)n1] | 1-[6-[6-(6-methylpyrazin-2-yl)pyrazolo[4,3-c]pyridin-1-yl]-2-pyridyl]azepan-3-amine | 400.48 |
| 188 | 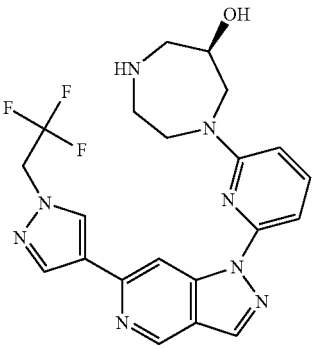 [SMILES: O[C@@H]1CNCCN(c2cccc(-n3ncc4cnc(-c5cnn(CC(F)(F)F)c5)cc43)n2)C1] | (R)-1-(6-(6-(1-(2,2,2-Trifluoroethyl)-1H-pyrazol-4-yl)-1H-pyrazolo[4,3-c]pyridin-1-yl)-pyridin-2-yl)-1,4-diazepan-6-ol | 458.44 |
| 189 | 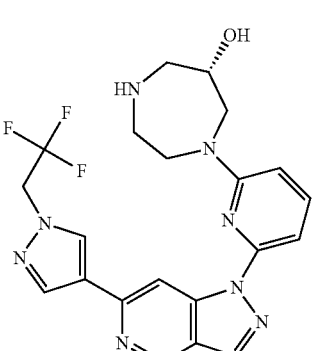 | (S)-1-(6-(6-(1-(2,2,2-Trifluoroethyl)-1H-pyrazol-4-yl)-1H-pyrazolo[4,3-c]pyridin-1-yl)-pyridin-2-yl)-1,4-diazepan-6-ol | 458.44 |
| 190 | 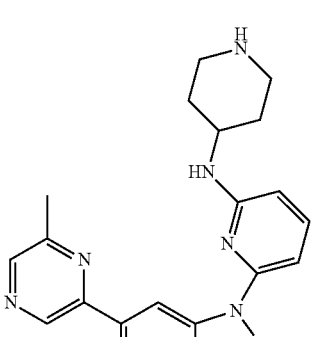 | 6-[6-(6-methylpyrazin-2-yl)pyrazolo[4,3-c]pyridin-1-yl]-N-(4-piperidyl)pyridin-2-amine | 386.453 |

TABLE 1-continued

| No. | Structure | IUPAC Name | MW |
|---|---|---|---|
| 191 | 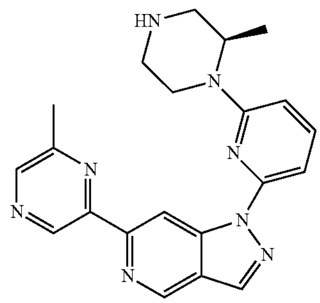 [SMILES: Cc1cncc(-c2cc3c(cn2)cnn3-c2cccc(N3CCNC[C@H]3C)n2)n1] | 1-[6-[(2R)-2-methylpiperazin-1-yl]-2-pyridyl]-6-(6-methylpyrazin-2-yl)pyrazolo[4,3-c]pyridine | 386.453 |
| 192 | 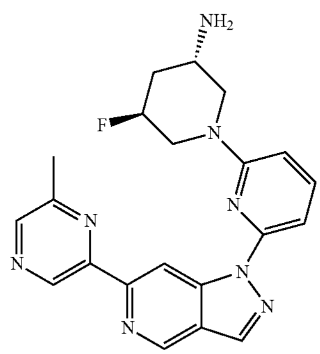 [SMILES: Cc1cncc(-c2cc3c(cn2)cnn3-c2cccc(N3C[C@@H](N)C[C@H](F)C3)n2)n1] | (3S,5S)-5-fluoro-1-[6-[6-(6-methylpyrazin-2-yl)pyrazolo[4,3-c]pyridin-1-yl]-2-pyridyl]piperidin-3-amine | 404.443 |
| 193 | 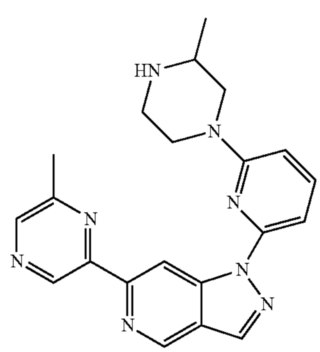 [SMILES: Cc1cncc(-c2cc3c(cn2)cnn3-c2cccc(N3CCNC(C)C3)n2)n1] | 1-[6-(3-methylpiperazin-1-yl)-2-pyridyl]-6-(6-methylpyrazin-2-yl)pyrazolo[4,3-c]pyridine | 386.453 |
| 194 | 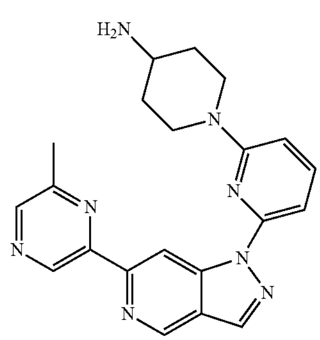 [SMILES: Cc1cncc(-c2cc3c(cn2)cnn3-c2cccc(N3CCC(N)CC3)n2)n1] | 1-[6-[6-(6-methylpyrazin-2-yl)pyrazolo[4,3-c]pyridin-1-yl]-2-pyridyl]piperidin-4-amine | 386.453 |

TABLE 1-continued
| No. | Structure | IUPAC Name | MW |
|---|---|---|---|
| 195 | 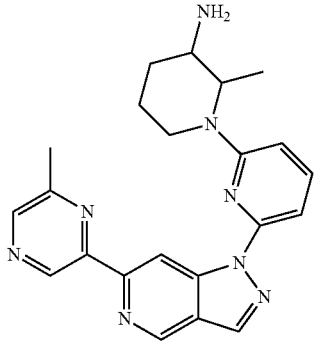 [SMILES: Cc1cncc(-c2cc3c(cn2)cnn3-c2cccc(N3CCCC(N)C3C)n2)n1] | 2-methyl-1-[6-[6-(6-methylpyrazin-2-yl)pyrazolo[4,3-c]pyridin-1-yl]-2-pyridyl]piperidin-3-amine | 400.48 |
| 196 | 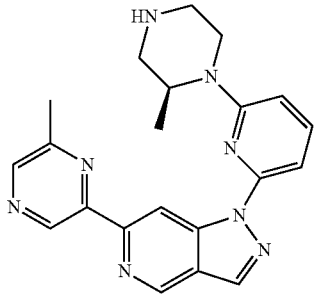 [SMILES: Cc1cncc(-c2cc3c(cn2)cnn3-c2cccc(N3CCNC[C@@H]3C)n2)n1] | 1-[6-[(2S)-2-methylpiperazin-1-yl]-2-pyridyl]-6-(6-methylpyrazin-2-yl)pyrazolo[4,3-c]pyridine | 386.453 |
| 197 | 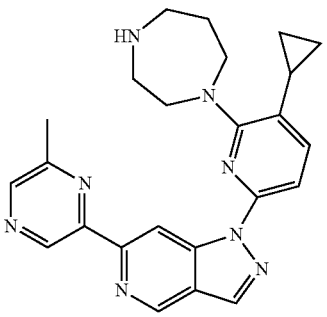 [SMILES: Cc1cncc(-c2cc3c(cn2)cnn3-c2ccc(C3CC3)c(N3CCCNCC3)n2)n1] | 1-[5-cyclopropyl-6-(1,4-diazepan-1-yl)-2-pyridyl]-6-(6-methylpyrazin-2-yl)pyrazolo[4,3-c]pyridine | 426.517 |
| 198 | 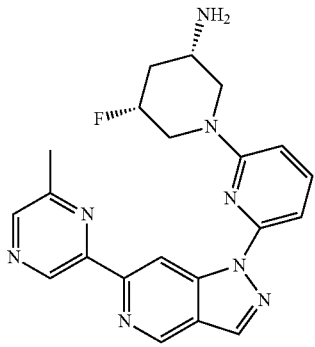 [SMILES: Cc1cncc(-c2cc3c(cn2)cnn3-c2cccc(N3C[C@@H](N)C[C@@H](F)C3)n2)n1] | (3S,5R)-5-fluoro-1-[6-[6-(6-methylpyrazin-2-yl)pyrazolo[4,3-c]pyridin-1-yl]-2-pyridyl]piperidin-3-amine | 404.443 |

TABLE 1-continued

| No. | Structure | IUPAC Name | MW |
|-----|-----------|------------|-----|
| 199 | 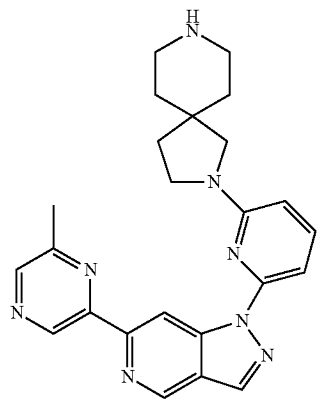 [SMILES: Cc1cncc(-c2cc3c(cn2)cnn3-c2cccc(N3CCC4(CCNCC4)C3)n2)n1] | 2-[6-[6-(6-methylpyrazin-2-yl)pyrazolo[4,3-c]pyridin-1-yl]-2-pyridyl]-2,8-diazaspiro[4.5]decane | 426.517 |
| 200 | 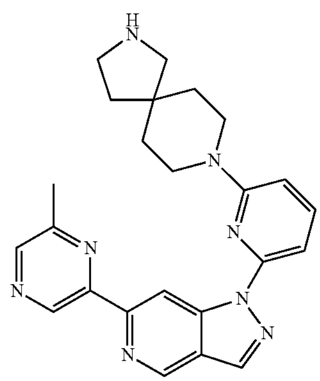 [SMILES: Cc1cncc(-c2cc3c(cn2)cnn3-c2cccc(N3CCC4(CCNC4)CC3)n2)n1] | 8-[6-[6-(6-methylpyrazin-2-yl)pyrazolo[4,3-c]pyridin-1-yl]-2-pyridyl]-2,8-diazaspiro[4.5]decane | 426.517 |
| 201 | 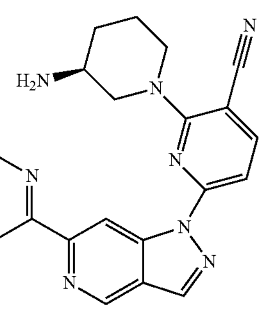 | 2-[(3S)-3-amino-1-piperidyl]-6-[6-(6-methylpyrazin-2-yl)pyrazolo[4,3-c]pyridin-1-yl]pyridine-3-carbonitrile | 411.462 |
| 202 | 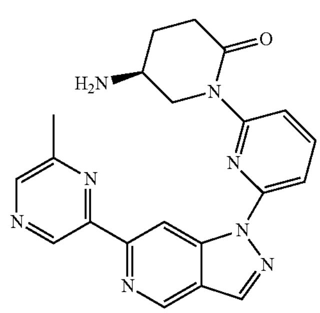 [SMILES: Cc1cncc(-c2cc3c(cn2)cnn3-c2cccc(N3C[C@@H](N)CCC3=O)n2)n1] | (5S)-5-amino-1-[6-[6-(6-methylpyrazin-2-yl)pyrazolo[4,3-c]pyridin-1-yl]-2-pyridyl]piperidin-2-one | 400.436 |

TABLE 1-continued
| No. | Structure | IUPAC Name | MW |
|---|---|---|---|
| 203 | 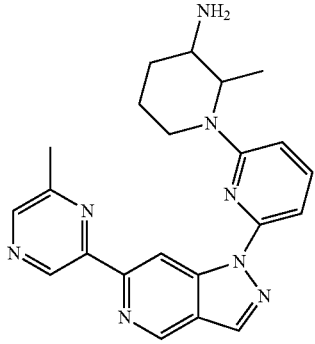 [SMILES: Cc1cncc(-c2cc3c(cn2)cnn3-c2cccc(N3CCCC(N)C3C)n2)n1] | 2-methyl-1-[6-[6-(6-methylpyrazin-2-yl)pyrazolo[4,3-c]pyridin-1-yl]-2-pyridyl]piperidin-3-amine | 400.48 |
| 204 | 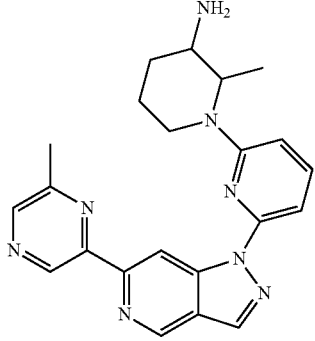 | 2-methyl-1-[6-[6-(6-methylpyrazin-2-yl)pyrazolo[4,3-c]pyridin-1-yl]-2-pyridyl]piperidin-3-amine | 400.48 |
| 205 | 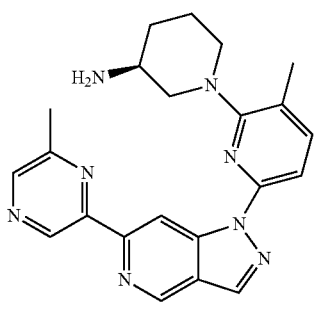 [SMILES: Cc1cncc(-c2cc3c(cn2)cnn3-c2ccc(C)c(N3CCC[C@H](N)C3)n2)n1] | (3S)-1-[3-methyl-6-[6-(6-methylpyrazin-2-yl)pyrazolo[4,3-c]pyridin-1-yl]-2-pyridyl]piperidin-3-amine | 400.48 |
| 206 | 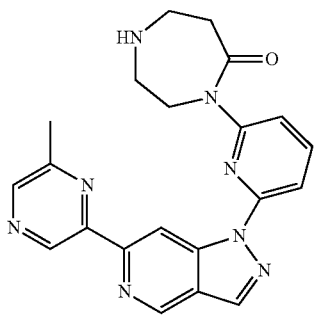 [SMILES: Cc1cncc(-c2cc3c(cn2)cnn3-c2cccc(N3CCNCCC3=O)n2)n1] | 4-[6-[6-(6-methylpyrazin-2-yl)pyrazolo[4,3-c]pyridin-1-yl]-2-pyridyl]-1,4-diazepan-5-one | 400.436 |

TABLE 1-continued

| No. | Structure | IUPAC Name | MW |
|---|---|---|---|
| 207 | 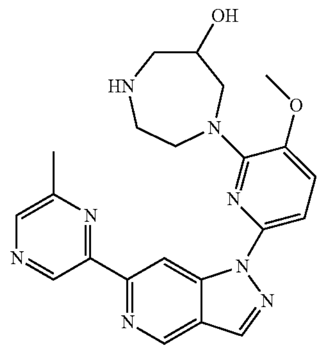 [SMILES: COc1ccc(-n2ncc3cnc(-c4cncc(C)n4)cc32)nc1N1CCNCC(O)C1] | 1-[3-methoxy-6-[6-(6-methylpyrazin-2-yl)pyrazolo[4,3-c]pyridin-1-yl]-2-pyridyl]-1,4-diazepan-6-ol | 432.478 |
| 208 | 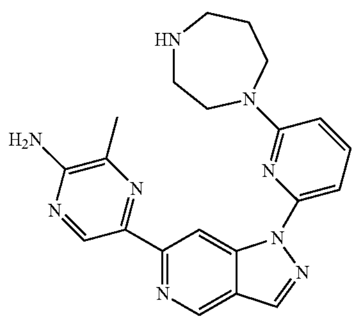 [SMILES: Cc1nc(-c2cc3c(cn2)cnn3-c2cccc(N3CCCNCC3)n2)cnc1N] | 5-[1-[6-(1,4-diazepan-1-yl)-2-pyridyl]pyrazolo[4,3-c]pyridin-6-yl]-3-methyl-pyrazin-2-amine | 401.468 |
| 209 | 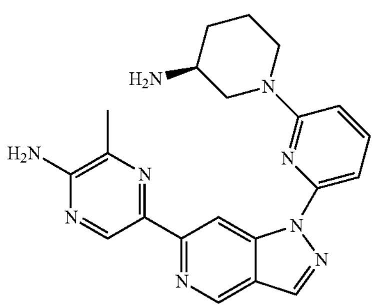 [SMILES: Cc1nc(-c2cc3c(cn2)cnn3-c2cccc(N3CCC[C@H](N)C3)n2)cnc1N] | 5-[1-[6-[(3S)-3-amino-1-piperidyl]-2-pyridyl]pyrazolo[4,3-c]pyridin-6-yl]-3-methyl-pyrazin-2-amine | 401.468 |
| 210 | 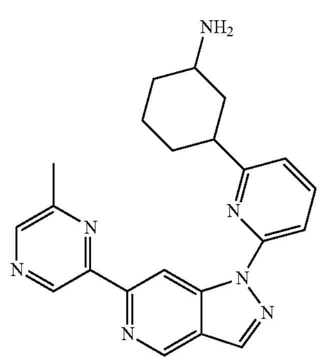 [SMILES: Cc1cncc(-c2cc3c(cn2)cnn3-c2cccc(C3CCCC(N)C3)n2)n1] | 3-[6-[6-(6-methylpyrazin-2-yl)pyrazolo[4,3-c]pyridin-1-yl]-2-pyridyl]cyclohexanamine | 385.465 |

TABLE 1-continued

| No. | Structure | IUPAC Name | MW |
|---|---|---|---|
| 211 | 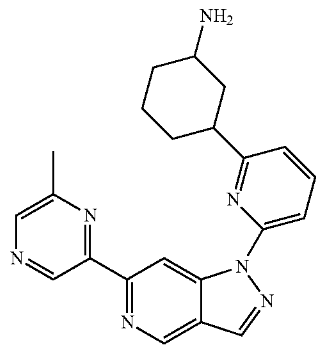 [SMILES: Cc1cncc(-c2cc3c(cn2)cnn3-c2cccc(C3CCCC(N)C3)n2)n1] | 3-[6-[6-(6-methylpyrazin-2-yl)pyrazolo[4,3-c]pyridin-1-yl]-2-pyridyl]cyclohexanamine | 385.465 |
| 212 | 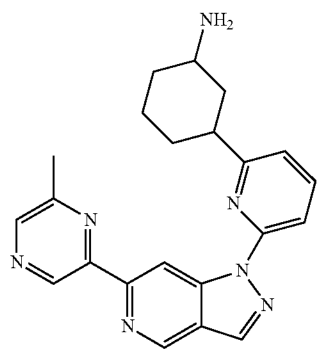 | 3-[6-[6-(6-methylpyrazin-2-yl)pyrazolo[4,3-c]pyridin-1-yl]-2-pyridyl]cyclohexanamine | 385.465 |
| 213 | 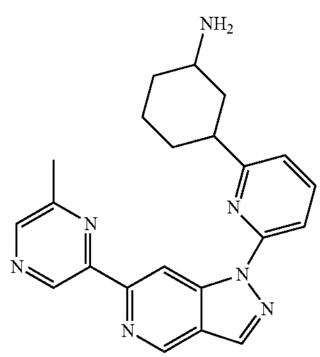 | 3-[6-[6-(6-methylpyrazin-2-yl)pyrazolo[4,3-c]pyridin-1-yl]-2-pyridyl]cyclohexanamine | 385.465 |
| 214 | 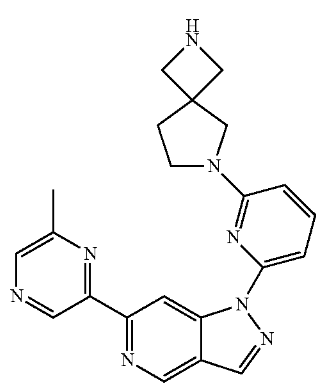 [SMILES: Cc1cncc(-c2cc3c(cn2)cnn3-c2cccc(N3CCC4(CNC4)C3)n2)n1] | 1-[6-(2,6-diazaspiro[3.4]octan-6-yl)-2-pyridyl]-6-(6-methylpyrazin-2-yl)pyrazolo[4,3-c]pyridine | 398.464 |

TABLE 1-continued
| No. | Structure | IUPAC Name | MW |
|---|---|---|---|
| 215 | 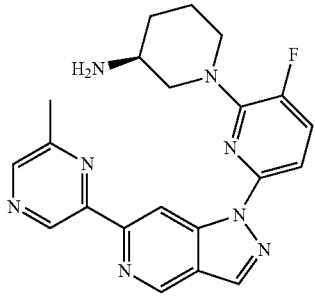 [SMILES: Cc1cncc(-c2cc3c(cn2)cnn3-c2ccc(F)c(N3CCC[C@H](N)C3)n2)n1] | (3S)-1-[3-fluoro-6-[6-(6-methylpyrazin-2-yl)pyrazolo[4,3-c]pyridin-1-yl]-2-pyridyl]piperidin-3-amine | 404.443 |
| 216 | 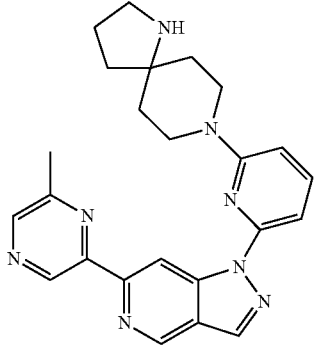 [SMILES: Cc1cncc(-c2cc3c(cn2)cnn3-c2cccc(N3CCC4(CCCN4)CC3)n2)n1] | 8-[6-[6-(6-methylpyrazin-2-yl)pyrazolo[4,3-c]pyridin-1-yl]-2-pyridyl]-1,8-diazaspiro[4.5]decane | 426.517 |
| 217 | 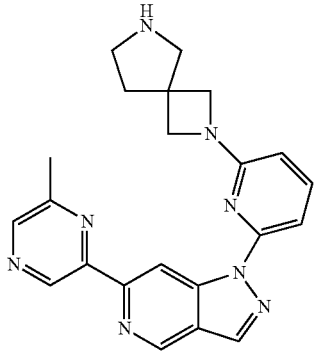 [SMILES: Cc1cncc(-c2cc3c(cn2)cnn3-c2cccc(N3CC4(CCNC4)C3)n2)n1] | 1-[6-(2,7-diazaspiro[3.4]octan-2-yl)-2-pyridyl]-6-(6-methylpyrazin-2-yl)pyrazolo[4,3-c]pyridine | 398.464 |
| 218 | 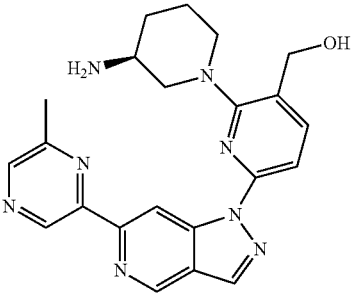 [SMILES: Cc1cncc(-c2cc3c(cn2)cnn3-c2ccc(CO)c(N3CCC[C@H](N)C3)n2)n1] | [2-[(3S)-3-amino-1-piperidyl]-6-[6-(6-methylpyrazin-2-yl)pyrazolo[4,3-c]pyridin-1-yl]-3-pyridyl]methanol | 416.479 |

TABLE 1-continued

| No. | Structure | IUPAC Name | MW |
|---|---|---|---|
| 219 | 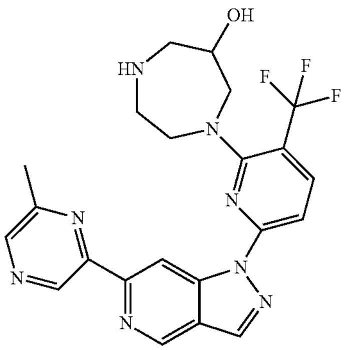 [SMILES: Cc1cncc(-c2cc3c(cn2)cnn3-c2ccc(C(F)(F)F)c(N3CCNCC(O)C3)n2)n1] | 1-[6-[6-(6-methylpyrazin-2-yl)pyrazolo[4,3-c]pyridin-1-yl]-3-(trifluoromethyl)-2-pyridyl]-1,4-diazepan-6-ol | 470.45 |
| 220 | 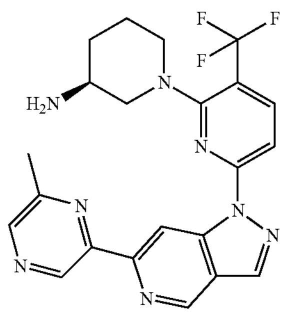 [SMILES: Cc1cncc(-c2cc3c(cn2)cnn3-c2ccc(C(F)(F)F)c(N3CCC[C@H](N)C3)n2)n1] | (3S)-1-[6-[6-(6-methylpyrazin-2-yl)pyrazolo[4,3-c]pyridin-1-yl]-3-(trifluoromethyl)-2-pyridyl]piperidin-3-amine | 454.451 |
| 221 | 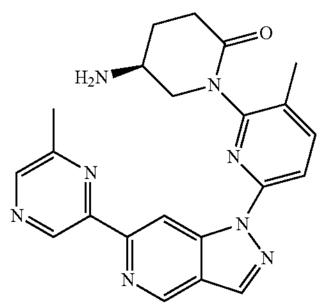 [SMILES: Cc1cncc(-c2cc3c(cn2)cnn3-c2ccc(C)c(N3C[C@@H](N)CCC3=O)n2)n1] | (5S)-5-amino-1-[3-methyl-6-[6-(6-methylpyrazin-2-yl)pyrazolo[4,3-c]pyridin-1-yl]-2-pyridyl]piperidin-2-one | 414.463 |
| 222 | 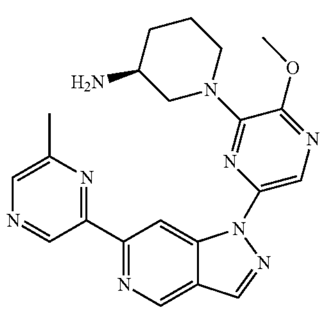 | (3S)-1-[3-methoxy-6-[6-(6-methylpyrazin-2-yl)pyrazolo[4,3-c]pyridin-1-yl]pyrazin-2-yl]piperidin-3-amine | 417.467 |
| 223 | 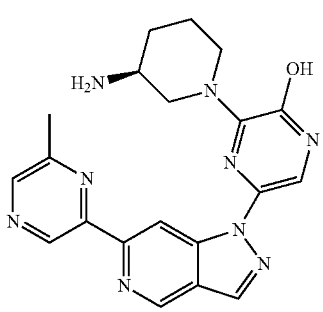 | 3-[(3S)-3-amino-1-piperidyl]-5-[6-(6-methylpyrazin-2-yl)pyrazolo[4,3-c]pyridin-1-yl]pyrazin-2-ol | 403.44 |

TABLE 1-continued

| No. | Structure | IUPAC Name | MW |
|---|---|---|---|
| 224 | 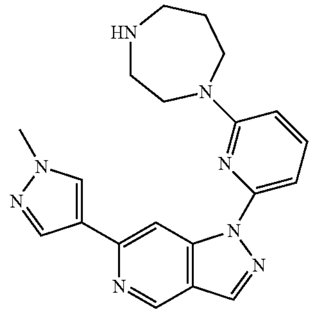 [SMILES: Cn1cc(-c2cc3c(cn2)cnn3-c2cccc(N3CCCNCC3)n2)cn1] | 1-[6-(1,4-diazepan-1-yl)-2-pyridyl]-6-(1-methylpyrazol-4-yl)pyrazolo[4,3-c]pyridine | 374.442 |
| 225 | 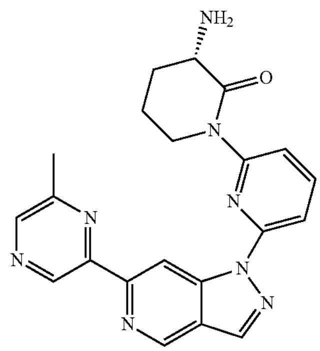 [SMILES: Cc1cncc(-c2cc3c(cn2)cnn3-c2cccc(N3CCC[C@H](N)C3=O)n2)n1] | (3S)-3-amino-1-[6-[6-(6-methylpyrazin-2-yl)pyrazolo[4,3-c]pyridin-1-yl]-2-pyridyl]piperidin-2-one | 400.436 |
| 226 | 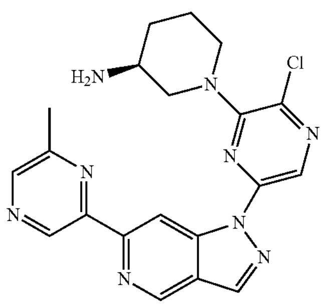 | (3S)-1-[3-chloro-6-[6-(6-methylpyrazin-2-yl)pyrazolo[4,3-c]pyridin-1-yl]pyrazin-2-yl]piperidin-3-amine | 421.886 |
| 227 | 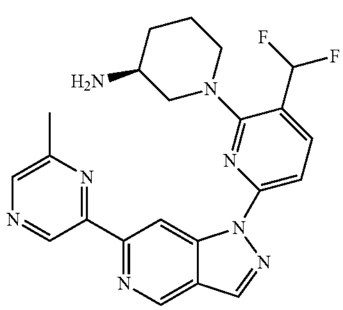 [SMILES: Cc1cncc(-c2cc3c(cn2)cnn3-c2ccc(C(F)F)c(N3CCC[C@H](N)C3)n2)n1] | (3S)-1-[3-(difluoromethyl)-6-[6-(6-methylpyrazin-2-yl)pyrazolo[4,3-c]pyridin-1-yl]-2-pyridyl]piperidin-3-amine | 436.46 |
| 228 | 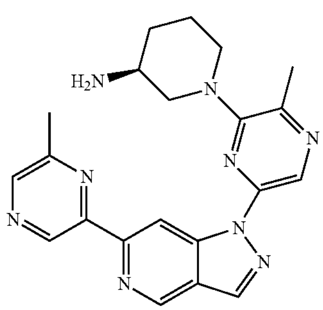 [SMILES: Cc1cncc(-c2cc3c(cn2)cnn3-c2cnc(C)c(N3CCC[C@H](N)C3)n2)n1] | (3S)-1-[3-methyl-6-[6-(6-methylpyrazin-2-yl)pyrazolo[4,3-c]pyridin-1-yl]pyrazin-2-yl]piperidin-3-amine | 401.468 |

TABLE 1-continued

| No. | Structure | IUPAC Name | MW |
|---|---|---|---|
| 229 | 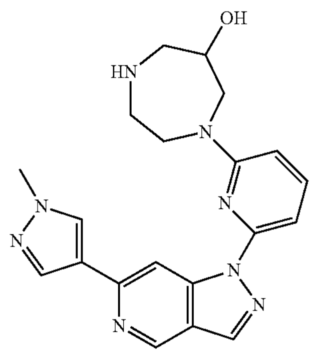 [SMILES: Cn1cc(-c2cc3c(cn2)cnn3-c2cccc(N3CCNCC(O)C3)n2)cn1] | 1-[6-[6-(1-methylpyrazol-4-yl)pyrazolo[4,3-c]pyridin-1-yl]-2-pyridyl]-1,4-diazepan-6-ol | 390.442 |
| 230 | 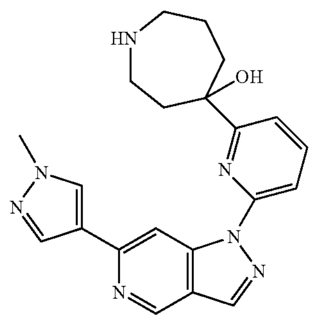 [SMILES: Cn1cc(-c2cc3c(cn2)cnn3-c2cccc(C3(O)CCCNCC3)n2)cn1] | 4-[6-[6-(1-methylpyrazol-4-yl)pyrazolo[4,3-c]pyridin-1-yl]-2-pyridyl]azepan-4-ol | 389.454 |
| 231 | 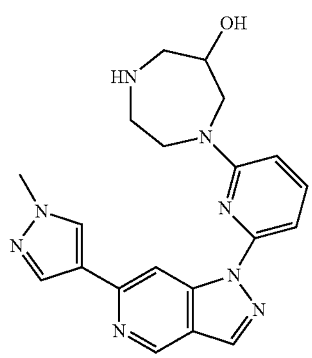 [SMILES: Cn1cc(-c2cc3c(cn2)cnn3-c2cccc(N3CCNCC(O)C3)n2)cn1] | 1-[6-[6-(1-methylpyrazol-4-yl)pyrazolo[4,3-c]pyridin-1-yl]-2-pyridyl]-1,4-diazepan-6-ol | 390.442 |
| 232 | 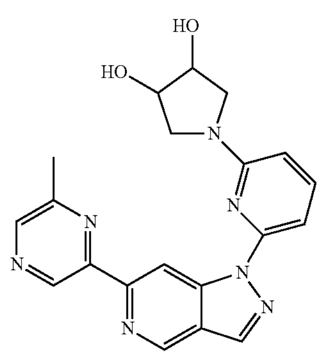 [SMILES: Cc1cncc(-c2cc3c(cn2)cnn3-c2cccc(N3CC(O)C(O)C3)n2)n1] | 1-[6-[6-(6-methylpyrazin-2-yl)pyrazolo[4,3-c]pyridin-1-yl]-2-pyridyl]pyrrolidine-3,4-diol | 389.411 |

TABLE 1-continued

| No. | Structure | IUPAC Name | MW |
|---|---|---|---|
| 233 | 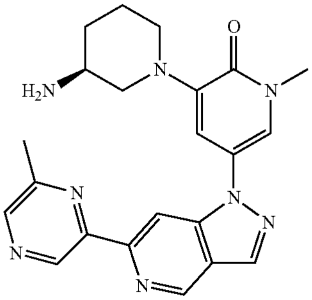 [SMILES: Cc1cncc(-c2cc3c(cn2)cnn3-c2cc(N3CCC[C@H](N)C3)c(=O)n(C)c2)n1] | 3-[(3S)-3-amino-1-piperidyl]-1-methyl-5-[6-(6-methylpyrazin-2-yl)pyrazolo[4,3-c]pyridin-1-yl]pyridin-2-one | 416.479 |
| 234 | 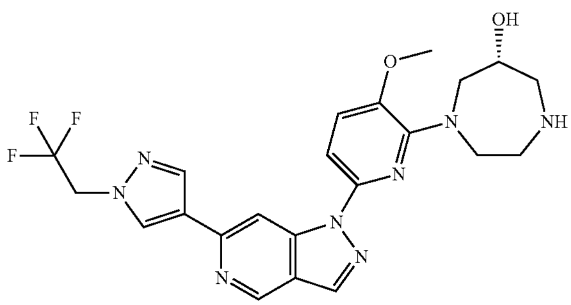 [SMILES: COc1ccc(-n2ncc3cnc(-c4cnn(CC(F)(F)F)c4)cc32)nc1N1CCNC[C@@H](O)C1] | 1-[3-methoxy-6-[6-[1-(2,2,2-trifluoroethyl)pyrazol-4-yl]pyrazolo[4,3-c]pyridin-1-yl]-2-pyridyl]-1,4-diazepan-6-ol | 488.466 |
| 235 | 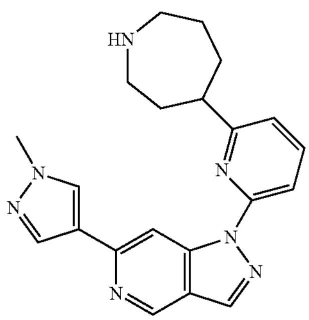 | 1-[6-(azepan-4-yl)-2-pyridyl]-6-(1-methylpyrazol-4-yl)pyrazolo[4,3-c]pyridine | 373.454 |
| 236 | 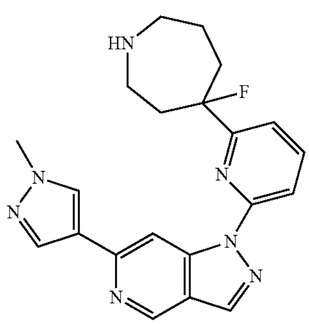 [SMILES: Cn1cc(-c2cc3c(cn2)cnn3-c2cccc(C3(F)CCCNCC3)n2)cn1] | 1-[6-(4-fluoroazepan-4-yl)-2-pyridyl]-6-(1-methylpyrazol-4-yl)pyrazolo[4,3-c]pyridine | 391.445 |
| 237 | 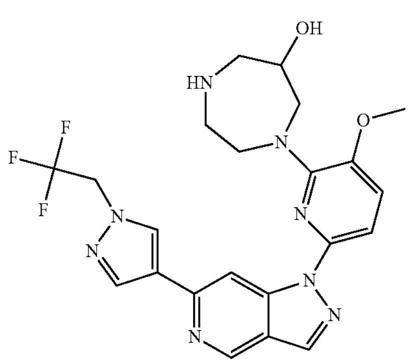 [SMILES: COc1ccc(-n2ncc3cnc(-c4cnn(CC(F)(F)F)c4)cc32)nc1N1CCNCC(O)C1] | 1-[3-methoxy-6-[6-[1-(2,2,2-trifluoroethyl)pyrazol-4-yl]pyrazolo[4,3-c]pyridin-1-yl]-2-pyridyl]-1,4-diazepan-6-ol | 488.466 |

TABLE 1-continued

| No. | Structure | IUPAC Name | MW |
|---|---|---|---|
| 238 | 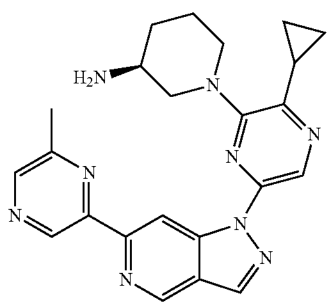 [SMILES: Cc1cncc(-c2cc3c(cn2)cnn3-c2cnc(C3CC3)c(N3CCC[C@H](N)C3)n2)n1] | (3S)-1-[3-cyclopropyl-6-[6-(6-methylpyrazin-2-yl)pyrazolo[4,3-c]pyridin-1-yl]pyrazin-2-yl]piperidin-3-amine | 427.505 |
| 239 | 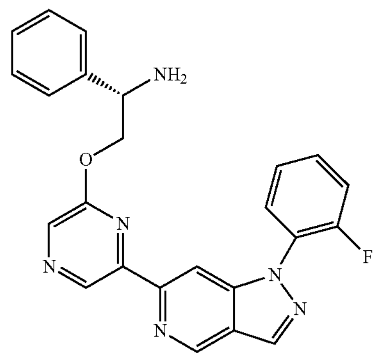 [SMILES: N[C@H](COc1cncc(-c2cc3c(cn2)cnn3-c2ccccc2F)n1)c1ccccc1] | (S)-2-((6-(1-(2-fluorophenyl)-1H-pyrdzolo[4,3-c]pyridin-6-yl)pyrazin-2-yl)oxy)-1-phenylethanamine | 426.45 |
| 240 | 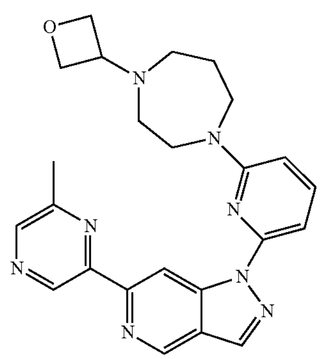 [SMILES: Cc1cncc(-c2cc3c(cn2)cnn3-c2cccc(N3CCCN(C4COC4)CC3)n2)n1] | 6-(6-methylpyrazin-2-yl)-1-[6-[4-(oxetan-3-yl)-1,4-diazepan-1-yl]-2-pyridyl]pyrazolo[4,3-c]pyridine | 442.516 |
| 241 | 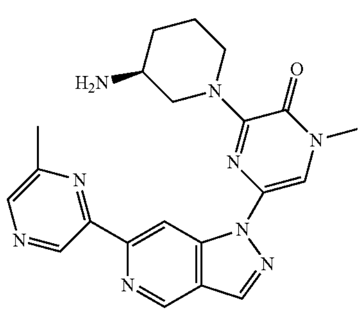 [SMILES: Cc1cncc(-c2cc3c(cn2)cnn3-c2cn(C)c(=O)c(N3CCC[C@H](N)C3)n2)n1] | 3-[(3S)-3-amino-1-piperidyl]-1-methyl-5-[6-(6-methylpyrazin-2-yl)pyrazolo[4,3-c]pyridin-1-yl]pyrazin-2-one | 417.467 |

TABLE 1-continued

| No. | Structure | IUPAC Name | MW |
|---|---|---|---|
| 242 | 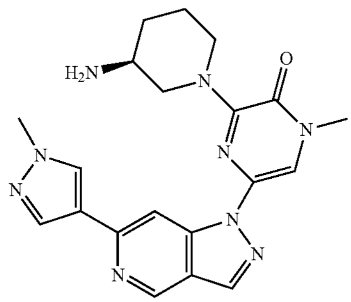 [SMILES: Cn1cc(-c2cc3c(cn2)cnn3-c2cn(C)c(=O)c(N3CCC[C@H](N)C3)n2)cn1] | 3-[(3S)-3-amino-1-piperidyl]-1-methyl-5-[6-(1-methylpyrazol-4-yl)pyrazolo[4,3-c]pyridin-1-yl]pyrazin-2-one | 405.456 |
| 243 | 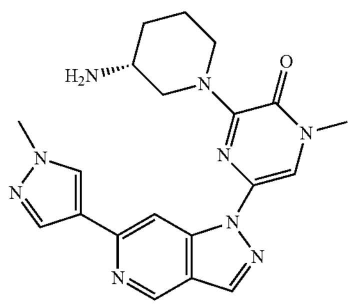 [SMILES: Cn1cc(-c2cc3c(cn2)cnn3-c2cn(C)c(=O)c(N3CCC[C@@H](N)C3)n2)cn1] | 3-[(3R)-3-amino-1-piperidyl]-1-methyl-5-[6-(1-methylpyrazol-4-yl)pyrazolo[4,3-c]pyridin-1-yl]pyrazin-2-one | 405.456 |
| 244 | 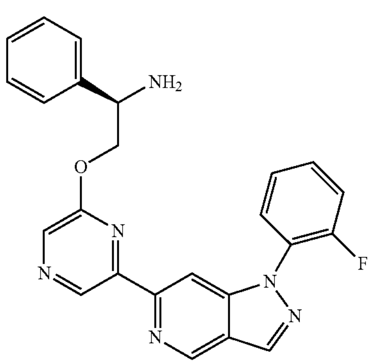 [SMILES: N[C@@H](COc1cncc(-c2cc3c(cn2)cnn3-c2ccccc2F)n1)c1ccccc1] | (R)-2-((6-(1-(2-fluorophenyl)-1H-pyrazolo[4,3-c]pyridin-6-yl)pyrazin-2-yl)oxy)-1-phenylethanamine | 426.45 |
| 245 | 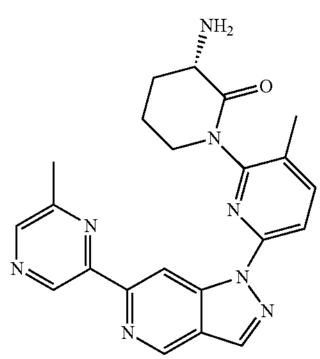 [SMILES: Cc1cncc(-c2cc3c(cn2)cnn3-c2ccc(C)c(N3CCC[C@H](N)C3=O)n2)n1] | (3S)-3-amino-1-[3-methyl-6-[6-(6-methylpyrazin-2-yl)pyrazolo[4,3-c]pyridin-1-yl]-2-pyridyl]piperidin-2-one | 414.463 |

TABLE 1-continued

| No. | Structure | IUPAC Name | MW |
|---|---|---|---|
| 246 | 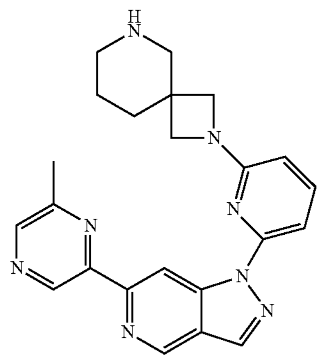 [SMILES: Cc1cncc(-c2cc3c(cn2)cnn3-c2cccc(N3CC4(CCCNC4)C3)n2)n1] | 1-(6-(2,6-diazaspiro[3.5]nonan-2-yl)pyridin-2-yl)-6-(6-methylpyrazin-2-yl)-1H-pyrazolo[4,3-c]pyridine | 412.49 |
| 247 | 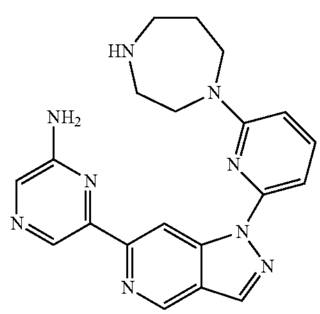 [SMILES: Nc1cncc(-c2cc3c(cn2)cnn3-c2cccc(N3CCCNCC3)n2)n1] | 6-[1-[6-(1,4-diazepan-1-yl)-2-pyridyl]pyrazolo[4,3-c]pyridin-6-yl]pyrazin-2-amine | 387.441 |
| 248 | 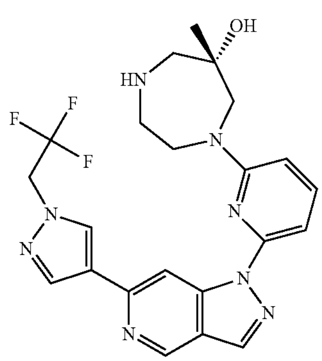 [SMILES: C[C@]1(O)CNCCN(c2cccc(-n3ncc4cnc(-c5cnn(CC(F)(F)F)c5)cc43)n2)C1] | (S)-6-methyl-1-(6-(6-(1-(2,2,2-trifluoroethyl)-1H-pyrazol-4-yl)-1H-pyrazolo[4,3-c]pyridin-1-yl)pyridin-2-yl)-1,4-diazepan-6-ol | 472.466 |
| 249 | 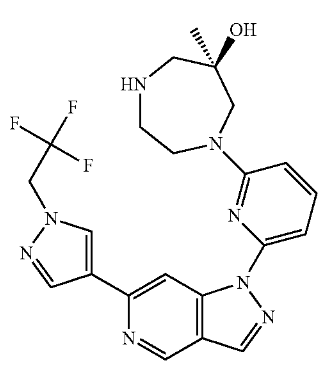 [SMILES: C[C@@]1(O)CNCCN(c2cccc(-n3ncc4cnc(-c5cnn(CC(F)(F)F)c5)cc43)n2)C1] | (R)-6-methyl-1-(6-(6-(1-(2,2,2-trifluoroethyl)-1H-pyrazol-4-yl)-1H-pyrazolo[4,3-c]pyridin-1-yl)pyridin-2-yl)-1,4-diazepan-6-ol | 472.466 |

TABLE 1-continued

| No. | Structure | IUPAC Name | MW |
|---|---|---|---|
| 250 | 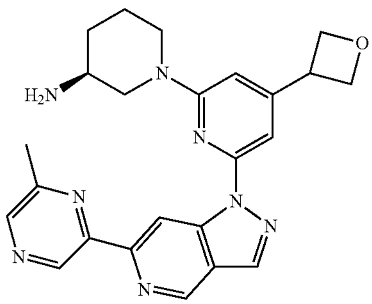 [SMILES: Cc1cncc(-c2cc3c(cn2)cnn3-c2cc(C3COC3)cc(N3CCC[C@H](N)C3)n2)n1] | (3S)-1-[6-[6-(6-methylpyrazin-2-yl)pyrazolo[4,3-c]pyridin-1-yl]-4-(oxetan-3-yl)-2-pyridyl]piperidin-3-amine | 442.516 |
| 251 | 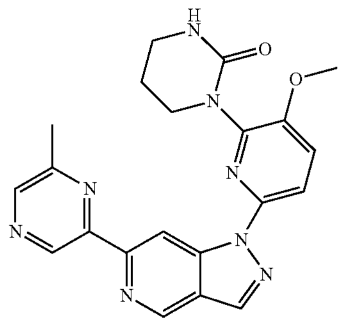 [SMILES: COc1ccc(-n2ncc3cnc(-c4cncc(C)n4)cc32)nc1N1CCCNC1=O] | 1-[3-methoxy-6-[6-(6-methylpyrazin-2-yl)pyrazolo[4,3-c]pyridin-1-yl]-2-pyridyl]hexahydropyrimidin-2-one | 416.436 |
| 252 | 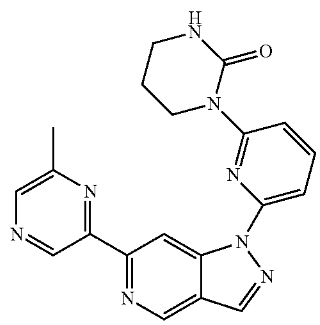 [SMILES: Cc1cncc(-c2cc3c(cn2)cnn3-c2cccc(N3CCCNC3=O)n2)n1] | 1-[6-[6-(6-methylpyrazin-2-yl)pyrazolo[4,3-c]pyridin-1-yl]-2-pyridyl]hexahydropyrimidin-2-one | 386.41 |
| 253 | 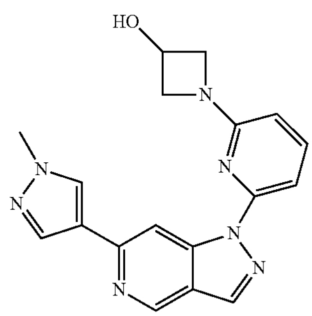 [SMILES: Cn1cc(-c2cc3c(cn2)cnn3-c2cccc(N3CC(O)C3)n2)cn1] | 1-[6-[6-(1-methylpyrazol-4-yl)pyrazolo[4,3-c]pyridin-1-yl]-2-pyridyl]azetidin-3-ol | 347.374 |
| 254 | 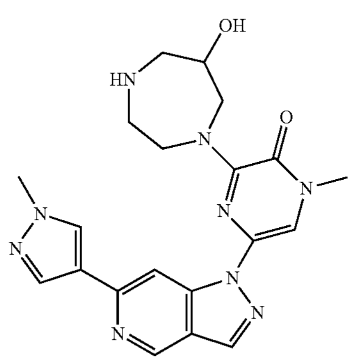 [SMILES: Cn1cc(-c2cc3c(cn2)cnn3-c2cn(C)c(=O)c(N3CCNCC(O)C3)n2)cn1] | 3-(6-hydroxy-1,4-diazepan-1-yl)-1-methyl-5-[6-(1-methylpyrazol-4-yl)pyrazolo[4,3-c]pyridin-1-yl]pyrazin-2-one | 421.456 |

TABLE 1-continued

| No. | Structure | IUPAC Name | MW |
|---|---|---|---|
| 255 | 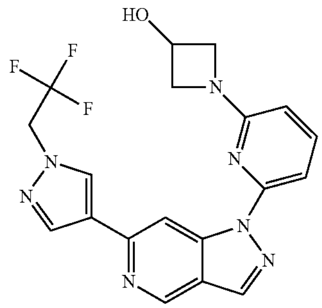 [SMILES: OC1CN(c2cccc(-n3ncc4cnc(-c5cnn(CC(F)(F)F)c5)cc43)n2)C1] | 1-[6-[6-[1-(2,2,2-trifluoroethyl)pyrazol-4-yl]pyrazolo[4,3-c]pyridin-1-yl]-2-pyridyl]azetidin-3-ol | 415.372 |
| 256 | 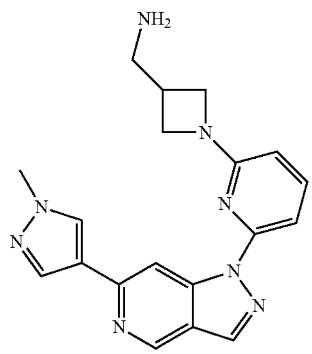 [SMILES: Cn1cc(-c2cc3c(cn2)cnn3-c2cccc(N3CC(CN)C3)n2)cn1] | [1-[6-[6-(1-methylpyrazol-4-yl)pyrazolo[4,3-c]pyridin-1-yl]-2-pyridyl]azetidin-3-yl]methanamine | 360.416 |
| 257 | 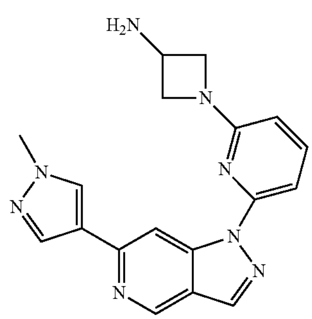 [SMILES: Cn1cc(-c2cc3c(cn2)cnn3-c2cccc(N3CC(N)C3)n2)cn1] | 1-[6-[6-(1-methylpyrazol-4-yl)pyrazolo[4,3-c]pyridin-1-yl]-2-pyridyl]azetidin-3-amine | 346.389 |
| 258 | 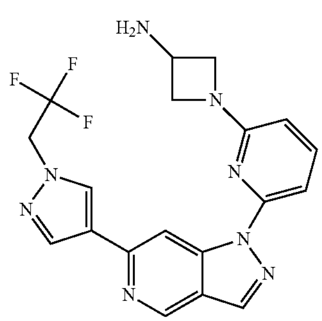 [SMILES: NC1CN(c2cccc(-n3ncc4cnc(-c5cnn(CC(F)(F)F)c5)cc43)n2)C1] | 1-[6-[6-[1-(2,2,2-trifluoroethyl)pyrazol-4-yl]pyrazolo[4,3-c]pyridin-1-yl]-2-pyridyl]azetidin-3-amine | 414.387 |

| No. | Structure | IUPAC Name | MW |
|---|---|---|---|
| 259 | 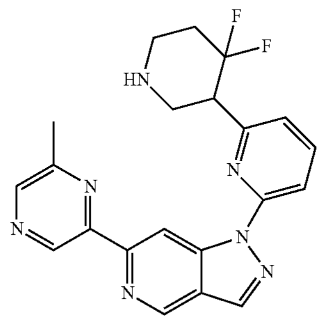 | 1-[6-(4,4-difluoro-3-piperidyl)-2-pyridyl]-6-(6-methylpyrazin-2-yl)pyrazolo[4,3-c]pyridine | 407.419 |
| 260 | 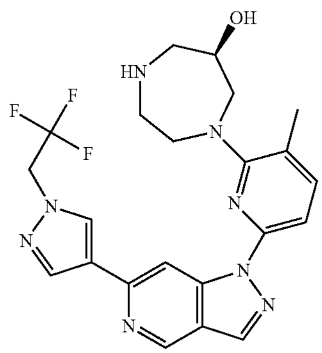 | (R)-1-(3-methyl-6-(6-(1-(2,2,2-trifluoroethyl)-1H-pyrazol-4-yl)-1H-pyrazolo[4,3-c]pyridin-1-yl)pyridin-2-yl)-1,4-diazepan-6-ol | 472.466 |
| 261 | 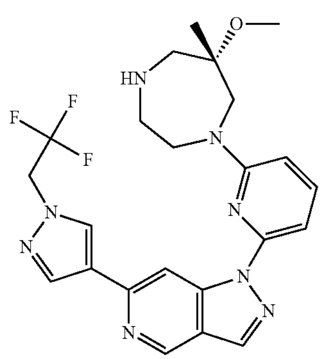 [SMILES: CO[C@@]1(C)CNCCN(c2cccc(-n3ncc4cnc(-c5cnn(CC(F)(F)F)c5)cc43)n2)C1] | (S)-1-(6-(6-Methoxy-6-methyl-1,4-diazepan-1-yl)pyridin-2-yl)-6-(1-(2,2,2-trifluoroethyl)-1H-pyrazol-4-yl)-1H-pyrazolo[4,3-c]pyridine | 486.493 |
| 262 | 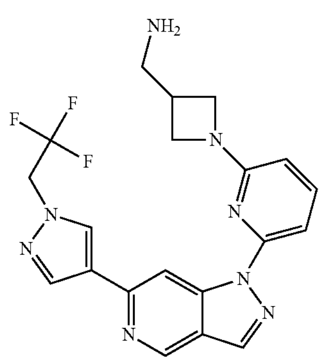 [SMILES: NCC1CN(c2cccc(-n3ncc4cnc(-c5cnn(CC(F)(F)F)c5)cc43)n2)C1] | [1-[6-[6-[1-(2,2,2-trifluoroethyl)pyrazol-4-yl]pyrazolo[4,3-c]pyridin-1-yl]-2-pyridyl]azetidin-3-yl]methanamine | 428.414 |

TABLE 1-continued

| No. | Structure | IUPAC Name | MW |
|---|---|---|---|
| 263 | 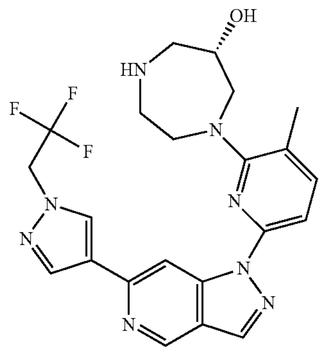 | (S)-1-(3-methyl-6-(6-(1-(2,2,2-trifluoroethyl)-1H-pyrazol-4-yl)-1H-pyrazolo[4,3-c]pyridin-1-yl)pyridin-2-yl)-1,4-diazepan-6-ol | 472.466 |
| 264 | 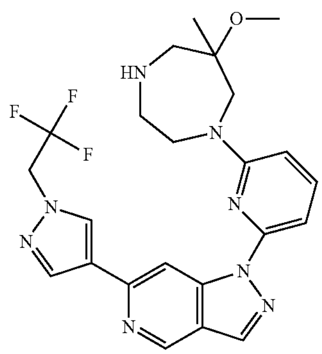 [SMILES: COC1(C)CNCCN(c2cccc(-n3ncc4cnc(-c5cnn(CC(F)(F)F)c5)cc43)n2)C1] | (R)-1-(6-(6-Methoxy-6-methyl-1,4-diazepan-1-yl)pyridin-2-yl)-6-(1-(2,2,2-trifluoroethyl)-1H-pyrazol-4-yl)-1H-pyrazolo[4,3-c]pyridine | 486.493 |
| 265 | 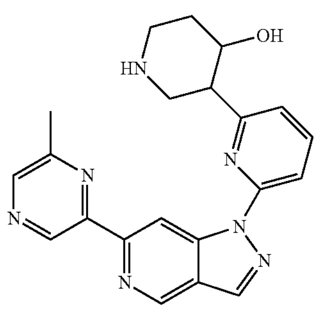 [SMILES: Cc1cncc(-c2cc3c(cn2)cnn3-c2cccc(C3CNCCC3O)n2)n1] | 3-[6-[6-(6-methylpyrazin-2-yl)pyrazolo[4,3-c]pyridin-1-yl]-2-pyridyl]piperidin-4-ol | 387.438 |
| 266 | 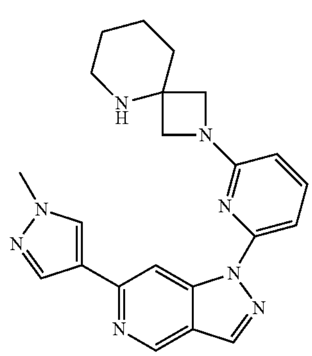 [SMILES: Cn1cc(-c2cc3c(cn2)cnn3-c2cccc(N3CC4(CCCCN4)C3)n2)cn1] | 1-[6-(2,5-diazaspiro[3.5]nonan-2-yl)-2-pyridyl]-6-(1-methylpyrazol-4-yl)pyrazolo[4,3-c]pyridine | 400.48 |

TABLE 1-continued

| No. | Structure | IUPAC Name | MW |
|---|---|---|---|
| 267 | 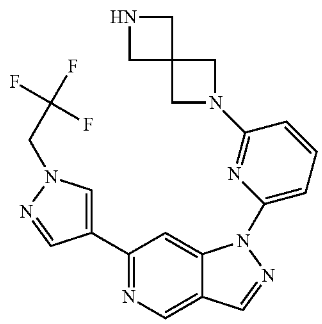 [SMILES: FC(F)(F)Cn1cc(-c2cc3c(cn2)cnn3-c2cccc(N3CC4(CNC4)C3)n2)cn1] | 1-[6-(2,6-diazaspiro[3.3]heptan-2-yl)-2-pyridyl]-6-[1-(2,2,2-trifluoroethyl)pyrazol-4-yl]pyrazolo[4,3-c]pyridine | 440.424 |
| 268 | 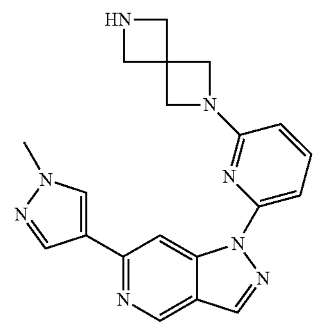 [SMILES: Cn1cc(-c2cc3c(cn2)cnn3-c2cccc(N3CC4(CNC4)C3)n2)cn1] | 1-[6-(2,6-diazaspiro[3.3]heptan-2-yl)-2-pyridyl]-6-(1-methylpyrazol-4-yl)pyrazolo[4,3-c]pyridine | 372.426 |
| 269 | 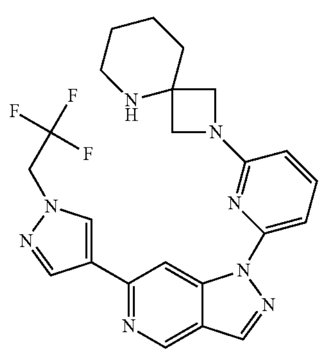 [SMILES: FC(F)(F)Cn1cc(-c2cc3c(cn2)cnn3-c2cccc(N3CC4(CCCCN4)C3)n2)cn1] | 1-[6-(2,5-diazaspiro[3.5]nonan-2-yl)-2-pyridyl]-6-[1-(2,2,2-trifluoroethyl)pyrazol-4-yl]pyrazolo[4,3-c]pyridine | 468.478 |
| 270 | 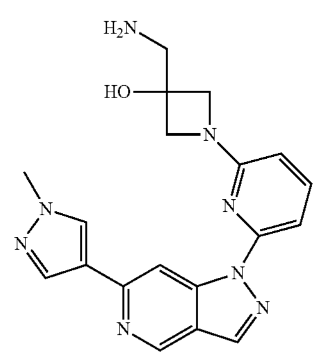 [SMILES: Cn1cc(-c2cc3c(cn2)cnn3-c2cccc(N3CC(O)(CN)C3)n2)cn1] | 3-(aminomethyl)-1-[6-[6-(1-methylpyrazol-4-yl)pyrazolo[4,3-c]pyridin-1-yl]-2-pyridyl]azetidin-3-ol | 376.415 |

TABLE 1-continued

| No. | Structure | IUPAC Name | MW |
|---|---|---|---|
| 271 | 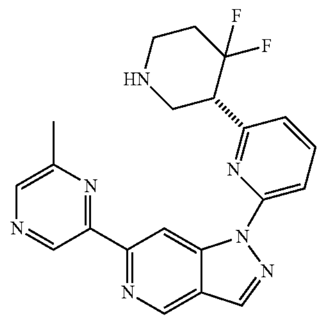 | (S)-1-(6-(4,4-difluoropiperidin-3-yl)pyridin-2-yl)-6-(6-methylpyrazin-2-yl)-1H-pyrazolo[4,3-c]pyridine | 407.419 |
| 272 | 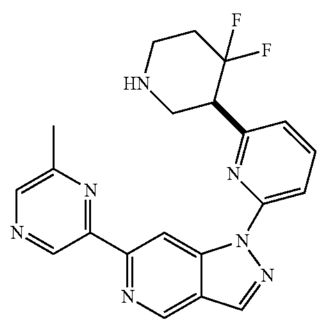 | (R)-1-(6-(4,4-difluoropiperidin-3-yl)pyridin-2-yl)-6-(6-methylpyrazin-2-yl)-1H-pyrazolo[4,3-c]pyridine | 407.419 |
| 273 | 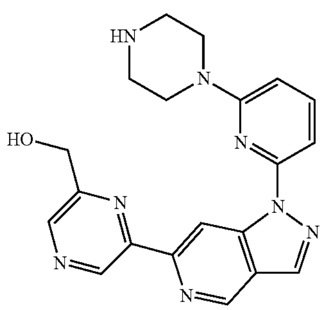 [SMILES: OCc1cncc(-c2cc3c(cn2)cnn3-c2cccc(N3CCNCC3)n2)n1] | [6-[1-(6-piperazin-1-yl-2-pyridyl)pyrazolo[4,3-c]pyridin-6-yl]pyrazin-2-yl]methanol | 388.426 |
| 274 | 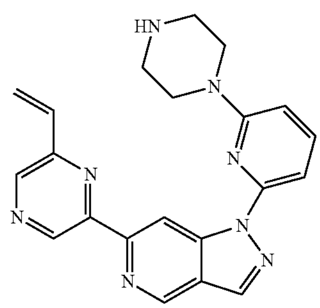 [SMILES: C=Cc1cncc(-c2cc3c(cn2)cnn3-c2cccc(N3CCNCC3)n2)n1] | 1-(6-piperazin-1-yl-2-pyridyl)-6-(6-vinylpyrazin-2-yl)pyrazolo[4,3-c]pyridine | 384.437 |
| 275 | 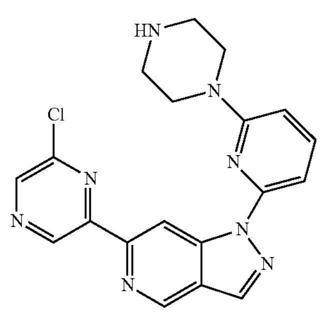 [SMILES: Clc1cncc(-c2cc3c(cn2)cnn3-c2cccc(N3CCNCC3)n2)n1] | 6-(6-chloropyrazin-2-yl)-1-(6-piperazin-1-yl-2-pyridyl)pyrazolo[4,3-c]pyridine | 392.845 |

TABLE 1-continued

| No. | Structure | IUPAC Name | MW |
|---|---|---|---|
| 276 | 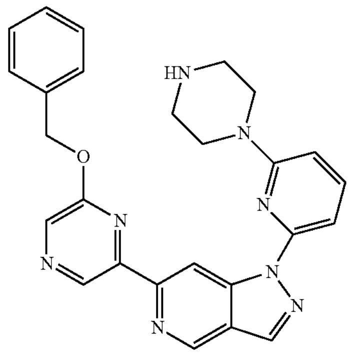 [SMILES: c1ccc(COc2cncc(-c3cc4c(cn3)cnn4-c3cccc(N4CCNCC4)n3)n2)cc1] | 6-(6-benzyloxypyrazin-2-yl)-1-(6-piperazin-1-yl-2-pyridyl)pyrazolo[4,3-c]pyridine | 464.522 |
| 277 | 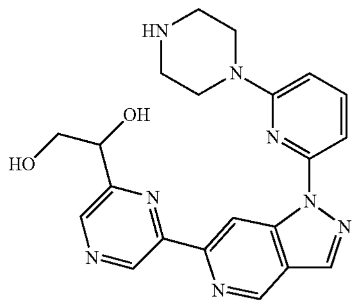 [SMILES: OCC(O)c1cncc(-c2cc3c(cn2)cnn3-c2cccc(N3CCNCC3)n2)n1] | 1-[6-[1-(6-piperazin-1-yl-2-pyridyl)pyrazolo[4,3-c]pyridin-6-yl]pyrazin-2-yl]ethane-1,2-diol | 418.452 |
| 278 | 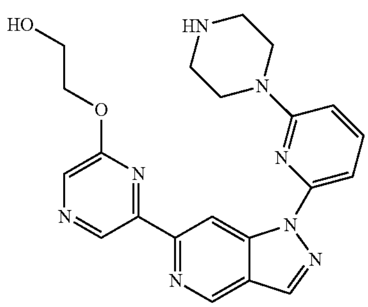 [SMILES: OCCOc1cncc(-c2cc3c(cn2)cnn3-c2cccc(N3CCNCC3)n2)n1] | 2-[6-[1-(6-piperazin-1-yl-2-pyridyl)pyrazolo[4,3-c]pyridin-6-yl]pyrazin-2-yl]oxyethanol | 418.452 |
| 279 | 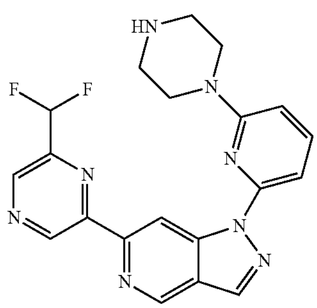 [SMILES: FC(F)c1cncc(-c2cc3c(cn2)cnn3-c2cccc(N3CCNCC3)n2)n1] | 6-[6-(difluoromethyl)pyrazin-2-yl]-1-(6-piperazin-1-yl-2-pyridyl)pyrazolo[4,3-c]pyridine | 408.407 |
| 280 | 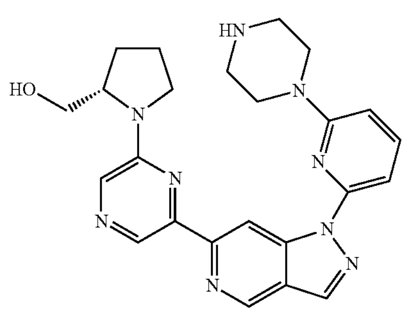 [SMILES: OC[C@@H]1CCCN1c1cncc(-c2cc3c(cn2)cnn3-c2cccc(N3CCNCC3)n2)n1] | [(2S)-1-[6-[1-(6-piperazin-1-yl-2-pyridyl)pyrazolo[4,3-c]pyridin-6-yl]pyrazin-2-yl]pyrrolidin-2-yl]methanol | 457.531 |

TABLE 1-continued

| No. | Structure | IUPAC Name | MW |
|---|---|---|---|
| 281 | 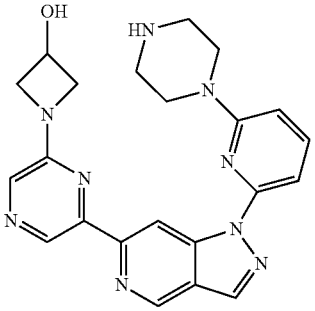 [SMILES: OC1CN(c2cncc(-c3cc4c(cn3)cnn4-c3cccc(N4CCNCC4)n3)n2)C1] | 1-[6-[1-(6-piperazin-1-yl-2-pyridyl)pyrazolo[4,3-c]pyridin-6-yl]pyrazin-2-yl]azetidin-3-ol | 429.478 |
| 282 | 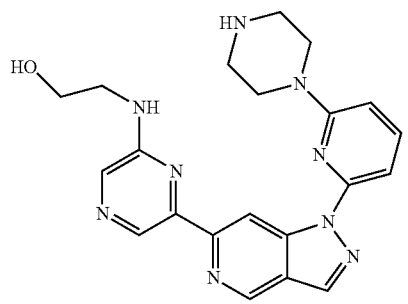 [SMILES: OCCNc1cncc(-c2cc3c(cn2)cnn3-c2cccc(N3CCNCC3)n2)n1] | 2-[[6-[1-(6-piperazin-1-yl-2-pyridyl)pyrazolo[4,3-c]pyridin-6-yl]pyrazin-2-yl]amino]ethanol | 417.467 |
| 283 | 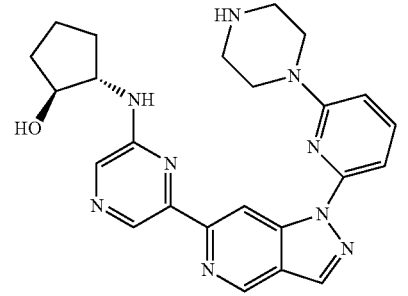 [SMILES: O[C@H]1CCC[C@@H]1Nc1cncc(-c2cc3c(cn2)cnn3-c2cccc(N3CCNCC3)n2)n1] | (1S,2S)-2-[[6-[1-(6-piperazin-1-yl-2-pyridyl)pyrazolo[4,3-c]pyridin-6-yl]pyrazin-2-yl]amino]cyclopentanol | 457.531 |
| 284 | 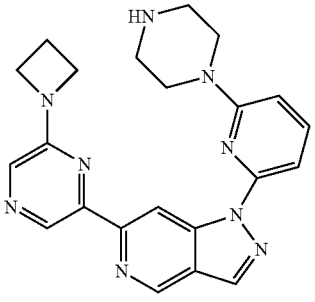 [SMILES: c1cc(N2CCNCC2)nc(-n2ncc3cnc(-c4cncc(N5CCC5)n4)cc32)c1] | 6-[6-(azetidin-1-yl)pyrazin-2-yl]-1-(6-piperazin-1-yl-2-pyridyl)pyrazolo[4,3-c]pyridine | 413.478 |
| 285 | 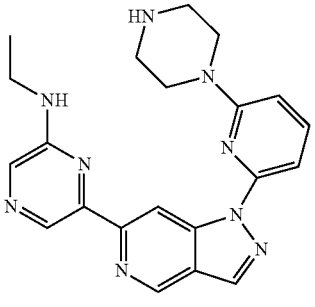 [SMILES: CCNc1cncc(-c2cc3c(cn2)cnn3-c2cccc(N3CCNCC3)n2)n1] | N-ethyl-6-[1-(6-piperazin-1-yl-2-pyridyl)pyrazolo[4,3-c]pyridin-6-yl]pyrazin-2-amine | 401.468 |

TABLE 1-continued

| No. | Structure | IUPAC Name | MW |
|---|---|---|---|
| 286 | 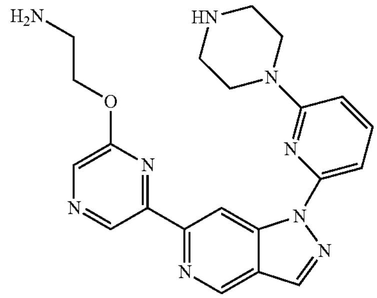 [SMILES: NCCOc1cncc(-c2cc3c(cn2)cnn3-c2cccc(N3CCNCC3)n2)n1] | 2-[6-[1-(6-piperazin-1-yl-2-pyridyl)pyrazolo[4,3-c]pyridin-6-yl]pyrazin-2-yl]oxyethanamine | 417.467 |
| 287 | 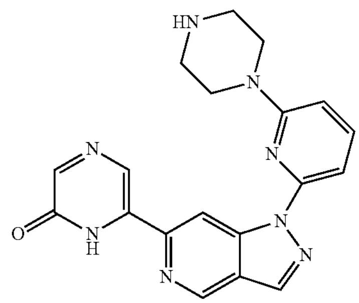 [SMILES: O=c1cncc(-c2cc3c(cn2)cnn3-c2cccc(N3CCNCC3)n2)[nH]1] | 6-[1-(6-piperazin-1-yl-2-pyridyl)pyrazolo[4,3-c]pyridin-6-yl]-1H-pyrazin-2-one | 374.399 |
| 288 | 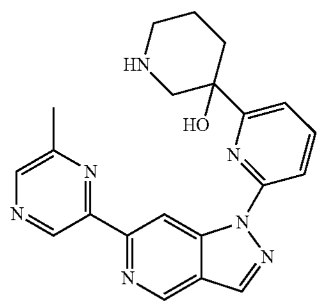 [SMILES: Cc1cncc(-c2cc3c(cn2)cnn3-c2cccc(C3(O)CCCNC3)n2)n1] | 3-(6-(6-(6-methylpyrazin-2-yl)-1H-pyrazolo[4,3-c]pyridin-1-yl)pyridin-2-yl)piperidin-3-ol | 387.44 |
| 289 | 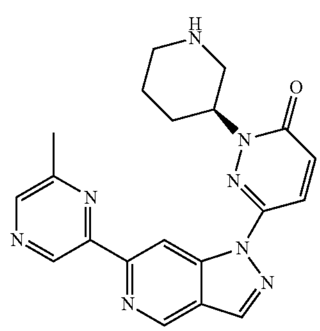 [SMILES: Cc1cncc(-c2cc3c(cn2)cnn3-c2ccc(=O)n([C@H]3CCCNC3)n2)n1] | (S)-6-(6-(6-methylpyrazin-2-yl)-1H-pyrazolo[4,3-c]pyridin-1-yl)-2-(piperidin-3-yl)pyridazin-3(2H)-one | 388.43 |
| 290 | 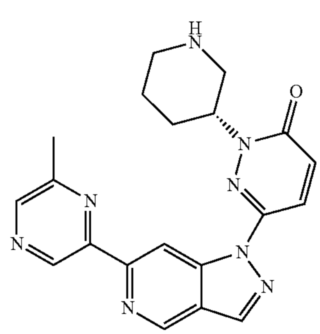 [SMILES: Cc1cncc(-c2cc3c(cn2)cnn3-c2ccc(=O)n([C@@H]3CCCNC3)n2)n1] | (R)-6-(6-(6-methylpyrazin-2-yl)-1H-pyrazolo[4,3-c]pyridin-1-yl)-2-(piperidin-3-yl)pyridazin-3(2H)-one | 388.43 |

TABLE 1-continued

| No. | Structure | IUPAC Name | MW |
|---|---|---|---|
| 291 | 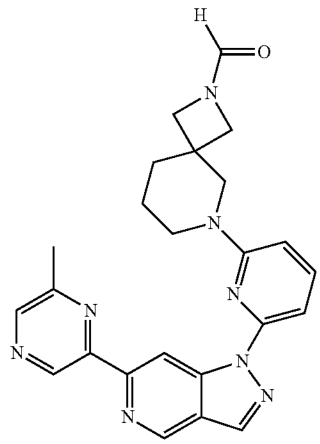 [SMILES: Cc1cncc(-c2cc3c(cn2)cnn3-c2cccc(N3CCCC4(CN(C=O)C4)C3)n2)n1] | 6-(6-(6-(6-methylpyrazin-2-yl)-1H-pyrazolo[4,3-c]pyridin-1-yl)pyridin-2-yl)-2,6-diazaspiro[3.5]nonane-2-carbaldehyde | 440.50 |
| 292 | 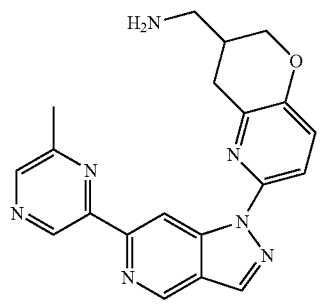 [SMILES: Cc1cncc(-c2cc3c(cn2)cnn3-c2ccc3c(n2)CC(CN)CO3)n1] | (6-(6-(6-methylpyrazin-2-yl)-1H-pyrazolo[4,3-c]pyridin-1-yl)-3,4-dihydro-2H-pyrano[3,2-b]pyridin-3-yl)methanamine | 373.41 |
| 293 | 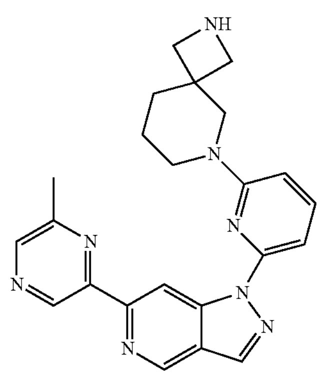 [SMILES: Cc1cncc(-c2cc3c(cn2)cnn3-c2cccc(N3CCCC4(CNC4)C3)n2)n1] | 1-(6-(2,6-diazaspiro[3.5]nonan-6-yl)pyridin-2-yl)-6-(6-methylpyrazin-2-yl)-1H-pyrazolo[4,3-c]pyridine | 412.49 |
| 294 | 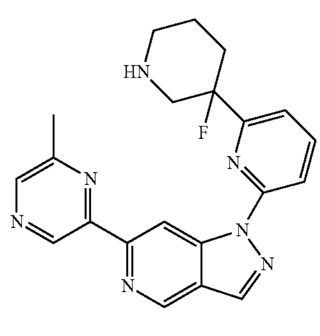 [SMILES: Cc1cncc(-c2cc3c(cn2)cnn3-c2cccc(C3(F)CCCNC3)n2)n1] | 1-(6-(3-fluoropiperidin-3-yl)pyridin-2-yl)-6-(6-methylpyrazin-2-yl)-1H-pyrazolo[4,3-c]pyridine | 389.43 |

TABLE 1-continued

| No. | Structure | IUPAC Name | MW |
|---|---|---|---|
| 295 | 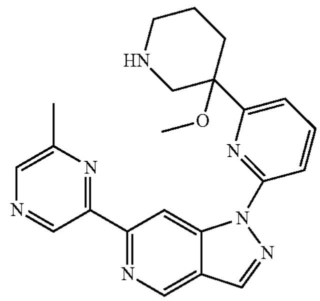 [SMILES: COC1(c2cccc(-n3ncc4cnc(-c5cncc(C)n5)cc43)n2)CCCNC1] | 1-(6-(3-methoxypiperidin-3-yl)pyridin-2-yl)-6-(6-methylpyrazin-2-yl)-1H-pyrazolo[4,3-c]pyridine | 401.46 |
| 296 | 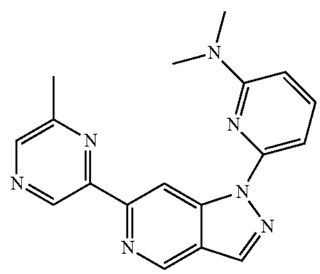 [SMILES: Cc1cncc(-c2cc3c(cn2)cnn3-c2cccc(N(C)C)n2)n1] | N,N-dimethyl-6-(6-(6-methylpyrazin-2-yl)-1H-pyrazolo[4,3-c]pyridin-1-yl)pyridin-2-amine | 331.37 |
| 297 | 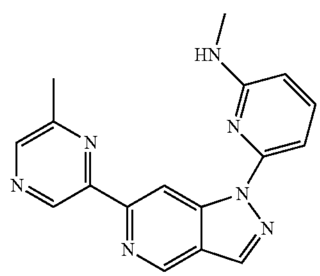 [SMILES: CNc1cccc(-n2ncc3cnc(-c4cncc(C)n4)cc32)n1] | N-methyl-6-(6-(6-methylpyrazin-2-yl)-1H-pyrazolo[4,3-c]pyridin-1-yl)pyridin-2-amine | 317.35 |
| 298 | 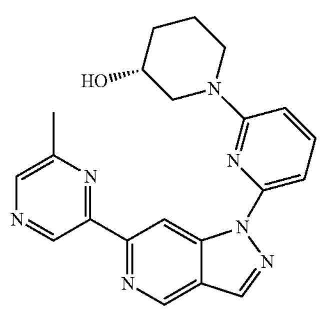 [SMILES: Cc1cncc(-c2cc3c(cn2)cnn3-c2cccc(N3CCC[C@@H](O)C3)n2)n1] | (R)-1-(6-(6-(6-methylpyrazin-2-yl)-1H-pyrazolo[4,3-c]pyridin-1-yl)pyridin-2-yl)piperidin-3-ol | 387.44 |
| 299 | 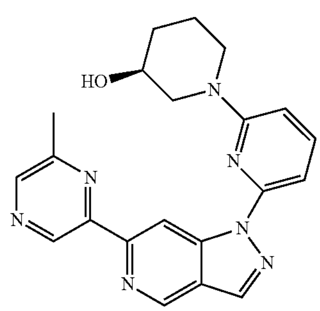 [SMILES: Cc1cncc(-c2cc3c(cn2)cnn3-c2cccc(N3CCC[C@H](O)C3)n2)n1] | (S)-1-(6-(6-(6-methylpyrazin-2-yl)-1H-pyrazolo[4,3-c]pyridin-1-yl)pyridin-2-yl)piperidin-3-ol | 387.44 |

TABLE 1-continued

| No. | Structure | IUPAC Name | MW |
|---|---|---|---|
| 300 | 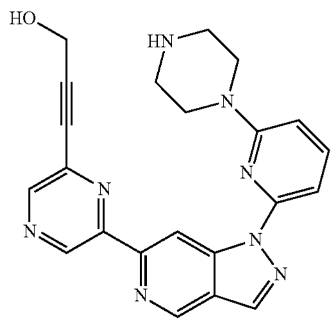 [SMILES: OCC#Cc1cncc(-c2cc3c(cn2)cnn3-c2cccc(N3CCNCC3)n2)n1] | 3-(6-(1-(6-(piperazin-1-yl)pyridin-2-yl)-1H-pyrazolo[4,3-c]pyridin-6-yl)pyrazin-2-yl)prop-2-yn-1-ol | 412.45 |
| 301 | 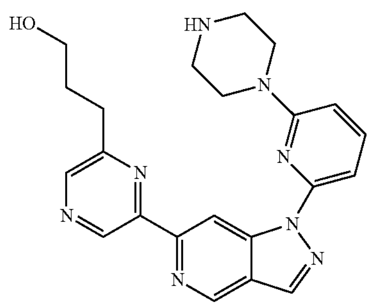 [SMILES: OCCCc1cncc(-c2cc3c(cn2)cnn3-c2cccc(N3CCNCC3)n2)n1] | 3-(6-(1-(6-(piperazin-1-yl)pyridin-2-yl)-1H-pyrazolo[4,3-c]pyridin-6-yl)pyrazin-2-yl)propan-1-ol | 416.48 |

TABLE 2

| No. | Structure | IUPAC Name | MW |
|---|---|---|---|
| 302 | 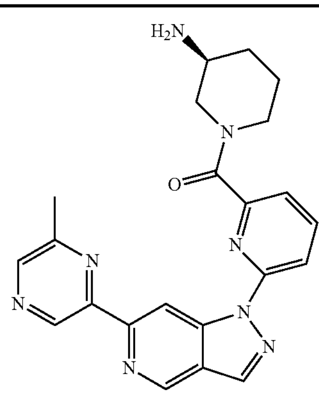 | (S)-(3-aminopiperidin-1-yl)(6-(6-(6-methylpyrazin-2-yl)-1H-pyrazolo[4,3-c]pyridin-1-yl)pyridin-2-yl)methanone | 414.46 |
| 303 | 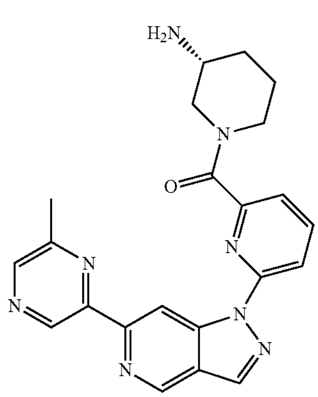 [SMILES: Cc1cncc(-c2cc3c(cn2)cnn3-c2cccc(C(=O)N3CCC[C@@H](N)C3)n2)n1] | (R)-(3-aminopiperidin-1-yl)(6-(6-(6-methylpyrazin-2-yl)-1H-pyrazolo[4,3-c]pyridin-1-yl)pyridin-2-yl)methanone | 414.46 |

TABLE 2-continued

| No. | Structure | IUPAC Name | MW |
| --- | --- | --- | --- |
| 304 | 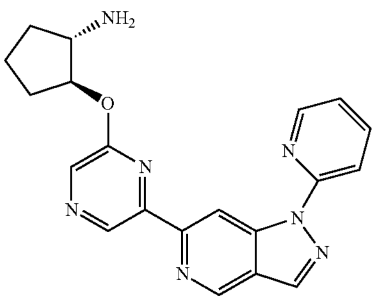 [SMILES: N[C@H]1CCC[C@@H]1Oc1cncc(-c2cc3c(cn2)cnn3-c2ccccn2)n1] | (1S,2S)-2-(6-(1-(pyridin-2-yl)-1H-pyrazolo[4,3-c]pyridin-6-yl)pyrazin-2-yloxy)cyclopentanamine | 373.41 |
| 305 | 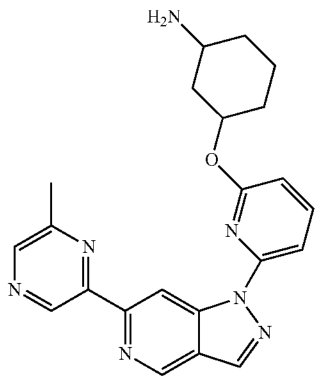 [SMILES: Cc1cncc(-c2cc3c(cn2)cnn3-c2cccc(OC3CCCC(N)C3)n2)n1] | 3-(6-(6-(6-methylpyrazin-2-yl)-1H-pyrazolo[4,3-c]pyridin-1-yl)pyrazin-2-yloxy)cyclohexanamine | 401.46 |
| 306 | 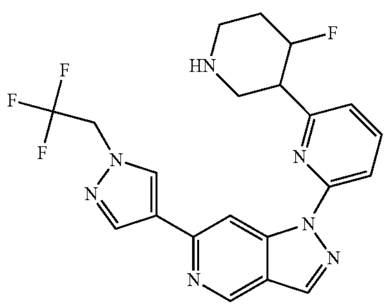 [SMILES: FC1CCNCC1c1cccc(-n2ncc3cnc(-c4cnn(CC(F)(F)F)c4)cc32)n1] | 1-(6-(4-fluoropiperidin-3-yl)pyridin-2-yl)-6-(1-(2,2,2-trifluoroethyl)-1H-pyrazol-4-yl)-1H-pyrazolo[4,3-c]pyridine | 445.42 |
| 307 | 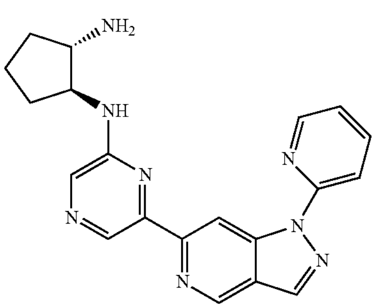 [SMILES: N[C@H]1CCC[C@@H]1Nc1cncc(-c2cc3c(cn2)cnn3-c2ccccn2)n1] | (1S,2S)-N1-(6-(1-(pyridin-2-yl)-1H-pyrazolo[4,3-c]pyridin-6-yl)pyrazin-2-yl)cyclopentane-1,2-diamine | 372.43 |
| 308 | 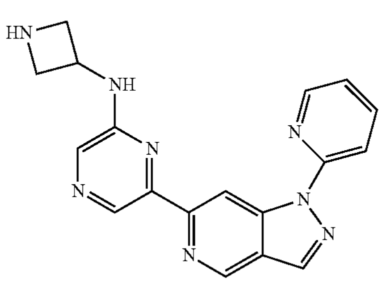 [SMILES: c1ccc(-n2ncc3cnc(-c4cncc(NC5CNC5)n4)cc32)nc1] | N-(azetidin-3-yl)-6-(1-(pyridin-2-yl)-1H-pyrazolo[4,3-c]pyridin-6-yl)pyrazin-2-amine | 344.37 |

TABLE 2-continued

| No. | Structure | IUPAC Name | MW |
|---|---|---|---|
| 309 | 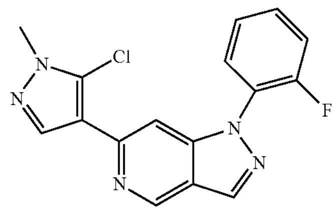 [SMILES: Cn1ncc(-c2cc3c(cn2)cnn3-c2ccccc2F)c1Cl] | 6-(5-chloro-1-methyl-1H-pyrazol-4-yl)-1-(2-fluorophenyl)-1H-pyrazolo[4,3-c]pyridine | 327.74 |
| 310 | 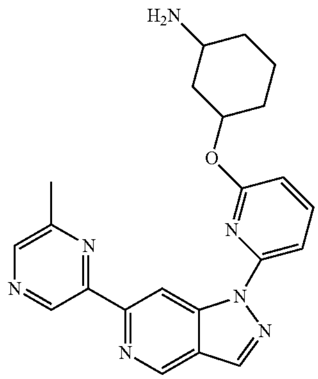 [SMILES: Cc1cncc(-c2cc3c(cn2)cnn3-c2cccc(OC3CCCC(N)C3)n2)n1] | 3-(6-(6-(6-methylpyrazin-2-yl)-1H-pyrazolo[4,3-c]pyridin-1-yl)pyridin-2-yloxy)cyclohexanamine | 401.46 |
| 311 | 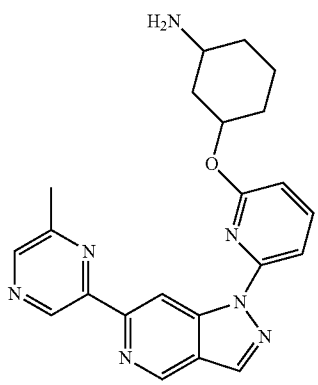 [SMILES: Cc1cncc(-c2cc3c(cn2)cnn3-c2cccc(OC3CCCC(N)C3)n2)n1] | 3-(6-(6-(6-methylpyrazin-2-yl)-1H-pyrazolo[4,3-c]pyridin-1-yl)pyridin-2-yloxy)cyclohexanamine | 401.46 |
| 312 | 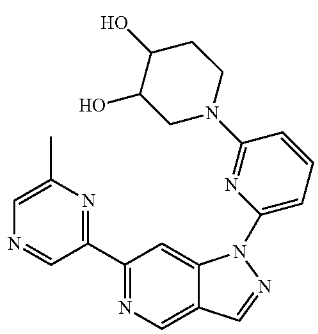 [SMILES: Cc1cncc(-c2cc3c(cn2)cnn3-c2cccc(N3CCC(O)C(O)C3)n2)n1] | 1-(6-(6-(6-methylpyrazin-2-yl)-1H-pyrazolo[4,3-c]pyridin-1-yl)pyridin-2-yl)piperidine-3,4-diol | 403.44 |
| 313 | 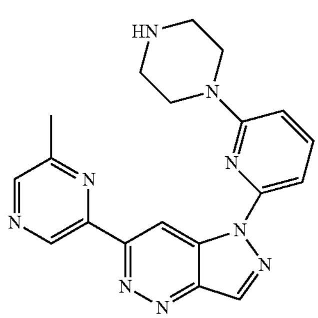 [SMILES: Cc1cncc(-c2cc3c(cnn3-c3cccc(N4CCNCC4)n3)nn2)n1] | 6-(6-methylpyrazin-2-yl)-1-(6-(piperazin-1-yl)pyridin-2-yl)-1H-pyrazolo[4,3-c]pyridazine | 373.41 |

TABLE 2-continued

| No. | Structure | IUPAC Name | MW |
|---|---|---|---|
| 314 | 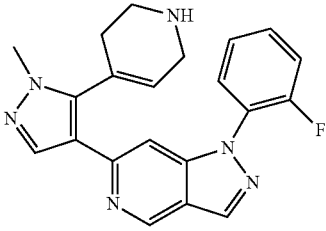 [SMILES: Cn1ncc(-c2cc3c(cn2)cnn3-c2ccccc2F)c1C1=CCNCC1] | 1-(2-fluorophenyl)-6-(1-methyl-5-(1,2,3,6-tetrahydropyridin-4-yl)-1H-pyrazol-4-yl)-1H-pyrazolo[4,3-c]pyridine | 374.41 |
| 315 | 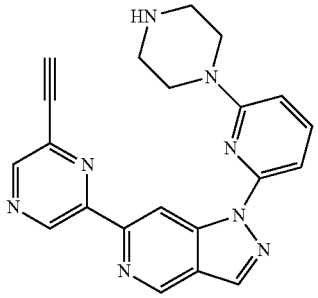 [SMILES: C#Cc1cncc(-c2cc3c(cn2)cnn3-c2cccc(N3CCNCC3)n2)n1] | 6-(6-ethynylpyrazin-2-yl)-1-(6-(piperazin-1-yl)pyridin-2-yl)-1H-pyrazolo[4,3-c]pyridine | 382.42 |
| 316 | 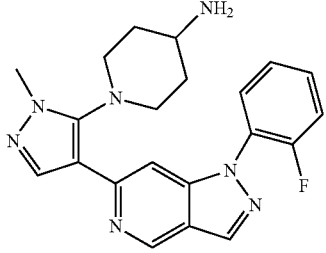 [SMILES: Cn1ncc(-c2cc3c(cn2)cnn3-c2ccccc2F)c1N1CCC(N)CC1] | 1-(4-(1-(2-fluorophenyl)-1H-pyrazolo[4,3-c]pyridin-6-yl)-1-methyl-1H-pyrazol-5-yl)piperidin-4-amine | 391.44 |
| 317 | 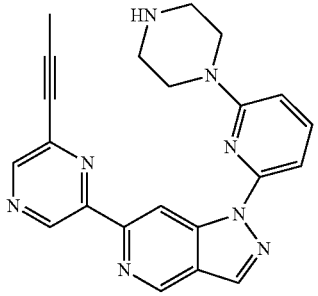 [SMILES: CC#Cc1cncc(-c2cc3c(cn2)cnn3-c2cccc(N3CCNCC3)n2)n1] | 1-(6-(piperazin-1-yl)pyridin-2-yl)-6-(6-(prop-1-ynyl)pyrazin-2-yl)-1H-pyrazolo[4,3-c]pyridine | 396.45 |

The present invention includes a composition (e.g., a pharmaceutical composition) comprising a compound of Formula I, and/or solvates, hydrates and/or salts thereof, and a carrier (a pharmaceutically acceptable carrier). The present invention also includes a composition (e.g., a pharmaceutical composition) comprising a compound of Formula I and/or solvates, hydrates and/or salts thereof, and a carrier (a pharmaceutically acceptable carrier), further comprising a second chemotherapeutic agent such as those described herein. The present compositions are useful for inhibiting abnormal cell growth or treating a hyperproliferative disorder such as cancer in a mammal (e.g., human). For example, the present compounds and compositions are useful for treating multiple myeloma, lymphoma, acute myeloid leukemia, prostate cancer, breast cancer, hepatocellular carcinoma, pancreatic cancer, and/or colorectal cancer in a mammal (e.g., human).

The present invention includes a method of inhibiting abnormal cell growth or treating a hyperproliferative disorder such as cancer in a mammal (e.g., human) comprising administering to said mammal a therapeutically effective amount of a compound of Formula I, and/or solvates, hydrates and/or salts thereof, or a composition thereof. For example, the present invention includes a method of treating multiple myeloma, lymphoma, acute myeloid leukemia, prostate cancer, breast cancer, hepatocellular carcinoma, pancreatic cancer, and/or colorectal cancer in a mammal (e.g., human), comprising administering to said mammal a therapeutically effective amount of a compound of Formula I, and/or solvates, hydrates and/or salts thereof) or a composition thereof.

The present invention includes a method of inhibiting abnormal cell growth or treating a hyperproliferative disorder such as cancer in a mammal (e.g., human) comprising administering to said mammal a therapeutically effective amount of a compound of Formula I, and/or solvates, hydrates and/or salts thereof, or a composition thereof, in combination with a second chemotherapeutic agent such as those described herein. For example, the present invention includes a method of treating multiple myeloma, lymphoma, acute myeloid leukemia, prostate cancer, breast cancer, hepatocellular carcinoma, pancreatic cancer, and/or colorectal cancer in a mammal (e.g., human), comprising administering to said mammal a therapeutically effective amount of a compound of Formula I, and/or solvates, hydrates and/or salts thereof, or a composition thereof, in combination with a second chemotherapeutic agent such as those described herein.

The present invention includes a method of treating lymphoma in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as an anti-B-cell antibody therapeutic (e.g., Rituxan and/or Dacetuzumab), gemcitabine, corticosteroids (e.g., prednisolone and/or dexamethasone), chemotherapy cocktails (e.g., CHOP (cyclophosphamide, doxorubicin, vincristine, prednisolone) and/or ICE (isfosfamide, cytoxan, etoposide)), a combination of biologics and chemotherapy (e.g., Rituxan-ICE, Dacetuzumab-Rituxan-ICE, R-Gem, and/or D-R-Gem), an Akt inhibitor, a PI3K inhibitor (e.g, GDC-0941 (Genentech) and/or GDC-0980 (Genentech)), rapamycin, a rapamycin analog, mTOR inhibitor such as everolimus or sirolimus, a MEK inhibitor (GDC-0973), and a Bcl-2 inhibitor (ABT-263 or ABT-199).

The present invention includes a method of treating multiple myeloma in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as melphalan, "Imids" (immuno-modulators, e.g., thalidomide, lenalidomide, and/or pomolidamide), corticosteroids (e.g., dexamethasone and/or prednisolone), and bortezomib or other proteasome inhibitor.

The present invention includes a method of treating multiple myeloma, chronic lymphocytic leukemia (CLL), or acute myeloid leukemia (AML) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as cytarabine (araC), anthracyclines (e.g., daunorubicin and/or idarubicin), anti-myeloid antibody therapeutics (e.g., SGN-33), anti-myeloid antibody-drug conjugates (e.g., MYLOTARG®).

The present invention includes a method of treating chronic lymphocytic leukemia (CLL) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as fludarabine, cyclophosphamide, anti-B-cell antibody therapeutics (e.g., Rituxan and/or Dacetuzumab).

The present invention includes a method of treating chronic myeloid leukemia (CML) in a mammal (e.g., human) comprising administering to said mammal a therapeutically effective amount of a compound of Formula I, and/or solvates, hydrates and/or salts thereof, or a composition thereof, either alone or in combination with a second chemotherapeutic agent such as a BCR-abl inhibitor (e.g., imatinib, nilotinib, and/or dasatinib).

The present invention includes a method of treating myelodysplastic diseases (MDS) and myeloproliferative disorders including polycythemia vera (PV), essential thrombocytosis (ET) or myelofibrosis (MF), in a mammal (e.g., human) comprising administering to said mammal a therapeutically effective amount of a compound of Formula I, and/or solvates, hydrates and/or salts thereof, or a composition thereof, either alone or in combination.

The present invention includes a method of using the present compounds for in vitro, in situ, and in vivo diagnosis or treatment of mammalian cells, organisms, or associated pathological conditions.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic agents, for example those described herein. Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension for parenteral injection as a sterile solution, suspension or emulsion for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of Formula I compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tabletting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

Administration of Formula I Compounds

The Formula I compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Compounds of the present invention are useful for treating hyperproliferative diseases, conditions and/or disorders including, but not limited to, those characterized by over expression of Pim kinases, e.g. Pim-1, Pim-2 and Pim-3 kinases. Accordingly, another aspect of this invention includes methods of treating or preventing diseases or conditions that can be treated or prevented by inhibiting Pim kinase. In one embodiment, the method comprises administering to a mammal in need thereof a therapeutically effective amount of a compound of Formula I, or a stereoisomer, geometric isomer, tautomer, or pharmaceutically acceptable salt thereof. In one embodiment, a human patient is treated with a compound of Formula I and a pharmaceutically acceptable carrier, adjuvant, or vehicle, wherein said compound of Formula I is present in an amount to detectably inhibit Pim kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a Formula I compound for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a Formula I compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the Formula I compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16$^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention comprising a Formula I compound will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the Formula I compound administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16$^{th}$ edition, Osol, A. Ed. (1980).

Sustained-release preparations of Formula I compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400), and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise solely an emulsifier, it may also comprise a mixture of at least one emulsifier and a fat or oil, or both a fat and an oil. A hydrophilic emulsifier included together with a lipophilic emulsifier may act as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as a hyperproliferative disorder (e.g., cancer). In certain embodiments, a compound of Formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Formula I Compounds

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, may be useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. The kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or II or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

5-Azaindazole compounds of Formula I are also known as pyrazolo[4,3-c]pyridine with the numbering scheme as:

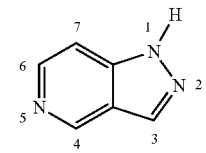

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The General Procedures and Examples provide exemplary methods for preparing Formula I compounds. Those skilled in the art will appreciate that other synthetic routes may be used to synthesize the Formula I compounds. Although specific starting materials and reagents are depicted and discussed in the Figures, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

General Preparative Procedures

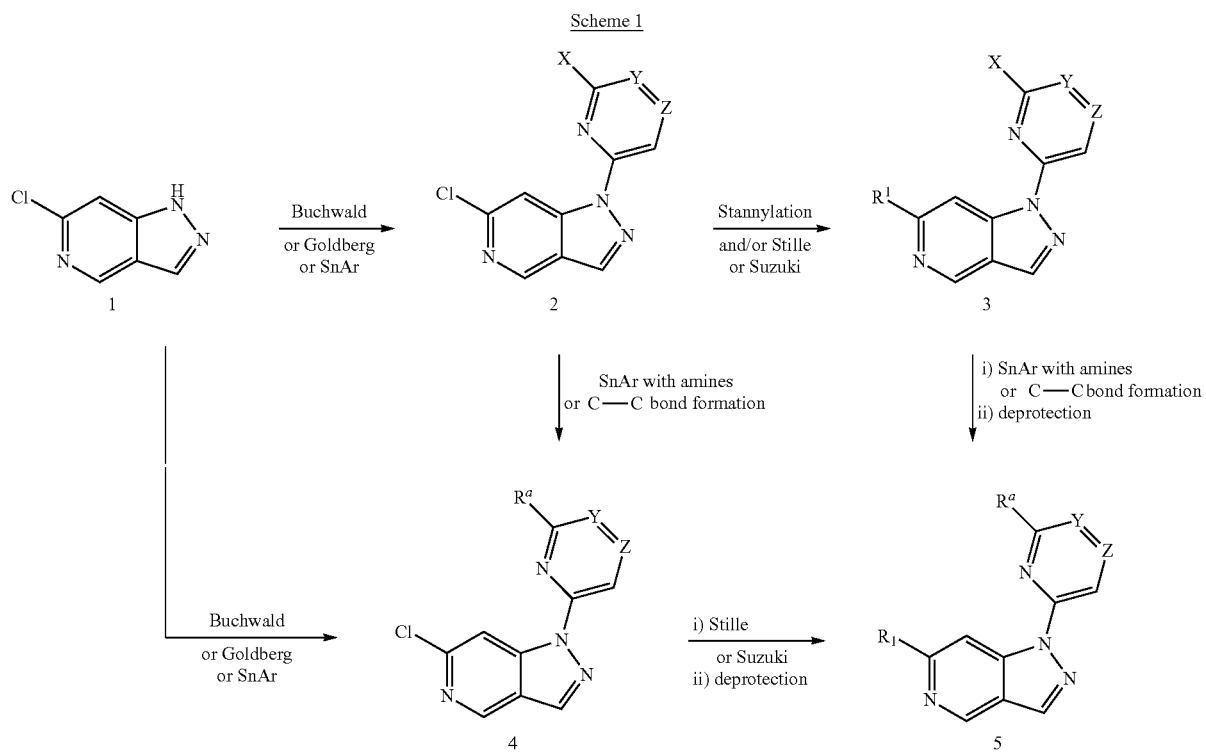

Scheme 1 shows a general synthesis of compounds 5. Substituted 6-chloro N-pyridyl 5-azaindazoles (Y=Z=CH) 2 may be made through, but not limited by, Buchwald, Goldberg or nucleophilic aromatic substitution (SnAr) reaction starting from 6-chloro-5-azaindazole 1. Installment of $R^2$ group by SnAr reaction with various amines, or C—C bond formation reaction with or without transition metal catalysis furnishes compounds 4. Alternatively, compounds 4 may be made directly from 6-chloro-5-azaindazole 1 with $R^a$ group already installed on the pyridine precursor. Subsequent Stille or Suzuki reaction, followed by deprotection may provide targeted compounds 5 with various $R^1$, $R^a$ substitutions. In an alternative sequence, compounds 5 can be accomplished through a three or four step synthesis starting from compounds 2. First, installment of $R^1$ group via stannylation, followed by Stille reaction or Suzuki reaction with boronic acid/ester furnishes compounds 3. Second, the addition of $R^a$ group may be accomplished either through SnAr reaction with various amines, or C—C bond formation reaction with or without transition metal catalysis. Lastly, under acidic, basic, oxidative or reductive condition, deprotection may yield the compounds 5. Similarly, substituted N-pyrimidinyl 5-azaindazoles (Y=N, Z=CH) and substituted N-pyrazinyl 5-azaindazoles (Y=CH, Z=N) 5 may be synthesized.

Scheme 2

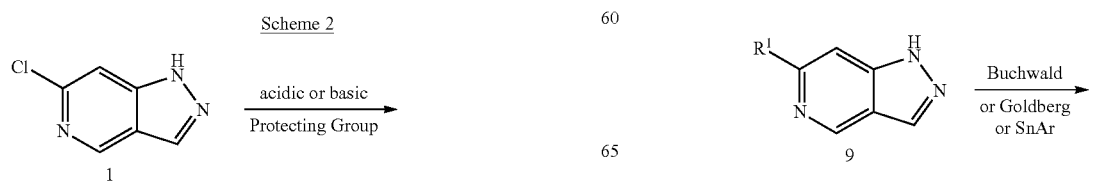

-continued

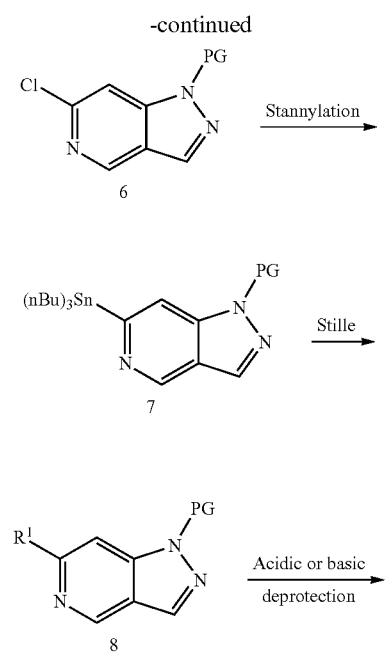

-continued

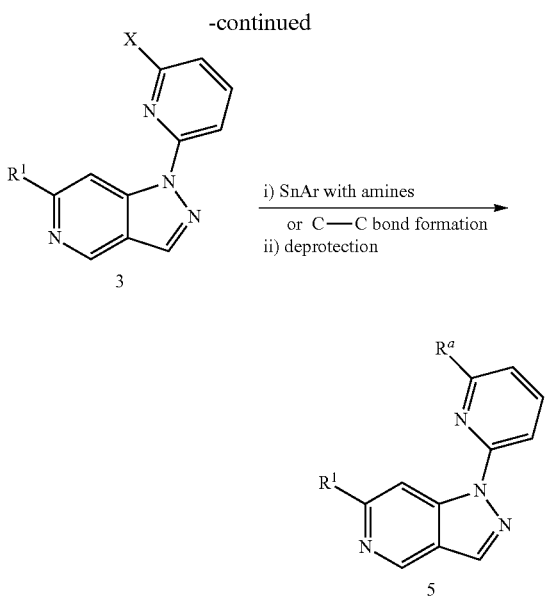

Scheme 2 shows a general synthesis of compounds 5. Protection of the 6-chloro-5-azaindazole 1 either under basic or acidic condition may yield compounds 6. Alternatively the 6-position can be other halo, such as Br or I, or leaving group. The protecting groups (PG) include but are not limited to tetrahydropyranyl, 2-(trimethylsilyl)ethoxy]methyl or acetyl group, or other nitrogen-protecting group known in the literature. Subsequent stannylation reaction, followed by Stille reaction starting from compounds 6 may furnish compounds 8. Compounds 9 may be made by the removal of protecting groups through either acidic or basic conditions. Substituted N-pyridyl 5-azaindazoles 3 may be synthesized through, but not limited by, Buchwald, Goldberg or nucleophilic aromatic substitution (SnAr) reaction starting from 6-chloro-5-azaindazole 9. Installment of $R^a$ group by SnAr reaction with various amines, or C—C bond formation reaction with or without transition metal catalysis, followed by deprotection furnishes compounds 5.

Scheme 3

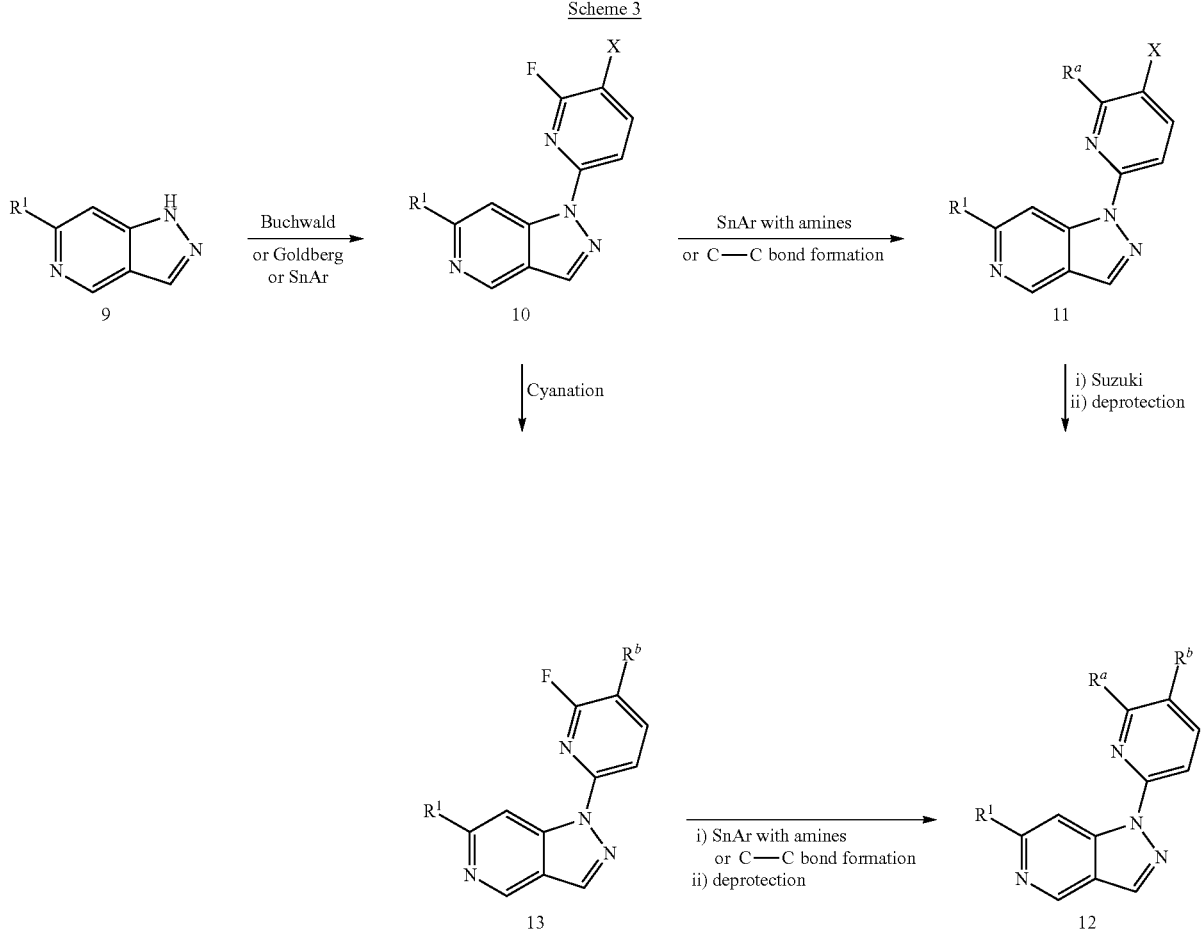

Scheme 3 shows a general synthesis of compounds 12. Compounds 10 may be synthesized through, but not limited by, Buchwald, Goldberg or nucleophilic aromatic substitution (SnAr) reaction starting from 6-chloro-5-azaindazoles 9. Cyanation of compounds 10 under suitable conditions may furnish compounds 13. Installment of $R^a$ group can be accomplished through, but not limited to, SnAr reaction with various amines or C—C bond formation reaction with or without transition metal catalysis. Subsequent deprotection under various conditions may furnish compounds 12. Alternatively, compounds 12 may be made through a different sequence with installment of $R^a$ group first followed by $R^b$ group.

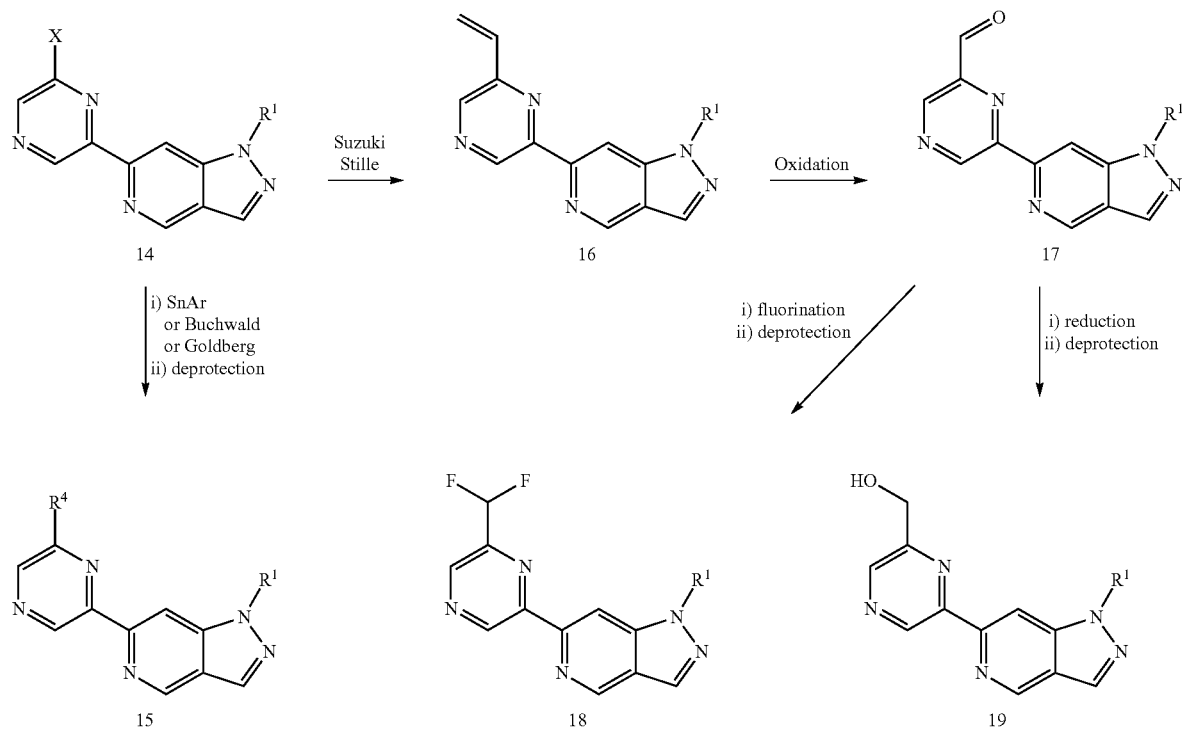

Scheme 4

Scheme 4 shows a general synthesis of compounds 15, 18 and 19. Compounds 15 may be synthesized through, but not limited by, Buchwald, Goldberg or nucleophilic aromatic substitution (SnAr) reaction starting from compounds 14, followed by deprotection reaction if needed under suitable conditions. Installment of a vinyl group can be accomplished through either Suzuki or Stille reaction to furnish compounds 16. Through either one step or step wise oxidative cleavage of compounds 16 may yield aldehydes 17. Subsequent fluorination or reduction reaction followed by deprotection reaction if needed under suitable conditions may result in compounds 18 or 19.

EXAMPLES

Example 1

6-(1-ethylpyrazol-4-yl)-1-(6-piperazin-1-yl-2-pyridyl)pyrazolo[4,3-c]pyridine 101

Step A: Preparation of 6-chloro-1-(6-fluoro-2-pyridyl)pyrazolo[4,3-c]pyridine

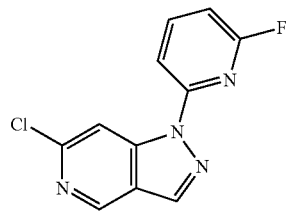 [SMILES: Fc1cccc(-n2ncc3cnc(Cl)cc32)n1]

Method I: A solution of 6-chloro-1H-pyrazolo[4,3-c]pyridine (3.78 g, 24.6 mmol), cesium carbonate (16.1 g, 49.2 mmol) and 2,6-difluoropyridine (3.40 g, 29.5 mmol) in dimethyl sulfoxide; 50.0 mL was stirred at 70° C. 2 h. The reaction was quenched by pouring into water then extracted with EtOAc. The organic layers was dried with sodium sulfate, filtered, and concentrated in vacuum. The crude product was purified by flash chromatography (EtOAc/Heptane eluted at 25% EtOAc) to give the desired product 3.2 g in 52% yield. MS (ESI) m/z: 249.2 [M+H]$^+$ Method II: A mixture of 6-chloro-1H-pyrazolo[4,3-c]pyridine (13.778 mmol, 2115.9 mg), 2-bromo-6-fluoro-pyridine (15.156 mmol, 2667.3 mg), N,N'-Dimethylethylenediamine (13.778 mmol; 1.215 g; 1.37 mL), Copper iodide (13.778 mmol; 2650.5 mg), and potassium carbonate (15.156 mmol; 2.12 g) in 1,4-Dioxane (10 mL) was purged with Argon, then sealed and stirred at 100° C. for 20 hours. The mixture was cooled to room temperature, and then filtered through Celite. The filtrate was concentrated; the residue was purified on silica and eluted with 0 to 100% Ethyl acetate in Heptane to give 6-Chloro-1-(6-fluoro-2-pyridyl)pyrazolo[4,3-c]pyridine as an off-white solid (1.90 g, 55%) MS (ESI) m/z: 249 [M+H]$^+$ Step B: Preparation of tert-butyl 4-[6-(6-chloropyrazolo[4,3-c]pyridin-1-yl)-2-pyridyl]piperazine-1-carboxylate

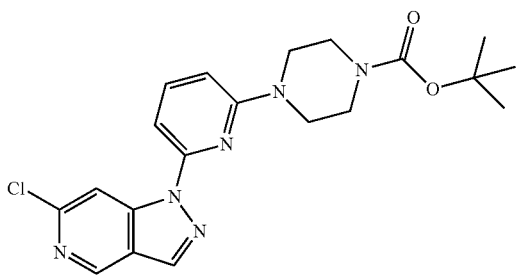 [SMILES: CC(C)(C)OC(=O)N1CCN(c2cccc(-n3ncc4cnc(Cl)cc43)n2)CC1]

A solution of 6-chloro-1-(6-fluoro-2-pyridyl)pyrazolo[4,3-c]pyridine (100 mg, 0.40 mmol) and 1-N-Boc-piperazine (380 mg, 2.0 mmol) in dimethyl sulfoxide (3.0 mL) was heated at 95° C. 4 h. The reaction was quenched with water and extracted with EtOAc. The organic layers was dried with sodium sulfate, filtered, and concentrated in vacuum. The crude product was purified by flash chromatography (EtOAc/Heptane 25% EtOAc) to give the desired product 110 mg 66% yield. MS (ESI) m/z: 415.1 [M+H]$^+$ Step C: 6-(1-ethyl-1H-pyrazol-4-yl)-1-(6-(piperazin-1-yl)pyridin-2-yl)-1H-pyrazolo[4,3-c]pyridine

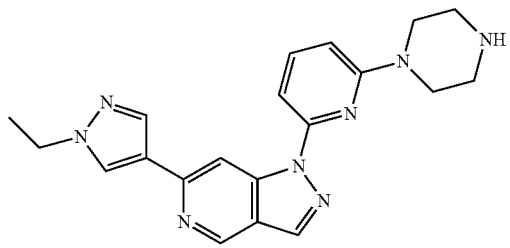 [SMILES: CCn1cc(-c2cc3c(cn2)cnn3-c2cccc(N3CCNCC3)n2)cn1]

A mixture of tert-butyl 4-[6-(6-chloropyrazolo[4,3-c]pyridin-1-yl)-2-pyridyl]piperazine-1-carboxylate (0.5112 mmol; 212.1 mg), 1-ethyl-4-(4,4,5,5-tetramethyl-1,3,2-dioxaborolan-2-yl)pyrazole (1.022 mmol; 227.1 mg), [1,1'-bis(diphenylphosphino)ferrocene]dichloropalladium(II) dichloromethane adduct (0.05112 mmol; 42.6 mg), potassium acetate hydrate (0.7668 mmol; 0.77 mL) and sodium carbonate decahydrate (0.7668 mmol; 0.77 mL) in Acetonitrile (10 mL) in a pressure tube was heated under microwave at 150° C. for 15 min. The mixture was cooled to room temperature. The layers were separated. The aqueous layer was extracted with EtOAc. The combined organic layer was concentrated. The residue was purified on silica eluted with 0 to 6% MeOH in DCM to afford tert-butyl 4-(6-(6-(1-ethyl-1H-pyrazol-4-yl)-1H-pyrazolo[4,3-c]pyridin-1-yl)pyridin-2-yl)piperazine-1-carboxylate as a dark tan solid.

A mixture of tert-butyl 4-(6-(6-(1-ethyl-1H-pyrazol-4-yl)-1H-pyrazolo[4,3-c]pyridin-1-yl)pyridin-2-yl)piperazine-1-carboxylate (0.2486 mmol; 118 mg) in DCM (5 mL) and TFA (5 mL) was stirred at room temperature overnight. The mixture was concentrated and the residue was purified by reverse phase HPLC to afford 6-(1-ethyl-1H-pyrazol-4-yl)-1-(6-(piperazin-1-yl)pyridin-2-yl)-1H-pyrazolo[4,3-c]pyridine 101 (47.5 mg, 50%). $^1$H NMR (400 MHz, DMSO) δ 9.15-9.11 (s, 1H), 8.67-8.65 (s, 1H), 8.54-8.51 (s, 1H), 8.27-8.24 (s, 1H), 7.91-7.88 (s, 1H), 7.78-7.72 (t, J=8.1 Hz, 1H), 7.24-7.18 (d, J=7.7 Hz, 1H), 6.80-6.74 (d, J=8.4 Hz, 1H), 4.26-4.17 (q, J=7.3 Hz, 2H), 3.65-3.56 (m, 4H), 2.96-2.86 (m, 4H), 1.46-1.41 (t, J=7.3 Hz, 3H); MS (ESI) m/z: 375.1 [M+H]$^+$ Example 2

6-(1-methyl-1H-pyrazol-4-yl)-1-(6-(piperazin-1-yl)pyridin-2-yl)-1H-pyrazolo[4,3-c]pyridine 102

Following the procedures as described in EXAMPLE 1 and starting with 1-methyl-4-(4,4,5,5-tetramethyl-1,3,2-dioxaborolan-2-yl)pyrazole, having the structure:

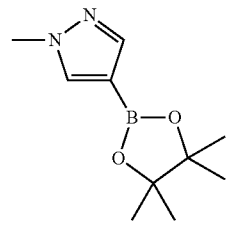

102 was obtained as an off-white solid (174 mg, 32%) over two steps. $^1$H NMR (400 MHz, DMSO) δ 9.17-9.07 (s, 1H), 8.71-8.57 (s, 1H), 8.56-8.47 (s, 1H), 8.26-8.15 (s, 1H), 7.91-7.82 (s, 1H), 7.80-7.69 (t, J=8.1 Hz, 1H), 7.26-7.15 (d, J=7.7 Hz, 1H), 6.81-6.73 (d, J=8.4 Hz, 1H), 3.99-3.82 (s, 3H), 3.66-3.52 (m, 4H), 2.96-2.85 (m, 4H); MS (ESI) m/z: 361.2 [M+H]$^+$ Example 3

1-(6-(1,4-diazepan-1-yl)pyridin-2-yl)-6-(5-isopropylpyridin-3-yl)-1H-pyrazolo[4,3-c]pyridine 103

Following the procedures as described in EXAMPLE 8 and starting with 1,4-diazepane, 103 was obtained as an off-white solid (29.4 mg, 24%). $^1$H NMR (400 MHz, DMSO) δ 9.36-9.28 (s, 1H), 9.09-9.04 (d, J=2.0 Hz, 1H), 9.03-9.01 (s, 1H), 8.66-8.61 (s, 1H), 8.59-8.55 (d, J=2.1 Hz, 1H), 8.30-8.24 (t, J=2.0 Hz, 1H), 7.76-7.65 (t, J=8.1 Hz, 1H), 7.23-7.16 (d, J=7.7 Hz, 1H), 6.65-6.58 (d, J=8.5 Hz, 1H), 3.93-3.72 (dt, J=10.0, 5.5 Hz, 4H), 3.12-3.03 (dt, J=14.0, 7.0 Hz, 1H), 2.99-2.90 (m, 2H), 2.73-2.66 (m, 2H), 1.91-1.80 (m, 2H), 1.33-1.30 (d, J=6.9 Hz, 6H); MS (ESI) m/z: 414.1 [M+H]$^+$

Example 4

6-(5-ethylpyridin-3-yl)-1-(6-(piperazin-1-yl)pyridin-2-yl)-1H-pyrazolo[4,3-c]pyridine 104

Following the procedures as described in EXAMPLE 8 and starting with 6-(5-ethylpyridin-3-yl)-1-(6-fluoropyridin-2-yl)-1H-pyrazolo[4,3-c]pyridine and piperazine, 104 was obtained as an off-white solid (22.3 mg, 18%) over 2 steps. $^1$H NMR (400 MHz, DMSO) δ 9.35-9.27 (s, 1H), 9.16-9.08 (d, J=2.0 Hz, 1H), 9.08-9.01 (s, 1H), 8.67-8.59 (s, 1H), 8.57-8.50 (d, J=1.9 Hz, 1H), 8.30-8.21 (s, 1H), 7.85-7.73 (m, 2H), 7.66-7.44 (m, 2H), 7.28-7.23 (d, J=7.7 Hz, 1H), 6.85-6.78 (d, J=8.4 Hz, 1H), 3.65-3.57 (m, 4H), 2.98-2.81 (m, 4H), 2.79-2.70 (q, J=7.6 Hz, 2H), 1.75-1.52 (m, 3H), 1.32-1.24 (t, J=7.6 Hz, 3H).; MS (ESI) m/z: 386.2 [M+H]$^+$

Example 5

6-(5-isopropylpyridin-3-yl)-1-(6-(piperazin-1-yl)pyridin-2-yl)-1H-pyrazolo[4,3-c]pyridine 105

Following the procedures as described in EXAMPLE 8 and starting with piperazine, 105 was obtained as an off-white solid (26.6 mg, 22%). $^1$H NMR (400 MHz, DMSO) δ 9.37-9.27 (s, 1H), 9.12-9.06 (d, J=2.0 Hz, 1H), 9.05-9.02 (s, 1H), 8.67-8.62 (s, 1H), 8.60-8.55 (d, J=2.0 Hz, 1H), 8.34-8.27 (t, J=2.0 Hz, 1H), 7.80-7.72 (t, J=8.1 Hz, 1H), 7.29-7.21 (d, J=7.7 Hz, 1H), 6.86-6.77 (d, J=8.4 Hz, 1H), 3.66-3.58 (m, 4H), 3.12-3.03 (dt, J=13.8, 6.9 Hz, 1H), 2.93-2.82 (m, 4H), 1.34-1.30 (d, J=6.9 Hz, 6H); MS (ESI) m/z: 400.2 [M+H]$^+$

Example 6

1-(6-(6-(5-ethylpyridin-3-yl)-1H-pyrazolo[4,3-c]pyridin-1-yl)pyridin-2-yl)-1,4-diazepan-6-ol 106

Following the procedures as described in EXAMPLE 8 and starting with 6-(5-ethylpyridin-3-yl)-1-(6-fluoropyridin-2-yl)-1H-pyrazolo[4,3-c]pyridine and 1,4-diazepan-6-ol, 106 was obtained as an off-white solid (49.4 mg, 12%). MS (ESI) m/z: 416.1 [M+H]$^+$

Example 7

(R)-1-(6-(6-(5-isopropylpyridin-3-yl)-1H-pyrazolo[4,3-c]pyridin-1-yl)pyridin-2-yl)piperidin-3-amine 107

Following the procedures as described in EXAMPLE 8 and starting with tert-butyl N-[(3R)-3-piperidyl]carbamate, 107 was obtained as an off-white solid (33.5 mg, 27%) over two steps. $^1$H NMR (400 MHz, DMSO) δ 9.38-9.29 (s, 1H), 9.14-9.09 (d, J=2.0 Hz, 1H), 9.06-9.00 (s, 1H), 8.67-8.61 (s, 1H), 8.60-8.55 (d, J=2.0 Hz, 1H), 8.36-8.30 (s, 1H), 7.79-7.70 (t, J=8.1 Hz, 1H), 7.23-7.14 (d, J=7.7 Hz, 1H), 6.84-6.78 (d, J=8.5 Hz, 1H), 4.31-4.13 (m, 3H), 3.13-3.04 (dt, J=13.7, 6.6 Hz, 3H), 2.87-2.79 (m, 1H), 2.80-2.72 (m, 2H), 1.96-1.75 (m, 2H), 1.68-1.52 (dd, J=24.1, 11.8 Hz, 2H), 1.33-1.30 (d, J=7.0 Hz, 7H); MS (ESI) m/z: 414.1 [M+H]$^+$

Example 8

(3S)-1-[6-[6-(5-isopropyl-3-pyridyl)pyrazolo[4,3-c]pyridin-1-yl]-2-pyridyl]piperidin-3-amine 108

Step A: Preparation of 3-bromo-5-isopropenyl-pyridine

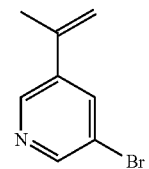

A mixture of [1,1'-bis(diphenylphosphino)ferrocene]dichloropalladium(II) dichloromethane adduct; 98.0 mass %, potassium acetate hydrate (7.4997 mmol; 3.7 mL), sodium carbonate decahydrate (7.4997 mmol; 3.7 mL), Acetonitrile (15 mL) and 3,5-dibromopyridine (4.9998 mmol; 1184.4 mg) in 2-isopropenyl-4,4,5,5-tetramethyl-1,3,2-dioxaborolane (4.9998 mmol; 840.0 mg; 0.940 mL) in a pressure tube was heated under microwave at 120° C. for 3 min. The mixture was cooled to room temperature. The layers were separated. The aqueous layer was extracted with EtOAc. The combined organic layer was concentrated. The residue was purified on silica eluted with 0 to 10% MeOH in DCM to afford 3-bromo-5-isopropenyl-pyridine as a dark tan solid (512.6 mg, 52%).

Step B: Preparation of 3-(prop-1-en-2-yl)-5-(4,4,5,5-tetramethyl-1,3,2-dioxaborolan-2-yl)pyridine

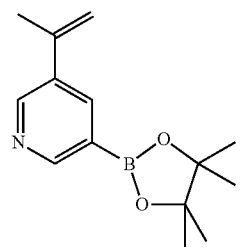 [SMILES: C=C(C)c1cncc(B2OC(C)(C)C(C)(C)O2)c1]

A mixture of 3-bromo-5-isopropenyl-pyridine 3-bromo-5-isopropenyl-pyridine (5.1767 mmol; 1025.3 mg), 4,4,5,5-tetramethyl-2-(4,4,5,5-tetramethyl-1,3,2-dioxaborolan-2-yl)-1,3,2-dioxaborolane (7.7651 mmol; 1972 mg), potassium acetate (7.7651 mmol; 762.10 mg), and [1,1'-bis(diphenylphosphino)ferrocene]dichloropalladium(II) dichloromethane adduct (0.25884 mmol; 216 mg) in 1,4-Dioxane (15 mL) in a pressure tube was purged with Nitrogen for 1 minute, then sealed and heated at 85° C. overnight. The reaction mixture was filtered hot through Celite. The filter cake was washed with EtOAc. The filtrated washed with water, and brine. The organic layer was dried with MgSO4, and then concentrated to afford 3-(prop-1-en-2-yl)-5-(4,4,5,5-tetramethyl-1,3,2-dioxaborolan-2-yl)pyridine, which was used without purification.

Step C: Preparation of 1-(6-fluoropyridin-2-yl)-6-(5-isopropylpyridin-3-yl)-1H-pyrazolo[4,3-c]pyridine

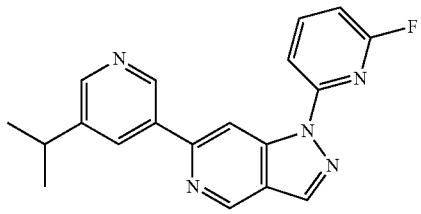

A mixture of 6-chloro-1-(6-fluoro-2-pyridyl)pyrazolo[4,3-c]pyridine (1.759 mmol; 437.3 mg), 3-isopropenyl-5-(4,4,5,5-tetramethyl-1,3,2-dioxaborolan-2-yl)pyridine (2.638 mmol; 646.6 mg), [1,1'-bis(diphenylphosphino)ferrocene]dichloropalladium(II) dichloromethane adduct (0.1759 mmol; 147 mg), potassium acetate hydrate (2.638 mmol; 1.3 mL) and sodium carbonate (2.638 mmol; 1.3 mL) in Acetonitrile (10 mL) in a pressure tube was heated under microwave at 150° C. for 5 min. The mixture was cooled to room temperature. The layers were separated. The aqueous layer was extracted with EtOAc. The combined organic layer was concentrated. The residue was purified on silica eluted with 0 to 6% MeOH in DCM to afford 1-(6-fluoro-2-pyridyl)-6-(5-isopropenyl-3-pyridyl)pyrazolo[4,3-c]pyridine.

To a solution of the aforesaid 1-(6-fluoro-2-pyridyl)-6-(5-isopropenyl-3-pyridyl)pyrazolo[4,3-c]pyridine in Ethanol (50 mL) in a 250 mL round bottom flask was added Pearlman's catalyst (0.3523 mmol; 247.4 mg). The flask was vacuumed and connected with a balloon of Hydrogen. The mixture was stirred at room temperature for 16 hours. The mixture was filtered through Celite. The filtrate was concentrated. The residue was purified on silica eluted with 0 to 5% MeOH in DCM to afford 1-(6-fluoropyridin-2-yl)-6-(5-isopropylpyridin-3-yl)-1H-pyrazolo[4,3-c]pyridine (479.2 mg, 82%).

Step D: tert-butyl N-[(3S)-1-[6-[6-(5-isopropyl-3-pyridyl)pyrazolo[4,3-c]pyridin-1-yl]-2-pyridyl]-3-piperidyl]carbamate

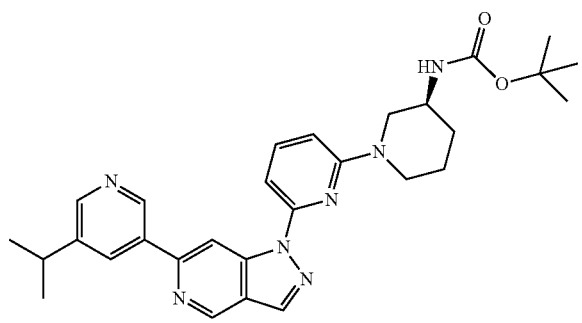 [SMILES: CC(C)c1cncc(-c2cc3c(cn2)cnn3-c2cccc(N3CCC[C@H](NC(=O)OC(C)(C)C)C3)n2)c1]

A mixture of 1-(6-fluoro-2-pyridyl)-6-(5-isopropyl-3-pyridyl)pyrazolo[4,3-c]pyridine (0.3032 mmol; 120.0 mg), tert-butyl N-[(3S)-3-piperidyl]carbamate (0.9095 mmol; 182.2 mg), and N-methylmorpholine (3.032 mmol; 310 mg; 0.337 mL) in 1-Methyl-2-pyrrolidinone (3 mL) in a sealed pressure vial was heated at 120° C. overnight. The mixture was cooled to room temperature, and then partitioned between EtOAc and water. The organic layer was concentrated to afford tert-butyl N-[(3S)-1-[6-[6-(5-isopropyl-3-pyridyl)pyrazolo[4,3-c]pyridin-1-yl]-2-pyridyl]-3-piperidyl]carbamate, which was used without purification.

The aforesaid tert-butyl N-[(3S)-1-[6-[6-(5-isopropyl-3-pyridyl)pyrazolo[4,3-c]pyridin-1-yl]-2-pyridyl]-3-piperidyl]carbamate in DCM (5 mL) and TFA (5 mL) was stirred at room temperature for 1 h. The mixture was concentrated and the residue was purified by reverse phase HPLC to afford 108 (33.9 mg, 37%). $^1$H NMR (400 MHz, DMSO) δ 9.35-9.30 (s, 1H), 9.13-9.10 (d, J=2.0 Hz, 1H), 9.06-9.02 (s, 1H), 8.66-8.61 (s, 1H), 8.58-8.55 (d, J=2.0 Hz, 1H), 8.35-8.31 (d, J=1.9 Hz, 1H), 7.78-7.70 (t, J=8.1 Hz, 1H), 7.23-7.17 (d, J=7.7 Hz, 1H), 6.84-6.78 (d, J=8.5 Hz, 1H), 4.32-4.14 (dd, J=37.4, 11.8 Hz, 2H), 3.12-3.01 (td, J=12.8, 5.7 Hz, 2H), 2.87-2.70 (ddd, J=15.5, 13.1, 7.6 Hz, 2H), 1.96-1.74 (m, 2H), 1.64-1.51 (dd, J=24.5, 11.5 Hz, 2H), 1.33-1.31 (d, J=7.0 Hz, 6H); MS (ESI) m/z: 414.1 [M+H]$^+$

Example 9

5-[1-(6-piperazin-1-yl-2-pyridyl)pyrazolo[4,3-c]pyridin-6-yl]thiazole 109

A solution of 5-[1-(6-fluoro-2-pyridyl)pyrazolo[4,3-c]pyridin-6-yl]thiazole (50 mg, 0.17 mmol) and 1-N-boc-piperazine (175 mg, 0.921 mmol) in dimethyl sulfoxide; 2.0 mL was heated at 95° C. for 8 h. The reaction was quenched with water and extracted with EtOAc. The organic layers was dried with sodium sulfate, filtered, and concentrated in vacuum to give tert-butyl 4-[6-(6-thiazol-5-ylpyrazolo[4,3-c]pyridin-1-yl)-2-pyridyl]piperazine-1-carboxylate:

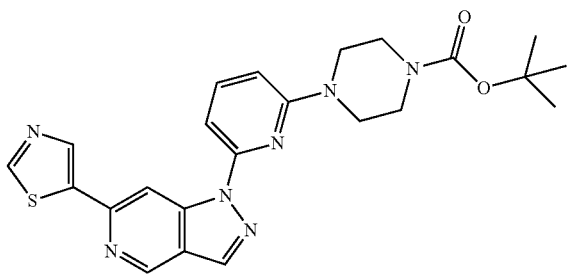 [SMILES: CC(C)(C)OC(=O)N1CCN(c2cccc(-n3ncc4cnc(-c5cncs5)cc43)n2)CC1]

A mixture of tert-butyl 4-[6-(6-thiazol-5-ylpyrazolo[4,3-c]pyridin-1-yl)-2-pyridyl]piperazine-1-carboxylate in hydrogen chloride (4 mol/l) in dioxane (1.5 mL, 6.0 mmol) and dioxane 1.0 mL was stirred at RT 14 h. The reaction was concentrated. The crude product was submitted for reverse phase HPLC to give 109 (44 mg) in 72% yield. MS (ESI) m/z: 364.1. $^1$H NMR (400 MHz, DMSO) δ 9.20 (d, J=8.2 Hz, 2H), 8.94 (s, 1H), 8.64-8.59 (m, 1H), 8.43 (s, 1H), 7.77 (t, J=8.1 Hz, 1H), 7.23 (d, J=7.7 Hz, 1H), 6.81 (d, J=8.4 Hz, 1H), 3.65-3.57 (m, 4H), 2.96-2.88 (m, 4H)

Example 10

(3R)-1-[6-(6-thiazol-5-ylpyrazolo[4,3-c]pyridin-1-yl)-2-pyridyl]piperidin-3-amine 110

Following the procedures in preparation of Example 9, 110 was obtained. MS (ESI) m/z: 378.1. $^1$H NMR (400 MHz, DMSO) δ 9.19 (d, J=13.5 Hz, 2H), 8.96 (s, 1H), 8.60 (d, J=9.0 Hz, 2H), 7.74 (t, J=8.1 Hz, 1H), 7.18 (d, J=7.7 Hz, 1H), 6.81 (d, J=8.5 Hz, 1H), 4.22 (dd, J=10.2, 6.2 Hz, 2H), 3.15-3.04 (m, 1H), 2.91-2.74 (m, 2H), 2.00-1.90 (m, 1H), 1.90-1.80 (m, 1H), 1.79-1.50 (m, 3H), 1.41-1.27 (m, 1H).

Example 11

6-(5-cyclopropylpyridin-3-yl)-1-(6-(piperazin-1-yl)pyridin-2-yl)-1H-pyrazolo[4,3-c]pyridine 111

Following the procedures as described in EXAMPLE 8 and starting with 6-(5-cyclopropylpyridin-3-yl)-1-(6-fluoropyridin-2-yl)-1H-pyrazolo[4,3-c]pyridine and piperazine, 111 was obtained as an off-white solid (41.7 mg, 31%). $^1$H NMR (400 MHz, DMSO) δ 9.33-9.28 (s, 1H), 9.06-8.99 (d, J=2.5 Hz, 2H), 8.66-8.61 (s, 1H), 8.50-8.45 (d, J=2.1 Hz, 1H), 8.09-8.03 (t, J=2.0 Hz, 1H), 7.81-7.73 (t, J=8.1 Hz, 1H), 7.29-7.20 (d, J=7.7 Hz, 1H), 6.85-6.76 (d, J=8.5 Hz, 1H), 3.65-3.56 (m, 4H), 2.94-2.84 (m, 4H), 2.13-2.04 (m, 1H), 1.12-1.04 (m, 2H), 0.88-0.81 (m, 2H); MS (ESI) m/z: 398.2 [M+H]$^+$

Example 12

6-(5-cyclopropylpyridin-3-yl)-1-(6-(piperazin-1-yl)pyridin-2-yl)-1H-pyrazolo[4,3-c]pyridine 112

Following the procedures as described in EXAMPLE 8 and starting with 6-(5-cyclopropylpyridin-3-yl)-1-(6-fluoropyridin-2-yl)-1H-pyrazolo[4,3-c]pyridine and 1,4-diazepane, 112 was obtained as an off-white solid (30.9 mg, 22%). $^1$H NMR (400 MHz, DMSO) δ 9.37-9.25 (s, 1H), 9.04-8.98 (s, 2H), 8.67-8.59 (s, 1H), 8.51-8.45 (d, J=2.1 Hz, 1H), 8.05-7.99 (t, J=2.1 Hz, 1H), 7.74-7.66 (dd, J=14.5, 6.5 Hz, 1H), 7.24-7.15 (t, J=7.4 Hz, 1H), 6.65-6.58 (d, J=8.5 Hz, 1H), 3.90-3.73 (dt, J=10.0, 5.5 Hz, 4H), 3.00-2.91 (m, 2H), 2.75-2.65 (dd, J=13.3, 7.3 Hz, 2H), 2.12-2.04 (m, 1H), 1.91-1.81 (m, 2H), 1.12-1.03 (m, 2H), 0.88-0.81 (m, 2H).; MS (ESI) m/z: 412.2 [M+H]$^+$

Example 13

(S)-1-(6-(3-methylpiperazin-1-yl)pyridin-2-yl)-6-(5-(oxetan-3-yl)pyridin-3-yl)-1H-pyrazolo[4,3-c]pyridine 113

Following the procedures as described in EXAMPLE 8 and starting with 1-(6-fluoropyridin-2-yl)-6-(5-(oxetan-3-yl)pyridin-3-yl)-1H-pyrazolo[4,3-c]pyridine and (S)-2-methylpiperazine, 113 was obtained as an off-white solid (26.3 mg, 24%). $^1$H NMR (400 MHz, DMSO) δ 9.39-9.28 (m, 1H), 9.20-9.11 (d, J=2.1 Hz, 1H), 9.11-9.02 (s, 1H), 8.72-8.61 (m, 2H), 8.60-8.53 (t, J=2.1 Hz, 1H), 7.84-7.67 (t, J=8.1 Hz, 1H), 7.32-7.18 (d, J=7.7 Hz, 1H), 6.87-6.76 (d, J=8.5 Hz, 1H), 5.08-4.98 (dd, J=8.2, 6.2 Hz, 2H), 4.76-4.68 (t, J=6.3 Hz, 2H), 4.48-4.35 (m, 1H), 4.28-4.13 (dd, J=20.9, 11.0 Hz, 2H), 3.06-2.88 (ddd, J=19.7, 14.7, 7.1 Hz, 2H), 2.87-2.73 (m, 2H), 2.60-2.53 (m, 1H), 2.39-2.31 (d, J=7.7 Hz, 1H), 1.09-0.99 (dd, J=14.9, 6.2 Hz, 3H); MS (ESI) m/z: 428.2 [M+H]$^+$

Example 14

6-(5-(oxetan-3-yl)pyridin-3-yl)-1-(6-(piperazin-1-yl)pyridin-2-yl)-1H-pyrazolo[4,3-c]pyridine 114

Following the procedures as described in EXAMPLE 8 and starting with 1-(6-fluoropyridin-2-yl)-6-(5-(oxetan-3-yl)pyridin-3-yl)-1H-pyrazolo[4,3-c]pyridine and piperazine, 114 was obtained as an off-white solid (14.3 mg, 13%). $^1$H NMR (400 MHz, DMSO) δ 9.36-9.31 (s, 1H), 9.20-9.14 (d, J=2.1 Hz, 1H), 9.10-9.05 (s, 1H), 8.70-8.62 (m, 2H), 8.57-8.52 (t, J=2.0 Hz, 1H), 7.81-7.74 (t, J=8.1 Hz, 1H), 7.28-7.22 (d, J=7.7 Hz, 1H), 6.85-6.78 (d, J=8.4 Hz, 1H), 5.08-5.00 (dd, J=8.3, 6.1 Hz, 2H), 4.77-4.70 (t, J=6.3 Hz, 2H), 4.47-4.38 (m, 1H), 3.65-3.56 (m, 4H), 2.99-2.75 (m, 4H).; MS (ESI) m/z: 414.2 [M+H]$^+$

Example 15

1-(6-(6-(5-cyclopropylpyridin-3-yl)-1H-pyrazolo[4,3-c]pyridin-1-yl)pyridin-2-yl)-1,4-diazepan-6-ol 115

Following the procedures as described in EXAMPLE 8 and starting with 6-(5-cyclopropylpyridin-3-yl)-1-(6-fluoropyridin-2-yl)-1H-pyrazolo[4,3-c]pyridine and 1,4-diazepan-6-ol, 115 was obtained as an off-white solid (25.1 mg, 17%). $^1$H NMR (400 MHz, DMSO) δ 9.31-9.27 (s, 1H), 9.07-9.00 (dd, J=16.3, 6.5 Hz, 2H), 8.65-8.59 (d, J=5.6 Hz, 1H), 8.48-8.44 (t, J=2.8 Hz, 1H), 8.09-8.03 (t, J=2.0 Hz, 1H), 7.73-7.67 (t, J=8.1 Hz, 1H), 7.20-7.14 (d, J=7.7 Hz, 1H), 6.73-6.68 (d, J=8.5 Hz, 1H), 4.82-4.73 (s, 1H), 4.03-3.87 (m, 3H), 3.74-3.57 (m, 2H), 3.02-2.93 (t, J=5.4 Hz, 2H), 2.87-2.75 (dd, J=13.8, 3.8 Hz, 1H), 2.70-2.60 (dd, J=13.8, 5.9 Hz, 1H), 2.15-2.03 (m, 1H), 1.10-1.02 (m, 2H), 0.92-0.82 (m, 2H); MS (ESI) m/z: 428.2 [M+H]$^+$

Example 16

1-(6-(6-(5-(oxetan-3-yl)pyridin-3-yl)-1H-pyrazolo[4,3-c]pyridin-1-yl)pyridin-2-yl)-1,4-diazepan-6-ol 116

Following the procedures as described in EXAMPLE 8 and starting with 1-(6-fluoropyridin-2-yl)-6-(5-(oxetan-3-yl)pyridin-3-yl)-1H-pyrazolo[4,3-c]pyridine and 1,4-diazepan-6-ol, 116 was obtained as an off-white solid (7.2 mg, 6%). $^1$H NMR (400 MHz, DMSO) δ 9.35-9.29 (s, 1H), 9.23-9.16 (dd, J=8.9, 2.0 Hz, 1H), 9.11-9.04 (d, J=8.6 Hz, 1H), 8.77-8.62 (m, 2H), 8.55-8.46 (dd, J=15.4, 8.6 Hz, 1H), 7.74-7.67 (t, J=8.1 Hz, 1H), 7.21-7.16 (d, J=7.7 Hz, 1H), 6.77-6.68 (dd, J=8.5, 2.9 Hz, 1H), 5.69-5.45 (d, J=72.4 Hz, 1H), 5.06-5.00 (dd, J=8.1, 6.2 Hz, 1H), 4.81-4.70 (dd, J=13.5, 6.7 Hz, 2H), 4.48-4.40 (m, 1H), 4.06-3.85 (dd, J=32.4, 13.9 Hz, 3H), 3.74-3.53 (m, 2H), 3.00-2.93 (d, J=2.3 Hz, 2H), 2.83-2.77 (dd, J=13.8, 3.8 Hz, 1H), 2.70-2.62 (dd, J=13.2, 6.0 Hz, 1H); MS (ESI) m/z: 444.2 [M+H]$^+$

Example 17

(S)-1-(3-chloro-6-(6-(5-ethylpyridin-3-yl)-1H-pyrazolo[4,3-c]pyridin-1-yl)pyridin-2-yl)piperidin-3-amine 117

Step A: 2-[(6-chloropyrazolo[4,3-c]pyridin-1-yl)methoxy]ethyl-trimethyl-silane

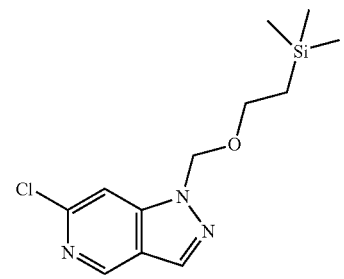 [SMILES: C[Si](C)(C)CCOCn1ncc2cnc(Cl)cc21]

To a mixture of 6-chloro-1H-pyrazolo[4,3-c]pyridine (12.82 mmol; 1968 mg) in Dichloromethane (50 mL) was added N,N-Diisopropylethylamine (38.45 mmol, 6.7 mL). 2-(Trimethylsilyl)ethoxymethyl chloride (19.22 mmol; 3205 mg; 3.40 mL) was then added dropwise at room temperature. The resulting mixture was stirred overnight. The mixture was partitioned between DCM and water. The organic layer was concentrated and the residue was purified on silica eluted with 0 to 6% MeOH in DCM to afford 2-[(6-chloropyrazolo[4,3-c]pyridin-1-yl)methoxy]ethyl-trimethyl-silane (590 mg, 13%).

Step B: trimethyl-[2-[[6-(5-vinyl-3-pyridyl)pyrazolo[4,3-c]pyridin-1-yl]methoxy]ethyl]silane

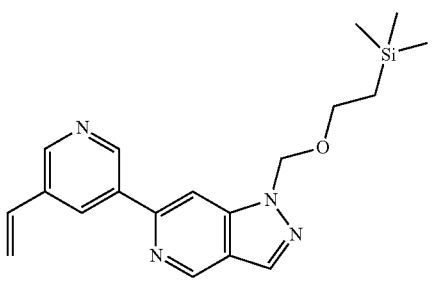 [SMILES: C=Cc1cncc(-c2cc3c(cn2)cnn3COCC[Si](C)(C)C)c1]

A mixture of 2-[(6-chloropyrazolo[4,3-c]pyridin-1-yl)methoxy]ethyl-trimethyl-silane (1.074 mmol; 304.8 mg), 3-(4,4,5,5-tetramethyl-1,3,2-dioxaborolan-2-yl)-5-vinyl-pyridine (1.611 mmol; 372.3 mg), [1,1'-bis(diphenylphosphino)ferrocene]dichloropalladium(II) dichloromethane adduct (0.1074 mmol; 89.5 mg), potassium acetate (1.611 mmol; 1.6 mL) and sodium carbonate (1.611 mmol; 1.6 mL) in Acetonitrile (10 mL) in a pressure tube was heated under microwave at 150° C. for 5 min. The mixture was cooled to room temperature. The layers were separated. The aqueous layer was extracted with EtOAc. The combined organic layer was concentrated. The residue was purified on silica eluted with 0 to 6% MeOH in DCM to afford trimethyl-[2-[[6-(5-vinyl-3-pyridyl)pyrazolo[4,3-c]pyridin-1-yl]methoxy]ethyl]silane (543.4 mg, 86%).

Step C: 6-(5-ethyl-3-pyridyl)-1H-pyrazolo[4,3-c]pyridine

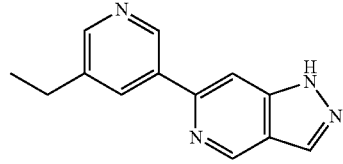 [SMILES: CCc1cncc(-c2cc3[nH]ncc3cn2)c1]

To a solution of trimethyl-[2-[[6-(5-vinyl-3-pyridyl)pyrazolo[4,3-c]pyridin-1-yl]methoxy]ethyl]silane (543.4 mg) in Ethanol (50 mL) in a 250 mL round bottom flask was added Pearlman's catalyst (0.1850 mmol; 129.9 mg). The flask was vacuumed and connected with a balloon of Hydrogen. The mixture was stirred at room temperature overnight. The mixture was filtered through Celite. The filtrate was concentrated. The residue was purified on silica eluted with 0 to 5% MeOH in DCM to afford 2-[[6-(5-ethyl-3-pyridyl)pyrazolo[4,3-c]pyridin-1-yl]methoxy]ethyl-trimethyl-silane (87 mg, 27%).

A solution of 2-[[6-(5-ethyl-3-pyridyl)pyrazolo[4,3-c]pyridin-1-yl]methoxy]ethyl-trimethyl-silane (0.2456 mmol; 106.8 mg) and anisole (1.228 mmol; 133 mg; 0.134 ml) in hydrogen chloride, 4.0 M in 1,4-dioxane (20 mmol; 5 ml) was stirred at room temperature overnight. The mixture was concentrated to afford 6-(5-ethyl-3-pyridyl)-1H-pyrazolo[4,3-c]pyridine (~95.9 mg), which was used without purification.

Step D: 1-(5-chloro-6-fluoro-2-pyridyl)-6-(5-ethyl-3-pyridyl)pyrazolo[4,3-c]pyridine

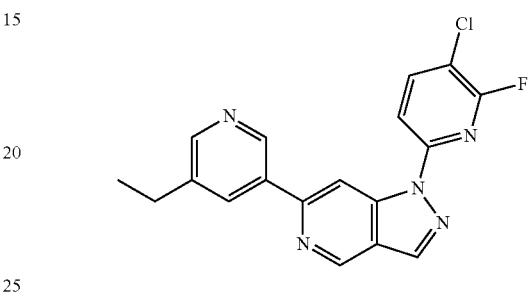

To a solution of the aforesaid 6-(5-ethyl-3-pyridyl)-1H-pyrazolo[4,3-c]pyridine (0.264 mmol; 95.9 mg) and 6-bromo-3-chloro-2-fluoro-pyridine (0.396 mmol; 83.4 mg) in 1,4-Dioxane (10 mL) under Nitrogen was added cesium carbonate (0.528 mmol; 172 mg), Xantphos (0.0449 mmol; 26.0 mg), and Tris(dibenzylideneacetone)dipalladium(0) (0.0264 mmol; 24.2 mg). The resulting mixture was sealed in a pressure tube and heated at 100° C. for 17 hours. The reaction mixture cooled to room temperature, and filtered through Celite. The filter cake was washed with DCM. The filtrate was concentrated. The residue was purified on silica eluted with 0 to 6% MeOH in DCM to afford 1-(5-chloro-6-fluoro-2-pyridyl)-6-(5-ethyl-3-pyridyl)pyrazolo[4,3-c]pyridine (54.9 mg, 59%).

Step E: tert-butyl N-[(3S)-1-[3-chloro-6-[6-(5-ethyl-3-pyridyl)pyrazolo[4,3-c]pyridin-1-yl]-2-pyridyl]-3-piperidyl]carbamate

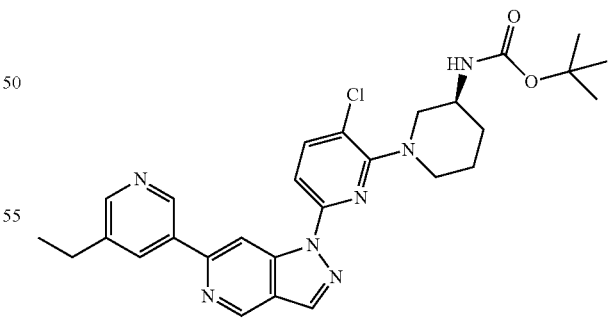

A mixture of 1-(5-chloro-6-fluoro-2-pyridyl)-6-(5-ethyl-3-pyridyl)pyrazolo[4,3-c]pyridine (0.155 mmol; 54.9 mg), tert-butyl N-[(3S)-3-piperidyl]carbamate (0.466 mmol; 93.2 mg), and N-Methylmorpholine (1.55 mmol; 159 mg; 0.172 mL) in 1-Methyl-2-pyrrolidinone (3 mL) in a sealed pressure vial was heated at 100° C. overnight. The mixture was poured into water. The precipitate was collect by filtration and dried on high vacuum to afford tert-butyl N-[(3S)-1-[3-chloro-6-[6-(5-ethyl-3-pyridyl)pyrazolo[4,3-c]pyridin-1-yl]-2-pyridyl]-3-piperidyl]carbamate (66.6 mg, 80%), which was used without further purification.

To a solution of tert-butyl N-[(3S)-1-[3-chloro-6-[6-(5-ethyl-3-pyridyl)pyrazolo[4,3-c]pyridin-1-yl]-2-pyridyl]-3-piperidyl]carbamate (0.0446 mmol; 23.8 mg) in Methanol (10 mL) was added hydrochloric acid, 4.0 M in 1,4-Dioxane (5 mL). The resulting mixture was stirred at room temperature overnight. The mixture was concentrated and the residue was purified by reverse phase HPLC to afford 117 (7.0 mg, 33%). $^1$H NMR (400 MHz, DMSO) δ 9.36-9.31 (s, 1H), 9.18-9.11 (m, 2H), 8.74-8.65 (s, 1H), 8.58-8.52 (d, J=1.9 Hz, 1H), 8.34-8.30 (s, 1H), 8.02-7.97 (d, J=8.4 Hz, 1H), 7.60-7.55 (d, J=8.4 Hz, 1H), 3.95-3.81 (dd, J=27.5, 10.2 Hz, 2H), 3.06-2.97 (t, J=10.2 Hz, 1H), 2.93-2.84 (t, J=9.5 Hz, 1H), 2.81-2.72 (m, 3H), 1.98-1.90 (d, J=12.6 Hz, 1H), 1.89-1.80 (d, J=13.3 Hz, 1H), 1.79-1.68 (d, J=12.9 Hz, 1H), 1.68-1.48 (s, 2H), 1.31-1.26 (t, J=7.6 Hz, 3H), 1.26-1.20 (m, 1H); MS (ESI) m/z: 434.2 [M+H]$^+$ Example 18

1-(6-(1,4-diazepan-1-yl)pyridin-2-yl)-6-(5-(oxetan-3-yl)pyridin-3-yl)-1H-pyrazolo[4,3-c]pyridine 118

Following the procedures as described in EXAMPLE 8 and starting with 1-(6-fluoropyridin-2-yl)-6-(5-(oxetan-3-yl)pyridin-3-yl)-1H-pyrazolo[4,3-c]pyridine and 1,4-diazepane, 118 was obtained as an off-white solid (22.8 mg, 18%). $^1$H NMR (400 MHz, DMSO) δ 9.36-9.33 (s, 1H), 9.18-9.13 (t, J=4.0 Hz, 1H), 9.10-9.05 (s, 1H), 8.68-8.62 (d, J=5.1 Hz, 2H), 8.55-8.50 (s, 1H), 7.74-7.69 (dd, J=13.8, 5.6 Hz, 1H), 7.23-7.18 (d, J=7.7 Hz, 1H), 6.65-6.61 (d, J=8.5 Hz, 1H), 5.07-5.00 (dd, J=8.3, 6.1 Hz, 2H), 4.76-4.69 (t, J=6.3 Hz, 2H), 4.48-4.36 (m, 1H), 3.90-3.83 (t, J=5.8 Hz, 2H), 3.83-3.77 (d, J=5.3 Hz, 2H), 3.01-2.93 (m, 2H), 2.75-2.69 (m, 2H), 1.89-1.83 (m, 2H); MS (ESI) m/z: 428.2 [M+H]$^+$ Example 19

3-methyl-5-[1-(6-piperazin-1-yl-2-pyridyl)pyrazolo[4,3-c]pyridin-6-yl]isothiazole 119

A solution of tert-butyl 4-[6-(6-chloropyrazolo[4,3-c]pyridin-1-yl)-2-pyridyl]piperazine-1-carboxylate (120 mg, 0.290 mmol) and palladium(0)tetrakis(triphenylphosphine) (34 mg, 0.0290 mmol) in N,N-dimethylacetamide 1.0 mL was added tributyl-(3-methylisothiazol-5-yl)stannane (224 mg, 0.579 mmol). The reaction mixture heated at 150° C. for 45 min in a microwave (Biotage Inc.). The reaction mixture was filtered through celite and concentrated. The crude product was diluted with EtOAc then washed with water. The organic layers was dried with sodium sulfate, filtered, and concentrated in vacuum. The crude product was purified by flash chromatography (EtOAc/Heptane eluted at 20% EtOAc) to give tert-butyl 4-[6-[6-(3-methylisothiazol-5-yl)pyrazolo[4,3-c]pyridin-1-yl]-2-pyridyl]piperazine-1-carboxylate (65 mg) 47% yield:

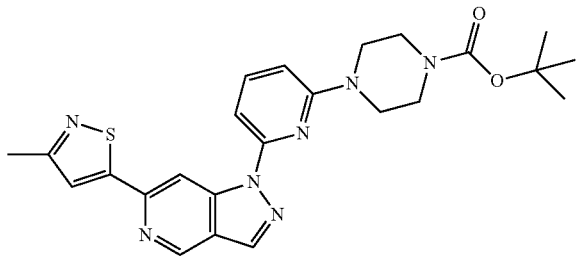 [SMILES: Cc1cc(-c2cc3c(cn2)cnn3-c2cccc(N3CCN(C(=O)OC(C)(C)C)CC3)n2)sn1]

A solution containing tert-butyl 4-[6-[6-(3-methylisothiazol-5-yl)pyrazolo[4,3-c]pyridin-1-yl]-2-pyridyl]piperazine-1-carboxylate (65 mg, 0.136 mmol) in hydrogen chloride (4 mol/l) in 1,4-dioxane (2.0 ml, 8.0 mmol) and 1,4-dioxane; 1.0 mL was stirred at RT for 18 h. The reaction was concentrated under vacuum. The crude product was submitted for reverse phase HPLC to give 118 (13 mg) 25% yield. $^1$H NMR (400 MHz, DMSO) δ 9.22 (s, 1H), 8.96 (s, 1H), 8.64 (s, 1H), 7.78 (t, J=8.1 Hz, 1H), 7.54 (s, 1H), 7.24 (d, J=7.7 Hz, 1H), 6.82 (d, J=8.5 Hz, 1H), 3.65-3.58 (m, 4H), 2.98-2.90 (m, 4H). MS (ESI) m/z: 378.1.

Example 20

5-[1-[6-(1 4-diazepan-1-yl)-2-pyridyl]pyrazolo[4,3-c]pyridin-6-yl]-3-methyl-isothiazole 120

Following the procedures in preparation of EXAMPLE 19, 120 was obtained. MS (ESI) m/z: 392.1. $^1$H NMR (400 MHz, DMSO) δ 9.22 (s, 1H), 8.92 (d, J=6.9 Hz, 1H), 8.64 (s, 1H), 7.74-7.67 (m, 1H), 7.54 (s, 1H), 7.17 (d, J=7.7 Hz, 1H), 6.64 (d, J=8.5 Hz, 1H), 3.86 (t, J=5.9 Hz, 2H), 3.83-3.76 (m, 2H), 3.04-2.97 (m, 2H), 2.73 (t, J=5.8 Hz, 2H), 1.90 (dd, J=11.6, 5.8 Hz, 2H).

Example 21

(S)-1-(6-(6-(5-ethylpyridin-3-yl)-1H-pyrazolo[4,3-c]pyridin-1-yl)pyridin-2-yl)-1,4-diazepan-6-ol 121

Racemic 1-(6-(6-(5-ethylpyridin-3-yl)-1H-pyrazolo[4,3-c]pyridin-1-yl)pyridin-2-yl)-1,4-diazepan-6-ol (30 mg) was purified by chiral HPLC to afford enantiomer 121 as an off-white solid (7.9 mg, 26%). $^1$H NMR (400 MHz, DMSO) δ 9.35-9.28 (s, 1H), 9.16-9.10 (t, J=4.0 Hz, 1H), 9.07-9.04 (s, 1H), 8.67-8.61 (s, 1H), 8.56-8.50 (d, J=1.8 Hz, 1H), 8.33-8.28 (s, 1H), 7.74-7.68 (t, J=8.1 Hz, 1H), 7.21-7.17 (d, J=7.7 Hz, 1H), 6.74-6.69 (t, J=7.5 Hz, 1H), 4.91-4.77 (s, 1H), 4.06-3.86 (m, 3H), 3.75-3.57 (m, 2H), 3.04-2.96 (m, 2H), 2.86-2.63 (m, 4H), 1.31-1.25 (t, J=7.6 Hz, 3H); MS (ESI) m/z: 416.1 [M+H]$^+$ Example 22

(R)-1-(6-(6-(5-ethylpyridin-3-yl)-1H-pyrazolo[4,3-c]pyridin-1-yl)pyridin-2-yl)-1,4-diazepan-6-ol 122

Racemic 1-(6-(6-(5-ethylpyridin-3-yl)-1H-pyrazolo[4,3-c]pyridin-1-yl)pyridin-2-yl)-1,4-diazepan-6-ol (30 mg) was purified by chiral HPLC to afford enantiomer 122 as an off-white solid (7.6 mg, 25%). $^1$H NMR (400 MHz, DMSO) δ 9.34-9.28 (s, 1H), 9.14-9.10 (d, J=1.8 Hz, 1H), 9.07-9.03 (s, 1H), 8.67-8.60 (s, 1H), 8.57-8.49 (d, J=1.8 Hz, 1H), 8.33-8.27 (s, 1H), 7.75-7.68 (t, J=8.1 Hz, 1H), 7.22-7.16 (d, J=7.7 Hz, 1H), 6.74-6.68 (d, J=8.5 Hz, 1H), 4.90-4.74 (s, 1H), 4.08-3.85 (m, 3H), 3.76-3.55 (m, 2H), 3.03-2.95 (t, J=5.4 Hz, 2H), 2.87-2.64 (m, 4H), 1.30-1.26 (t, J=7.6 Hz, 3H); MS (ESI) m/z: 416.1 [M+H]+

Example 23

6-(6-methylpyrazin-2-yl)-1-(6-(piperazin-1-yl)pyridin-2-yl)-1H-pyrazolo[4,3-c]pyridine 123

Step A: Preparation of trimethyl-(6-methylpyrazin-2-yl)stannane

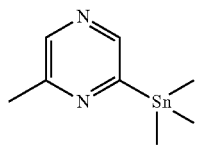

To a solution of 2-bromo-6-methyl-pyrazine (300 mg, 1.7 mmol), hexamethylditin (0.45 mL, 2.1 mmol), and tetrakis(triphenylphosphine) (142 mg, 0.123 mmol) in 1,4-dioxane 8.0 mL was purged with N2 for 5 min. The reaction mixture was stirred at 100° C. for 18 h. The reaction was filtered through celite. The crude product was used in next step. MS (ESI) m/z: 259.1

Step B: tert-butyl 4-[6-[6-(6-methylpyrazin-2-yl)pyrazolo[4,3-c]pyridin-1-yl]-2-pyridyl]piperazine-1-carboxylate

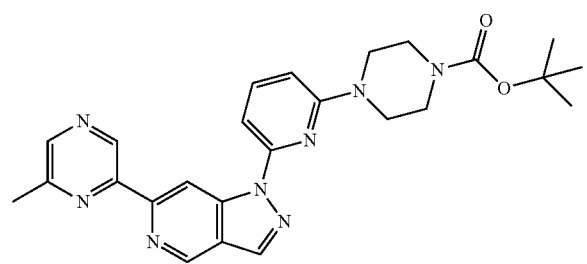 [SMILES: Cc1cncc(-c2cc3c(cn2)cnn3-c2cccc(N3CCN(C(=O)OC(C)(C)C)CC3)n2)n1]

A solution of tert-butyl 4-[6-(6-chloropyrazolo[4,3-c]pyridin-1-yl)-2-pyridyl]piperazine-1-carboxylate (90 mg; 0.22 mmol and palladium(0)tetrakis(triphenylphosphine) (25 mg, 0.022 mmol in N,N-dimethylacetamide; 2.0 mL was added trimethyl-(6-methylpyrazin-2-yl)stannane (112 mg; 0.436 mmol). The reaction mixture was heated at 150° C. for 45 min in a microwave (Biotage). The reaction mixture was filtered through celite and concentrated. The crude product was diluted with EtOAc then washed with water. The organic layers was dried with sodium sulfate, filtered, and concentrated in vacuum. The crude product was purified by flash chromatography (EtOAc/Heptane eluted at 50% EtOAc) to give tert-butyl 4-[6-[6-(6-methylpyrazin-2-yl)pyrazolo[4,3-c]pyridin-1-yl]-2-pyridyl]piperazine-1-carboxylate 60 mg in 58% yield.

A solution of tert-butyl 4-[6-[6-(6-methylpyrazin-2-yl)pyrazolo[4,3-c]pyridin-1-yl]-2-pyridyl]piperazine-1-carboxylate (60 mg, 0.1270 mmol) in 1,4-dioxane; 1.0 mL and hydrogen chloride (4 mol/L) in 1,4-dioxane (2.0 mL, 8.0 mmol) was stirred at RT 18 h. The reaction was concentrated and submitted for reverse phase HPLC to give 123 (26 mg) in 32% yield. MS (ESI) m/z: 373.2. 1H NMR (400 MHz, DMSO) δ 9.59 (s, 1H), 9.46 (s, 1H), 9.31 (s, 1H), 8.66 (s, 1H), 8.62 (s, 1H), 7.77 (t, J=8.1 Hz, 1H), 7.27 (d, J=7.7 Hz, 1H), 6.80 (d, J=8.4 Hz, 1H), 3.67-3.60 (m, 4H), 2.96-2.89 (m, 4H), 2.63 (s, 3H).

Example 24

(3S)-1-[6-[6-(3-methylisothiazol-5-yl)pyrazolo[4,3-c]pyridin-1-yl]-2-pyridyl]piperidin-3-amine 124

Following the procedures in preparation of EXAMPLE 19, 124 was obtained. MS (ESI) m/z: 392.2. 1H NMR (400 MHz, DMSO) δ 9.22 (s, 1H), 9.00 (s, 1H), 8.64 (s, 1H), 7.92 (s, 1H), 7.74 (t, J=8.1 Hz, 1H), 7.21 (d, J=7.7 Hz, 1H), 6.82 (d, J=8.5 Hz, 1H), 4.36 (d, J=8.9 Hz, 1H), 4.13 (d, J=12.8 Hz, 1H), 3.08-2.98 (m, 1H), 2.89-2.77 (m, 2H), 2.48 (s, 3H), 1.97 (d, J=9.9 Hz, 1H), 1.88-1.80 (m, 2H), 1.60 (dd, J=24.6, 11.9 Hz, 1H), 1.42-1.29 (m, 1H).

Example 25

1-(6-(1,4-diazepan-1-yl)pyridin-2-yl)-6-(1-ethyl-1H-pyrazol-4-yl)-1H-pyrazolo[4,3-c]pyridine 125

Following the procedures as described in EXAMPLE 8 and starting with 1-ethyl-4-(4,4,5,5-tetramethyl-1,3,2-dioxaborolan-2-yl)-1H-pyrazole and 1,4-diazepane, 125 was obtained as an off-white solid (21.5 mg, 17%). 1H NMR (400 MHz, DMSO) δ 9.15-9.09 (s, 1H), 8.55-8.48 (s, 1H), 8.29-8.21 (s, 1H), 7.92-7.86 (s, 1H), 7.71-7.65 (t, J=8.0 Hz, 1H), 7.17-7.12 (d, J=7.7 Hz, 1H), 6.62-6.56 (d, J=8.5 Hz, 1H), 4.24-4.19 (d, J=7.3 Hz, 2H), 3.88-3.84 (t, J=6.0 Hz, 2H), 3.82-3.77 (m, 2H), 3.02-2.95 (m, 2H), 2.76-2.69 (m, 2H), 1.90-1.86 (m, 2H), 1.45-1.42 (t, J=7.3 Hz, 3H).; MS (ESI) m/z: 389.2 [M+H]+

Example 26

(S)-6-(1-ethyl-1H-pyrazol-4-yl)-1-(6-(3-methylpiperazin-1-yl)pyridin-2-yl)-1H-pyrazolo[4,3-c]pyridine 126

Following the procedures as described in EXAMPLE 8 and starting with 1-ethyl-4-(4,4,5,5-tetramethyl-1,3,2-dioxaborolan-2-yl)-1H-pyrazole and (S)-2-methylpiperazine, 126 was obtained as an off-white solid (19.7 mg, 16%). 1H NMR (400 MHz, DMSO) δ 9.18-9.09 (s, 1H), 8.72-8.60 (s, 1H), 8.56-8.47 (s, 1H), 8.30-8.25 (s, 1H), 7.96-7.89 (s, 1H), 7.78-7.71 (t, J=8.1 Hz, 1H), 7.24-7.17 (d, J=7.7 Hz, 1H), 6.82-6.75 (d, J=8.4 Hz, 1H), 4.27-4.13 (m, 4H), 3.09-3.01 (d, J=11.4 Hz, 1H), 2.99-2.89 (m, 1H), 2.89-2.76 (m, 2H), 2.63-2.55 (m, 1H), 1.47-1.39 (t, J=7.3 Hz, 3H), 1.13-1.06 (d, J=6.2 Hz, 3H); MS (ESI) m/z: 389.0 [M+H]+

Example 27

(S)-1-(6-(6-(1-ethyl-1H-pyrazol-4-yl)-1H-pyrazolo[4,3-c]pyridin-1-yl)pyridin-2-yl)pyrrolidin-3-ol 127

Following the procedures as described in EXAMPLE 8 and starting with 1-ethyl-4-(4,4,5,5-tetramethyl-1,3,2-dioxaborolan-2-yl)-1H-pyrazole and (S)-pyrrolidin-3-ol, 127 was obtained as an off-white solid (18.6 mg, 14%). 1H NMR (400 MHz, DMSO) δ 9.19-9.05 (s, 1H), 8.92-8.78 (s, 1H), 8.55-8.46 (s, 1H), 8.34-8.20 (d, J=8.3 Hz, 1H), 7.99-7.91 (s, 1H), 7.73-7.64 (t, J=8.0 Hz, 1H), 7.19-7.09 (d, J=7.7 Hz, 1H), 6.42-6.35 (d, J=8.3 Hz, 1H), 5.15-5.01 (d, J=3.7 Hz, 1H), 4.57-4.47 (s, 1H), 4.26-4.16 (q, J=7.3 Hz, 2H), 3.80-3.71 (d, J=6.4 Hz, 1H), 3.72-3.60 (s, 2H), 3.58-3.45 (d, J=10.6 Hz, 1H), 2.20-2.09 (ddd, J=13.1, 8.6, 4.6 Hz, 1H), 2.06-1.97 (d, J=3.3 Hz, 1H), 1.48-1.40 (q, J=7.5 Hz, 3H).; MS (ESI) m/z: 376.2 [M+H]$^+$ Example 28

(R)-1-(6-(6-(1-ethyl-1H-pyrazol-4-yl)-1H-pyrazolo[4,3-c]pyridin-1-yl)pyridin-2-yl)pyrrolidin-3-ol 128

Following the procedures as described in EXAMPLE 8 and starting with 1-ethyl-4-(4,4,5,5-tetramethyl-1,3,2-dioxaborolan-2-yl)-1H-pyrazole and (R)-pyrrolidin-3-ol, 128 was obtained as an off-white solid (18.6 mg, 14%). $^1$H NMR (400 MHz, DMSO) δ 9.19-9.05 (s, 1H), 8.92-8.78 (s, 1H), 8.55-8.46 (s, 1H), 8.34-8.20 (d, J=8.3 Hz, 1H), 7.99-7.91 (s, 1H), 7.73-7.64 (t, J=8.0 Hz, 1H), 7.19-7.09 (d, J=7.7 Hz, 1H), 6.42-6.35 (d, J=8.3 Hz, 1H), 5.15-5.01 (d, J=3.7 Hz, 1H), 4.57-4.47 (s, 1H), 4.26-4.16 (q, J=7.3 Hz, 2H), 3.80-3.71 (d, J=6.4 Hz, 1H), 3.72-3.60 (s, 2H), 3.58-3.45 (d, J=10.6 Hz, 1H), 2.20-2.09 (ddd, J=13.1, 8.6, 4.6 Hz, 1H), 2.06-1.97 (d, J=3.3 Hz, 1H), 1.48-1.40 (q, J=7.5 Hz, 3H).; MS (ESI) m/z: 376.2 [M+H]$^+$ Example 29

1-(6-(6-(1-ethyl-1H-pyrazol-4-yl)-1H-pyrazolo[4,3-c]pyridin-1-yl)pyridin-2-yl)piperidin-4-ol 129

Following the procedures as described in EXAMPLE 8 and starting with 1-ethyl-4-(4,4,5,5-tetramethyl-1,3,2-dioxaborolan-2-yl)-1H-pyrazole and piperidin-4-ol, 129 was obtained as an off-white solid (23.8 mg, 19%). $^1$H NMR (400 MHz, DMSO) δ 9.18-9.07 (s, 1H), 8.70-8.60 (s, 1H), 8.57-8.49 (s, 1H), 8.30-8.22 (s, 1H), 7.94-7.84 (s, 1H), 7.80-7.66 (t, J=8.1 Hz, 1H), 7.26-7.10 (d, J=7.7 Hz, 1H), 6.88-6.73 (d, J=8.4 Hz, 1H), 4.87-4.71 (d, J=4.2 Hz, 1H), 4.26-4.18 (q, J=7.3 Hz, 2H), 4.18-4.08 (dt, J=9.0, 4.3 Hz, 2H), 3.88-3.77 (dt, J=12.7, 4.3 Hz, 1H), 3.40-3.31 (m, 2H), 1.98-1.88 (dd, J=8.7, 4.4 Hz, 2H), 1.59-1.47 (m, 2H), 1.47-1.39 (t, J=7.3 Hz, 3H); MS (ESI) m/z: 390.2 [M+H]$^+$ Example 30

6-(6-methoxypyrazin-2-yl)-1-(6-piperazin-1-yl-2-pyridyl)pyrazolo[4,3-c]pyridine 130

Following the procedures in preparation of EXAMPLE 23, 130 was obtained. MS (ESI) m/z: 389.2. $^1$H NMR (400 MHz, DMSO) δ 9.33 (s, 1H), 9.28 (s, 1H), 9.25 (s, 1H), 8.68 (s, 1H), 8.40 (s, 1H), 7.79 (t, J=8.1 Hz, 1H), 7.26 (d, J=7.7 Hz, 1H), 6.84 (d, J=8.4 Hz, 1H), 4.08 (s, 3H), 3.65-3.58 (m, 5H), 2.90-2.83 (m, 4H).

Example 31

1-(6-(3,3-dimethylpiperazin-1-yl)pyridin-2-yl)-6-(1-ethyl-1H-pyrazol-4-yl)-1H-pyrazolo[4,3-c]pyridine 131

Following the procedures as described in EXAMPLE 8 and starting with 1-ethyl-4-(4,4,5,5-tetramethyl-1,3,2-dioxaborolan-2-yl)-1H-pyrazole and 2,2-dimethylpiperazine, 131 was obtained as an off-white solid (14.2 mg, 11%). $^1$H NMR (400 MHz, DMSO) δ 9.23-9.05 (s, 1H), 8.69-8.58 (s, 1H), 8.57-8.48 (d, J=5.7 Hz, 1H), 8.33-8.20 (s, 1H), 7.98-7.88 (s, 1H), 7.75-7.68 (t, J=8.1 Hz, 1H), 7.21-7.12 (d, J=7.7 Hz, 1H), 6.82-6.75 (d, J=8.5 Hz, 1H), 4.25-4.17 (q, J=7.3 Hz, 2H), 3.64-3.54 (m, 2H), 3.46-3.41 (s, 2H), 3.00-2.88 (m, 2H), 1.47-1.39 (t, J=7.3 Hz, 3H), 1.19-1.06 (s, 6H); MS (ESI) m/z: 403.2 [M+H]$^+$ Example 32

1-(6-(6-(1-ethyl-1H-pyrazol-4-yl)-1H-pyrazolo[4,3-c]pyridin-1-yl)pyridin-2-yl)piperidin-4-amine 132

Following the procedures as described in EXAMPLE 8 and starting with 1-ethyl-4-(4,4,5,5-tetramethyl-1,3,2-dioxaborolan-2-yl)-1H-pyrazole and tert-butyl piperidin-4-ylcarbamate, 132 was obtained as an off-white solid (15.2 mg, 12%) over 2 steps. $^1$H NMR (400 MHz, DMSO) δ 9.18-9.06 (s, 1H), 8.68-8.62 (s, 1H), 8.56-8.48 (d, J=4.4 Hz, 1H), 8.31-8.21 (s, 1H), 7.93-7.85 (s, 1H), 7.77-7.68 (t, J=8.1 Hz, 1H), 7.23-7.14 (d, J=7.7 Hz, 1H), 6.85-6.75 (d, J=8.5 Hz, 1H), 4.36-4.26 (d, J=13.1 Hz, 2H), 4.27-4.16 (q, J=7.3 Hz, 2H), 3.20-3.10 (dd, J=18.0, 6.6 Hz, 2H), 2.96-2.87 (td, J=9.9, 4.9 Hz, 1H), 1.92-1.83 (dd, J=12.7, 2.9 Hz, 2H), 1.47-1.41 (t, J=7.3 Hz, 3H), 1.41-1.30 (m, 2H); MS (ESI) m/z: 389.2 [M+H]$^+$ Example 34

(R)-1-(6-(6-(1-ethyl-1H-pyrazol-4-yl)-1H-pyrazolo[4,3-c]pyridin-1-yl)pyridin-2-yl)piperidin-3-amine 134

Following the procedures as described in EXAMPLE 8 and starting with 1-ethyl-4-(4,4,5,5-tetramethyl-1,3,2-dioxaborolan-2-yl)-1H-pyrazole and (R)-tert-butyl piperidin-3-ylcarbamate, 134 was obtained as an off-white solid (15.3 mg, 12%) over 2 steps. $^1$H NMR (400 MHz, DMSO) δ 9.17-9.08 (s, 1H), 8.72-8.65 (s, 1H), 8.54-8.50 (s, 1H), 8.49-8.43 (s, 1H), 8.09-7.98 (d, J=15.0 Hz, 1H), 7.78-7.65 (t, J=8.1 Hz, 1H), 7.23-7.12 (d, J=7.7 Hz, 1H), 6.83-6.70 (d, J=8.5 Hz, 1H), 4.37-4.29 (d, J=10.4 Hz, 1H), 4.26-4.11 (m, 3H), 3.09-2.99 (m, 1H), 2.89-2.72 (m, 2H), 2.00-1.91 (d, J=9.4 Hz, 1H), 1.90-1.73 (m, 2H), 1.67-1.53 (dd, J=24.3, 12.1 Hz, 1H), 1.46-1.39 (t, J=7.3 Hz, 3H), 1.39-1.28 (ddd, J=15.9, 12.4, 3.7 Hz, 1H); MS (ESI) m/z: 389.2 [M+H]$^+$ Example 35

(S)-1-(6-(6-(1-ethyl-1H-pyrazol-4-yl)-1H-pyrazolo[4,3-c]pyridin-1-yl)pyridin-2-yl)pyrrolidin-3-amine 135

Following the procedures as described in EXAMPLE 8 and starting with 1-ethyl-4-(4,4,5,5-tetramethyl-1,3,2-dioxaborolan-2-yl)-1H-pyrazole and (S)-tert-butyl pyrrolidin- 3-ylcarbamate, 135 was obtained as an off-white solid (11.1 mg, 8.5%) over 2 steps. $^1$H NMR (400 MHz, DMSO) δ 9.14-9.09 (s, 1H), 8.90-8.83 (d, J=16.8 Hz, 1H), 8.57-8.46 (d, J=16.4 Hz, 1H), 8.33-8.23 (d, J=12.5 Hz, 1H), 7.98-7.91 (d, J=8.6 Hz, 1H), 7.71-7.65 (t, J=8.0 Hz, 1H), 7.17-7.10 (d, J=7.7 Hz, 1H), 6.41-6.33 (d, J=8.3 Hz, 1H), 4.26-4.16 (q, J=7.3 Hz, 2H), 3.82-3.65 (m, 3H), 3.65-3.54 (s, 1H), 2.22-2.14 (dt, J=18.7, 6.2 Hz, 1H), 1.90-1.78 (m, 1H), 1.47-1.41 (q, J=7.0 Hz, 3H); MS (ESI) m/z: 375.2 [M+H]$^+$ Example 36

(R)-1-(6-(6-(1-ethyl-1H-pyrazol-4-yl)-1H-pyrazolo[4,3-c]pyridin-1-yl)pyridin-2-yl)pyrrolidin-3-amine 136

Following the procedures as described in EXAMPLE 8 and starting with 1-ethyl-4-(4,4,5,5-tetramethyl-1,3,2-dioxaborolan-2-yl)-1H-pyrazole and (R)-tert-butyl pyrrolidin-3-ylcarbamate, 136 was obtained as an off-white solid (14.5 mg, 12%) over 2 steps. $^1$H NMR (400 MHz, DMSO) δ 9.16-9.08 (s, 1H), 8.90-8.85 (s, 1H), 8.52-8.50 (s, 1H), 8.29-8.25 (s, 1H), 7.99-7.92 (m, 1H), 7.71-7.65 (t, J=8.0 Hz, 1H), 7.16-7.10 (d, J=7.7 Hz, 1H), 6.38-6.33 (d, J=8.3 Hz, 1H), 4.26-4.16 (q, J=7.3 Hz, 2H), 3.83-3.65 (m, 3H), 3.64-3.54 (s, 1H), 2.22-2.12 (dt, J=12.6, 6.3 Hz, 1H), 1.89-1.79 (td, J=12.9, 6.4 Hz, 1H), 1.47-1.41 (t, J=7.3 Hz, 3H); MS (ESI) m/z: 375.2 [M+H]$^+$ Example 37

(3S)-1-[6-[6-(6-methylpyrazin-2-yl)pyrazolo[4,3-c]pyridin-1-yl]-2-pyridyl]piperidin-3-amine 137

Following the procedures in preparation of EXAMPLE 23, 137 was obtained. $^1$H NMR (400 MHz, DMSO) δ 9.59 (s, 1H), 9.46 (s, 1H), 9.32 (s, 1H), 8.66 (s, 1H), 8.62 (s, 1H), 7.75 (t, J=8.1 Hz, 1H), 7.21 (d, J=7.7 Hz, 1H), 6.81 (d, J=8.5 Hz, 1H), 4.40 (d, J=13.0 Hz, 1H), 4.15 (d, J=11.2 Hz, 1H), 3.17-3.07 (m, 1H), 2.89-2.75 (m, 2H), 2.64 (s, 3H), 1.98-1.81 (m, 2H), 1.69-1.57 (m, 1H), 1.40-1.27 (m, 1H). MS (ESI) m/z: 387.2.

Example 38

1-[6-(1 4-diazepan-1-yl)-2-pyridyl]-6-(6-methylpyrazin-2-yl)pyrazolo[4,3-c]pyridine 138

Following the procedures in preparation of EXAMPLE 23, 138 was obtained. MS (ESI) m/z: 387.2. $^1$H NMR (400 MHz, DMSO) δ 9.64 (s, 1H), 9.46 (s, 1H), 9.32 (s, 1H), 8.66 (s, 1H), 8.62 (s, 1H), 7.71 (t, J=8.1 Hz, 1H), 7.21 (t, J=6.8 Hz, 1H), 6.63 (d, J=8.4 Hz, 1H), 3.89 (dd, J=15.6, 9.7 Hz, 4H), 3.08-3.00 (m, 2H), 2.78-2.70 (m, 2H), 2.61 (s, 3H), 1.93 (dd, J=11.5, 6.0 Hz, 2H).

Example 39

(S)-1-(3-cyclopropyl-6-(6-(5-ethylpyridin-3-yl)-1H-pyrazolo[4,3-c]pyridin-1-yl)pyridin-2-yl)piperidin-3-amine 139

Step A: tert-butyl N-[(3S)-1-[3-cyclopropyl-6-[6-(5-ethyl-3-pyridyl)pyrazolo[4,3-c]pyridin-1-yl]-2-pyridyl]-3-piperidyl]carbamate

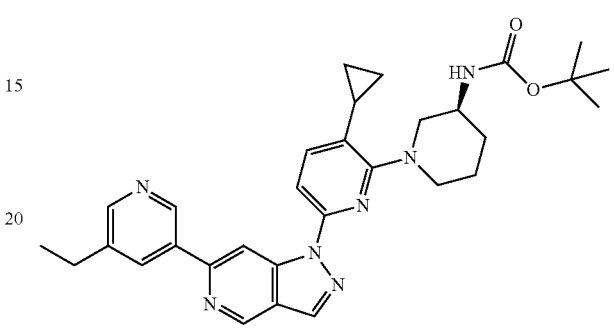

A mixture of tert-butyl N-[(3S)-1-[3-chloro-6-[6-(5-ethyl-3-pyridyl)pyrazolo[4,3-c]pyridin-1-yl]-2-pyridyl]-3-piperidyl]carbamate (0.0801 mmol; 42.8 mg), potassium cyclopropyl trifluoroborate (0.120 mmol; 18.3 mg), butyldi-1-adamantylphosphine (0.0240 mmol; 9.07 mg), cesium carbonate (0.240 mmol; 78.3 mg) and palladium (II) acetate (0.0160 mmol; 3.60 mg) in Water (0.5 mL) and Toluene (4.5 mL) was purged with Argon for 1 minute. The reaction mixture in a pressure tube was stirred at 105° C. for 3 days. The layers were separated. The organic later was concentrated. The residue was purified on silica eluted with 0 to 5% MeOH in DCM to afford tert-butyl N-[(3S)-1-[3-cyclopropyl-6-[6-(5-ethyl-3-pyridyl)pyrazolo[4,3-c]pyridin-1-yl]-2-pyridyl]-3-piperidyl]carbamate (32.2 mg, 74%).

Step B

To a solution of tert-butyl N-[(3S)-1-[3-cyclopropyl-6-[6-(5-ethyl-3-pyridyl)pyrazolo[4,3-c]pyridin-1-yl]-2-pyridyl]-3-piperidyl]carbamate (0.0597 mmol; 32.2 mg) in Methanol (10 mL) was added hydrochloric acid, 4.0 M in 1,4-Dioxane (5 mL). The resulting mixture was stirred at room temperature overnight. The mixture was concentrated and the residue was purified by reverse phase HPLC to afford 139 as an off-white solid (20 .mg, 7.4%). MS (ESI) m/z: 440.3 [M+H]$^+$ Example 40

1-(6-(6-(1-ethyl-1H-pyrazol-4-yl)-1H-pyrazolo[4,3-c]pyridin-1-yl)pyridin-2-yl)azepan-4-amine 140

Following the procedures as described in EXAMPLE 8 and starting with 1-ethyl-4-(4,4,5,5-tetramethyl-1,3,2-dioxaborolan-2-yl)-1H-pyrazole and tert-butyl azepan-4-ylcarbamate, 140 was obtained as an off-white solid (16.2 mg, 12%) over 2 steps. $^1$H NMR (400 MHz, DMSO) δ 9.15-9.11 (s, 1H), 8.70-8.65 (d, J=9.8 Hz, 1H), 8.54-8.47 (d, J=8.1 Hz, 1H), 8.28-8.25 (d, J=7.4 Hz, 1H), 7.95-7.87 (s, 1H), 7.73-7.66 (dd, J=10.5, 5.7 Hz, 1H), 7.18-7.12 (d, J=7.7 Hz, 1H), 6.60-6.54 (t, J=6.6 Hz, 1H), 4.25-4.18 (q, J=7.3 Hz, 2H), 3.95-3.86 (s, 1H), 3.85-3.77 (m, 1H), 3.75-3.58 (ddd, J=20.2, 14.0, 9.4 Hz, 2H), 2.94-2.85 (dd, J=12.2, 6.3 Hz, 1H), 2.07-1.96 (m, 2H), 1.83-1.74 (m, 1H), 1.74-1.66 (d, J=14.4 Hz, 1H), 1.65-1.56 (ddd, J=13.0, 9.1, 4.5 Hz, 1H), 1.46-1.41 (t, J=7.3 Hz, 3H), 1.42-1.34 (dd, J=14.2, 4.0 Hz, 1H); MS (ESI) m/z: 403.2 [M+H]⁺

Example 41

1-(6-(1,4-diazepan-1-yl)pyridin-2-yl)-6-(5-methyl-pyridin-3-yl)-1H-pyrazolo[4,3-c]pyridine 141

Following the procedures as described in EXAMPLE 8 and starting with (5-methylpyridin-3-yl)boronic acid and 1,4-diazepane, 141 was obtained as an off-white solid (23.3 mg, 22%) over 2 steps. ¹H NMR (400 MHz, DMSO) δ 9.33-9.29 (s, 1H), 9.08-8.99 (m, 2H), 8.64-8.61 (s, 1H), 8.53-8.48 (d, J=1.5 Hz, 1H), 8.24-8.21 (s, 1H), 7.74-7.67 (t, J=8.1 Hz, 1H), 7.21-7.16 (d, J=7.7 Hz, 1H), 6.65-6.59 (d, J=8.5 Hz, 1H), 3.88-3.83 (t, J=6.0 Hz, 2H), 3.82-3.74 (m, 2H), 3.02-2.95 (m, 2H), 2.75-2.69 (m, 2H), 2.45-2.40 (s, 3H), 1.92-1.83 (m, 2H); MS (ESI) m/z: 386.2 [M+H]⁺

Example 42

(R)-6-(1-ethyl-1H-pyrazol-4-yl)-1-(6-(3-ethylpiperazin-1-yl)pyridin-2-yl)-1H-pyrazolo[4,3-c]pyridine 142

Following the procedures as described in EXAMPLE 8 and starting with 1-ethyl-4-(4,4,5,5-tetramethyl-1,3,2-dioxaborolan-2-yl)-1H-pyrazole and (R)-tert-butyl 2-ethylpiperazine-1-carboxylate, 142 was obtained as an off-white solid (12.7 mg, 10%) over 2 steps. ¹H NMR (400 MHz, DMSO) δ 9.18-9.06 (s, 1H), 8.67-8.59 (s, 1H), 8.56-8.49 (s, 1H), 8.31-8.25 (s, 1H), 7.95-7.90 (s, 1H), 7.78-7.70 (t, J=8.1 Hz, 1H), 7.23-7.15 (d, J=7.7 Hz, 1H), 6.84-6.76 (d, J=8.5 Hz, 1H), 4.27-4.15 (m, 4H), 3.10-3.03 (d, J=11.7 Hz, 1H), 3.01-2.93 (td, J=11.8, 3.0 Hz, 1H), 2.86-2.77 (td, J=11.6, 3.0 Hz, 1H), 2.68-2.56 (m, 2H), 1.48-1.38 (m, 5H), 0.94-0.87 (t, J=7.5 Hz, 3H); MS (ESI) m/z: 403.2 [M+H]⁺

Example 43

N-(6-(6-(1-ethyl-1H-pyrazol-4-yl)-1H-pyrazolo[4,3-c]pyridin-1-yl)pyridin-2-yl)azepan-3-amine 143

Following the procedures as described in EXAMPLE 8 and starting with 1-ethyl-4-(4,4,5,5-tetramethyl-1,3,2-dioxaborolan-2-yl)-1H-pyrazole and tert-butyl 3-aminoazepane-1-carboxylate, 143 was obtained as an off-white solid (3.6 mg, 2.8%) over 2 steps. MS (ESI) m/z: 403.2 [M+H]⁺

Example 44

1-(6-piperazin-1-yl-2-pyridyl)-6-pyrazin-2-yl-pyrazolo[4,3-c]pyridine 144

A solution of tert-butyl 4-[6-(6-chloropyrazolo[4,3-c]pyridin-1-yl)-2-pyridyl]piperazine-1-carboxylate (40 mg, 0.096 mmol) and palladium(0)tetrakis(triphenylphosphine) (11 mg, 0.0095 mmol) in N,N-dimethylacetamide 1 mL was added (2-pyrazinyl)tributyltin (0.064 mL, 0.19 mmol). The reaction mixture heated at 150° C. for 45 min in biotage microwave. The reaction mixture was filtered through celite and concentrated. The crude product was diluted with EtOAc then washed with water. The organic layers was dried with sodium sulfate, filtered, and concentrated in vacuum. The crude product was purified by flash chromatography (EtOAc/Heptane eluted at 20% EtOAc) to give tert-butyl 4-[6-(6-pyrazin-2-ylpyrazolo[4,3-c]pyridin-1-yl)-2-pyridyl]piperazine-1-carboxylate 30 mg 67% yield.

To a solution of tert-butyl 4-[6-(6-pyrazin-2-ylpyrazolo[4,3-c]pyridin-1-yl)-2-pyridyl]piperazine-1-carboxylate (30 mg, 0.065 mmol) in hydrogen chloride (4 mol/l) in 1,4-dioxane (1.5 ml, 6.0 mmol) and 1,4-dioxane; 1.5 mL was stirred at RT 18 h. The reaction was concentrated and submitted for reverse phase HPLC to give 144 (12 mg) in 34% yield. MS (ESI) m/z: 359.1. ¹H NMR (400 MHz, DMSO) δ 9.70 (s, 1H), 9.65 (d, J=1.1 Hz, 1H), 9.34 (s, 1H), 8.78-8.74 (m, 1H), 8.72 (d, J=2.4 Hz, 1H), 8.68 (d, J=5.3 Hz, 1H), 7.77 (t, J=8.1 Hz, 1H), 7.25 (d, J=7.7 Hz, 1H), 6.79 (d, J=8.4 Hz, 1H), 3.67-3.61 (m, 4H), 2.97-2.90 (m, 4H).

Example 45

1-(6-(1,4-Diazepan-1-yl)pyridin-2-yl)-6-(1-tert-butyl-1H-pyrazol-4-yl)-1H-pyrazolo[4,3-c]pyridine 145

Step A: tert-Butyl 4-(6-Bromopyridin-2-yl)-1,4-diazepane-1-carboxylate

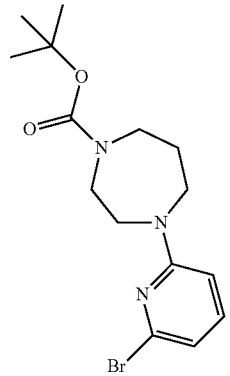 [SMILES: CC(C)(C)OC(=O)N1CCCN(c2cccc(Br)n2)CC1]

A mixture of 2-bromo-6-fluoropyridine (500 mg, 2.8 mmol), tert-butyl 1,4-diazepane-1-carboxylate (568 mg, 2.8 mmol) in DIPEA (1.83 g, 14.2 mmol) in ethanol (10 mL) was heated at 100° C. for 16 hours. The reaction mixture was concentrated under reduced pressure and the residue was diluted with EtOAc (100 mL). The solution was washed with brine, dried over Na₂SO₄, and concentrated under reduced pressure to afford tert-butyl 4-(6-bromopyridin-2-yl)-1,4-diazepane-1-carboxylate as a colorless oil (500 mg, 50%). MS (ESI) m/z: 356 [M+H]⁺.

Step B: tert-Butyl 4-(6-(6-Chloro-1H-pyrazolo[4,3-c]pyridin-1-yl)pyridin-2-yl)-1,4-diazepane-1-carboxylate

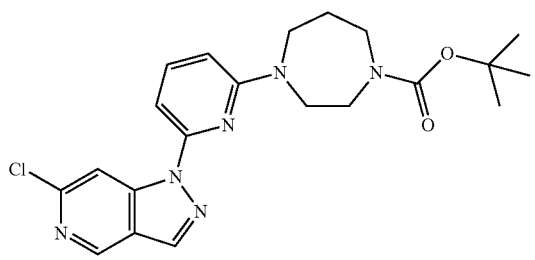 [SMILES: CC(C)(C)OC(=O)N1CCCN(c2cccc(-n3ncc4cnc(Cl)cc43)n2)CC1]

To a mixture of tert-butyl 4-(6-bromopyridin-2-yl)-1,4-diazepane-1-carboxylate (2.55 g, 7.16 mmol) and 6-chloro-1H-pyrazolo[4,3-c]pyridine (1.0 g, 6.51 mmol) in 1,4-dioxane (20 mL) was added CuI (494 mg, 2.6 mmol), $K_2CO_3$ (3.6 g, 26 mmol), and $N^1,N^2$-dimethylethane-1,2-diamine (460 mg, 5.2 mmol). The mixture was heated at 100° C. for 3 hours, which was monitored by LCMS. After completion of the reaction, it was concentrated under reduced pressure. The crude was purified by silica gel chromatography using petroleum ether/EtOAc (2/1) as eluting solvents to afford tert-butyl 4-(6-(6-chloro-1H-pyrazolo[4,3-c]pyridin-1-yl)pyridin-2-yl)-1,4-diazepane-1-carboxylate as a yellow solid (1.6 g, 57%). MS (ESI) m/z: 429 [M+H]$^+$.

Step C: 1-tert-Butyl-1H-pyrazole

A mixture of 1,1,3,3-tetramethoxypropane (3.7 g, 22.6 mmol), tert-butylhydrazine hydrochloride (2.8 g, 22.6 mmol), and conc. HCl (6 mL, 72 mmol) in EtOH (30 mL) was heated at reflux overnight. The reaction mixture was poured into water and the resulting mixture was extracted with ether (30 mL×3). The combined organics was washed with brine (20 mL), dried over $MgSO_4$, and concentrated under reduced pressure to afford 1-tert-butyl-1H-pyrazole as a white solid (2.5 g, 89%). MS (ESI) m/z: 125 [M+H]$^+$.

Step D: 4-Bromo-1-tert-butyl-1H-pyrazole

To a suspension of $Na_2CO_3$ (3.6 g, 33.9 mmol) in $CH_2Cl_2$ (30 mL) was added 1-tert-butyl-1H-pyrazole (2.1 g, 17 mmol) and $Br_2$ (0.9 mL). The mixture was stirred at room temperature overnight. The formed solid was removed by filtration and the filter cake was washed with $CH_2Cl_2$ (30 mL). The filtrates were washed with water (20 mL) and brine (20 mL), dried ($MgSO_4$), and concentrated under reduced pressure to afford crude 4-bromo-1-tert-butyl-1H-pyrazole (2.9 g, 85%), which was used in next step without further purification. MS (ESI) m/z: 203 [M+H]$^+$.

Step E: 1-tert-Butyl-4-(4,4,5,5-tetramethyl-1,3,2-dioxaborolan-2-yl)-1H-pyrazole A mixture of 4-bromo-1-tert-butyl-1H-pyrazole (3.3 g, 16.3 mmol), bis(pinacolato)diboron (8.3 g, 32.6 mmol), $PdCl_2$(dppf) (1.8 g, 2.4 mmol), and KOAc (3.2 g, 32.6 mmol) in 1,4-dioxane (60 mL) was heated at reflux for 15 hours. After the completion of the reaction, the mixture was filtered and the filter cake was washed with EtOAc (100 mL). The filtrate was concentrated under reduced pressure. The residue was purified by silica gel chromatography using heptane/ethyl acetate (10% to 50%) as eluting solvents to afford 1-tert-butyl-4-(4,4,5,5-tetramethyl-1,3,2-dioxaborolan-2-yl)-1H-pyrazole as white solid (1.0 g, 25%). MS (ESI) m/z: 251 [M+H]$^+$.

Step F: tert-Butyl 4-(6-(6-(1-tert-Butyl-1H-pyrazol-4-yl)-1H-pyrazolo[4,3-c]pyridin-1-yl)pyridin-2-yl)-1,4-diazepane-1-carboxylate

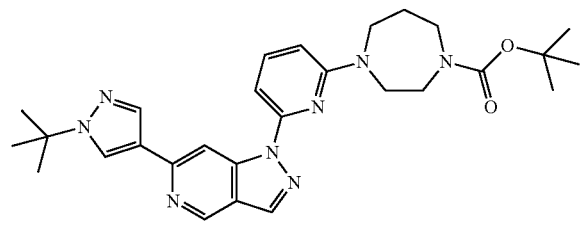 [SMILES: CC(C)(C)OC(=O)N1CCCN(c2cccc(-n3ncc4cnc(-c5cnn(C(C)(C)C)c5)cc43)n2)CC1]

A mixture of 1-tert-butyl-4-(4,4,5,5-tetramethyl-1,3,2-dioxaborolan-2-yl)-1H-pyrazole (220 mg, 0.88 mmol), tert-butyl 4-(6-(6-chloro-1H-pyrazolo[4,3-c]pyridin-1-yl)pyridin-2-yl)-1,4-diazepane-1-carboxylate (377 mg, 0.88 mmol), and Pd(dppf)$Cl_2$ (64 mg, 0.088 mmol) in 1,4-dioxane (20 mL) and $Na_2CO_3$ (2.0 M, 5 mL) under nitrogen was heated at 100° C. for 20 hours. The crude product was purified by silica gel chromatography using petroleum ether: EtOAc (50%-100%) as eluting solvents to afford tert-butyl 4-(6-(6-(1-tert-butyl-1H-pyrazol-4-yl)-1H-pyrazolo[4,3-c]pyridin-1-yl)pyridin-2-yl)-1,4-diazepane-1-carboxylate as a yellow solid (240 mg, 53%). MS (ESI) m/z: 517 [M+H]$^+$.

Step G

A solution of tert-butyl 4-(6-(6-(1-tert-butyl-1H-pyrazol-4-yl)-1H-pyrazolo[4,3-c]pyridin-1-yl)pyridin-2-yl)-1,4-diazepane-1-carboxylate (100 mg, 0.19 mmol) and TFA (2 mL) in DCM (4 mL) was stirred at room temperature for 4 hours. The reaction mixture was concentrated under reduced pressure to afford a residue. The residue was diluted with MeOH (10 mL), neutralized with 28% ammonia solution, concentrated, and purified by preparative HPLC to afford 145 as a white solid (45 mg, 56%). $^1$H-NMR (500 MHz, CD$_3$OD) δ (ppm) 9.03 (s, 1H), 8.71 (d, J=6.5 Hz, 1H), 8.36 (s, 1H), 8.28 (s, 1H), 7.98 (s, 1H), 7.65-7.68 (m, 1H), 7.25 (d, J=7.5 Hz, 1H), 6.58 (d, J=8.5 Hz, 1H), 3.90-3.94 (m, 4H), 3.14-3.16 (m, 2H), 2.91-2.94 (m, 2H), 2.05-2.10 (m, 2H), 1.68 (s, 9H); MS (ESI) m/z: 417 [M+H]$^+$.

Example 46

1-(6-(1,4-Diazepan-1-yl)pyridin-2-yl)-6-(1-isopropyl-1H-pyrazol-4-yl)-1H-pyrazolo[4,3-c]pyridine 146

Following the procedures as described in Example 61 and starting with tert-butyl 4-(6-(6-(1H-pyrazol-4-yl)-1H-pyrazolo[4,3-c]pyridin-1-yl)pyridin-2-yl)-1,4-diazepane-1-carboxylate and 2-bromopropane, 146 was obtained as a yellow solid (90 mg, 75%) over two steps. $^1$H-NMR (500 MHz, CD$_3$OD) δ (ppm) 8.93 (s, 1H), 8.54 (s, 1H), 8.25 (s, 1H), 8.10 (s, 1H), 7.86 (s, 1H), 7.55-7.59 (m, 1H), 7.15 (d, J=7.5 Hz, 1H), 6.47 (d, J=8.0 Hz, 1H), 4.56-4.63 (m, 1H), 3.78-3.82 (m, 4H), 3.06-3.08 (m, 2H), 2.85-2.87 (m, 2H), 1.98-2.02 (m, 2H), 1.57 (d, J=6.5 Hz, 6H); MS (ESI) m/z: 403 [M+H]⁺.

Example 47

1-(6-(1,4-Diazepan-1-yl)pyridin-2-yl)-6-(1-cyclobutyl-1H-pyrazol-4-yl)-1H-pyrazolo[4,3-c]pyridine 147

Following the procedures as described in Example 61 and starting with tert-butyl 4-(6-(6-(1H-pyrazol-4-yl)-1H-pyrazolo[4,3-c]pyridin-1-yl)pyridin-2-yl)-1,4-diazepane-1-carboxylate and bromocyclobutane, 147 was obtained as a yellow solid (40 mg, 35%) over two steps. ¹H-NMR (500 MHz, CD₃OD) δ (ppm): 9.02 (s, 1H), 8.66 (s, 1H), 8.34 (s, 1H), 8.18 (s, 1H), 7.95 (s, 1H), 7.66-7.69 (m, 1H), 7.25 (d, J=7.5 Hz, 1H), 6.59 (d, J=8.5 Hz, 1H), 4.91-4.96 (m, 1H), 3.90-3.95 (m, 4H), 3.20-3.22 (m, 2H), 3.00-3.02 (m, 2H), 2.52-2.63 (m, 4H), 2.08-2.13 (m, 2H), 1.92-1.99 (m, 2H); MS (ESI) m/z: 415 [M+H]⁺.

Example 48

5-(1-(6-(1,4-diazepan-1-yl)pyridin-2-yl)-1H-pyrazolo[4,3-c]pyridin-6-yl)-2-methylpyridazin-3(2H)-one 148

A solution of 4-chloro-1H-pyridazin-6-one (6.000 mmol; 783.2 mg), Iodomethane (7.200 mmol; 1032 mg; 0.453 mL), and potassium carbonate (9.000 mmol; 1256 mg) in DMF (12 mL) was stirred at room temperature overnight. The mixture was filtered. The filtrate was partitioned between EtOAc and water. The organic layer was concentrated. The residue was purified on silica eluted with 0 to 40% EtOAc in DCM to afford 5-chloro-2-methyl-pyridazin-3-one as an off-white solid (514.7, 59%).

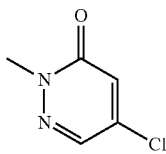

To a mixture of 5-chloro-2-methyl-pyridazin-3-one (3.560 mmol; 514.7 mg), bis(pinacolato)diboron (5.687 mmol; 1459 mg) and potassium acetate (7.121 mmol; 720.5 mg) in 1,4-Dioxane (12 mL) in a pressure tube under Nitrogen was added X-PHOS (0.4273 mmol; 142.3 mg) and tris(dibenzylideneacetone)dipalladium(0); (0.1780 mmol; 163.0 mg). The tube was sealed and heated at 90° C. for 2 h. The reaction mixture was filtered hot through Celite. The filter cake was washed with EtOAc. The filtrated washed with water, and brine. The organic layer was dried with MgSO4, and then concentrated to afford 2-methyl-5-(4,4,5,5-tetramethyl-1,3,2-dioxaborolan-2-yl)pyridazin-3-one, which was used without further purification.

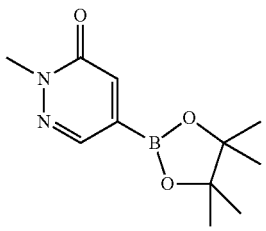

A mixture of 6-chloro-1-[6-(1,4-diazepan-1-yl)-2-pyridyl]pyrazolo[4,3-c]pyridine (0.3190 mmol; 104.9 mg), 2-methyl-5-(4,4,5,5-tetramethyl-1,3,2-dioxaborolan-2-yl)pyridazin-3-one (0.4786 mmol; 113.0 mg), [1,1'-bis(diphenylphosphino)ferrocene]dichloropalladium(II) dichloromethane adduct (0.03190 mmol; 26.6 mg), potassium acetate (0.4786 mmol; 0.48 mL) and sodium carbonate (0.4786 mmol; 0.48 mL) in Acetonitrile (10 mL) in a pressure tube was heated under microwave at 150° C. for 15 min. The mixture was filtered through Celite. The filtrated was concentrated. The residue was purified on silica eluted with 10% MeOH in DCM with 1% NH4OH. The product obtained (29 mg, purity>90%) was further purified by reverse phase HPLC to afford 148 as an off-white solid (10.9 mg, 8.5%). ¹H NMR (400 MHz, DMSO) δ 9.39-9.31 (s, 1H), 9.08-9.01 (s, 1H), 8.72-8.65 (s, 1H), 8.56-8.51 (d, J=2.1 Hz, 1H), 8.31-8.22 (s, 1H), 7.76-7.69 (t, J=8.1 Hz, 1H), 7.42-7.38 (d, J=2.1 Hz, 1H), 7.22-7.18 (d, J=7.7 Hz, 1H), 6.69-6.62 (d, J=8.5 Hz, 1H), 3.87-3.79 (m, 4H), 3.74-3.72 (s, 3H), 3.05-3.00 (m, 2H), 2.83-2.77 (m, 2H), 1.94-1.87 (m, 2H); MS (ESI) m/z: 403.2 [M+H]⁺.

Example 49

6-(6-ethylpyrazin-2-yl)-1-(6-piperazin-1-yl-2-pyridyl)pyrazolo[4,3-c]pyridine 149

Following the procedures in preparation of EXAMPLE 23, 149 was obtained. MS (ESI) m/z: 387.2. ¹H NMR (400 MHz, DMSO) δ 9.55 (s, 1H), 9.50 (s, 1H), 9.33 (s, 1H), 8.66 (d, J=3.9 Hz, 2H), 7.77 (t, J=8.1 Hz, 1H), 7.27 (d, J=7.7 Hz, 1H), 6.81 (d, J=8.5 Hz, 1H), 3.67-3.58 (m, 4H), 2.91 (dd, J=8.9, 4.5 Hz, 6H), 1.36 (t, J=7.6 Hz, 3H).

Example 50

1-[6-(1 4-diazepan-1-yl)-2-pyridyl]-6-(6-ethylpyrazin-2-yl)pyrazolo[4 3-c]pyridine 150

Following the procedures in preparation of EXAMPLE 23, 150 was obtained. MS (ESI) m/z: 401.2. ¹H NMR (400 MHz, DMSO) δ 9.60 (d, J=6.4 Hz, 1H), 9.49 (s, 1H), 9.32 (s, 1H), 8.66 (d, J=2.8 Hz, 2H), 7.72 (dd, J=14.7, 6.6 Hz, 1H), 7.20 (d, J=7.7 Hz, 1H), 6.62 (d, J=8.5 Hz, 1H), 3.91 (t, J=6.0 Hz, 2H), 3.85-3.78 (m, 2H), 3.01-2.94 (m, 2H), 2.90 (q, J=7.6 Hz, 3H), 2.72-2.64 (m, 3H), 1.94-1.84 (m, 2H), 1.35 (t, J=7.6 Hz, 3H).

Example 51

3-ethyl-5-[1-(6-piperazin-1-yl-2-pyridyl)pyrazolo[4,3-c]pyridin-6-yl]pyrimidin-4-one 151

Following the procedures in preparation of EXAMPLE 23, 151 was obtained. MS (ESI) m/z: 403.2. ¹H NMR (400 MHz, DMSO) δ 9.80 (s, 1H), 9.23 (s, 1H), 9.02 (s, 1H), 8.65

(s, 1H), 8.59 (s, 1H), 7.74 (t, J=8.1 Hz, 1H), 7.25 (d, J=7.7 Hz, 1H), 6.74 (d, J=8.4 Hz, 1H), 4.08 (q, J=7.1 Hz, 2H), 3.65-3.57 (m, 4H), 2.96-2.83 (m, 4H), 1.36 (t, J=7.1 Hz, 3H).

Example 52

2-(4-(1-(6-(1,4-Diazepan-1-yl)pyridin-2-yl)-1H-pyrazolo[4,3-c]pyridin-6-yl)-1H-pyrazol-1-yl)ethanol 152

Following the procedures as described in Example 61 and starting with tert-butyl 4-(6-(6-(1H-pyrazol-4-yl)-1H-pyrazolo[4,3-c]pyridin-1-yl)pyridin-2-yl)-1,4-diazepane-1-carboxylate and oxirane, 152 was obtained as a light yellow solid (102 mg, 71%) over two steps. $^1$H NMR (500 MHz, CDCl$_3$) δ (ppm) 8.941-8.942 (d, J=0.5 Hz, 1H), 8.57 (s, 1H), 8.17 (s, 1H), 8.07 (s, 1H), 7.86 (s, 1H), 7.57-7.60 (t, J=16 Hz, 1H), 7.22-7.26 (t, J=20.5 Hz, 1H), 6.36-6.37 (d, J=8 Hz, 1H), 4.30-4.32 (t, J=9.5 Hz, 2H), 4.05-4.07 (t, J=9.5 Hz, 2H), 3.77-3.82 (m, 4H), 3.11-3.13 (t, J=10.5 Hz, 2H), 2.88-2.91 (t, J=11.5 Hz, 2H), 2.26 (s, 2H), 1.97-2.01 (m, 2H); MS (ESI) m/z: 405 [M+H]$^+$.

Example 53

1-(6-(1,4-Diazepan-1-yl)pyridin-2-yl)-6-(1-(2-fluoroethyl)-1H-pyrazol-4-yl)-1H-pyrazolo[4,3-c]pyridine 153

Following the procedures as described in Example 61 and starting with tert-butyl 4-(6-(6-(1H-pyrazol-4-yl)-1H-pyrazolo[4,3-c]pyridin-1-yl)pyridin-2-yl)-1,4-diazepane-1-carboxylate and 1-bromo-2-fluoroethane, 153 was obtained as a yellow solid (60 mg, 87.5%) over two steps. $^1$H NMR (500 MHz, DMSO-d$_6$) δ (ppm) 9.12 (s, 1H), 8.63 (s, 1H), 8.51 (s, 1H), 8.28 (s, 1H), 7.95 (s, 1H), 7.49-7.66 (m, 1H), 7.13-7.15 (d, J=7.5 Hz, 1H), 6.55-6.57 (d, J=8.5 Hz, 1H), 4.88-4.90 (m, 1H), 4.73-4.80 (m, 1H), 4.54-4.58 (m, 1H), 4.49-4.52 (m, 1H), 3.77-3.83 (m, 4H), 2.97-2.99 (m, 2H), 2.70-2.72 (m, 2H), 1.87-1.89 (m, 2H); MS (ESI) m/z: 407 [M+H]$^+$.

Example 54

1-(6-(1,4-Diazepan-1-yl)pyridin-2-yl)-6-(1-(2,2,2-trifluoroethyl)-1H-pyrazol-4-yl)-1H-pyrazolo[4,3-c]pyridine 154

Following the procedures as described in Example 61 and starting with tert-butyl 4-(6-(6-(1H-pyrazol-4-yl)-1H-pyrazolo[4,3-c]pyridin-1-yl)pyridin-2-yl)-1,4-diazepane-1-carboxylate and 2,2,2-trifluoroethyl trifluoromethanesulfonate, 154 was obtained as white solid (45 mg, 31%) over two steps. $^1$H NMR (500 MHz, CDCl$_3$) δ (ppm) 9.060-9.062 (d, J=1 Hz, 1H), 8.76 (s, 1H), 8.24 (s, 1H), 8.16 (s, 1H), 8.05 (s, 1H), 7.60-7.63 (t, J=16 Hz, 1H), 7.26-7.28 (t, J=7.5 Hz, 1H), 6.42-6.43 (d, J=8.5 Hz, 1H), 4.75-4.78 (t, J=16.5 Hz, 2H), 3.86-3.92 (m, 4H), 3.15-3.17 (t, J=10.5 Hz, 2H), 2.90-2.92 (t, J=11.5 Hz, 2H), 2.01-2.03 (t, J=11.5 Hz, 2H); MS (ESI) m/z: 443 [M+H]$^+$.

Example 55

2-(4-(1-(6-(1,4-Diazepan-1-yl)pyridin-2-yl)-1H-pyrazolo[4,3-c]pyridin-6-yl)-1H-pyrazol-1-yl)acetonitrile 155

Following the procedures as described in Example 61 and starting with tert-butyl 4-(6-(6-(1H-pyrazol-4-yl)-1H-pyrazolo[4,3-c]pyridin-1-yl)pyridin-2-yl)-1,4-diazepane-1-carboxylate and 2-bromoacetonitrile, 155 was obtained as a white solid (25 mg, 18.5%) over two steps. $^1$H NMR (500 MHz, CDCl$_3$) δ (ppm) 9.064-9.065 (d, J=0.5 Hz, 1H), 8.75 (s, 1H), 8.25 (s, 1H), 8.19 (s, 1H), 8.05 (s, 1H), 7.61-7.64 (t, J=16.5 Hz, 1H), 7.28 (s, 1H), 6.43-6.45 (d, J=8.5 Hz, 1H), 5.15 (s, 2H), 3.88-3.92 (m, 4H), 3.17-3.19 (t, J=11 Hz, 2H), 2.92-2.94 (t, J=11 Hz, 2H), 2.02-2.05 (t, J=12 Hz, 2H); MS (ESI) m/z: 400 [M+H]$^+$.

Example 56

(3S)-1-[6-[6-(6-ethylpyrazin-2-yl)pyrazolo[4,3-c]pyridin-1-yl]-2-pyridyl]piperidin-3-amine 156

Step A: Preparation of 6-(6-ethylpyrazin-2-yl)-1-(6-fluoro-2-pyridyl)pyrazolo[4,3-c]pyridine

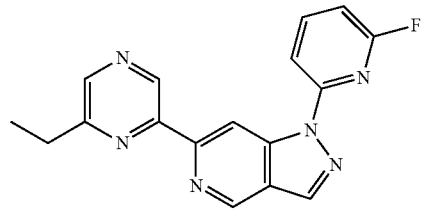 [SMILES: CCc1cncc(-c2cc3c(cn2)cnn3-c2cccc(F)n2)n1]

To a solution of 6-chloro-1-(6-fluoro-2-pyridyl)pyrazolo[4,3-c]pyridine (85 mg; 0.34 mmol) and tetrakis(triphenylphosphine)palladium (40 mg, 0.034 mmol) in N,N-dimethylacetamide; 2.0 mL was added (6-ethylpyrazin-2-yl)-trimethyl-stannane (185 mg, 0.684 mmol). The reaction was purged with N2 for 5 min then heated at 150° C. for 45 min in biotage microwave. The reaction mixture was filtered through celite and concentrated. The crude product was diluted with EtOAc then washed with water. The organic layers was dried with sodium sulfate, filtered, and concentrated in vacuum. The crude product was purified by flash chromatography (EtOAc/Heptane eluted at 50% EtOAc) to give 6-(6-ethylpyrazin-2-yl)-1-(6-fluoro-2-pyridyl)pyrazolo[4,3-c]pyridine (45 mg) in 41% yield. MS (ESI) m/z: 321.2

Step B: (S)-tert-butyl(1-(6-(6-(6-ethylpyrazin-2-yl)-1H-pyrazolo[4,3-c]pyridin-1-yl)pyridin-2-yl)piperidin-3-yl)carbamate

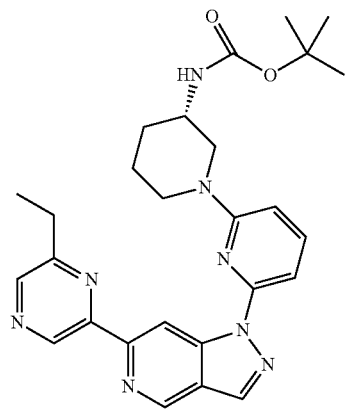 [SMILES: CCc1cncc(-c2cc3c(cn2)cnn3-c2cccc(N3CCC[C@H](NC(=O)OC(C)(C)C)C3)n2)n1]

A solution containing 6-(6-ethylpyrazin-2-yl)-1-(6-fluoro-2-pyridyl)pyrazolo[4,3-c]pyridine (75 mg, 0.23 mmol) and tert-butyl N-[(3S)-3-piperidyl]carbamate (234 mg, 1.17 mmol) in methyl sulfoxide 2.0 mL was heated 95° C. The reaction was quenched with water then extracted with EtOAc. The organic layers was dried with sodium sulfate, filtered, and concentrated in vacuum. The crude product was purified by flash chromatography (EtOAc/Heptane eluted at 65% EtOAc) to give (S)-tert-butyl(1-(6-(6-(6-ethylpyrazin-2-yl)-1H-pyrazolo[4,3-c]pyridin-1-yl)pyridin-2-yl)piperidin-3-yl)carbamate (80 mg) in 68% yield.

Step C

A solution of (5)-tert-butyl(1-(6-(6-(6-ethylpyrazin-2-yl)-1H-pyrazolo[4,3-c]pyridin-1-yl)pyridin-2-yl)piperidin-3-yl)carbamate (80 mg, 0.16 mmol) in hydrogen chloride (4 mol/l) in 1,4-dioxane (2.0 ml, 8.0 mmol) and 1,4-dioxane 2.0 mL was stirred at RT 18 h. The reaction was concentrated and submitted for reverse phase HPLC to give 156 (47 mg) in 50% yield. $^1$H NMR (400 MHz, DMSO) δ 9.55 (s, 1H), 9.49 (s, 1H), 9.33 (s, 1H), 8.66 (d, J=4.9 Hz, 2H), 7.75 (t, J=8.1 Hz, 1H), 7.21 (d, J=7.7 Hz, 1H), 6.82 (d, J=8.5 Hz, 1H), 4.42 (d, J=13.1 Hz, 1H), 4.12 (d, J=10.6 Hz, 1H), 3.17-3.06 (m, 1H), 2.93 (q, J=7.5 Hz, 2H), 2.88-2.71 (m, 2H), 1.84 (ddd, J=17.0, 13.4, 8.1 Hz, 2H), 1.58 (dd, J=24.7, 11.5 Hz, 1H), 1.35 (t, J=7.6 Hz, 3H). MS (ESI) m/z: 401.2.

Example 57

1-(6-(1,4-Diazepan-1-yl)pyridin-2-yl)-6-(1-(2-(methylsulfonyl)ethyl)-1H-pyrazol-4-yl)-1H-pyrazolo[4,3-c]pyridine 157

Following the procedures as described in Example 61 and starting with tert-butyl 4-(6-(6-(1H-pyrazol-4-yl)-1H-pyrazolo[4,3-c]pyridin-1-yl)pyridin-2-yl)-1,4-diazepane-1-carboxylate and 2-(methylsulfonyl)ethyl 4-methylbenzenesulfonate, 157 was obtained as a white solid (50 mg, 40.6%) over two steps. $^1$H NMR (500 MHz, DMSO-d$_6$) δ (ppm) 9.16 (s, 1H), 8.58 (s, 1H), 8.56 (s, 1H), 8.39 (s, 1H), 8.02 (s, 1H), 7.76-7.79 (t, J=16 Hz, 1H), 7.23-7.24 (d, J=7.5 Hz, 1H), 6.71-6.73 (d, J=8.5 Hz, 1H), 4.64-4.67 (t, J=13.5 Hz, 2H), 4.01-4.03 (t, J=9.5 Hz, 2H), 3.89-3.87 (t, J=11.5 Hz, 2H), 3.76-3.79 (t, J=14 Hz, 2H), 3.32 (s, 2H), 3.17-3.20 (t, J=10.5 Hz, 2H), 2.94 (s, 3H), 2.13-2.14 (d, J=4.5 Hz, 2H); MS (ESI) m/z: 467 [M+H]$^+$.

Example 58

1-(6-(1,4-Diazepan-1-yl)pyridin-2-yl)-6-(1-(oxetan-3-ylmethyl)-1H-pyrazol-4-yl)-1H-pyrazolo[4,3-c]pyridine 158

Following the procedures as described in Example 61 and starting with tert-butyl 4-(6-(6-(1H-pyrazol-4-yl)-1H-pyrazolo[4,3-c]pyridin-1-yl)pyridin-2-yl)-1,4-diazepane-1-carboxylate and oxetan-3-ylmethyl 4-methylbenzenesulfonate, 158 was obtained as a yellow solid (38 mg, 51%) over two steps. $^1$H-NMR (500 MHz, CD$_3$OD) δ (ppm): 9.16-9.19 (m, 1H), 8.86-8.77 (m, 3H), 8.43-8.47 (m, 1H), 7.66-7.73 (m, 1H), 7.18-7.26 (m, 1H), 6.63-6.66 (m, 1H), 4.81-4.83 (m, 2H), 4.60-4.64 (m, 2H), 3.75-3.97 (m, 7H), 3.61-3.64 (m, 1H), 3.46-3.48 (m, 1H), 3.10-3.12 (m, 1H), 2.88-2.90 (m, 1H), 1.98-2.07 (m, 2H); MS (ESI) m/z: 431 [M+H]$^+$.

Example 59

2-(4-(1-(6-(1,4-Diazepan-1-yl)pyridin-2-yl)-1H-pyrazolo[4,3-c]pyridin-6-yl)-1H-pyrazol-1-yl)acetamide 159

Following the procedures as described in Example 61 and starting with tert-butyl 4-(6-(6-(1H-pyrazol-4-yl)-1H-pyrazolo[4,3-c]pyridin-1-yl)pyridin-2-yl)-1,4-diazepane-1-carboxylate and 2-bromoacetonitrile, 159 was obtained as a white solid (12 mg, 36%) over two steps. $^1$H NMR (500 MHz, DMSO-d$_6$) δ (ppm) 9.11 (s, 1H), 8.64 (s, 1H), 8.46 (s, 1H), 8.20 (s, 1H), 7.91 (s, 1H), 7.64-7.70 (m, 1H), 7.14-7.16 (d, J=12.5 Hz, 3H), 6.56-6.59 (d, J=14 Hz, 1H), 4.83 (s, 1H), 3.78-3.88 (m, 6H), 2.74-2.78 (m, 3H), 1.88-1.92 (t, J=20 Hz, 2H); MS (ESI) m/z: 418 [M+H]$^+$.

Example 60

6-(6-methylpyrazin-2-yl)-1-[6-(1 2 3 6-tetrahydro-pyridin-4-yl)-2-pyridyl]pyrazolo[4,3-c]pyridine 160

Step A: tert-butyl 4-[6-(6-chloropyrazolo[4,3-c]pyridin-1-yl)-2-pyridyl]-3,6-dihydro-2H-pyridine-1-carboxylate

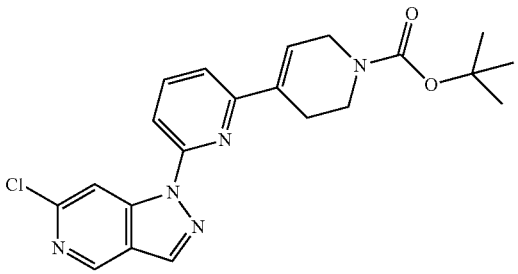 [SMILES: CC(C)(C)OC(=O)N1CC=C(c2cccc(-n3ncc4cnc(Cl)cc43)n2)CC1]

To a solution of 1-(6-bromo-2-pyridyl)-6-chloro-pyrazolo[4,3-c]pyridine (150 mg, 0.485 mmol), 4-(4,4,5,5-tetramethyl-[1,3,2]-dioxaborolan-2-yl)-3,6-dihydro-2 h-pyridine-1-carboxylic acid tert-butyl ester (180 mg, 0.581 mmol), and 1,1'-Bis(diphenylphosphino)ferrocenepalladium(II) chloride (32 mg, 0.039 mmol) in Acetonitrile 5.0 mL was added 1.00 M of Potassium acetate in Water (0.73 mL, 0.73 mmol) and 1.00 M of Sodium carbonate in Water (0.73 mL, 0.73 mmol). The reaction mixture was stirred at 95° C. for 2 h. The reaction was filtered through celite. The crude product was purified by flash chromatography (EtOAc/Heptane eluted at 35% EtOAc) to give tert-butyl 4-[6-(6-chloropyrazolo[4,3-c]pyridin-1-yl)-2-pyridyl]-3,6-dihydro-2H-pyridine-1-carboxylate (185 mg) in 92% yield. MS (ESI) m/z: 412.2

Step B: tert-butyl 4-[6-[6-(6-methylpyrazin-2-yl) pyrazolo[4,3-c]pyridin-1-yl]-2-pyridyl]-3,6-dihydro-2 h-pyridine-1-carboxylate

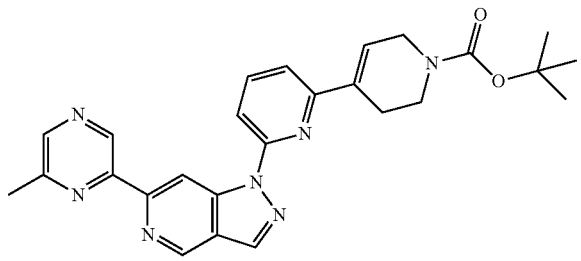 [SMILES: Cc1cncc(-c2cc3c(cn2)cnn3-c2cccc(C3=CCN(C(=O)OC(C)(C)C)CC3)n2)n1]

A solution of tert-butyl 4-[6-(6-chloropyrazolo[4,3-c]pyridin-1-yl)-2-pyridyl]-3,6-dihydro-2H-pyridine-1-carboxylate (200 mg, 0.486 mmol) and palladium(0)tetrakis(triphenylphosphine) (56 mg, 0.049 mmol) in N,N-dimethylacetamide 5.0 mL was added trimethyl-(6-methylpyrazin-2-yl)stannane (250 mg, 0.971 mmol). The reaction mixture heated at 145° C. for 40 min in microwave. The reaction mixture was filtered through celite and concentrated. The crude product was diluted with EtOAc then washed with water. The organic layers was dried with sodium sulfate, filtered, and concentrated in vacuum. The crude product was purified by flash chromatography (EtOAc/Heptane eluted at 65% EtOAc) to give the desired product 165 mg 72% yield.

Step C

A solution of tert-butyl 4-[6-[6-(6-methylpyrazin-2-yl)pyrazolo[4,3-c]pyridin-1-yl]-2-pyridyl]-3,6-dihydro-2 h-pyridine-1-carboxylate (40 mg, 0.085 mmol) in hydrogen chloride (4 mol/l) in 1,4-dioxane (1.0 mL, 4.0 mmol) and 1,4-dioxane 1.0 mL was stirred at RT 18 h. The reaction was concentrated. The crude product was diluted in water and washed with EtOAc to remove triphenylphosphine oxide by product. The aqueous layer was concentrated and submitted for reverse phase HPLC to give 160 17 mg 52% yield. $^1$H NMR (400 MHz, DMSO) δ 9.73 (s, 1H), 9.48 (s, 1H), 9.34 (s, 1H), 8.72 (s, 1H), 8.64 (s, 1H), 8.03 (t, J=7.9 Hz, 1H), 7.93 (d, J=8.1 Hz, 1H), 7.57 (d, J=7.7 Hz, 1H), 7.02 (s, 1H), 3.14 (s, 2H

Example 61

1-(6-(1,4-Diazepan-1-yl)pyridin-2-yl)-6-(1-(cyclopropylmethyl)-1H-pyrazol-4-yl)-1H-pyrazolo[4,3-c]pyridine 161

Step A: tert-Butyl 4-(6-Bromopyridin-2-yl)-1,4-diazepane-1-carboxylate

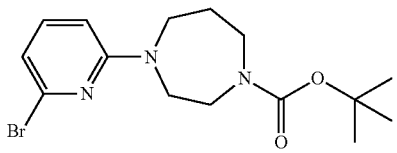 [SMILES: CC(C)(C)OC(=O)N1CCCN(c2cccc(Br)n2)CC1]

A mixture of 2-bromo-6-fluoropyridine (500 mg, 2.8 mmol), tert-butyl 1,4-diazepane-1-carboxylate (568 mg, 2.8 mmol) in DIPEA (1.83 g, 14.2 mmol) and ethanol (10 mL) was heated at 100° C. for 16 hours. After it was cooled, the solvent was removed under reduced pressure, and the residue was diluted with EtOAc (100 mL) and washed with brine. The organic layer was dried over Na$_2$SO$_4$ and concentrated under reduced pressure to afford tert-butyl 4-(6-bromopyridin-2-yl)-1,4-diazepane-1-carboxylate as a colorless oil (500 mg, 50%). MS (ESI) m/z: 356 [M+H]$^+$.

Step B: tert-Butyl 4-(6-(6-Chloro-1H-pyrazolo[4,3-c]pyridin-1-yl)pyridin-2-yl)-1,4-diazepane-1-carboxylate

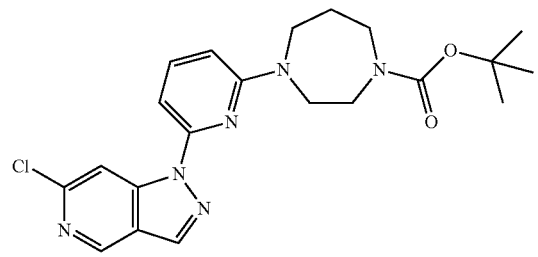

To a mixture of tert-butyl 4-(6-bromopyridin-2-yl)-1,4-diazepane-1-carboxylate (2.55 g, 7.16 mmol) and 6-chloro-1H-pyrazolo[4,3-c]pyridine (1.0 g, 6.51 mmol) in 1,4-dioxane (20 mL) was added CuI (494 mg, 2.6 mmol), K$_2$CO$_3$ (3.6 g, 26 mmol), and N$^1$,N$^2$-dimethylethane-1,2-diamine (460 mg, 5.2 mmol). The mixture was heated at 100° C. for 3 hours, which was monitored by LC-MS. The reaction mixture was concentrated under reduced pressure. The crude was purified by silica gel chromatography using petroleum ether/EtOAc (2/1) as eluting solvents to afford tert-butyl 4-(6-(6-chloro-1H-pyrazolo[4,3-c]-pyridin-1-yl)pyridin-2-yl)-1,4-diazepane-1-carboxylate as a yellow solid (1.6 g, 57%). MS (ESI) m/z: 429[M+H]$^+$.

Step C: tert-Butyl 4-(6-(6-(1H-Pyrazol-4-yl)-1H-pyrazolo[4,3-c]pyridin-1-yl)pyridin-2-yl)-1,4-diazepane-1-carboxylate

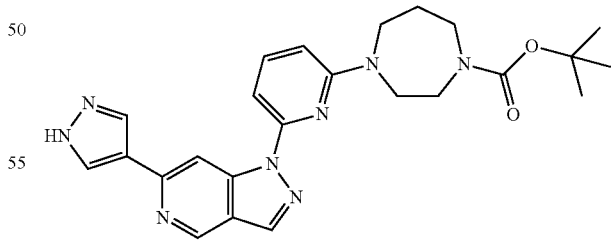

A suspension of tert-butyl 4-(6-(6-chloro-1H-pyrazolo[4,3-c]pyridin-1-yl)pyridin-2-yl)-1,4-diazepane-1-carboxylate (500 mg, 1.16 mmol), 4-(4,4,5,5-tetramethyl-1,3,2-dioxaborolan-2-yl)-1H-pyrazole (679 mg, 3.5 mmol), Pd(dppf)Cl$_2$ (47.5 mg, 0.058 mmol), and aqueous solution of Na$_2$CO$_3$ (saturated, 3 mL) in 1,4-dioxane (10 mL) under nitrogen was heated at 100° C. for 16 hours. The reaction mixture was filtered and the filtrate was concentrated under reduced pressure. The residue was purified by silica gel chromatography using petroleum ether/EtOAc (1/1) as eluting solvents to afford tert-butyl 4-(6-(6-(1H-pyrazol-4-yl)-1H-pyrazolo[4,3-c]pyridin-1-yl)pyridin-2-yl)-1,4-diazepane-1-carboxylate as a yellow solid (360 mg, 67%). MS (ESI) m/z: 461 [M+H]⁺.

Step D: tert-Butyl 4-(6-(6-(1-(Cyclopropylmethyl)-1H-pyrazol-4-yl)-1H-pyrazolo[4,3-c]pyridin-1-yl)pyridin-2-yl)-1,4-diazepane-1-carboxylate

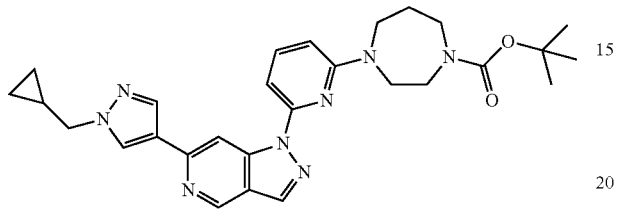

A suspension of 4-(6-(6-(1H-pyrazol-4-yl)-1H-pyrazolo[4,3-c]pyridin-1-yl)pyridin-2-yl)-1,4-diazepane-1-carboxylate (200 mg, 0.43 mmol), (bromomethyl)cyclopropane (100 mg, 0.65 mmol), and K₂CO₃ (120 mg, 0.87 mmol) in DMF (10 mL) was stirred at room temperature for 18 hours. The reaction mixture was extracted with EtOAc (100 mL), washed with brine (50 mL), dried over MgSO₄, and concentrated under reduced pressure. The crude was purified by silica gel chromatography using petroleum ether/EtOAc (2/1) as eluting solvents to afford tert-butyl 4-(6-(6-(1-(cyclopropylmethyl)-1H-pyrazol-4-yl)-1H-pyrazolo[4,3-c]pyridin-1-yl)pyridin-2-yl)-1,4-diazepane-1-carboxylate as a white solid (200 mg, 89.6%). MS (ESI) m/z: 515 [M+H]⁺.

Step E

A solution of tert-butyl 4-(6-(6-(1-(cyclopropylmethyl)-1H-pyrazol-4-yl)-1H-pyrazolo[4,3-c]-pyridin-1-yl)pyridin-2-yl)-1,4-diazepane-1-carboxylate (200 mg, 0.39 mmol) in HCl/MeOH (2M, 10 mL) was stirred at room temperature for 3 hours. The reaction mixture was concentrated under reduced pressure. The crude was purified by reverse phase preparative HPLC to afford 161 as a yellow solid (70 mg, 43.5%). ¹H NMR (500 MHz, CDCl₃) δ (ppm) 9.055-9.057 (d, J=1 Hz, 1H), 8.74 (s, 1H), 8.23 (s, 1H), 8.17 (s, 1H), 7.97 (s, 1H), 7.60-7.63 (t, J=16 Hz, 1H), 7.28 (s, 1H), 6.41-6.43 (d, J=8 Hz, 1H), 4.04-4.06 (d, J=7 Hz, 2H), 3.89-3.94 (m, 4H), 3.17-3.19 (t, J=11 Hz, 2H), 2.91-2.93 (t, J=11.5 Hz, 2H), 2.03-2.06 (t, J=12.5 Hz, 2H), 1.35-1.36 (m, 1H), 0.69-0.73 (m, 2H), 0.43-0.46 (m, 2H); MS (ESI) m/z: 415 [M+H]⁺.

Example 62

1-(6-(1,4-Diazepan-1-yl)pyridin-2-yl)-6-(1-(2,2-difluoroethyl)-1H-pyrazol-4-yl)-1H-pyrazolo[4,3-c]pyridine 162

Following the procedures as described in Example 61 and starting with tert-butyl 4-(6-(6-(1H-pyrazol-4-yl)-1H-pyra-zolo[4,3-c]pyridin-1-yl)pyridin-2-yl)-1,4-diazepane-1-carboxylate and 1,1-difluoro-2-iodoethane, 162 was obtained as a light yellow solid (21 mg, 14.5%) over two steps. ¹H NMR (500 MHz, CDCl₃) δ (ppm) 9.060-9.062 (d, J=1 Hz, 1H), 8.74 (s, 1H), 8.24 (s, 1H), 8.11 (s, 1H), 8.04 (s, 1H), 7.61-7.64 (t, J=16 Hz, 1H), 7.26-7.28 (t, J=10.5 Hz, 1H), 6.42-6.44 (d, J=8.5 Hz, 1H), 6.04-6.26 (m, 1H), 4.51-4.57 (m, 2H), 3.89-3.93 (m, 4H), 3.17-3.19 (t, J=11 Hz, 2H), 2.92-2.94 (t, J=11 Hz, 2H), 2.02-2.05 (m, 2H); MS (ESI) m/z: 425 [M+H]⁺.

Example 63

1-(6-(1,4-diazepan-1-yl)pyrazin-2-yl)-6-(1-ethyl-1H-pyrazol-4-yl)-1H-pyrazolo[4,3-c]pyridine 163

Step A: tert-butyl 4-(6-bromopyrazin-2-yl)-1,4-diazepane-1-carboxylate

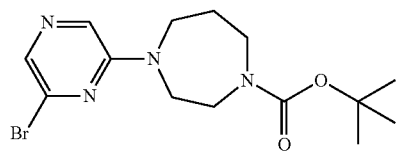 [SMILES: CC(C)(C)OC(=O)N1CCCN(c2cncc(Br)n2)CC1]

A mixture of 2,6-dibromopyrazine (5.0198 mmol; 1194.1 mg), tert-butyl 1,4-diazepane-1-carboxylate (5.271 mmol; 1055.6 mg), and triethylamine (15.06 mmol; 1539 mg; 2.12 mL) in IPA (10 mL) in a sealed pressure vial was heated at 120° C. overnight. The mixture was cooled to room temperature, and then concentrated. The residue was purified on silica elute with 0 to 100% EtOAc in Heptane to afford tert-butyl 4-(6-bromopyrazin-2-yl)-1,4-diazepane-1-carboxylate (1.6965 g, 95%). MS (ESI) m/z: 357 [M+H]⁺

Step B: tert-butyl 4-[6-(6-chloropyrazolo[4,3-c]pyridin-1-yl)pyrazin-2-yl]-1,4-diazepane-1-carboxylate

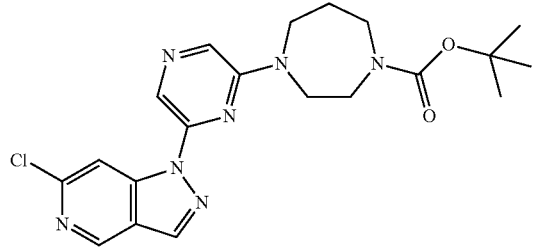 [SMILES: CC(C)(C)OC(=O)N1CCCN(c2cncc(-n3ncc4cnc(Cl)cc43)n2)CC1]

A mixture of 6-chloro-1H-pyrazolo[4,3-c]pyridine (2.0 mmol; 307 mg), tert-butyl 4-(6-bromopyrazin-2-yl)-1,4-diazepane-1-carboxylate (2.199 mmol; 785.5 mg), N,N'-Dimethylethylenediamine (4.0 mmol; 352.4 mg; 0.398 mL), cuprous iodide (2.0 mmol; 380.72 mg), and potassium carbonate (2.1990 mmol; 307 mg) in 1,4-Dioxane (15 mL) was purged with Argon, then sealed and stirred at 110° C. overnight. The mixture was cooled to room temperature, then filtered through Celite. The filtrate was concentrated; the residue was purified on silica eluted with 0 to 100% EtOAc in Heptane to afford tert-butyl 4-[6-[6-(6-chloropyrazolo[4,3-c]pyridin-1-yl)pyrazin-2-yl]-1,4-diazepane-1-carboxylate as an off-white solid (217.2 mg, 25%). MS (ESI) m/z: δ 430 [M+H]+

Step C: tert-butyl 4-[6-[6-(1-ethylpyrazol-4-yl)pyrazolo[4,3-c]pyridin-1-yl]pyrazin-2-yl]-1,4-diazepane-1-carboxylate

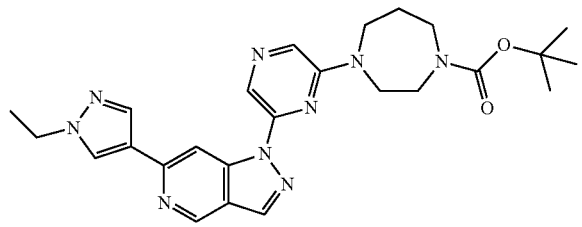 [SMILES: CCn1cc(-c2cc3c(cn2)cnn3-c2cncc(N3CCCN(C(=O)OC(C)(C)C)CC3)n2)cn1]

A mixture of tert-butyl 4-[6-(6-chloropyrazolo[4,3-c]pyridin-1-yl)pyrazin-2-yl]-1,4-diazepane-1-carboxylate (0.2526 mmol; 108.6 mg), 1-ethyl-4-(4,4,5,5-tetramethyl-1,3,2-dioxaborolan-2-yl)pyrazole (0.3789 mmol; 84.16 mg), [1,1'-bis(diphenylphosphino)ferrocene]dichloropalladium(II) dichloromethane adduct (0.02526 mmol; 21.1 mg), potassium acetate (0.3789 mmol; 0.38 mL) and sodium carbonate (0.3789 mmol; 0.38 mL) in Acetonitrile (10 mL) in a pressure tube was heated under microwave at 150° C. for 15 min. The mixture was cooled to room temperature. The layers were separated. The aqueous layer was extracted with EtOAc. The combined organic layers were concentrated. The residue was purified on silica eluted with 0 to 5% MeOH in DCM with 1% NH4OH to afford tert-butyl 4-[6-[6-(1-ethylpyrazol-4-yl)pyrazolo[4,3-c]pyridin-1-yl]pyrazin-2-yl]-1,4-diazepane-1-carboxylate (127 mg, ~100%).

Step D

To a solution of tert-butyl 4-[6-[6-(1-ethylpyrazol-4-yl)pyrazolo[4,3-c]pyridin-1-yl]pyrazin-2-yl]-1,4-diazepane-1-carboxylate (0.2596 mmol; 127.1 mg) in Methanol (5 mL) was added hydrochloric acid, 4.0 M in 1,4-Dioxane (5 mL). The resulting mixture was stirred at room temperature overnight. The mixture was concentrated and the residue was purified by reverse phase HPLC to afford 163 as an off-white solid (34.9 mg, 34%). $^1$H NMR (400 MHz, DMSO) δ 9.17-9.12 (s, 1H), 8.60-8.56 (s, 1H), 8.55-8.52 (s, 1H), 8.39-8.36 (s, 1H), 8.27-8.24 (s, 1H), 8.12-8.08 (s, 1H), 7.91-7.85 (s, 1H), 4.25-4.17 (q, J=7.3 Hz, 2H), 3.92-3.80 (dt, J=10.3, 5.5 Hz, 4H), 3.05-2.95 (m, 2H), 2.79-2.71 (m, 2H), 1.95-1.82 (m, 2H), 1.46-1.40 (t, J=7.3 Hz, 3H); MS (ESI) m/z: 390.2 [M+H]+

Example 64

3-(1-(6-(1,4-diazepan-1-yl)pyrazin-2-yl)-1H-pyrazolo[4,3-c]pyridin-6-yl)-5-methylpyridin-2-ol 164

Step A: tert-butyl 4-[6-[6-(2-fluoro-5-methyl-3-pyridyl)pyrazolo[4,3-c]pyridin-1-yl]pyrazin-2-yl]-1,4-diazepane-1-carboxylate

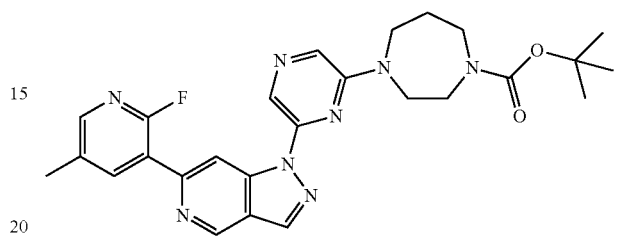

A mixture of tert-butyl 4-[6-[6-(6-chloropyrazolo[4,3-c]pyridin-1-yl)pyrazin-2-yl]-1,4-diazepane-1-carboxylate (0.2526 mmol; 108.6 mg), 2-fluoro-5-methyl-3-(4,4,5,5-tetramethyl-1,3,2-dioxaborolan-2-yl)pyridine (0.3789 mmol; 89.84 mg), [1,1'-bis(diphenylphosphino)ferrocene]dichloropalladium(II) dichloromethane adduct (0.02526 mmol; 21.1 mg), potassium acetate (0.3789 mmol; 0.38 mL) and sodium carbonate (0.3789 mmol; 0.38 mL) in Acetonitrile (10 mL) in a pressure tube was heated under microwave at 150° C. for 15 min. The mixture was cooled to room temperature. The layers were separated. The aqueous layer was extracted with EtOAc. The combined organic layers were concentrated. The residue was purified on silica eluted with 0 to 5% MeOH in DCM with 1% NH4OH to afford tert-butyl 4-[6-[6-(2-fluoro-5-methyl-3-pyridyl)pyrazolo[4,3-c]pyridin-1-yl]pyrazin-2-yl]-1,4-diazepane-1-carboxylate (106.6 mg, 84%).

Step B

To a solution of tert-butyl 4-[6-[6-(2-fluoro-5-methyl-3-pyridyl)pyrazolo[4,3-c]pyridin-1-yl]pyrazin-2-yl]-1,4-diazepane-1-carboxylate (0.2113 mmol; 106.6 mg) in Methanol (5 mL) was added hydrochloric acid, 4.0 M in 1,4-Dioxane (5 mL). The resulting mixture was stirred at room temperature overnight. The mixture was concentrated and the residue was purified by reverse phase HPLC to afford 164 as a by-product (18.7 mg, 22%). $^1$H NMR (400 MHz, DMSO) δ 9.89-9.85 (s, 1H), 9.25-9.20 (s, 1H), 8.64-8.60 (s, 1H), 8.56-8.52 (d, J=2.6 Hz, 1H), 8.41-8.38 (s, 1H), 8.08-8.05 (s, 1H), 7.33-7.30 (s, 1H), 3.95-3.84 (m, 4H), 2.99-2.93 (m, 2H), 2.71-2.66 (m, 2H), 2.15-2.13 (s, 3H), 1.88-1.81 (m, 2H); MS (ESI) m/z: 403.2 [M+H]+

Example 65

6-(6-cyclopropylpyrazin-2-yl)-1-(6-piperazin-1-yl-2-pyridyl)pyrazolo[4,3-c]pyridine 165

Following the procedures in preparation of EXAMPLE 23, 165 was obtained. MS (ESI) m/z: 399.2. $^1$H NMR (400 MHz, DMSO) δ 9.40 (s, 1H), 9.32 (s, 1H), 9.28 (s, 1H), 8.66 (s, 1H), 8.62 (s, 1H), 7.77 (t, J=8.1 Hz, 1H), 7.24 (d, J=7.7 Hz, 1H), 6.82 (d, J=8.5 Hz, 1H), 3.66-3.59 (m, 4H), 2.91-2.85 (m, 4H), 2.35-2.27 (m, 1H), 1.21-1.06 (m, =4H).

Example 66

6-(6-methylpyrazin-2-yl)-1-[6-(4-piperidyl)-2-pyridyl]pyrazolo[4,3-c]pyridine 166

Step A: tert-butyl 4-[6-[6-(6-methylpyrazin-2-yl)pyrazolo[4,3-c]pyridin-1-yl]-2-pyridyl]piperidine-1-carboxylate

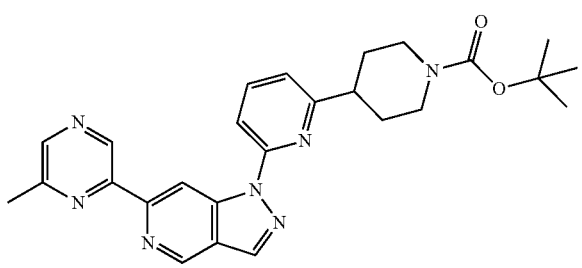 [SMILES: Cc1cncc(-c2cc3c(cn2)cnn3-c2cccc(C3CCN(C(=O)OC(C)(C)C)CC3)n2)n1]

A mixture of tert-butyl 4-[6-[6-(6-methylpyrazin-2-yl)pyrazolo[4,3-c]pyridin-1-yl]-2-pyridyl]-3,6-dihydro-2H-pyridine-1-carboxylate (125 mg, 0.266 mmol) and palladium on activated carbon, reduced 10% (28 mg, 0.0266 mmol) in ethanol 10.0 mL was stirred under H2 balloon at 40° C. 18 h. The reaction was filtered through celite and wash with MeOH. The crude product was carried to next step.

Step B

A mixture of tert-butyl 4-[6-[6-(6-methylpyrazin-2-yl)pyrazolo[4,3-c]pyridin-1-yl]-2-pyridyl]piperidine-1-carboxylate; B; 110 mg; 0.2332 mmol in hydrogen chloride (4 mol/L) in 1,4-dioxane (2.0 ml, 8.0 mmol) and 1,4-dioxane 2.0 mL was stirred at RT 18 h. The reaction was concentrated and submitted for reverse phase HPLC to give 166 (13 mg) in 13% yield. $^1$H NMR (400 MHz, DMSO) δ 9.80 (s, 1H), 9.46 (s, 1H), 9.34 (s, 1H), 8.71 (s, 1H), 8.63 (s, 1H), 7.99 (t, J=7.9 Hz, 1H), 7.87 (d, J=8.1 Hz, 1H), 7.29 (d, J=7.5 Hz, 1H), 3.15 (d, J=12.0 Hz, 2H), 2.94 (tt, J=11.8, 3.5 Hz, 1H), 2.76-2.67 (m, 2H), 2.66 (s, 3H), 2.01 (d, J=12.1 Hz, 2H), 1.85 (qd, J=12.2, 3.8 Hz, 2H). MS (ESI) m/z: 372.2.

Example 67

(3S)-1-[6-[6-(6-methylpyrazin-2-yl)pyrazolo[4,3-c]pyridin-1-yl]-2-pyridyl]pyrrolidin-3-amine 167

Following the procedures in preparation of EXAMPLE 23, 167 was obtained. MS (ESI) m/z: 373.2. $^1$H NMR (400 MHz, DMSO) δ 9.88 (s, 1H), 9.45 (s, 1H), 9.30 (s, 1H), 8.64 (s, 1H), 8.62 (s, 1H), 7.70 (t, J=8.0 Hz, 1H), 7.18 (d, J=7.7 Hz, 1H), 6.39 (d, J=8.3 Hz, 1H), 3.74 (dd, J=28.2, 23.7 Hz, 4H), 2.64 (s, 3H), 2.19 (td, J=12.6, 7.1 Hz, 1H), 1.92-1.78 (m, 2H).

Example 68

(3R)-1-[6-[6-(6-methylpyrazin-2-yl)pyrazolo[4,3-c]pyridin-1-yl]-2-pyridyl]pyrrolidin-3-amine 168

Following the procedures in preparation of EXAMPLE 23, 168 was obtained. MS (ESI) m/z: 373.2. $^1$H NMR (400 MHz, DMSO) δ 9.88 (s, 1H), 9.45 (s, 1H), 9.30 (s, 1H), 8.63 (s, 1H), 8.62 (s, 1H), 7.70 (t, J=8.0 Hz, 1H), 7.18 (d, J=7.7 Hz, 1H), 6.39 (d, J=8.3 Hz, 1H), 3.74 (dd, J=27.9, 23.5 Hz, 4H), 2.64 (s, 3H), 2.19 (td, J=12.6, 7.1 Hz, 1H), 1.90-1.80 (m, 2H).

Example 69

1-[6-(3-methylpiperazin-1-yl)-2-pyridyl]-6-(6-methylpyrazin-2-yl)pyrazolo[4,3-c]pyridine 169

Following the procedures in preparation of EXAMPLE 23, 169 was obtained. MS (ESI) m/z: 387.2. $^1$H NMR (400 MHz, DMSO) δ 9.56 (s, 1H), 9.46 (s, 1H), 9.32 (s, 1H), 8.66 (s, 1H), 8.63 (s, 1H), 7.76 (t, J=8.1 Hz, 1H), 7.24 (d, J=7.7 Hz, 1H), 6.81 (d, J=8.5 Hz, 1H), 4.37 (d, J=12.1 Hz, 1H), 4.17 (d, J=10.7 Hz, 1H), 3.08 (d, J=11.7 Hz, 1H), 2.98 (td, J=11.9, 2.9 Hz, 1H), 2.83 (dd, J=22.0, 9.9 Hz, 1H), 2.63 (s, 3H), 2.62-2.54 (m, 1H), 2.34 (d, J=12.3 Hz, 1H), 1.04 (d, J=6.3 Hz, 3H).

Example 70

6-(6-tert-butylpyrazin-2-yl)-1-(6-piperazin-1-yl-2-pyridyl)pyrazolo[4,3-c]pyridine 170

Following the procedures in preparation of EXAMPLE 23, 170 was obtained. MS (ESI) m/z: 415.2. $^1$H NMR (400 MHz, DMSO) δ 9.65 (s, 1H), 9.56 (d, J=1.2 Hz, 1H), 9.32 (s, 1H), 8.81 (d, J=1.3 Hz, 1H), 8.65 (s, 1H), 7.76 (t, J=8.1 Hz, 1H), 7.25 (d, J=7.7 Hz, 1H), 6.79 (d, J=8.4 Hz, 1H), 3.70-3.58 (m, 4H), 3.00-2.89 (m, 4H), 1.43 (s, 9H).

Example 71

6-methyl-1-[6-[6-(6-methylpyrazin-2-yl)pyrazolo[4,3-c]pyridin-1-yl]-2-pyridyl]piperidin-3-amine 171

Step A: tert-butyl N-[1-(6-bromo-2-pyridyl)-6-methyl-3-piperidyl]carbamate

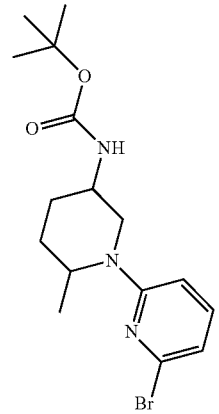 [SMILES: CC1CCC(NC(=O)OC(C)(C)C)CN1c1cccc(Br)n1]

A solution containing 2-bromo-6-fluoropyridine (0.95 mL, 6.65 mmol and tert-butyl 6-methylpiperidin-3-ylcarbamate (750 mg, 3.32 mmol) in methyl sulfoxide 5.0 ml was heated 95° C. 18 h. The reaction was quenched with water then extracted with EtOAc. The organic layers was dried with sodium sulfate, filtered, and concentrated in vacuum. The crude product was purified by flash chromatography (EtOAc/Heptane eluted at 30% EtOAc) to give tert-butyl N-[1-(6-bromo-2-pyridyl)-6-methyl-3-piperidyl]carbamate (480 mg) in 39% yield. MS (ESI) m/z: 371.2

Step B: tert-butyl N-[1-[6-(6-chloropyrazolo[4,3-c]pyridin-1-yl)-2-pyridyl]-6-methyl-3-piperidyl]carbamate

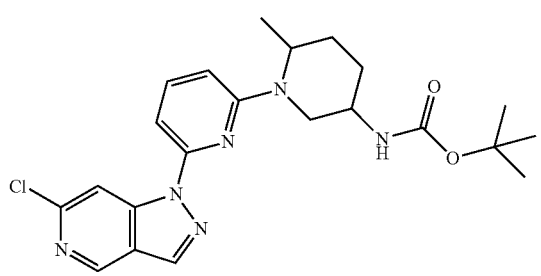 [SMILES: CC1CCC(NC(=O)OC(C)(C)C)CN1c1cccc(-n2ncc3cnc(Cl)cc32)n1]

A mixture of 6-chloro-1H-pyrazolo[4,3-c]pyridine (100 mg, 0.651 mmol), tert-butyl N-[1-(6-bromo-2-pyridyl)-6-methyl-3-piperidyl]carbamate (422 mg, 1.14 mmol), tris(dibenzylideneacetone)dipalladium(0) (59 mg, 0.065 mmol), xantphos (78 mg, 0.130 mmol), and sodium tert-butoxide (129 mg, 1.30 mmol) in toluene 6.0 mL was stirred at 100° C. 18 h. The reaction was filtered through celite. The crude product was purified by flash chromatography (EtOAc/Heptane) to give the desired product (185 mg) in 64% yield. MS (ESI) m/z: 443.2

Step C

Following the procedures in preparation of EXAMPLE 23, 171 was obtained. MS (ESI) m/z: 401.2. 1H NMR (400 MHz, DMSO) δ 9.47 (d, J=6.7 Hz, 2H), 9.33 (s, 1H), 8.66 (s, 1H), 8.62 (s, 1H), 7.75 (t, J=8.1 Hz, 1H), 7.21 (d, J=7.7 Hz, 1H), 6.75 (d, J=8.5 Hz, 1H), 5.05-4.92 (m, 1H), 4.06 (d, J=7.8 Hz, 1H), 2.71 (dd, J=6.1, 3.3 Hz, 2H), 2.65 (s, 3H), 1.92-1.70 (m, 2H), 1.70-1.41 (m, 2H), 1.27 (t, J=6.5 Hz, 3H).

Example 72

1-[6-[6-(6-ethylpyrazin-2-yl)pyrazolo[4,3-c]pyridin-1-yl]-2-pyridyl]-1 4-diazepan-6-ol 172

Following the procedures in preparation of EXAMPLE 56, 172 was obtained. MS (ESI) m/z: 417.2. $^1$H NMR (400 MHz, DMSO) δ 9.58 (s, 1H), 9.47 (d, J=4.1 Hz, 1H), 9.32 (s, 1H), 8.65 (d, J=4.1 Hz, 2H), 7.71 (t, J=8.1 Hz, 1H), 7.19 (d, J=7.7 Hz, 1H), 6.74 (d, J=8.5 Hz, 1H), 4.73 (s, 1H), 4.11 (dt, J=13.8, 5.1 Hz, 1H), 4.06-3.97 (m, 1H), 3.92 (s, 1H), 3.86-3.70 (m, 1H), 3.52 (dd, J=14.6, 6.9 Hz, 1H), 3.00 (t, J=5.4 Hz, 2H), 2.92 (q, J=7.5 Hz, 2H), 2.78 (dd, J=13.8, 3.9 Hz, 1H), 2.69-2.59 (m, 1H), 1.35 (t, J=7.6 Hz, 3H).

Example 73

1-(6-(1,4-Diazepan-1-yl)pyridin-2-yl)-6-(1-(difluoromethyl)-1H-pyrazol-4-yl)-1H-pyrazolo[4,3-c]pyridine 173

Step A: 1-(difluoromethyl)-4-(4,4,5,5-tetramethyl-1,3,2-dioxaborolan-2-yl)-1H-pyrazole

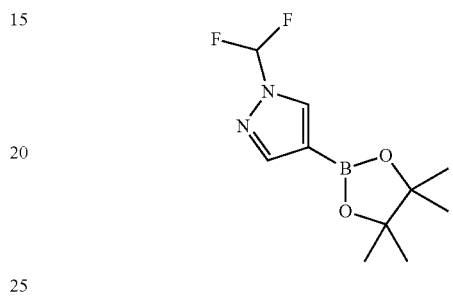

A suspension of 4-(4,4,5,5-tetramethyl-1,3,2-dioxaborolan-2-yl)-1H-pyrazole (516 mg, 2.66 mmol), CF$_2$ClCO$_2$Na (486 mg, 3.19 mmol), and 18-crown-6 (141 mg, 0.532 mmol) in CH$_3$CN (150 mL) was heated to reflux for 20 hours. After cooled to room temperature, the reaction mixture was poured into water and extracted with EtOAc. The extracts were washed with brine, dried over MgSO$_4$, and concentrated under reduced pressure to afford a crude 1-(difluoromethyl)-4-(4,4,5,5-tetramethyl-1,3,2-dioxaborolan-2-yl)-1H-pyrazole (500 mg), which was used for the next step without further purification. MS (ESI) m/z: 245 [M+H]$^+$.

Step B

Following the procedures as described in Example 45 and starting with tert-butyl 4-(6-(6-chloro-1H-pyrazolo[4,3-c]pyridin-1-yl)pyridin-2-yl)-1,4-diazepane-1-carboxylate and 1-(difluoromethyl)-4-(4,4,5,5-tetramethyl-1,3,2-dioxaborolan-2-yl)-1H-pyrazole, 173 was obtained as a white solid (80 mg, 35%) over three steps. $^1$H-NMR (500 MHz, CD$_3$OD) δ (ppm) 9.06 (s, 1H), 8.73 (s, 1H), 8.50 (s, 1H), 8.34 (s, 1H), 8.15 (s, 1H), 7.50-7.67 (m, 2H), 7.23 (d, J=7.5 Hz, 1H), 6.58 (d, J=8.0 Hz, 1H), 3.87-3.90 (m, 4H), 3.13-3.15 (m, 2H), 2.91-2.94 (m, 2H), 2.03-2.08 (m, 2H); MS (ESI) m/z: 411 [M+H]$^+$.

Example 74

1-(6-(1,4-Diazepan-1-yl)pyridin-2-yl)-6-(1-cyclopropyl-1H-pyrazol-4-yl)-1H-pyrazolo[4,3-c]pyridine 174

Following the procedures as described in Example 61 and starting with tert-butyl 4-(6-(6-(1H-pyrazol-4-yl)-1H-pyrazolo[4,3-c]pyridin-1-yl)pyridin-2-yl)-1,4-diazepane-1-carboxylate and cyclopropylboronic acid, 174 was obtained as a yellow solid (40 mg, 25%) over two steps. $^1$H NMR (500 MHz, DMSO-d$_6$) δ (ppm) 9.13 (s, 1H), 8.64 (s, 1H), 8.52 (s, 1H), 8.26 (s, 1H), 7.98 (s, 1H), 7.66-7.70 (t, J=16 Hz, 1H), 7.14-7.17 (t, J=14.5 Hz, 1H), 6.58-6.66 (m, 1H), 6.06-6.12 (m, 1H), 5.21-5.28 (m, 2H), 4.84-4.85 (d, J=10 Hz, 2H), 3.35-3.90 (m, 7H), 2.97-2.99 (t, J=10.5 Hz, 1H), 2.71-2.73 (t, J=12 Hz, 1H), 1.87-1.89 (t, J=10 Hz, 2H); MS (ESI) m/z: 401 [M+H]⁺.

Example 75

1-(6-(1,4-Diazepan-1-yl)pyridin-2-yl)-6-(pyrimidin-5-yl)-1H-pyrazolo[4,3-c]pyridine 175

Step A tert-Butyl 4-(6-(6-(Pyrimidin-5-yl)-1H-pyrazolo[4,3-c]pyridin-1-yl)pyridin-2-yl)-1,4-diazepane-1-carboxylate

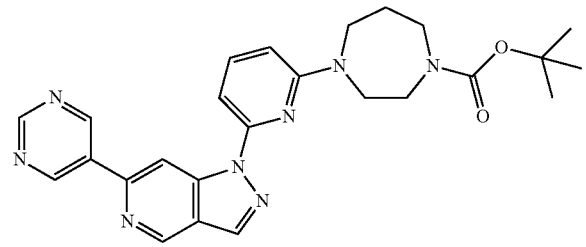 [SMILES: CC(C)(C)OC(=O)N1CCCN(c2cccc(-n3ncc4cnc(-c5cncnc5)cc43)n2)CC1]

A mixture of tert-butyl 4-(6-(6-chloro-1H-pyrazolo[4,3-c]pyridin-1-yl)pyridin-2-yl)-1,4-diazepane-1-carboxylate (427 mg, 1.0 mmol), pyrimidin-5-ylboronic acid (372 mg, 3.0 mmol), PdCl₂(dppf) (73 mg, 0.1 mmol), and aq. Solution of NaHCO₃ (318 mg, 3.0 mmol) in 1,4-dioxane (5.0 mL) in a sealed tube was purged with nitrogen and stirred at 100° C. for 16 hours. After it was cooled to room temperature, the reaction mixture was filtered. The filtrate was concentrated under reduced pressure. The crude product was purified by silica gel chromatography using petroleum ether:EtOAc (5:1~1:1) as eluting solvents to afford tert-butyl 4-(6-(6-(pyrimidin-5-yl)-1H-pyrazolo[4,3-c]pyridin-1-yl)pyridin-2-yl)-1,4-diazepane-1-carboxylate as yellow solid (350 mg, yield 74%). ESI (MS) m/z=473 [M+H]⁺

Step B

A suspension of tert-butyl 4-(6-(6-(pyrimidin-5-yl)-1H-pyrazolo[4,3-c]pyridin-1-yl)pyridin-2-yl)-1,4-diazepane-1-carboxylate (320 mg, 0.68 mmol) in a solution of HCl in MeOH (3.0 N, 20 mL) was stirred at room temperature for 4 hours. The reaction mixture was concentrated under reduced pressure. The residue was purified by prepared HPLC to afford 175 as a light yellow solid (220 mg, yield 87%). ¹H NMR (500 MHz, DMSO-d₆) δ (ppm) 9.43 (s, 1H), 9.39 (s, 1H), 9.35 (d, J=3.0 Hz, 1H), 9.28 (d, J=3.0 Hz, 1H), 9.06 (d, J=11.5 Hz, 1H), 8.66 (d, J=5.5 Hz, 1H), 7.70 (dd, J=8.0 and 16.5 Hz, 1H), 7.17 (dd, J=7.5 and 11.0 Hz, 1H), 6.61 (t, J=8.0 Hz, 1H), 3.83 (s, 2H), 3.77 (s, 2H), 3.56 (m, 1H), 2.95 (t, J=5.0 Hz, 2H), 2.70 (t, J=6.0 Hz, 2H), 1.84 (t, J=5.0 Hz, 2H). ESI (MS) m/z: 373 [M+1]⁺.

Example 76

(S)-1-(3-chloro-6-(6-(6-methylpyrazin-2-yl)-1H-pyrazolo[4,3-c]pyridin-1-yl)pyridin-2-yl)piperidin-3-amine 176

Step A: 6-chloro-1-(tetrahydro-2H-pyran-2-yl)-1H-pyrazolo[4,3-c]pyridine

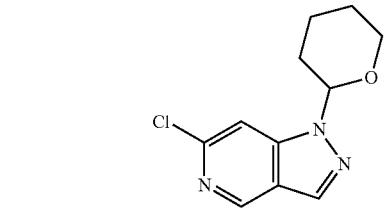 [SMILES: Clc1cc2c(cn1)cnn2C1CCCCO1]

A mixture of 6-chloro-1H-pyrazolo[4,3-c]pyridine (11.5 g, 0.075 mol) and 3,4-dihydro-2H-pyran (19 g, 0.225 mol) and Tos-OH (0.13 g 0.75 mmol) in 1,4-dioxane (175 mL) was heated at 110° C. overnight. The mixture was cooled to room temperature and concentrated. The crude product was purified by column chromatography on silica gel (petroleum ether/ethyl acetate 20:0~20:1) to afford a mixture of 6-chloro-1-(tetrahydro-2H-pyran-2-yl)-1H-pyrazolo[4,3-c]pyridine and 6-chloro-2-(tetrahydro-2H-pyran-2-yl)-2H-pyrazolo[4,3-c]pyridine (13.5 g, yield 76%) MS (ESI) m/z: m/z: 238 [M+H]⁺

Step B: 1-(tetrahydro-2H-pyran-2-yl)-6-(tributyl-stannyl)-1H-pyrazolo[4,3-c]pyridine

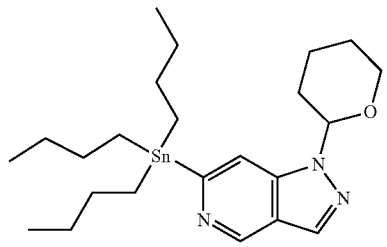 [SMILES: CCC[CH2][Sn]([CH2]CCC)([CH2]CCC)[c]1cc2c(cn1)cnn2C1CCCCO1]

To a mixture of 6-chloro-1-tetrahydropyran-2-yl-pyrazolo[4,3-c]pyridine (19.506 mmol; 4636.1 mg) in 1,4-dioxane (40 mL) under Argon was added lithium chloride (117.03 mmol; 4961.5 mg), bis(tributyltin (23.407 mmol; 14293 mg; 12.45 mL), tris(dibenzylideneacetone)dipalladium (0) (0.97528 mmol; 893.09 mg) and tricyclohexylphosphine (2.3407 mmol; 656.40 mg). The resulting mixture was sealed in a pressure tube and heated at 120° C. overnight. The mixture was filtered through Celite. The filter cake was washed with DCM. The filtrate was concentrated, and the residue was purified on silica eluted with 0 to 60% EtOAc in DCM to afford 1-(tetrahydro-2H-pyran-2-yl)-6-(tributyl-stannyl)-1H-pyrazolo[4,3-c]pyridine as a clear oil (7.1768 g, 74%).

Step C: 6-(6-methylpyrazin-2-yl)-1-tetrahydropyran-2-yl-pyrazolo[4,3-c]pyridine

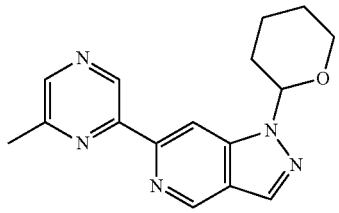 [SMILES: Cc1cncc(-c2cc3c(cn2)cnn3C2CCCCO2)n1]

A mixture of tributyl-(1-tetrahydropyran-2-ylpyrazolo[4,3-c]pyridin-6-yl)stannane (7.139 mmol; 3514.5 mg), 2-chloro-6-methyl-pyrazine (10.71 mmol; 1377 mg), tricyclohexylphosphine; (0.5140 mmol; 144.1 mg) and tris(dibenzylideneacetone)dipalladium (0) (0.2142 mmol; 196.1 mg) in N,N-Dimethylacetamide (15 mL) was purged with Argon for 1 min. The reaction mixture was sealed in a pressure vial and heated at 130° C. overnight. The mixture was partitioned between EtOAc and water. The organic layer was concentrated and the residue was purified on silica eluted with 0 to 100% EtOAc in DCM to afford 6-(6-methylpyrazin-2-yl)-1-tetrahydropyran-2-yl-pyrazolo[4,3-c]pyridine as a clear oil (1.3608 g, 60%).

Step D: 6-(6-methylpyrazin-2-yl)-1H-pyrazolo[4,3-c]pyridine

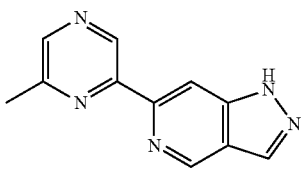 [SMILES: Cc1cncc(-c2cc3[nH]ncc3cn2)n1]

To a solution of 6-(6-methylpyrazin-2-yl)-1-tetrahydropyran-2-yl-pyrazolo[4,3-c]pyridine (4.29 mmol; 1360.8 mg) in Methanol (10 mL) was added hydrochloric acid, 4.0 M in 1,4-Dioxane (5 mL). The resulting mixture was stirred at room temperature overnight.

The mixture was concentrated and the residue was purified on silica eluted with 0 to 5% MeOH in DCM to afford 6-(6-methylpyrazin-2-yl)-1H-pyrazolo[4,3-c]pyridine as an off-white solid (759.5 mg, 88%).

Step E: 1-(5-chloro-6-fluoro-2-pyridyl)-6-(6-methylpyrazin-2-yl)pyrazolo[4,3-c]pyridine

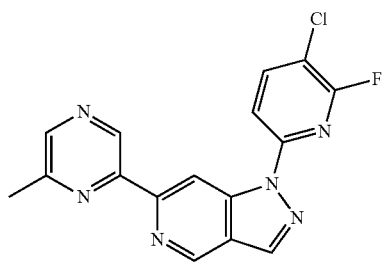 [SMILES: Cc1cncc(-c2cc3c(cn2)cnn3-c2ccc(Cl)c(F)n2)n1]

To a mixture of 6-(6-methylpyrazin-2-yl)-1H-pyrazolo[4,3-c]pyridine (1.325 mmol; 279.9 mg) and 6-bromo-3-chloro-2-fluoro-pyridine (1.988 mmol; 418.3 mg) in 1,4-Dioxane (10 mL) under Argon was added cesium carbonate (3.975 mmol; 1295 mg), Xantphos (0.2253 mmol; 130.4 mg), and tris(dibenzylideneacetone)dipalladium(0) (0.1325 mmol; 121.3 mg). The resulting mixture was sealed in a pressure tube and heated at 105° C. overnight. The reaction mixture cooled to room temperature, and filtered through Celite. The filter cake was washed with DCM. The filtrate was concentrated. The residue was purified on silica eluted with 0 to 6% MeOH in DCM to afford 1-(5-chloro-6-fluoro-2-pyridyl)-6-(6-methylpyrazin-2-yl)pyrazolo[4,3-c]pyridine (217.1 mg, 48%).

Step F: tert-butyl N-[(3S)-1-[3-chloro-6-[6-(6-methylpyrazin-2-yl)pyrazolo[4,3-c]pyridin-1-yl]-2-pyridyl]-3-piperidyl]carbamate

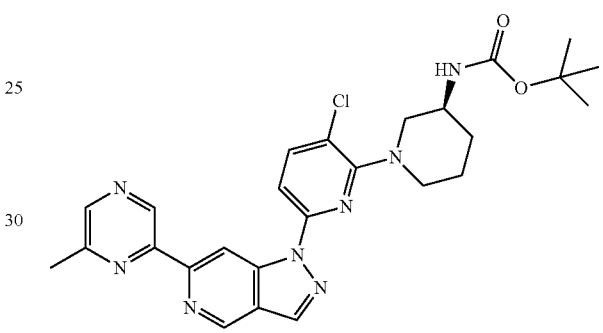

A mixture of 1-(5-chloro-6-fluoro-2-pyridyl)-6-(6-methylpyrazin-2-yl)pyrazolo[4,3-c]pyridine; (0.6372 mmol; 217.1 mg), tert-butyl N-[(3S)-3-piperidyl]carbamate (1.912 mmol; 382.9 mg), and N-Methylmorpholine (3.186 mmol; 326 mg; 0.354 mL) in 1-methyl-2-pyrrolidinone (3 mL) in a sealed pressure vial was heated at 100° C. overnight. The mixture was poured into water. The precipitate was collect by filtration, then purified on silica eluted with 0 to 6% MeOH in DCM to afford tert-butyl N-[(3S)-1-[3-chloro-6-[6-(6-methylpyrazin-2-yl)pyrazolo[4,3-c]pyridin-1-yl]-2-pyridyl]-3-piperidyl]carbamate (229.4 mg, 69%).

Step G

To a solution of tert-butyl N-[(3S)-1-[3-chloro-6-[6-(6-methylpyrazin-2-yl)pyrazolo[4,3-c]pyridin-1-yl]-2-pyridyl]-3-piperidyl]carbamate (0.140 mmol; 72.7 mg) in Methanol (5 mL) was added hydrochloric acid, 4.0 M in 1,4-Dioxane (5 mL). The resulting mixture was stirred at room temperature overnight. The mixture was concentrated and the residue was purified by reverse phase HPLC to afford 176 as an off-white solid (23.3 mg, 40%). $^1$H NMR (400 MHz, DMSO) δ 9.67-9.61 (s, 1H), 9.47-9.42 (s, 1H), 9.34-9.28 (s, 1H), 8.71-8.67 (s, 1H), 8.64-8.61 (s, 1H), 8.01-7.94 (d, J=8.4 Hz, 1H), 7.57-7.51 (d, J=8.4 Hz, 1H), 3.91-3.83 (d, J=8.8 Hz, 1H), 3.81-3.72 (d, J=12.3 Hz, 1H), 3.25-3.19 (m, 1H), 2.97-2.89 (m, 1H), 2.77-2.71 (dd, J=11.9, 9.1 Hz, 1H), 2.67-2.62 (d, J=8.6 Hz, 3H), 1.98-1.87 (dd, J=16.2, 6.5 Hz, 2H), 1.84-1.40 (dd, J=32.9, 22.1 Hz, 3H), 1.36-1.23 (td, J=13.5, 4.6 Hz, 1H); MS (ESI) m/z: 421.1 [M+H]$^+$

Example 77

6-[1-(6-piperazin-1-yl-2-pyridyl)pyrazolo[4,3-c]pyridin-6-yl]pyrazine-2-carbonitrile 177

Following the procedures in preparation of EXAMPLE 23, 177 was obtained. MS (ESI) m/z: 384.1. ¹H NMR (400 MHz, DMSO) δ 9.89 (s, 1H), 9.61 (s, 1H), 9.38 (s, 1H), 9.29 (s, 1H), 8.71 (s, 1H), 7.78 (t, J=8.1 Hz, 1H), 7.30 (d, J=7.7 Hz, 1H), 6.82 (d, J=8.5 Hz, 1H), 3.68-3.60 (m, 4H), 3.02-2.95 (m, 4H).

Example 78

1-(6-(1,4-Diazepan-1-yl)pyrazin-2-yl)-6-(1-(2,2,2-trifluoroethyl)-1H-pyrazol-4-yl)-1H-pyrazolo[4,3-c]pyridine 178

Step A: tert-Butyl 4-(6-Bromopyrazin-2-yl)-1,4-diazepane-1-carboxylate

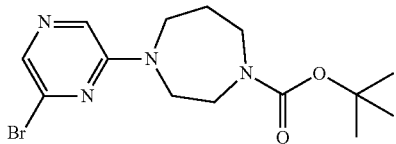 [SMILES: CC(C)(C)OC(=O)N1CCCN(c2cncc(Br)n2)CC1]

A mixture of 2,6-dibromopyrazine (0.47 g, 2 mmol), tert-butyl 1,4-diazepane-1-carboxylate (0.4 g, 2 mmol), and DIPEA (0.78 g, 6 mmol) in EtOH (10 mL) was heated at 100° C. for 15 hours. The reaction mixture was concentrated under reduced pressure to give a residue. The residue was purified by silica gel chromatography using petroleum ether/ethyl acetate (5% to 50%) as eluting solvents to afford tert-butyl 4-(6-bromopyrazin-2-yl)-1,4-diazepane-1-carboxylate as colorless oil (0.5 g, 70%). MS (ESI) m/z: 357 [M+H]⁺.

Step B: tert-Butyl 4-(6-(6-Chloro-1H-pyrazolo[4,3-c]pyridin-1-yl)pyrazin-2-yl)-1,4-diazepane-1-carboxylate

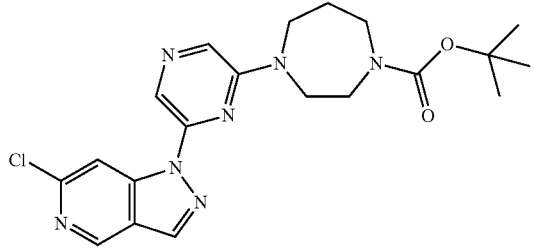 [SMILES: CC(C)(C)OC(=O)N1CCCN(c2cncc(-n3ncc4cnc(Cl)cc43)n2)CC1]

To a mixture of tert-butyl 4-(6-bromopyrazin-2-yl)-1,4-diazepane-1-carboxylate (0.45 g, 1.26 mmol) and 6-chloro-1H-pyrazolo[4,3-c]pyridine (192 mg, 1.26 mmol) in dioxane (10 mL) was added CuI (19 mg, 0.1 mmol), N¹,N²-dimethylethane-1,2-diamine (6.3 mmol, 0.55 g), K₂CO₃ (3.78 mmol, 0.53 g). The reaction mixture was heated at 100° C., which was monitored by LCMS. After completion of the reaction, it was concentrated under reduced pressure. The crude material was purified by silica gel chromatography using petroleum ether/ethyl acetate (5% to 50%) as eluting solvents to afford tert-butyl 4-(6-(6-chloro-1H-pyrazolo[4,3-c]pyridin-1-yl)pyrazin-2-yl)-1,4-diazepane-1-carboxylate as yellow solid (0.4 g, 74%). MS (ESI) m/z: δ 430 [M+H]⁺.

Step C: tert-Butyl 4-(6-(6-(1H-Pyrazol-4-yl)-1H-pyrazolo[4,3-c]pyridin-1-yl)pyrazin-2-yl)-1,4-diazepane-1-carboxylate

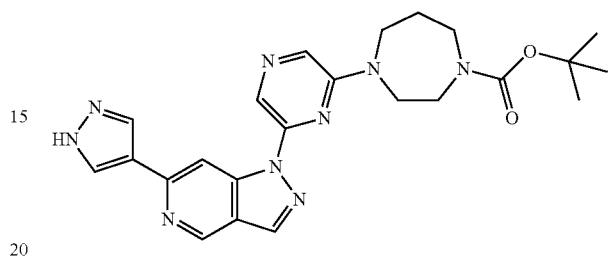

A suspension of tert-butyl 4-(6-(6-chloro-1H-pyrazolo[4,3-c]pyridin-1-yl)pyrazin-2-yl)-1,4-diazepane-1-carboxylate (400 mg, 0.93 mmol), 4-(4,4,5,5-tetramethyl-1,3,2-dioxaborolan-2-yl)-1H-pyrazole (271 mg, 1.4 mmol), Pd(dppf)Cl₂ (81 mg, 0.093 mmol) and a solution of Na₂CO₃ (2.0 M, 1.5 mL) in 1,4-dioxane (6 mL) under argon in a sealed vial was heated at 120° C. for 1 hour. The reaction mixture was filtered and the filtrate was concentrated under reduced pressure to give a residue. The residue was purified by silica gel chromatography using petroleum ether/ethyl acetate (10% to 60%) as eluting solvents to afford tert-butyl 4-(6-(6-(1H-pyrazol-4-yl)-1H-pyrazolo[4,3-c]pyridin-1-yl)pyrazin-2-yl)-1,4-diazepane-1-carboxylate as yellow solid (180 mg, 42%). MS (ESI) m/z: 462 [M+H]⁺.

Step D: tert-Butyl 4-(6-(6-(1-(2,2,2-Trifluoroethyl)-1H-pyrazol-4-yl)-1H-pyrazolo[4,3-c]-pyridin-1-yl)pyrazin-2-yl)-1,4-diazepane-1-carboxylate

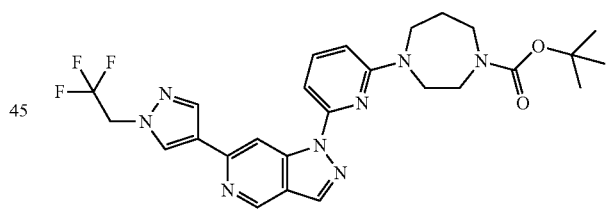

To a solution of tert-butyl 4-(6-(6-(1-(2,2,2-trifluoroethyl)-1H-pyrazol-4-yl)-1H-pyrazolo[4,3-c]pyridin-1-yl)pyrazin-2-yl)-1,4-diazepane-1-carboxylate (100 mg, 0.22 mmol) in DMF (10 mL) was added 2,2,2-trifluoroethyl trifluoromethanesulfonate (100 mg, 0.44 mmol). The reaction mixture was stirred at room temperature for 2 hours and was concentrated under reduced pressure. The residue was purified by silica gel chromatography using petroleum ether/ethyl acetate (10% to 60%) as eluting solvents to afford tert-butyl 4-(6-(6-(1-(2,2,2-trifluoroethyl)-1H-pyrazol-4-yl)-1H-pyrazolo[4,3-c]pyridin-1-yl)pyrazin-2-yl)-1,4-diazepane-1-carboxylate as white solid (80 mg, 80%). MS (ESI) m/z: 544 [M+H]⁺.

Step E

To a solution of tert-butyl 4-(6-(6-(1-(2,2,2-trifluoroethyl)-1H-pyrazol-4-yl)-1H-pyrazolo[4,3-c]pyridin-1-yl)

pyrazin-2-yl)-1,4-diazepane-1-carboxylate (80 mg, 0.147 mmol) in 1,4-dioxane (6 mL) was added a solution of HCl/1,4-dioxane (3.8 M, 6 mL). The reaction mixture was stirred at room temperature for 2 hours and concentrated under reduced pressure to give a crude product. The crude was purified by reverse phase preparative HPLC to afford 178 as a white solid (55 mg, 84%). $^1$H NMR (500 MHz, DMSO-d$_6$) δ (ppm) 9.17 (s, 1H), 8.60 (s, 1H), 8.54 (s, 1H), 8.37 (d, J=6.0 Hz, 2H), 8.09 (s, 1H), 8.02 (s, 1H), 5.26 (Q, J=9.2 Hz, 2H), 3.86 (s, 2H), 3.81 (s, 2H), 3.01 (t, J=5.5 Hz, 2H), 2.76 (t, J=5.5 Hz, 2H), 1.89 (t, J=5.5 Hz, 2H). MS (ESI) m/z: 444 [M+H]$^+$.

Example 79

1-(2-(1,4-Diazepan-1-yl)pyrimidin-4-yl)-6-(1-(2,2,2-trifluoroethyl)-1H-pyrazol-4-yl)-1H-pyrazolo-[4,3-c]pyridine 179

Following the procedures as described in Example 78 and starting with 2,4-dichloropyrimidine, 179 was obtained as a white solid (80 mg, 9.5%) over five steps. $^1$H NMR (500 MHz, DMSO-d$_6$) δ (ppm) 9.18 (s, 1H), 8.68 (s, 1H), 8.64 (s, 1H), 8.45 (d, J=4.5 Hz, 1H), 8.39 (s, 1H), 8.04 (s, 1H), 7.12 (d, J=5.0 Hz, 1H), 5.27 (Q, J=9.2 Hz, 2H), 3.98 (s, 2H), 3.89 (s, 2H), 3.13 (s, 1H), 2.95 (s, 1H), 2.82 (s, 2H), 2.01 (s, 1H), 1.81 (s, 1H). MS (ESI) m/z: 444 [M+H]$^+$.

Example 80

1-(6-(1,4-Diazepan-1-yl)pyridin-2-yl)-6-(1H-pyrazol-4-yl)-1H-pyrazolo[4,3-c]pyridine 180

Following the procedures as described in Example 61 and starting with tert-butyl 4-(6-(6-(1H-pyrazol-4-yl)-1H-pyrazolo[4,3-c]pyridin-1-yl)pyridin-2-yl)-1,4-diazepane-1-carboxylate, 180 was obtained as a yellow solid (62 mg, 65.9%) over one step. $^1$H NMR (500 MHz, MeOD) δ (ppm) 9.084-9.086 (d, J=1 Hz, 1H), 8.68 (s, 1H), 8.41 (s, 1H), 8.15 (s, 2H), 7.77-7.80 (t, J=16.5 Hz, 1H), 7.36-7.38 (d, J=8 Hz, 1H), 6.71-6.73 (d, J=8 Hz, 1H), 4.16-4.19 (t, J=11 Hz, 2H), 3.97-3.99 (t, J=12.5 Hz, 2H), 3.51-3.53 (t, J=11 Hz, 2H), 3.37-3.39 (t, J=11 Hz, 2H), 2.29-2.31 (t, J=11 Hz, 2H), 1.32-1.34 (t, J=14.5 Hz, 2H); MS (ESI) m/z: 361 [M+H]$^+$.

Example 81

(S)-1-(3-cyclopropyl-6-(6-(6-methylpyrazin-2-yl)-1H-pyrazolo[4,3-c]pyridin-1-yl)pyridin-2-yl)piperidin-3-amine 181

Step A: tert-butyl N-[(3S)-1-[3-cyclopropyl-6-[6-(6-methylpyrazin-2-yl)pyrazolo[4,3-c]pyridin-1-yl]-2-pyridyl]-3-piperidyl]carbamate

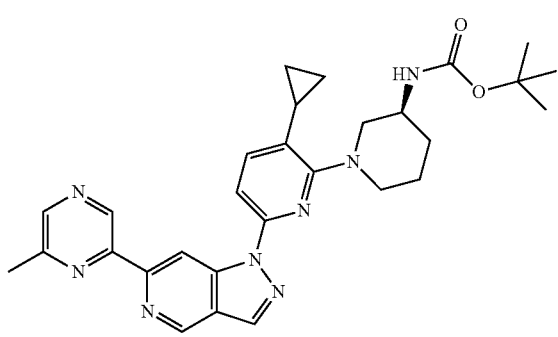 [SMILES: Cc1cncc(-c2cc3c(cn2)cnn3-c2ccc(C3CC3)c(N3CCC[C@H](NC(=O)OC(C)(C)C)C3)n2)n1]

A mixture of tert-butyl N-[(3S)-1-[3-chloro-6-[6-(6-methylpyrazin-2-yl)pyrazolo[4,3-c]pyridin-1-yl]-2-pyridyl]-3-piperidyl]carbamate (0.2225 mmol; 115.9 mg), potassium cyclopropyl trifluoroborate (0.3337 mmol; 50.90 mg), butyldi-1-adamantylphosphine (0.06674 mmol; 25.19 mg), cesium carbonate (0.6674 mmol; 217.4 mg) and palladium (II) acetate (0.04449 mmol; 9.994 mg) in water (0.5 mL) and Toluene (4.5 mL) was purged with Argon for 1 minute. The reaction mixture in a pressure tube was stirred at 105° C. for 3 days. The layers were separated. The organic later was concentrated. The residue was purified on silica eluted with 0 to 5% MeOH in DCM to afford tert-butyl N-[(3S)-1-[3-cyclopropyl-6-[6-(6-methylpyrazin-2-yl)pyrazolo[4,3-c]pyridin-1-yl]-2-pyridyl]-3-piperidyl]carbamate (129 mg, ~100%).

Step B

To a solution of tert-butyl N-[(3S)-1-[3-cyclopropyl-6-[6-(6-methylpyrazin-2-yl)pyrazolo[4,3-c]pyridin-1-yl]-2-pyridyl]-3-piperidyl]carbamate (0.2224 mmol; 117.1 mg) in Methanol (5 mL) was added hydrochloric acid, 4.0 M in 1,4-Dioxane (5 mL). The resulting mixture was stirred at room temperature overnight. The mixture was concentrated and the residue was purified by reverse phase HPLC to afford 181 as an off-white solid (46.0 mg, 49%). $^1$H NMR (400 MHz, DMSO) δ 9.75-9.71 (s, 1H), 9.47-9.44 (s, 1H), 9.33-9.29 (s, 1H), 8.67-8.61 (d, J=9.6 Hz, 2H), 7.55-7.51 (d, J=8.2 Hz, 1H), 7.49-7.43 (d, J=8.2 Hz, 1H), 3.86-3.78 (d, J=10.8 Hz, 1H), 3.65-3.58 (s, 1H), 3.16-3.09 (s, 1H), 2.89-2.81 (m, 1H), 2.68-2.65 (s, 3H), 2.12-2.04 (m, 1H), 2.02-1.93 (d, J=8.9 Hz, 2H), 1.81-1.69 (m, 1H), 1.48-1.37 (d, J=8.7 Hz, 1H), 1.20-1.11 (m, 1H), 1.09-0.99 (m, 1H), 0.91-0.84 (m, 1H), 0.75-0.67 (s, 1H); MS (ESI) m/z: 427.2 [M+H]$^+$ Example 82

6-methyl-1-[6-[6-(6-methylpyrazin-2-yl)pyrazolo[4,3-c]pyridin-1-yl]-2-pyridyl]piperidin-3-amine 182

Compound 182 was obtained as the second peak from SFC chiral separation of Example 71. MS (ESI) m/z: 401.2. 1H NMR (400 MHz, DMSO) δ 9.48 (s, 1H), 9.45 (s, 1H), 9.33 (s, 1H), 8.67 (s, 1H), 8.62 (s, 1H), 7.77 (t, J=8.1 Hz, 1H), 7.23 (d, J=7.7 Hz, 1H), 6.75 (d, J=8.5 Hz, 1H), 5.03 (s, 1H), 4.09 (d, J=8.8 Hz, 1H), 2.80 (dd, J=19.2, 10.2 Hz, 2H), 2.64 (s, 3H), 1.94-1.72 (m, 3H), 1.66-1.51 (m, 1H), 1.27 (d, J=6.8 Hz, 3H).

Example 83

6-methyl-1-[6-[6-(6-methylpyrazin-2-yl)pyrazolo[4,3-c]pyridin-1-yl]-2-pyridyl]piperidin-3-amine 183

Compound 183 was obtained as the first peak from SFC chiral separation of Example 71. MS (ESI) m/z: 401.2. 1H NMR (400 MHz, DMSO) δ 9.48 (s, 1H), 9.45 (s, 1H), 9.33 (s, 1H), 8.67 (s, 1H), 8.62 (s, 1H), 7.76 (t, J=8.1 Hz, 1H), 7.22 (d, J=7.7 Hz, 1H), 6.75 (d, J=8.5 Hz, 1H), 5.01 (s, 1H), 4.13-3.92 (m, 2H), 2.81-2.73 (m, 2H), 2.65 (s, 3H), 1.96-1.69 (m, 2H), 1.55 (dd, J=14.9, 8.1 Hz, 1H), 1.26 (d, J=6.8 Hz, 3H).

Example 84

1-[6-(5-methyl-1 4-diazepan-1-yl)-2-pyridyl]-6-(6-methylpyrazin-2-yl)pyrazolo[4,3-c]pyridine 184

Following the procedures in preparation of EXAMPLE 23, 184 was obtained. MS (ESI) m/z: 401.2. 1H NMR (400

MHz, DMSO) δ 9.65 (s, 1H), 9.45 (s, 1H), 9.31 (s, 1H), 8.65 (s, 1H), 8.62 (s, 1H), 7.70 (t, J=8.1 Hz, 1H), 7.20 (d, J=7.7 Hz, 1H), 6.59 (d, J=8.5 Hz, 1H), 4.01 (d, J=12.7 Hz, 2H), 3.86-3.73 (m, 1H), 3.62 (t, J=10.1 Hz, 1H), 3.20 (d, J=13.9 Hz, 1H), 2.98-2.87 (m, 1H), 2.71-2.62 (m, 1H), 2.61 (s, 3H), 2.13-2.02 (m, 1H), 1.54-1.40 (m, 1H), 1.00 (d, J=6.4 Hz, 3H).

Example 85

1-[6-(3-methylpiperazin-1-yl)-2-pyridyl]-6-(6-methylpyrazin-2-yl)pyrazolo[4,3-c]pyridine 185

Compound 185 was obtained as the second peak from SFC chiral separation of Example 69. MS (ESI) m/z: 387.2. 1H NMR (400 MHz, DMSO) δ 9.56 (s, 1H), 9.47 (s, 1H), 9.32 (s, 1H), 8.66 (s, 1H), 8.63 (s, 1H), 7.77 (t, J=8.1 Hz, 1H), 7.25 (d, J=7.7 Hz, 1H), 6.82 (d, J=8.5 Hz, 1H), 4.39 (d, J=12.3 Hz, 1H), 4.19 (d, J=11.3 Hz, 1H), 3.12 (d, J=11.8 Hz, 1H), 3.07-2.98 (m, 1H), 2.94-2.82 (m, 2H), 2.63 (s, 3H), 1.06 (d, J=6.3 Hz, 3H).

Example 86

(S)-1-(3-methoxy-6-(6-(6-methylpyrazin-2-yl)-1H-pyrazolo[4,3-c]pyridin-1-yl)pyridin-2-yl)piperidin-3-amine 186

Step A: tert-butyl N-[(3S)-1-(6-bromo-3-methoxy-2-pyridyl)-3-piperidyl]carbamate

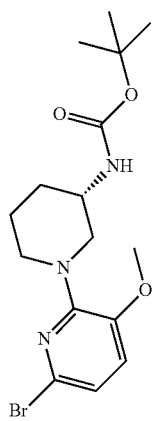 [SMILES: COc1ccc(Br)nc1N1CCC[C@H](NC(=O)OC(C)(C)C)C1]

A mixture of 6-bromo-2-fluoro-3-methoxy-pyridine (2.030 mmol; 418.1 mg), tert-butyl N-[(3S)-3-piperidyl]carbamate (3.044 mmol; 609.7 mg), and N-Methylmorpholine (6.089 mmol; 622 mg; 0.676 mL) in 1-methyl-2-pyrrolidinone (5 mL) in a sealed pressure vial was heated at 120° C. overnight. The mixture was poured into water, and extracted with EtOAc. The organic layer was concentrated. The residue was purified on silica eluted with 0 to 40% EtOAc in Heptane to afford tert-butyl N-[(3S)-1-(6-bromo-3-methoxy-2-pyridyl)-3-piperidyl]carbamate (743.5 mg, 95%).

Step B: tert-butyl N-[(3S)-1-[3-methoxy-6-[6-(6-methylpyrazin-2-yl)pyrazolo[4,3-c]pyridin-1-yl]-2-pyridyl]-3-piperidyl]carbamate

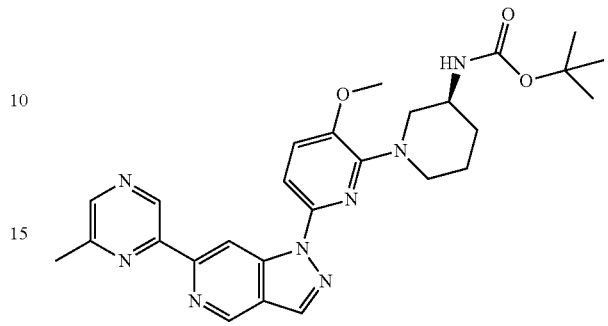

A mixture of 6-(6-methylpyrazin-2-yl)-1H-pyrazolo[4,3-c]pyridine (0.4734 mmol; 100.0 mg), tert-butyl N-[(3S)-1-(6-bromo-3-methoxy-2-pyridyl)-3-piperidyl]carbamate (0.5681 mmol, 219.5 mg), N,N'-Dimethylethylenediamine (0.4734 mmol; 41.73 mg; 0.0471 mL), copper iodide (0.4734 mmol; 91.08 mg), and potassium carbonate (0.5208 mmol; 72.70 mg) in 1,4-Dioxane (10 mL) was purged with Argon, then sealed and stirred at 100° C. overnight. The mixture was cooled to room temperature, and then filtered through Celite. The filtrate was concentrated; the residue was purified on silica eluted with 0 to 100% EtOAc in DCM to afford tert-butyl N-[(3S)-1-[3-methoxy-6-[6-(6-methylpyrazin-2-yl)pyrazolo[4,3-c]pyridin-1-yl]-2-pyridyl]-3-piperidyl]carbamate as a tan solid (142.5 mg, 58%).

Step C

To a solution of tert-butyl N-[(3S)-1-[3-methoxy-6-[6-(6-methylpyrazin-2-yl)pyrazolo[4,3-c]pyridin-1-yl]-2-pyridyl]-3-piperidyl]carbamate (0.2758 mmol; 142.5 mg) in Methanol (10 mL) was added hydrochloric acid, 4.0 M in 1,4-Dioxane (5 mL). The resulting mixture was stirred at room temperature overnight. The mixture was concentrated and the residue was purified by reverse phase HPLC to afford 186 as an off-white solid (105.6 mg, 91%). $^1$H NMR (400 MHz, DMSO) δ 9.66-9.62 (s, 1H), 9.48-9.44 (s, 1H), 9.33-9.28 (s, 1H), 8.65-8.61 (d, J=3.5 Hz, 2H), 7.54-7.45 (dd, J=21.6, 8.5 Hz, 2H), 4.02-3.96 (d, J=10.3 Hz, 1H), 3.90-3.84 (d, J=11.7 Hz, 4H), 3.03-2.96 (d, J=9.0 Hz, 1H), 2.89-2.82 (m, 1H), 2.65-2.61 (s, 3H), 1.98-1.86 (t, J=10.6 Hz, 2H), 1.78-1.67 (d, J=10.2 Hz, 1H), 1.45-1.35 (dd, J=19.2, 8.9 Hz, 1H); MS (ESI) m/z: 417.2 [M+H]$^+$

Example 87

1-[6-[6-(6-methylpyrazin-2-yl)pyrazolo[4,3-c]pyridin-1-yl]-2-pyridyl]azepan-3-amine 187

Following the procedures in preparation of EXAMPLE 23, 187 was obtained. MS (ESI) m/z: 401.2. 1H NMR (400 MHz, DMSO) δ 9.64 (s, 1H), 9.46 (s, 1H), 9.32 (s, 1H), 8.66 (s, 1H), 8.62 (s, 1H), 7.73 (t, J=8.0 Hz, 1H), 7.21 (d, J=7.7 Hz, 1H), 6.73 (d, J=8.5 Hz, 1H), 4.39-4.29 (m, 1H), 4.06 (d, J=12.5 Hz, 1H), 2.63 (s, 3H), 2.11 (s, 1H), 1.76 (s, 3H), 1.44 (d, J=10.3 Hz, 1H), 1.27 (d, J=9.6 Hz, 1H).

Example 88 and 89

(R)-1-(6-(6-(1-(2,2,2-Trifluoroethyl)-1H-pyrazol-4-yl)-1H-pyrazolo[4,3-c]pyridin-1-yl)-pyridin-2-yl)-1,4-diazepan-6-ol 188 and (S)-1-(6-(6-(1-(2,2,2-Trifluoroethyl)-1H-pyrazol-4-yl)-1H-pyrazolo[4,3-c]pyridin-1-yl)-pyridin-2-yl)-1,4-diazepan-6-ol 189

Step A: 1-(6-Bromopyridin-2-yl)-1,4-diazepan-6-ol

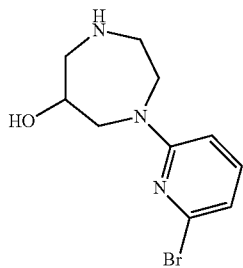 [SMILES: OC1CNCCN(c2cccc(Br)n2)C1]

A mixture of 2-bromo-6-fluoropyridine (477 mg, 2.7 mmol), 1,4-diazepan-6-ol (350 mg, 3 mmol), and DIPEA (1.94 g, 15 mmol) in ethanol (10 mL) was heated at 100° C. for 16 hours. After it was cooled, the reaction mixture was concentrated under reduced pressure. The residue was diluted with EtOAc (100 mL) and washed with brine. The organic layer was dried over $Na_2SO_4$ and concentrated under reduced pressure to afford 1-(6-bromopyridin-2-yl)-1,4-diazepan-6-ol as a colorless oil (400 mg, 48.9%). MS (ESI) m/z: 272 [M+H]$^+$.

Step B: tert-Butyl 4-(6-Bromopyridin-2-yl)-6-hydroxy-1,4-diazepane-1-carboxylate

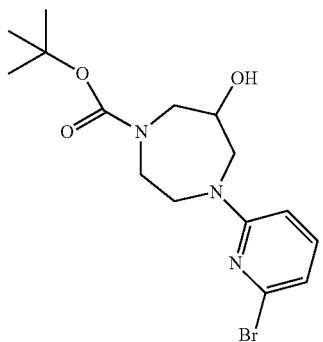 [SMILES: CC(C)(C)OC(=O)N1CCN(c2cccc(Br)n2)CC(O)C1]

A mixture of 1-(6-bromopyridin-2-yl)-1,4-diazepan-6-ol (400 mg, 1.47 mmol), $Boc_2O$ (354 mg, 1.62 mmol) and $Et_3N$ (157 mg, 1.55 mmol) in DCM (10 mL) was stirred at room temperature for 16 hours. The reaction mixture was washed with brine, dried over $Na_2SO_4$, and concentrated under reduced pressure to afford tert-butyl 4-(6-bromopyridin-2-yl)-6-hydroxy-1,4-diazepane-1-carboxylate as a colorless oil (500 mg, 91%). MS (ESI) m/z: 372 [M+H]$^+$.

Step C: tert-Butyl 4-(6-(6-Chloro-1H-pyrazolo[4,3-c]pyridin-1-yl)pyridine-2-yl)-6-hydroxy-1,4-diazepane-1-carboxylate

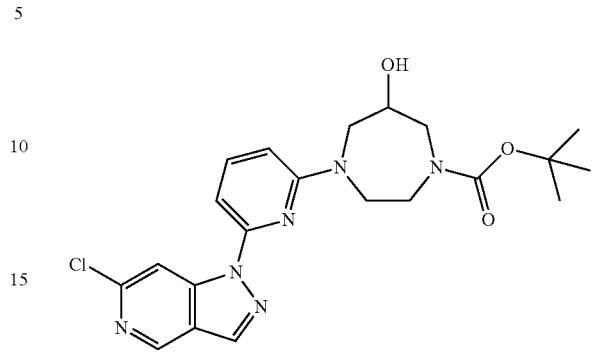

To a mixture of tert-butyl 4-(6-bromopyridin-2-yl)-6-hydroxy-1,4-diazepane-1-carboxylate (550 mg, 1.48 mmol) and 6-chloro-1H-pyrazolo[4,3-c]pyridine (207 mg, 1.34 mmol) in 1,4-dioxane (20 mL) was added CuI (102 mg, 0.54 mmol), $K_2CO_3$ (743 g, 5.4 mmol), and $N^1,N^2$-dimethylethane-1,2-diamine (95 mg, 1.08 mmol). The reaction mixture was heated at 100° C. for 3 hours, which was monitored by LCMS. After completion of the reaction, it was concentrated under reduced pressure. The crude was purified by silica gel chromatography using petroleum ether/EtOAc (2/1) as eluting solvents to afford tert-butyl 4-(6-(6-chloro-1H-pyrazolo[4,3-c]pyridin-1-yl)pyridin-2-yl)-6-hydroxy-1,4-diazepane-1-carboxylate as a light yellow solid (160 mg, 24.3%). MS (ESI) m/z: 445[M+H]$^+$.

Step D: tert-Butyl 4-(6-(6-(1H-Pyrazol-4-yl)-1H-pyrazolo[4,3-c]pyridin-1-yl)pyridin-2-yl)-6-hydroxy-1,4-diazepane-1-carboxylate

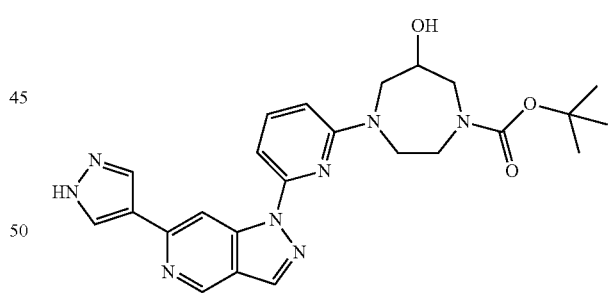

A suspension of tert-butyl 4-(6-(6-chloro-1H-pyrazolo[4,3-c]pyridin-1-yl)Pyridine-2-yl)-6-hydroxy-1,4-diazepane-1-carboxylate (160 mg, 0.36 mmol), 4-(4,4,5,5-tetramethyl-1,3,2-dioxaborolan-2-yl)-1H-pyrazole (140 mg, 0.72 mmo), Pd(dppf)$Cl_2$ (147 mg, 0.18 mmol), and aq. $Na_2CO_3$ (2.0 M, 1 mL) in 1,4-dioxane (10 mL) under nitrogen was heated at 100° C. for 16 hours. The reaction mixture was filtered and the filtrate was concentrated under reduced pressure. The residue was purified by silica gel chromatography using EtOAc as eluting solvent to afford tert-butyl 4-(6-(6-(1H-pyrazol-4-yl)-1H-pyrazolo[4,3-c]pyridin-1-yl)pyridin-2-yl)-6-hydroxy-1,4-diazepane-1-carboxylate as a yellow solid (60 mg, 35%). MS (ESI) m/z: 477 [M+H]$^+$.

Step E: tert-Butyl(±)-6-Hydroxy-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate

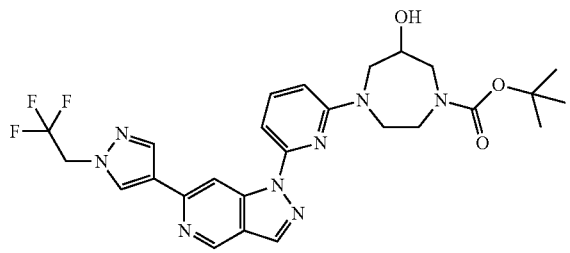 [SMILES: CC(C)(C)OC(=O)N1CCN(c2cccc(-n3ncc4cnc(-c5cnn(CC(F)(F)F)c5)cc43)n2)CC(O)C1]

A suspension of tert-butyl 4-(6-(6-(1H-pyrazol-4-yl)-1H-pyrazolo[4,3-c]pyridin-1-yl)pyridin-2-yl)-6-hydroxy-1,4-diazepane-1-carboxylate (150 mg, 0.32 mmol), 2,2,2-trifluoroethyl trifluoromethanesulfonate (110 mg, 0.48 mmol), and K$_2$CO$_3$ (87 mg, 0.64 mmol) in DMF (10 mL) was stirred at room temperature for 18 hours, which was monitored by LCMS. After completion of the reaction, the reaction mixture was quenched with EtOAc (100 mL), washed with brine (50 mL), dried over MgSO$_4$, concentrated under reduced pressure. The residue was purified by silica gel chromatography using petroleum ether/EtOAc (1/1) as eluting solvents to afford tert-butyl(±)-6-hydroxy-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate as a white solid (82 mg, 46.5%). MS (ESI) m/z: 559 [M+H]$^+$.

Step F: tert-Butyl(R)-6-Hydroxy-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate and tert-Butyl(S)-6-Hydroxy-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate

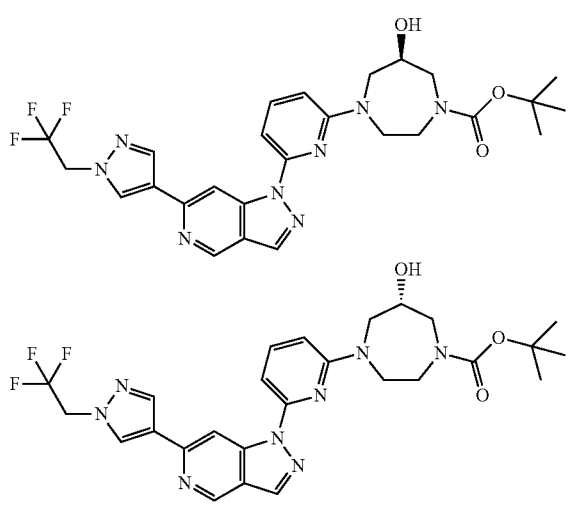

tert-Butyl(±)-6-hydroxy-4-(6-(6-(1-(2,2,2-trifluoroethyl)-1H-pyrazol-4-yl)-1H-pyrazolo-[4,3-c]pyridin-1-yl)pyridin-2-yl)-1,4-diazepane-1-carboxylate was separated by chiral preparative HPLC to afford tert-butyl(S)-6-hydroxy-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (70 mg) and tert-butyl(R)-6-hydroxy-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (70 mg).

Step G

A mixture of tert-butyl(S)-6-hydroxy-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (70 mg, 0.13 mmol) in HCl/MeOH (4.0 M, 10 mL) was stirred at room temperature for 3 hours, which was monitored by LCMS. After completion of the reaction, the reaction mixture was concentrated under reduced pressure. The crude material was purified by reverse phase prep-HPLC to afford (R)-1-(6-(6-(1-(2,2,2-trifluoroethyl)-1H-pyrazol-4-yl)-1H-pyrazolo[4,3-c]pyridine-1-yl)pyridin-2-yl)-1,4-diazepan-6-ol 188 as a white solid (30 mg, 52.6%). $^1$H NMR (500 MHz, DMSO-d$_6$) δ (ppm) 9.16 (s, 1H), 8.74 (s, 1H), 8.55 (s, 1H), 8.49 (s, 1H), 8.21 (s, 1H), 7.69 (t, J=16 Hz, 1H), 7.17 (d, J=7.5 Hz, 1H), 6.66 (d, J=8 Hz, 1H), 5.18-5.24 (m, 2H), 4.93 (d, J=5.5 Hz, 1H), 3.96 (t, J=8.5 Hz, 1H), 3.88 (m, 2H), 3.56-3.64 (m, 2H), 2.98 (t, J=10.5 Hz, 2H), 2.80-2.84 (m, 1H), 2.64-2.72 (m, 1H); MS (ESI) m/z: 459 [M+H]$^+$.

Step H

Following the procedures as described in Step G and starting with tert-butyl(R)-6-hydroxy-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate, 189 was obtained as a yellow solid (41 mg, 71.9%). $^1$H NMR (500 MHz, DMSO-d$_6$) δ (ppm) 9.16 (s, 1H), 8.74 (s, 1H), 8.55 (s, 1H), 8.49 (s, 1H), 8.21 (s, 1H), 7.69 (t, J=16 Hz, 1H), 7.17 (d, J=7.5 Hz, 1H), 6.66 (d, J=8 Hz, 1H), 5.18-5.24 (m, 2H), 4.93 (d, J=5.5 Hz, 1H), 3.96 (t, J=8.5 Hz, 1H), 3.88 (m, 2H), 3.56-3.64 (m, 2H), 2.98 (t, J=10.5 Hz, 2H), 2.80-2.84 (m, 1H), 2.64-2.72 (m, 1H); MS (ESI) m/z: 459 [M+H]$^+$.

Example 90

6-[6-(6-methylpyrazin-2-yl)pyrazolo[4,3-c]pyridin-1-yl]-N-(4-piperidyl)pyridin-2-amine 190

Following the procedures in preparation of EXAMPLE 23, 190 was obtained. MS (ESI) m/z: 387.2. 1H NMR (400 MHz, DMSO) δ 9.45 (s, 1H), 9.42 (s, 1H), 9.32 (s, 1H), 8.64 (s, 2H), 8.35 (s, 1H), 7.61 (t, J=8.0 Hz, 1H), 7.10 (d, J=7.7 Hz, 1H), 6.54 (d, J=8.2 Hz, 1H), 4.17 (s, 1H), 3.08-2.97 (m, 2H), 2.71 (d, J=9.7 Hz, 1H), 2.67 (s, 3H), 2.06 (s, 2H), 1.64 (d, J=9.1 Hz, 2H).

Example 91

1-[6-[(2R)-2-methylpiperazin-1-yl]-2-pyridyl]-6-(6-methylpyrazin-2-yl)pyrazolo[4,3-c]pyridine 191

Following the procedures in preparation of EXAMPLE 71, 191 was obtained. MS (ESI) m/z: 387.2. 1H NMR (400 MHz, DMSO) δ 9.52 (s, 1H), 9.48 (s, 1H), 9.32 (s, 1H), 8.66 (s, 1H), 8.62 (s, 1H), 7.76 (t, J=8.1 Hz, 1H), 7.26 (d, J=7.7 Hz, 1H), 6.75 (d, J=8.5 Hz, 1H), 4.60 (s, 1H), 4.06 (d, J=12.1 Hz, 1H), 3.19-3.08 (m, 3H), 2.99 (dt, J=19.3, 7.8 Hz, 2H), 2.84-2.74 (m, 1H), 2.64 (s, 3H), 1.28 (d, J=6.6 Hz, 3H).

Example 92

(3S,5S)-5-fluoro-1-[6-[6-(6-methylpyrazin-2-yl)pyrazolo[4,3-c]pyridin-1-yl]-2-pyridyl]piperidin-3-amine 192

Following the procedures in preparation of EXAMPLE 23, 192 was obtained. MS (ESI) m/z: 405.2.

Example 93

1-[6-(3-methylpiperazin-1-yl)-2-pyridyl]-6-(6-methylpyrazin-2-yl)pyrazolo[4,3-c]pyridine 193

Compound 193 was obtained as the first peak from SFC chiral separation of EXAMPLE 69. MS (ESI) m/z: 387.2. 1H NMR (400 MHz, DMSO) δ 9.54 (s, 1H), 9.47 (s, 1H), 9.33 (s, 1H), 8.67 (s, 1H), 8.64 (s, 1H), 7.80 (t, J=8.1 Hz, 1H), 7.28 (d, J=7.7 Hz, 1H), 6.86 (d, J=8.5 Hz, 1H), 4.43 (d, J=12.4 Hz, 1H), 4.25 (d, J=12.0 Hz, 1H), 3.17-3.06 (m, 1H), 3.03-2.91 (m, 2H), 2.83-2.71 (m, 1H), 2.64 (s, 3H), 1.12 (d, J=6.3 Hz, 3H).

Example 94

1-[6-[6-(6-methylpyrazin-2-yl)pyrazolo[4,3-c]pyridin-1-yl]-2-pyridyl]piperidin-4-amine 194

Following the procedures in preparation of EXAMPLE 23, 194 was obtained. MS (ESI) m/z: 387.2. 1H NMR (400 MHz, DMSO) δ 9.61 (s, 1H), 9.47 (s, 1H), 9.33 (s, 1H), 8.67 (s, 1H), 8.64 (s, 1H), 7.77 (t, J=8.1 Hz, 1H), 7.27 (d, J=7.7 Hz, 1H), 6.86 (d, J=8.5 Hz, 1H), 4.43 (d, J=13.3 Hz, 2H), 2.65 (s, 3H), 1.98 (d, J=10.4 Hz, 2H), 1.48 (dd, J=20.4, 11.1 Hz, 2H).

Example 95

2-methyl-1-[6-[6-(6-methylpyrazin-2-yl)pyrazolo[4,3-c]pyridin-1-yl]-2-pyridyl]piperidin-3-amine 195

Following the procedures in preparation of EXAMPLE 71, 195 was obtained. MS (ESI) m/z: 401.2. 1H NMR (400 MHz, DMSO) δ 9.47 (d, J=5.9 Hz, 2H), 9.33 (s, 1H), 8.66 (s, 1H), 8.62 (s, 1H), 7.78 (t, J=8.1 Hz, 1H), 7.21 (d, J=7.7 Hz, 1H), 6.77 (d, J=8.5 Hz, 1H), 4.66-4.55 (m, 1H), 4.42 (d, J=13.7 Hz, 1H), 3.10-3.00 (m, 2H), 2.64 (s, 3H), 1.92-1.83 (m, 1H), 1.65 (dt, J=21.6, 10.4 Hz, 3H), 1.19 (d, J=6.8 Hz, 3H).

Example 96

1-[6-[(2S)-2-methylpiperazin-1-yl]-2-pyridyl]-6-(6-methylpyrazin-2-yl)pyrazolo[4,3-c]pyridine 196

Following the procedures in preparation of EXAMPLE 71, 196 was obtained. MS (ESI) m/z: 387.1. 1H NMR (400 MHz, DMSO) δ 9.53 (s, 1H), 9.48 (s, 1H), 9.33 (s, 1H), 8.67 (s, 1H), 8.63 (s, 1H), 7.76 (t, J=8.1 Hz, 1H), 7.27 (d, J=7.7 Hz, 1H), 6.75 (d, J=8.5 Hz, 1H), 4.61 (s, 1H), 4.07 (d, J=12.0 Hz, 1H), 2.98 (dd, J=20.6, 13.3 Hz, 2H), 2.79 (t, J=10.8 Hz, 1H), 2.64 (s, 3H), 1.29 (d, J=6.6 Hz, 3H).

Example 97

1-(5-cyclopropyl-6-(1,4-diazepan-1-yl)pyridin-2-yl)-6-(6-methylpyrazin-2-yl)-1H-pyrazolo[4,3-c]pyridine 197

Following the procedures as described in EXAMPLE 81 and starting with 6-bromo-3-chloro-2-fluoropyridine, and tert-butyl 1,4-diazepane-1-carboxylate, 197 was obtained as an off-white solid (31.6 mg, 48%) over 4 steps. $^1$H NMR (400 MHz, DMSO) δ 9.66-9.61 (s, 1H), 9.48-9.42 (s, 1H), 9.33-9.27 (s, 1H), 8.66-8.60 (d, J=7.9 Hz, 2H), 7.53-7.49 (d, J=8.1 Hz, 1H), 7.39-7.34 (d, J=8.1 Hz, 1H), 3.94-3.84 (m, 4H), 3.10-3.06 (m, 2H), 2.91-2.84 (m, 2H), 2.65-2.61 (s, 3H), 2.03-1.91 (tt, J=11.5, 5.6 Hz, 3H), 1.05-0.92 (m, 3H), 0.78-0.71 (q, J=5.7 Hz, 2H); MS (ESI) m/z: 427.2 [M+H]$^+$

Example 98

(3S,5R)-5-fluoro-1-[6-[6-(6-methylpyrazin-2-yl)pyrazolo[4,3-c]pyridin-1-yl]-2-pyridyl]piperidin-3-amine 198

Following the procedures in preparation of EXAMPLE 23, 198 was obtained. MS (ESI) m/z: 405.1. 1H NMR (400 MHz, DMSO) δ 9.58 (s, 1H), 9.47 (s, 1H), 9.33 (s, 1H), 8.67 (s, 1H), 8.63 (s, 1H), 7.78 (t, J=8.1 Hz, 1H), 7.25 (d, J=7.7 Hz, 1H), 6.85 (d, J=8.5 Hz, 1H), 5.10 (d, J=47.2 Hz, 1H), 4.71 (t, J=13.0 Hz, 1H), 4.29 (d, J=9.9 Hz, 1H), 2.96-2.86 (m, 1H), 2.65 (s, 3H), 2.20 (d, J=11.5 Hz, 1H), 1.69 (dt, J=24.6, 11.4 Hz, 1H).

Example 99

2-[6-[6-(6-methylpyrazin-2-yl)pyrazolo[4,3-c]pyridin-1-yl]-2-pyridyl]-2 8-diazaspiro[4.5]decane 199

Following the procedures in preparation of EXAMPLE 23, 199 was obtained. MS (ESI) m/z: 427.1. 1H NMR (400 MHz, DMSO) δ 9.82 (s, 1H), 9.46 (s, 1H), 9.31 (s, 1H), 8.64 (d, J=6.3 Hz, 2H), 7.73 (t, J=8.0 Hz, 1H), 7.20 (d, J=7.7 Hz, 1H), 6.46 (d, J=8.3 Hz, 1H), 3.86 (s, 2H), 3.00-2.83 (m, 6H), 2.63 (s, 3H), 2.02 (t, J=7.0 Hz, 2H), 1.67 (s, 4H).

Example 100

8-[6-[6-(6-methylpyrazin-2-yl)pyrazolo[4,3-c]pyridin-1-yl]-2-pyridyl]-2 8-diazaspiro[4.5]decane 200

Following the procedures in preparation of EXAMPLE 23, 200 was obtained. MS (ESI) m/z: 427.1. 1H NMR (400 MHz, DMSO) δ 9.62 (s, 1H), 9.48 (s, 1H), 9.33 (s, 1H), 8.67 (s, 1H), 8.64 (s, 1H), 7.77 (t, J=8.1 Hz, 1H), 7.26 (d, J=7.7 Hz, 1H), 6.87 (d, J=8.5 Hz, 1H), 3.91-3.80 (m, 2H), 3.78-3.68 (m, 2H), 3.13-3.07 (m, 2H), 2.89 (s, 2H), 2.65 (s, 3H), 1.79 (t, J=7.2 Hz, 2H), 1.71 (t, J=5.3 Hz, 4H).

Example 101

(S)-2-(3-aminopiperidin-1-yl)-6-(6-(6-methyl-pyrazin-2-yl)-1H-pyrazolo[4,3-c]pyridin-1-yl)nicotinonitrile 201

Step A: 1-(5-bromo-6-fluoro-2-pyridyl)-6-chloro-pyrazolo[4,3-c]pyridine and 6-chloro-1-(6-fluoro-5-iodo-2-pyridyl)pyrazolo[4,3-c]pyridine

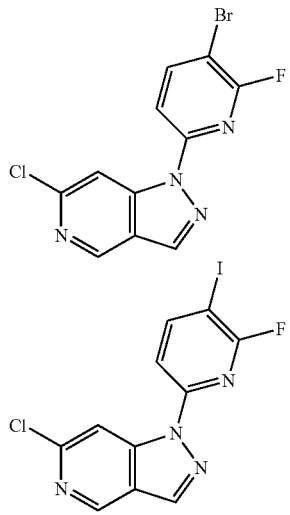

A mixture of 6-chloro-1H-pyrazolo[4,3-c]pyridine (2.045 mmol; 314.0 mg), 3-bromo-2-fluoro-6-iodo-pyridine (2.249 mmol; 679.0 mg), N,N'-Dimethylethylenediamine (0.2045 mmol; 18.02 mg; 0.0203 mL), copper iodide (2.045 mmol; 393.3 mg), and potassium carbonate (2.249 mmol; 314.0 mg) in 1,4-Dioxane (10 mL) was purged with Argon, then sealed and stirred at 100° C. for 20 hours. The mixture was cooled to room temperature, and then filtered through Celite. The filtrate was concentrated; the residue was purified on silica eluted with 0 to 100% EtOAc in Heptane to afford a mixture of 1-(5-bromo-6-fluoro-2-pyridyl)-6-chloro-pyrazolo[4,3-c]pyridine (~80 mg, 12%) and 6-chloro-1-(6-fluoro-5-iodo-2-pyridyl)pyrazolo[4,3-c]pyridine (~163 mg, 21%).

Step B: 6-(6-chloropyrazolo[4,3-c]pyridin-1-yl)-2-fluoro-pyridine-3-carbonitrile

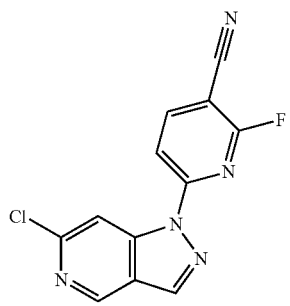 [SMILES: N#Cc1ccc(-n2ncc3cnc(Cl)cc32)nc1F]

A suspension of 1-(5-bromo-6-fluoro-2-pyridyl)-6-chloro-pyrazolo[4,3-c]pyridine (0.7437 mmol; 243.6 mg), zinc cyanide (0.4462 mmol; 53.47 mg; 0.0289 mL), and tetrakis(triphenylphosphine)palladium(0); (0.03719 mmol; 43.1 mg) in DMF (5 mL) was degassed and then heated at 120° C. for 3 hours. The mixture was cooled to room temperature, and then partitioned between EtOAc and brine. The organic layer was concentrated and the residue was purified on silica eluted with 0 to 60% EtOAc in Heptane to afford 6-(6-chloropyrazolo[4,3-c]pyridin-1-yl)-2-fluoro-pyridine-3-carbonitrile as a white solid (143.2 mg, 70%).

Step C: trimethyl-(6-methylpyrazin-2-yl)stannane

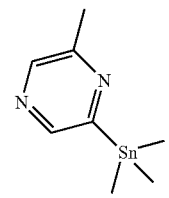

A mixture of 2-chloro-6-methyl-pyrazine (3.357 mmol; 431.6 mg), hexamethylditin (4.03 mmol; 1361 mg; 0.861 mL), and tetrakis(triphenylphosphine)palladium(0) (0.2756 mmol; 318.5 mg) in 1,4-Dioxane (10 mL) was purged with Argon. The resulting mixture was sealed in a pressure tube and heated at 100° C. overnight. The mixture was cooled to room temperature, and filtered through Celite. The filter cake was washed with DCM. The filtrate was concentrated to afford trimethyl-(6-methylpyrazin-2-yl)stannane, which was used without purification.

Step D: tert-butyl N-[(3S)-1-[3-cyano-6-[6-(6-methylpyrazin-2-yl)pyrazolo[4,3-c]pyridin-1-yl]-2-pyridyl]-3-piperidyl]carbamate

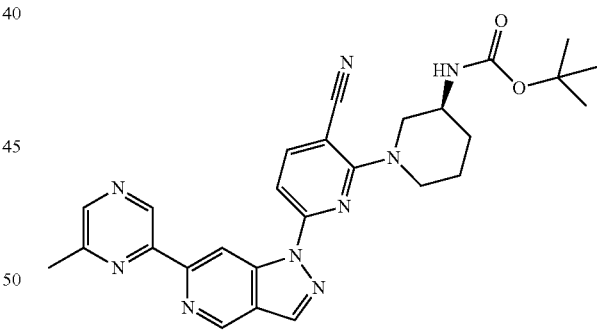

A mixture of [(3S)-1-[6-(6-chloropyrazolo[4,3-c]pyridin-1-yl)-3-cyano-2-pyridyl]-3-piperidyl]carbamic acid (0.5166 mmol; 205.5 mg), trimethyl-(6-methylpyrazin-2-yl)stannane (0.7749 mmol; 199.1 mg), and palladium(0)tetrakis (triphenylphosphine); (0.05166 mmol; 59.8 mg) in N,N-Dimethylacetamide (12 mL) was purged with Argon. The reaction mixture was sealed in a pressure vial and heated at 150° C. for 2 hours. The mixture was cooled to room temperature, and then partitioned between EtOAc and water. The organic layer was concentrated and the residue was purified on silica eluted with 0 to 5% MeOH in DCM to afford tert-butyl N-[(3S)-1-[3-cyano-6-[6-(6-methylpyrazin-2-yl)pyrazolo[4,3-c]pyridin-1-yl]-2-pyridyl]-3-piperidyl]carbamate as a yellow solid (248.6 mg, 94%).

Step E

To a solution of tert-butyl N-[(3S)-1-[3-cyano-6-[6-(6-methylpyrazin-2-yl)pyrazolo[4,3-c]pyridin-1-yl]-2-pyridyl]-3-piperidyl]carbamate (0.4859 mmol; 248.6 mg) in dichloromethane (8 mL) was added TFA (2 mL). The resulting mixture was stirred at room temperature for 4 hours. The mixture was concentrated and the residue was purified by reverse phase HPLC to afford 201 was obtained as an off-white solid (361.6 mg, 18%). $^1$H NMR (400 MHz, DMSO) δ 9.61-9.55 (s, 1H), 9.48-9.44 (s, 1H), 9.37-9.33 (s, 1H), 8.80-8.75 (s, 1H), 8.66-8.62 (s, 1H), 8.26-8.19 (m, 2H), 7.48-7.44 (d, J=8.4 Hz, 1H), 4.29-4.19 (dd, J=10.7, 6.9 Hz, 2H), 3.00-2.94 (m, 1H), 2.66-2.62 (s, 3H), 2.03-1.89 (dd, J=18.5, 10.2 Hz, 2H), 1.80-1.66 (m, 1H), 1.49-1.37 (m, 1H); MS (ESI) m/z: 412.2 [M+H]$^+$

Example 102

(5S)-5-amino-1-[6-[6-(6-methylpyrazin-2-yl)pyrazolo[4,3-c]pyridin-1-yl]-2-pyridyl]piperidin-2-one 202

Step A: tert-butyl N-[(3S)-1-[6-[6-(6-methylpyrazin-2-yl)pyrazolo[4,3-c]pyridin-1-yl]-2-pyridyl]-6-oxo-3-piperidyl]carbamate

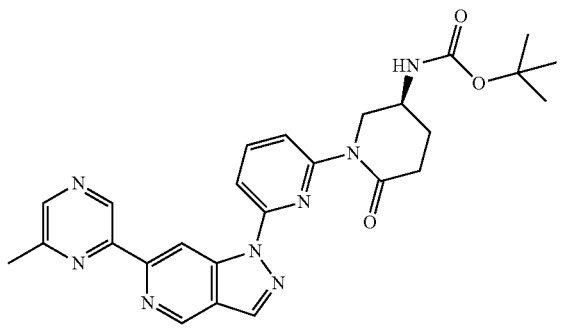 [SMILES: Cc1cncc(-c2cc3c(cn2)cnn3-c2cccc(N3C[C@@H](NC(=O)OC(C)(C)C)CCC3=O)n2)n1]

A mixture of 6-(6-methylpyrazin-2-yl)-1H-pyrazolo[4,3-c]pyridine (75 mg, 0.36 mmol), tert-butyl N-[(3S)-1-(6-bromo-2-pyridyl)-6-oxo-3-piperidyl]carbamate (158 mg, 0.426 mmol), tris(dibenzylideneacetone)dipalladium(0) (32 mg, 0.036 mmol), xantphos (42 mg, 0.071 mmol), and sodium tert-butoxide (70 mg, 0.71 mmol) in toluene 6.0 mL was stirred at 100° C. 18 h. The reaction was filtered through celite. The crude product was purified by flash chromatography (EtOAc/Heptane eluted at 100% EtOAc) to give tert-butyl N-[(3S)-1-[6-[6-(6-methylpyrazin-2-yl)pyrazolo[4,3-c]pyridin-1-yl]-2-pyridyl]-6-oxo-3-piperidyl]carbamate (50 mg) in 28% yield.

Step B

A solution of tert-butyl N-[(3S)-1-[6-[6-(6-methylpyrazin-2-yl)pyrazolo[4,3-c]pyridin-1-yl]-2-pyridyl]-6-oxo-3-piperidyl]carbamate (45 mg, 0.15 mmol) in hydrogen chloride (4 mol/l) in 1,4-dioxane (2.0 ml, 8.0 mmol) and 1,4-dioxane 2.0 mL was stirred at RT 18 h. The reaction was diluted with water then wash with EtOAc. The aqueous layer was basified with 1M NaOH to pH 10 and extracted with EtOAc. The organic layers was dried with sodium sulfate, filtered, and concentrated in vacuum. The crude product was submitted for reverse phase HPLC to give 202 (11 mg) in 18% yield. MS (ESI) m/z: 401.1. 1H NMR (400 MHz, DMSO) δ 9.61 (s, 1H), 9.47 (s, 1H), 9.35 (s, 1H), 8.73 (s, 1H), 8.63 (s, 1H), 8.04 (t, J=8.1 Hz, 1H), 7.83 (d, J=7.9 Hz, 1H), 7.76 (d, J=8.1 Hz, 1H), 4.24 (dd, J=12.2, 3.8 Hz, 1H), 3.94 (dd, J=12.3, 6.3 Hz, 1H), 3.49 (s, 1H), 2.75 (dd, J=12.2, 5.3 Hz, 1H), 2.69 (s, 3H), 2.63-2.55 (m, 1H), 2.10 (dd, J=13.0, 4.3 Hz, 1H), 1.85-1.72 (m, 1H).

Example 103

2-methyl-1-[6-[6-(6-methylpyrazin-2-yl)pyrazolo[4,3-c]pyridin-1-yl]-2-pyridyl]piperidin-3-amine 203

Compound 203 was obtained as the first peak from SFC chiral separation of EXAMPLE 71. MS (ESI) m/z: 401.1. 1H NMR (400 MHz, DMSO) δ 9.47 (d, J=7.6 Hz, 2H), 9.32 (s, 1H), 8.66 (s, 1H), 8.62 (s, 1H), 7.76 (t, J=8.1 Hz, 1H), 7.21 (d, J=7.7 Hz, 1H), 6.77 (d, J=8.5 Hz, 1H), 4.62-4.49 (m, 1H), 4.41 (d, J=13.7 Hz, 1H), 3.09-2.97 (m, 2H), 2.64 (s, 3H), 1.86 (d, J=13.0 Hz, 1H), 1.74-1.49 (m, 3H), 1.17 (d, J=6.8 Hz, 3H).

Example 104

2-methyl-1-[6-[6-(6-methylpyrazin-2-yl)pyrazolo[4,3-c]pyridin-1-yl]-2-pyridyl]piperidin-3-amine 204

Compound 204 was obtained as the second peak from SFC chiral separation of EXAMPLE 71. MS (ESI) m/z: 401.1. 1H NMR (400 MHz, DMSO) δ 9.47 (d, J=5.4 Hz, 2H), 9.32 (d, J=0.9 Hz, 1H), 8.65 (d, J=10.3 Hz, 1H), 8.61 (d, J=5.5 Hz, 1H), 7.81-7.73 (m, 1H), 7.21 (d, J=7.7 Hz, 1H), 6.77 (d, J=8.5 Hz, 1H), 4.63-4.52 (m, 1H), 4.41 (d, J=14.2 Hz, 1H), 3.10-2.99 (m, 2H), 2.64 (s, 3H), 1.86 (d, J=12.0 Hz, 1H), 1.76-1.52 (m, 3H), 1.19 (d, J=6.8 Hz, 3H).

Example 105

(S)-1-(3-methyl-6-(6-(6-methylpyrazin-2-yl)-1H-pyrazolo[4,3-c]pyridin-1-yl)pyridin-2-yl)piperidin-3-amine 205

Step A: 6-bromo-2-fluoro-3-methyl-pyridine

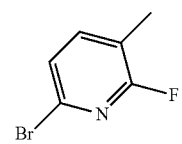

To Diisopropylamine (22.001 mmol; 2240 mg; 3.13 mL) in THF (40 mL) at 0° C. was added N-Butyllithium (2.5 mol/L) in Hexane (24.001 mmol; 9.6 mL). The reaction was stirred at 0° C. for 0.5 h, and then cooled to −78° C. 2-bromo-6-fluoro-pyridine (20.001 mmol; 3520.0 mg) in THF (10 mL) was added dropwise. The mixture was stirred at −78° C. for 3 h. Iodomethane (22.001 mmol; 3122.8 mg; 1.37 mL) was added slowly. The mixture was allowed to warm to room temperature with stirring for 1 hour. The reaction was quenched with water (~50 mL) and stirred overnight. The layers were separated. The organic layer was concentrated, and the residue was purified on silica eluted with 0 to 5% EtOAc in Heptane to afford 6-bromo-2-fluoro-3-methyl-pyridine as a white solid (2.08 g, 55%).

Step B

Following the procedures as described in EXAMPLE 86 and starting with tert-butyl N-[(3S)-3-piperidyl]carbamate, 6-bromo-2-fluoro-3-methyl-pyridine, and 6-(6-methyl-pyrazin-2-yl)-1H-pyrazolo[4,3-c]pyridine, 205 was obtained as an off-white solid (4.4 mg, 4.5%) over 3 steps. $^1$H NMR (400 MHz, DMSO) δ 9.75-9.70 (s, 1H), 9.48-9.44 (s, 1H), 9.33-9.29 (s, 1H), 8.68-8.61 (d, J=12.1 Hz, 2H), 8.38-8.15 (s, 1H), 7.78-7.74 (d, J=8.1 Hz, 1H), 7.59-7.55 (d, J=8.0 Hz, 1H), 2.90-2.84 (m, 1H), 2.67-2.63 (s, 3H), 2.37-2.32 (s, 3H), 2.04-1.95 (d, J=9.2 Hz, 2H), 1.80-1.68 (d, J=9.4 Hz, 1H), 1.57-1.47 (d, J=8.6 Hz, 1H); MS (ESI) m/z: 433.1 [M+H]$^+$ Example 106

4-[6-[6-(6-methylpyrazin-2-yl)pyrazolo[4,3-c]pyridin-1-yl]-2-pyridyl]-1 4-diazepan-5-one 206

Following the procedures in preparation of Example 102, 206 was obtained. MS (ESI) m/z: 401.1.

Example 107

1-(3-methoxy-6-(6-(6-methylpyrazin-2-yl)-1H-pyrazolo[4,3-c]pyridin-1-yl)pyridin-2-yl)-1,4-diazepan-6-ol 207

Step A: 1-(6-bromo-3-methoxy-2-pyridyl)-1,4-diazepan-6-ol

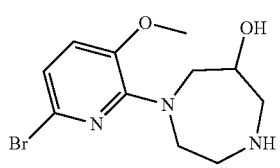 [SMILES: COc1ccc(Br)nc1N1CCNCC(O)C1]

A mixture of 6-bromo-2-fluoro-3-methoxy-pyridine (2.660 mmol; 547.9 mg), 1,4-diazepan-6-ol dihydrobromide (3.989 mmol; 1109 mg), and N,N'-diisopropylethylamine (10.64 mmol; 1389 mg; 1.87 mL) in Isopropanol (10 mL) in a sealed pressure vial was heated at 100° C. overnight. The mixture was cooled to room temperature and concentrated. The residue was purified on silica eluted with 0 to 10% MeOH in DCM to afford 1-(6-bromo-3-methoxy-2-pyridyl)-1,4-diazepan-6-ol (301.2 mg, 37%).

Step B: tert-butyl 4-(6-bromo-3-methoxy-2-pyridyl)-6-hydroxy-1,4-diazepane-1-carboxylate

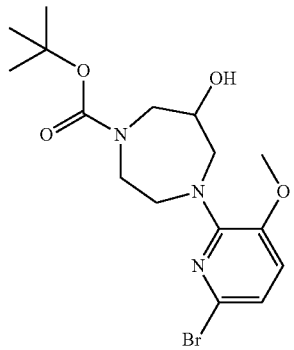 [SMILES: COc1ccc(Br)nc1N1CCN(C(=O)OC(C)(C)C)CC(O)C1]

A mixture of 1-(6-bromo-3-methoxy-2-pyridyl)-1,4-diazepan-6-ol (0.9968 mmol; 301.2 mg), tert-butoxycarbonyl tert-butyl carbonate (1.495 mmol; 326.3 mg), and sodium bicarbonate (9.968 mmol; 837.4 mg) in dichloromethane (20 Ml) was stirred at room temperature overnight. The mixture was concentrated, and the residue was purified on silica eluted with 0 to 40% EtOAc in DCM to afford tert-butyl 4-(6-bromo-3-methoxy-2-pyridyl)-6-hydroxy-1,4-diazepane-1-carboxylate (262.5 mg, 65%).

Step C

Following the procedures as described in EXAMPLE 86 and starting with 6-(6-methylpyrazin-2-yl)-1H-pyrazolo[4,3-c]pyridine and tert-butyl 4-(6-bromo-3-methoxy-2-pyridyl)-6-hydroxy-1,4-diazepane-1-carboxylate, 207 was obtained as an off-white solid (4.4 mg, 4.5%) over 2 steps. MS (ESI) m/z: 433.1 [M+H]$^+$ Example 108

5-(1-(6-(1,4-diazepan-1-yl)pyridin-2-yl)-1H-pyrazolo[4,3-c]pyridin-6-yl)-3-methylpyrazin-2-amine 208

Step A: tert-butyl N-[(3S)-1-[6-(6-chloropyrazolo[4,3-c]pyridin-1-yl)-2-pyridyl]-3-piperidyl]carbamate

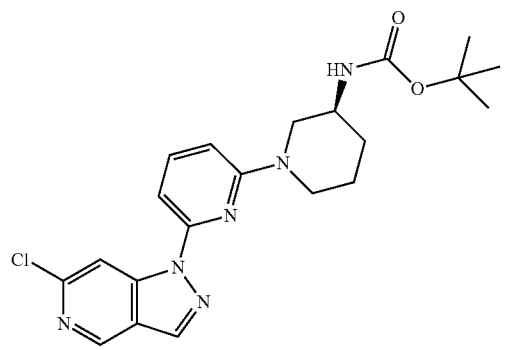 [SMILES: CC(C)(C)OC(=O)N[C@H]1CCCN(c2cccc(-n3ncc4cnc(Cl)cc43)n2)C1]

A mixture of 6-chloro-1-(6-fluoro-2-pyridyl)pyrazolo[4,3-c]pyridine (2.998 mmol; 745.3 mg), tert-butyl N-[(3S)-3-piperidyl]carbamate (4.496 mmol; 900.5 mg), and N-Methylmorpholine (8.993 mmol; 919 mg; 0.999 mL) in 1-methyl-2-pyrrolidinone (10 mL) in a sealed pressure vial was heated at 100° C. overnight. The mixture was poured into water. The precipitate was collect by filtration, then purified on silica eluted with 0 to 40% EtOAc in Heptane to afford tert-butyl N-[(3S)-1-[6-(6-chloropyrazolo[4,3-c]pyridin-1-yl)-2-pyridyl]-3-piperidyl]carbamate (1.0738 g, 84%).

Step B: tert-butyl 4-[6-(6-tributylstannylpyrazolo[4,3-c]pyridin-1-yl)-2-pyridyl]-1,4-diazepane-1-carboxylate

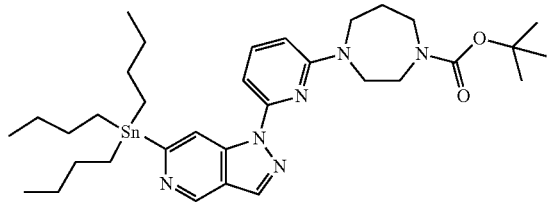 [SMILES: CCC[CH2][Sn]([CH2]CCC)([CH2]CCC)[c]1cc2c(cn1)cnn2-c1cccc(N2CCCN(C(=O)OC(C)(C)C)CC2)n1]

To a mixture of tert-butyl 4-[6-(6-chloropyrazolo[4,3-c]pyridin-1-yl)-2-pyridyl]-1,4-diazepane-1-carboxylate (1.234 mmol; 529.4 mg) in 1,4-Dioxane (40 mL) under Argon was added lithium chloride (7.406 mmol; 314.0 mg), bis(tributyltin (1.481 mmol; 904.5 mg; 0.7879 mL), tris(dibenzylideneacetone)dipalladium(0) (0.06172 mmol; 56.52 mg) and tricyclohexylphosphine (0.1481 mmol; 41.54 mg). The resulting mixture was sealed in a pressure tube and heated at 120° C. overnight. The mixture was cooled to room temperature and filtered through Celite. The filter cake was washed with DCM. The filtrate was concentrated, and the residue was purified on silica eluted with 0 to 40% EtOAc in Heptane to afford tert-butyl 4-[6-(6-tributylstannylpyrazolo[4,3-c]pyridin-1-yl)-2-pyridyl]-1,4-diazepane-1-carboxylate as a clear oil (400.0 mg, 47%).

Step C tert-butyl 4-[6-[6-(5-amino-6-methyl-pyrazin-2-yl)pyrazolo[4,3-c]pyridin-1-yl]-2-pyridyl]-1,4-diazepane-1-carboxylate

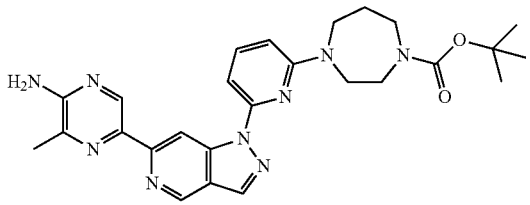 [SMILES: Cc1nc(-c2cc3c(cn2)cnn3-c2cccc(N3CCCN(C(=O)OC(C)(C)C)CC3)n2)cnc1N]

A mixture of tert-butyl 4-[6-(6-tributylstannylpyrazolo[4,3-c]pyridin-1-yl)-2-pyridyl]-1,4-diazepane-1-carboxylate (0.5852 mmol; 400 mg), 5-bromo-3-methyl-pyrazin-2-amine (1.170 mmol; 220.1 mg), tricyclohexylphosphine (0.1405 mmol; 39.39 mg) and tris(dibenzylideneacetone)dipalladium (0) (0.05852 mmol; 53.59 mg) in N,N-Dimethylacetamide (30 mL) was purged with Argon for 1 min. The reaction mixture was sealed in a Biotage microwave tube and heated under microwave at 150° C. for 45 min. The mixture was partitioned between EtOAc and water. The organic layer was concentrated and the residue was purified on silica eluted with 10% MeOH in DCM to afford tert-butyl 4-[6-[6-(5-amino-6-methyl-pyrazin-2-yl)pyrazolo[4,3-c]pyridin-1-yl]-2-pyridyl]-1,4-diazepane-1-carboxylate (115.0 mg, 39%).

Step D

To a solution of tert-butyl 4-[6-[6-(5-amino-6-methyl-pyrazin-2-yl)pyrazolo[4,3-c]pyridin-1-yl]-2-pyridyl]-1,4-diazepane-1-carboxylate (0.2293 mmol; 115 mg) in Methanol (10 mL) was added hydrochloric acid, 4.0 M in 1,4-Dioxane (5 mL). The resulting mixture was stirred at room temperature overnight. The mixture was concentrated and the residue was purified by reverse phase HPLC to afford 208 as an off-white solid (4.0 mg, 4.3%). MS (ESI) m/z: 402.1 [M+H]$^+$ Example 109

(S)-5-(1-(6-(3-aminopiperidin-1-yl)pyridin-2-yl)-1H-pyrazolo[4,3-c]pyridin-6-yl)-3-methylpyrazin-2-amine 209

Following the procedures as described in EXAMPLE 108 and starting (S)-tert-butyl piperidin-3-ylcarbamate, 209 was obtained as an off-white solid (52.8 mg, 56%) over 4 steps. $^1$H NMR (400 MHz, DMSO) δ 9.34-9.29 (s, 1H), 9.20-9.13 (s, 1H), 8.89-8.84 (s, 1H), 8.58-8.54 (s, 1H), 7.77-7.69 (t, J=8.1 Hz, 1H), 7.22-7.15 (d, J=7.7 Hz, 1H), 6.81-6.73 (d, J=8.5 Hz, 1H), 6.60-6.51 (s, 2H), 4.45-4.37 (d, J=13.2 Hz, 1H), 4.18-4.11 (d, J=10.5 Hz, 1H), 3.16-3.08 (dd, J=17.5, 6.7 Hz, 1H), 2.87-2.74 (dt, J=22.9, 9.5 Hz, 2H), 2.47-2.38 (s, 3H), 1.96-1.90 (d, J=12.7 Hz, 1H), 1.87-1.79 (m, 1H), 1.65-1.53 (d, J=12.8 Hz, 1H), 1.38-1.28 (m, 1H); MS (ESI) m/z: 402.1 [M+H]$^+$ Example 110

3-[6-[6-(6-methylpyrazin-2-yl)pyrazolo[4,3-c]pyridin-1-yl]-2-pyridyl]cyclohexanamine 210

Compound 210 was obtained as the third peak from SFC chiral separation of a mixture of four diastereoisomers. MS (ESI) m/z: 386.1. 1H NMR (400 MHz, DMSO) δ 9.68 (s, 1H), 9.49 (s, 1H), 9.37 (s, 1H), 8.74 (s, 1H), 8.66 (s, 1H), 8.07-8.02 (m, 1H), 7.92 (d, J=8.1 Hz, 1H), 7.31 (d, J=7.5 Hz, 1H), 2.65 (s, 3H), 2.35-2.21 (m, 1H), 2.19-2.02 (m, 3H), 1.96-1.72 (m, 4H).

Example 111

3-[6-[6-(6-methylpyrazin-2-yl)pyrazolo[4,3-c]pyridin-1-yl]-2-pyridyl]cyclohexanamine 211

Compound 211 was obtained as the first peak from SFC chiral separation of a mixture of four diastereoisomers. MS (ESI) m/z: 386.1. 1H NMR (400 MHz, DMSO) δ 9.68 (s, 1H), 9.49 (s, 1H), 9.37 (d, J=0.8 Hz, 1H), 8.74 (s, 1H), 8.66 (s, 1H), 8.07-8.02 (m, 1H), 7.92 (d, J=8.1 Hz, 1H), 7.31 (d, J=7.5 Hz, 1H), 2.65 (s, 3H), 2.36-2.22 (m, 2H), 2.19-2.03 (m, 4H), 1.93-1.72 (m, 4H).

Example 112

3-[6-[6-(6-methylpyrazin-2-yl)pyrazolo[4,3-c]pyridin-1-yl]-2-pyridyl]cyclohexanamine 212

Compound 212 was obtained as the second peak from SFC chiral separation of a mixture of four diastereoisomers.

MS (ESI) m/z: 386.1. 1H NMR (400 MHz, DMSO) δ 9.72 (s, 1H), 9.49 (s, 1H), 9.37 (s, 1H), 8.75 (s, 1H), 8.66 (s, 1H), 8.06-8.01 (m, 1H), 7.92 (d, J=8.1 Hz, 1H), 7.29 (d, J=7.4 Hz, 1H), 3.26 (s, 1H), 3.04 (t, J=12.1 Hz, 1H), 2.66 (s, 3H), 2.25-2.02 (m, 4H), 1.95 (dd, J=27.3, 12.1 Hz, 1H), 1.71-1.53 (m, 2H), 1.46 (dd, J=22.9, 10.7 Hz, 1H).

Example 113

3-[6-[6-(6-methylpyrazin-2-yl)pyrazolo[4,3-c]pyridin-1-yl]-2-pyridyl]cyclohexanamine 213

Compound 213 was obtained as the fourth peak from SFC chiral separation of a mixture of four diastereoisomers. MS (ESI) m/z: 386.1. 1H NMR (400 MHz, DMSO) δ 9.72 (s, 1H), 9.49 (s, 1H), 9.37 (s, 1H), 8.74 (s, 1H), 8.66 (s, 1H), 8.06-8.00 (m, 1H), 7.92 (d, J=8.2 Hz, 1H), 7.29 (d, J=7.5 Hz, 1H), 3.25 (s, 1H), 3.04 (t, J=12.1 Hz, 1H), 2.66 (s, 3H), 2.27-2.02 (m, 4H), 1.94 (dd, J=25.3, 12.8 Hz, 1H), 1.73-1.39 (m, 3H).

Example 114

1-[6-(2 6-diazaspiro[3.4]octan-6-yl)-2-pyridyl]-6-(6-methylpyrazin-2-yl)pyrazolo[4,3-c]pyridine 214

Following the procedures in preparation of EXAMPLE 23, 214 was obtained. MS (ESI) m/z: 399.1. 1H NMR (400 MHz, DMSO) δ 9.80 (s, 1H), 9.45 (s, 1H), 9.30 (s, 1H), 8.64 (d, J=3.3 Hz, 1H), 8.39 (s, 1H), 7.73 (t, J=8.0 Hz, 1H), 7.20 (d, J=7.7 Hz, 1H), 6.42 (d, J=8.3 Hz, 1H), 3.73 (dd, J=21.9, 13.3 Hz, 6H), 3.62 (d, J=8.5 Hz, 2H), 2.65 (s, 3H), 2.32 (t, J=6.8 Hz, 2H).

Example 115

(S)-1-(3-fluoro-6-(6-(6-methylpyrazin-2-yl)-1H-pyrazolo[4,3-c]pyridin-1-yl)pyridin-2-yl)piperidin-3-amine 215

Step A: tert-butyl N-[(3S)-1-(6-chloro-3-fluoro-2-pyridyl)-3-piperidyl]carbamate

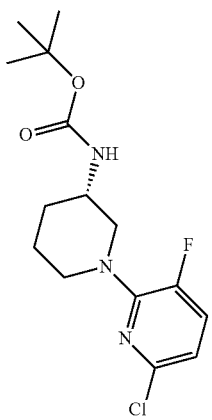 [SMILES: CC(C)(C)OC(=O)N[C@H]1CCCN(c2nc(Cl)ccc2F)C1]

A mixture of 2,6-dichloro-3-fluoro-pyridine (3.802 mmol; 631.1 mg), tert-butyl N-[(3S)-3-piperidyl]carbamate (3.992 mmol; 799.6 mg), potassium carbonate (7.605 mmol; 1051 mg), N,N'-Dimethylethylenediamine (0.3802 mmol; 33.52 mg; 0.0409 mL), and copper(I) iodide; (3.802 mmol; 724.1 mg) in 1,4-Dioxane (15 mL) was purged with Argon then sealed in a pressure tube and heated at 105° C. overnight. The reaction was cooled to room temperature, then filtered through Celite. The filtrate was concentrated and the residue was purified on silica eluted with 0 to 20% EtOAc in Heptane to afford tert-butyl N-[(3S)-1-(6-chloro-3-fluoro-2-pyridyl)-3-piperidyl]carbamate (279.2 mg, 22%) as a white solid.

Step B: tert-butyl N-[(3S)-1-[3-fluoro-6-[6-(6-methylpyrazin-2-yl)pyrazolo[4,3-c]pyridin-1-yl]-2-pyridyl]-3-piperidyl]carbamate

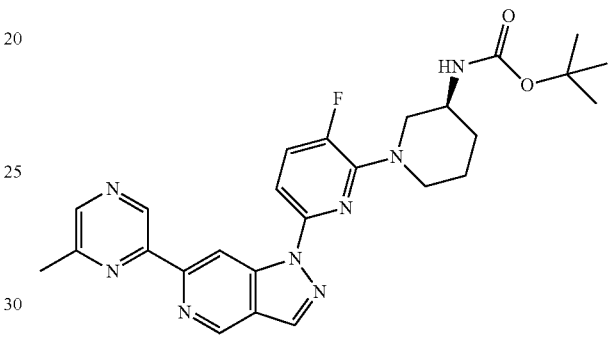

A mixture of 6-(6-methylpyrazin-2-yl)-1H-pyrazolo[4,3-c]pyridine (0.83325 mmol; 176 mg), tert-butyl N-[(3S)-1-(6-chloro-3-fluoro-2-pyridyl)-3-piperidyl]carbamate (0.8378 mmol; 276.3 mg), cesium carbonate (1.6665 mmol; 543.00 mg), Xantphos (0.14165 mmol; 84.500 mg), and tris(dibenzylideneacetone)dipalladium(0) (0.083325 mmol; 77.074 mg) in 1,4-Dioxane (10 mL) was purged with Argon, then sealed and stirred at 110° C. overnight. The mixture was cooled to room temperature and filtered through Celite. The filtrate was concentrated and the residue was purified on silica eluted with 0 to 100% EtOAc in Heptane to afford tert-butyl N-[(3S)-1-[3-fluoro-6-[6-(6-methylpyrazin-2-yl)pyrazolo[4,3-c]pyridin-1-yl]-2-pyridyl]-3-piperidyl]carbamate (113.1 mg, 16%).

Step C

A mixture of tert-butyl N-[(3S)-1-[3-fluoro-6-[6-(6-methylpyrazin-2-yl)pyrazolo[4,3-c]pyridin-1-yl]-2-pyridyl]-3-piperidyl]carbamate (0.1345 mmol; 113.1 mg) in TFA (1 mL) and dichloromethane (4 mL) was stirred at room temperature overnight. The mixture was concentrated and the residue was purified by reverse phase HPLC to afford 215 as an off-white solid (42.7 mg, 77%). $^1$H NMR (400 MHz, DMSO) δ 9.58-9.55 (s, 1H), 9.47-9.43 (s, 1H), 9.33-9.30 (s, 1H), 8.69-8.65 (s, 1H), 8.64-8.62 (s, 1H), 8.35-8.30 (s, 1H), 7.79-7.72 (dd, J=12.7, 8.5 Hz, 1H), 7.42-7.38 (dd, J=8.4, 2.0 Hz, 1H), 4.05-3.97 (d, J=8.5 Hz, 2H), 3.29-3.26 (d, J=10.8 Hz, 1H), 3.02-2.95 (m, 2H), 2.66-2.60 (s, 3H), 2.00-1.87 (t, J=14.1 Hz, 2H), 1.80-1.67 (m, 1H), 1.47-1.37 (d, J=10.5 Hz, 1H); MS (ESI) m/z: 405.1 [M+H]$^+$

Example 116

8-[6-[6-(6-methylpyrazin-2-yl)pyrazolo[4,3-c]pyridin-1-yl]-2-pyridyl]-1 8-diazaspiro[4.5]decane 216

Following the procedures in preparation of EXAMPLE 23, 216 was obtained. MS (ESI) m/z: 427.1. 1H NMR (400 MHz, DMSO) δ 9.61 (s, 1H), 9.46 (s, 1H), 9.32 (s, 1H), 8.66 (s, 1H), 8.62 (s, 1H), 7.74 (t, J=8.1 Hz, 1H), 7.23 (d, J=7.7 Hz, 1H), 6.83 (d, J=8.5 Hz, 1H), 3.87-3.70 (m, 4H), 2.87 (t, J=6.9 Hz, 2H), 2.63 (s, 3H), 1.79-1.68 (m, 2H), 1.68-1.60 (m, 3H), 1.60-1.52 (m, 3H).

Example 117

1-[6-(2 7-diazaspiro[3.4]octan-2-yl)-2-pyridyl]-6-(6-methylpyrazin-2-yl)pyrazolo[4,3-c]pyridine 217

Following the procedures in preparation of EXAMPLE 23, 217 was obtained. MS (ESI) m/z: 399.1. 1H NMR (400 MHz, DMSO) δ 9.82 (s, 1H), 9.46 (s, 1H), 9.31 (s, 1H), 8.65 (s, 1H), 8.63 (s, 1H), 7.75 (t, J=8.0 Hz, 1H), 7.26 (d, J=7.7 Hz, 1H), 6.37 (d, J=8.1 Hz, 1H), 4.16 (s, 4H), 3.20 (s, 2H), 3.02 (t, J=7.1 Hz, 3H), 2.62 (s, 2H), 2.14 (t, J=7.1 Hz, 2H).

Example 118

(S)-(2-(3-aminopiperidin-1-yl)-6-(6-(6-methylpyrazin-2-yl)-1H-pyrazolo[4,3-c]pyridin-1-yl)pyridin-3-yl)methanol 218

Step A: (6-bromo-2-fluoro-3-pyridyl)methanol

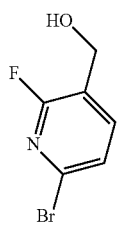

To Diisopropylamine (22.001 mmol; 2240 mg; 3.13 mL) in THF (40 mL) at 0° C. was added N-Butyllithium (2.5 mol/L) in Hexane (24.001 mmol; 9.6 mL). The reaction was stirred at 0° C. for 0.5 h, and then cooled to −78° C. 2-bromo-6-fluoro-pyridine (20.001 mmol; 3520.0 mg) in THF (10 mL) was added dropwise. The mixture was stirred at −78° C. for 2.5 h. Paraformaldehyde (40.002 mmol; 3603.3 mg) was added rapidly. The mixture was allowed to warm to room temperature and stirred overnight. The reaction was quenched with water. The layers were separated. The aqueous layer was extracted with EtOAc. The combined organic layers were concentrated and the residue was purified on silica eluted with 0 to 50% EtOAc in Heptane to afford (6-bromo-2-fluoro-3-pyridyl)methanol (1.4888 g, 36%).

Step B: tert-butyl N-[(3S)-1-[6-bromo-3-(hydroxymethyl)-2-pyridyl]-3-piperidyl]carbamate

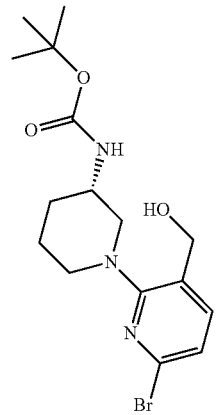 [SMILES: CC(C)(C)OC(=O)N[C@H]1CCCN(c2nc(Br)ccc2CO)C1]

A mixture of (6-bromo-2-fluoro-3-pyridyl)methanol (1.766 mmol; 363.8 mg), tert-butyl N-[(3S)-3-piperidyl]carbamate (2.649 mmol; 530.5 mg), and N-Methylmorpholine (5.298 mmol; 541 mg; 0.588 mL) in 1-methyl-2-pyrrolidinone (10 mL) in a sealed pressure vial was heated at 130° C. for 4 hours. The mixture was poured into water, and extracted with EtOAc. The organic layer was concentrated. The residue was purified on silica eluted with 0 to 100% EtOAc in Heptane to afford tert-butyl N-[(3S)-1-[6-bromo-3-(hydroxymethyl)-2-pyridyl]-3-piperidyl]carbamate (546.3 mg, 80%).

Step C

Following the procedures as described in EXAMPLE 86 and starting with 6-(6-methylpyrazin-2-yl)-1H-pyrazolo[4,3-c]pyridine and tert-butyl N-[(3S)-1-[6-bromo-3-(hydroxymethyl)-2-pyridyl]-3-piperidyl]carbamate, 218 was obtained as an off-white solid (40.8 mg, 68%) over 2 steps. 1H NMR (400 MHz, DMSO) δ 9.77-9.73 (s, 1H), 9.49-9.45 (s, 1H), 9.34-9.31 (s, 1H), 8.69-8.67 (s, 1H), 8.64-8.61 (s, 1H), 8.03-7.98 (d, J=8.1 Hz, 1H), 7.65-7.61 (d, J=8.1 Hz, 1H), 4.59-4.52 (d, J=2.9 Hz, 2H), 3.60-3.52 (d, J=12.4 Hz, 1H), 3.51-3.43 (d, J=9.8 Hz, 1H), 3.21-3.15 (d, J=10.4 Hz, 1H), 3.00-2.92 (s, 1H), 2.74-2.68 (d, J=12.0 Hz, 1H), 2.67-2.64 (s, 3H), 1.98-1.89 (d, J=9.4 Hz, 2H), 1.77-1.66 (m, 1H), 1.37-1.26 (d, J=10.0 Hz, 1H); MS (ESI) m/z: 417.1 [M+H]+

Example 119

1-(6-(6-(6-methylpyrazin-2-yl)-1H-pyrazolo[4,3-c]pyridin-1-yl)-3-(trifluoromethyl)pyridin-2-yl)-1,4-diazepan-6-ol 219

A mixture of 1-[6-fluoro-5-(trifluoromethyl)-2-pyridyl]-6-(6-methylpyrazin-2-yl)pyrazolo[4,3-c]pyridine (0.213 mmol; 79.9 mg), 1,4-diazepan-6-ol dihydrobromide (1.07 mmol; 297 mg), and cesium carbonate (2.13 mmol; 696 mg) in DMSO (2 mL) and IPA (4 mL) in a sealed pressure vial was heated at 120° C. overnight. The mixture was cooled to room temperature, and then filtered through Celite®. The filtrate was concentrated and the residue was purified by reverse phase HPLC to afford 219 as an off-white solid (10.8 mg, 11%). 1H NMR (400 MHz, DMSO) δ 9.59-9.53 (s, 1H), 9.48-9.43 (s, 1H), 9.38-9.33 (s, 1H), 8.79-8.75 (s, 1H), 8.66-8.62 (s, 1H), 8.22-8.17 (d, J=8.5 Hz, 1H), 7.57-7.52 (d, J=8.5 Hz, 1H), 4.76-4.67 (s, 1H), 3.98-3.88 (d, J=10.4 Hz, 3H), 3.75-3.66 (d, J=14.1 Hz, 1H), 3.65-3.55 (dd, J=15.3, 8.4 Hz, 1H), 3.15-3.07 (m, 1H), 3.06-2.99 (m, 1H), 2.87-2.79 (dd, J=13.7, 3.4 Hz, 1H), 2.76-2.68 (dd, J=13.6, 5.8 Hz, 1H), 2.69-2.62 (s, 3H); MS (ESI) m/z: 471.1 [M+H]$^+$ Example 120

(S)-1-(6-(6-(6-methylpyrazin-2-yl)-1H-pyrazolo[4,3-c]pyridin-1-yl)-3-(trifluoromethyl)pyridin-2-yl)piperidin-3-amine 120

Step A: 1-[6-fluoro-5-(trifluoromethyl)-2-pyridyl]-6-(6-methylpyrazin-2-yl)pyrazolo[4,3-c]pyridine

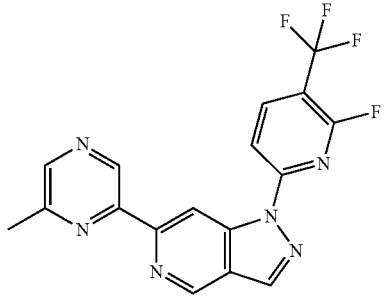 [SMILES: Cc1cncc(-c2cc3c(cn2)cnn3-c2ccc(C(F)(F)F)c(F)n2)n1]

To a mixture of 6-(6-methylpyrazin-2-yl)-1H-pyrazolo[4,3-c]pyridine (1.008 mmol; 213.0 mg) in Dimethylformamide (10 mL) at 0° C. was added sodium hydride (60% in mineral oil; 1.210 mmol; 48.40 mg). The resulting mixture was stirred for 10 min. 2,6-difluoro-3-(trifluoromethyl)pyridine (1.008 mmol; 184.6 mg) was then added. The reaction was stirred and allowed to warm to room temperature and stirred for 4 hours. The mixture was quenched with water, and extracted with EtOAc. The organic layer was washed with brine, and then concentrated. The residue was purified on silica eluted with 0 to 100% EtOAc in Heptane. 1-[6-fluoro-5-(trifluoromethyl)-2-pyridyl]-6-(6-methylpyrazin-2-yl)pyrazolo[4,3-c]pyridine was obtained as the most abundant isomer (173.6 mg, 46%).

Step B tert-butyl N-[(3S)-1-[6-[6-(6-methylpyrazin-2-yl)pyrazolo[4,3-c]pyridin-1-yl]-3-(trifluoromethyl)-2-pyridyl]-3-piperidyl]carbamate

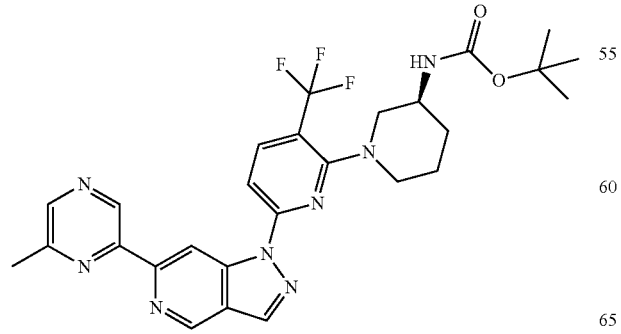

A mixture of 1-[6-chloro-5-(trifluoromethyl)-2-pyridyl]-6-(6-methylpyrazin-2-yl)pyrazolo[4,3-c]pyridine (0.0876 mmol; 59.7 mg), tert-butyl N-[(3S)-3-piperidyl]carbamate (0.263 mmol; 52.6 mg), and N-Methylmorpholine (0.263 mmol; 26.9 mg; 0.0292 mL) in 1-methyl-2-pyrrolidinone (3 mL) in a sealed pressure vial was heated at 120° C. overnight. The mixture was poured into water, and extracted with EtOAc. The organic layer was concentrated. The residue was purified on silica eluted with 0 to 100% EtOAc in Heptane to afford tert-butyl N-[(3S)-1-[6-[6-(6-methylpyrazin-2-yl)pyrazolo[4,3-c]pyridin-1-yl]-3-(trifluoromethyl)-2-pyridyl]-3-piperidyl]carbamate as a white solid (37.0 mg, 65%).

Step C

A mixture of tert-butyl N-[(3S)-1-[6-[6-(6-methylpyrazin-2-yl)pyrazolo[4,3-c]pyridin-1-yl]-3-(trifluoromethyl)-2-pyridyl]-3-piperidyl]carbamate (0.0569 mmol; 37.0 mg) in Methanol (5 mL) and hydrogen chloride, 4.0 M in 1,4-Dioxane (5 mL) was stirred at room temperature overnight. The mixture was concentrated and the residue was purified by reverse phase HPLC to afford 220 as an off-white solid (31.0 mg, 81%). $^1$H NMR (400 MHz, DMSO) δ 9.67-9.63 (s, 1H), 9.48-9.45 (s, 1H), 9.36-9.33 (s, 1H), 8.78-8.75 (s, 1H), 8.65-8.62 (s, 1H), 8.27-8.21 (d, J=8.5 Hz, 1H), 7.71-7.65 (d, J=8.5 Hz, 1H), 3.76-3.62 (dd, J=24.1, 11.7 Hz, 2H), 3.25-3.19 (d, J=11.2 Hz, 1H), 2.95-2.80 (dd, J=24.6, 13.2 Hz, 2H), 2.68-2.63 (d, J=9.0 Hz, 3H), 2.00-1.88 (d, J=14.4 Hz, 2H), 1.73-1.63 (d, J=13.2 Hz, 1H), 1.36-1.22 (dd, J=20.5, 8.6 Hz, 1H); MS (ESI) m/z: 455.1 [M+H]$^+$ Example 121

(5S)-5-amino-1-[3-methyl-6-[6-(6-methylpyrazin-2-yl)pyrazolo[4,3-c]pyridin-1-yl]-2-pyridyl]piperidin-2-one 221

Step A: tert-butyl N-[(3S)-1-(6-chloro-3-methyl-2-pyridyl)-6-oxo-3-piperidyl]carbamate

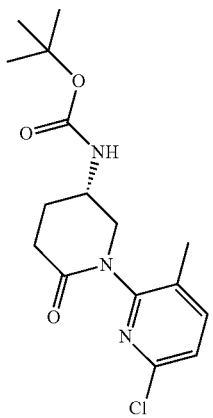 [SMILES: Cc1ccc(Cl)nc1N1C[C@@H](NC(=O)OC(C)(C)C)CCC1=O]

A solution containing 2-bromo-6-chloro-3-methylpyridine (487 mg, 2.24 mmol), tert-butyl N-[(3S)-6-oxo-3- piperidyl]carbamate (400 mg, 1.87 mmol), Copper(I) iodide (356 mg, 1.87 mmol), Potassium carbonate (310 mg, 2.24 mmol) and N,N'-Dimethylethylenediamine (329 mg, 3.73 mmol) in dioxane 12 mL was stirred at 110° C. 18 h. The reaction was filtered through celite and concentrated. The crude product was purified by flash chromatography (EtOAc/Heptane eluted at 50% EtOAc) to give the desired product 350 mg 38% yield. MS (ESI) m/z: 340.1.

Step B: tert-butyl N-[(3S)-1-[3-methyl-6-[6-(6-methylpyrazin-2-yl)pyrazolo[4,3-c]pyridin-1-yl]-2-pyridyl]-6-oxo-3-piperidyl]carbamate

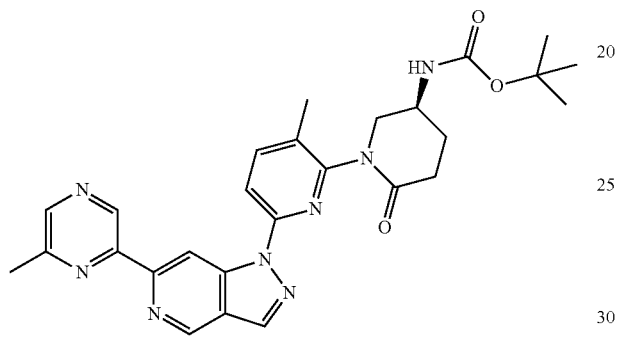

A mixture of 6-(6-methylpyrazin-2-yl)-1H-pyrazolo[4,3-c]pyridine (150 mg, 0.710 mmol), tert-butyl N-[(3S)-1-(6-chloro-3-methyl-2-pyridyl)-6-oxo-3-piperidyl]carbamate (497 mg, 1.42 mmol), tris(dibenzylideneacetone)dipalladium(0) (65 mg, 0.071 mmol), xantphos (84 mg, 0.14 mmol), and sodium tert-butoxide (140 mg, 1.42 mmol) in toluene 3.0 mL was stirred at 110° C. 18 h. The reaction was filtered through celite. The crude product was purified by flash chromatography (EtOAc/Heptane then MeOH/DCM eluted at 10% MeOH) to give the desired product 75 mg 20% yield. MS (ESI) m/z: 515.1.

Step C

A solution of tert-butyl N-[(3S)-1-[3-methyl-6-[6-(6-methylpyrazin-2-yl)pyrazolo[4,3-c]pyridin-1-yl]-2-pyridyl]-6-oxo-3-piperidyl]carbamate (63 mg, 0.12 mmol) in hydrogen chloride (4 mol/l) in 1,4-dioxane (2.0 ml, 8.0 mmol) and 1,4-dioxane 2.0 mL was stirred at RT 18 h. The reaction was concentrated in vacuum. The crude product was submitted for reverse phase HPLC to give 221 15 mg 29% yield. MS (ESI) m/z: 415.1. 1H NMR (400 MHz, DMSO) δ 9.61 (s, 1H), 9.48 (s, 1H), 9.35 (s, 1H), 8.73 (s, 1H), 8.64 (s, 1H), 7.98 (d, J=8.2 Hz, 1H), 7.93 (d, J=8.3 Hz, 1H), 4.27 (s, 1H), 3.86 (s, 1H), 3.59 (d, J=33.7 Hz, 1H), 3.40 (s, 1H), 2.68 (t, J=18.2 Hz, 3H), 2.20 (d, J=13.0 Hz, 3H), 2.10 (s, 1H), 1.85 (s, 2H).

Example 122

(3S)-1-[3-methoxy-6-[6-(6-methylpyrazin-2-yl)pyrazolo[4,3-c]pyridin-1-yl]pyrazin-2-yl]piperidin-3-amine 222

Step A: tert-butyl N-[(3S)-1-[3-methoxy-6-[6-(6-methylpyrazin-2-yl)pyrazolo[4,3-c]pyridin-1-yl] pyrazin-2-yl]-3-piperidyl]carbamate

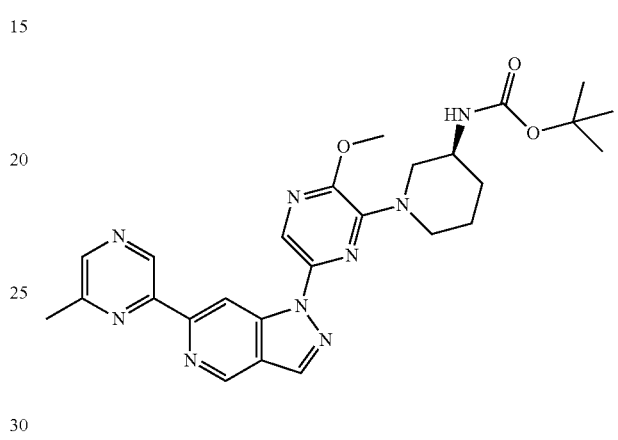

A mixture of 6-(6-methylpyrazin-2-yl)-1H-pyrazolo[4,3-c]pyridine (80 mg; 0.38 mmol), tert-butyl N-[(3S)-1-(6-bromo-3-methoxy-pyrazin-2-yl)-3-piperidyl]carbamate (181 mg, 0.4550 mmol), tris(dibenzylideneacetone)dipalladium(0) (35 mg, 0.038 mmol), xantphos (45 mg, 0.076 mmol), and sodium tert-butoxide (75 mg, 0.76 mmol) in toluene 3.0 mL was stirred at 110° C. 18 h. The reaction was filtered through celite. The crude product was purified by flash chromatography (EtOAc/Heptane eluted at 75% EtOAc) to give the desired product 112 mg 57% yield. MS (ESI) m/z: 518.1.

Step B

A solution of tert-butyl N-[(3S)-1-[3-methoxy-6-[6-(6-methylpyrazin-2-yl)pyrazolo[4,3-c]pyridin-1-yl]pyrazin-2-yl]-3-piperidyl]carbamate (75 mg, 0.15 mmol) in dichloromethane 4.0 ml and trifluoroacetic acid (0.80 mL, 10 mmol) was stirred at RT 4 h. The reaction was concentrated and submitted for reverse phase HPLC to give 222 (25 mg) in 41% yield. MS (ESI) m/z: 418.2. 1H NMR (400 MHz, DMSO) δ 9.45 (s, 2H), 9.32 (s, 1H), 8.67 (s, 1H), 8.63 (s, 1H), 8.15 (s, 1H), 4.24 (d, J=10.2 Hz, 1H), 4.06 (d, J=13.3 Hz, 1H), 4.00 (s, 3H), 3.09 (dd, J=24.2, 12.0 Hz, 3H), 2.63 (s, 3H), 1.94 (d, J=15.0 Hz, 2H), 1.76 (d, J=10.0 Hz, 1H), 1.49 (d, J=10.0 Hz, 1H).

Example 123

3-[(3S)-3-amino-1-piperidyl]-5-[6-(6-methylpyrazin-2-yl)pyrazolo[4 3-c]pyridin-1-yl]pyrazin-2-ol 223

A solution of tert-butyl N-[(3S)-1-[3-methoxy-6-[6-(6-methylpyrazin-2-yl)pyrazolo[4,3-c]pyridin-1-yl]pyrazin-2- yl]-3-piperidyl]carbamate (30 mg, 0.058 mmol) in hydrogen chloride (4 mol/l) in 1,4-dioxane (1.0 ml, 4.0 mmol) and 1,4-dioxane 1.0 mL was stirred at RT 2d. The reaction was concentrated and submitted for reverse phase HPLC to give 223 (7 mg, 27% yield. MS (ESI) m/z: 404.1. 1H NMR (400 MHz, DMSO) δ 9.44 (s, 1H), 9.28 (s, 1H), 9.25 (s, 1H), 8.61 (s, 1H), 8.57 (s, 1H), 7.23 (s, 1H), 4.74 (d, J=11.1 Hz, 1H), 4.44 (d, J=12.8 Hz, 1H), 2.92 (s, 2H), 2.62 (s, 3H), 1.88 (d, J=16.7 Hz, 2H), 1.68 (d, J=11.1 Hz, 1H), 1.39 (d, J=9.5 Hz, 1H).

Example 124

1-(6-(1,4-Diazepan-1-yl)pyridin-2-yl)-6-(1-methyl-1H-pyrazol-4-yl)-1H-pyrazolo[4,3-c]pyridine 224

Step A: tert-Butyl 4-(6-(6-Chloro-1H-pyrazolo[4,3-c]pyridin-1-yl)pyridin-2-yl)-1,4-diazepane-1-carboxylate

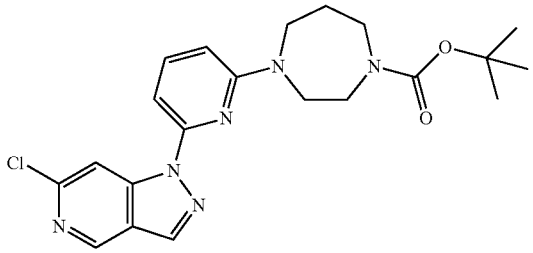 [SMILES: CC(C)(C)OC(=O)N1CCCN(c2cccc(-n3ncc4cnc(Cl)cc43)n2)CC1]

To a mixture of tert-butyl 4-(6-bromopyridin-2-yl)-1,4-diazepane-1-carboxylate (2.55 g, 7.16 mmol) from Example 45 and 6-chloro-1H-pyrazolo[4,3-c]pyridine (1.0 g, 6.51 mmol) in 1,4-dioxane (20 mL) was added CuI (494 mg, 2.6 mmol), K$_2$CO$_3$ (3.6 g, 26 mmol), and N$^1$,N$^2$-dimethylethane-1,2-diamine (460 mg, 5.2 mmol). The mixture was heated at 100° C. for 3 hours, which was monitored by LCMS. After completion of the reaction, the reaction mixture was concentrated under reduced pressure. The crude was purified by silica gel chromatography petroleum ether/EtOAc (2/1) as eluting solvents to afford tert-butyl 4-(6-(6-chloro-1H-pyrazolo[4,3-c]pyridin-1-yl)pyridin-2-yl)-1,4-diazepane-1-carboxylate as a yellow solid (1.6 g, 57%). MS (ESI) m/z: 429 [M+H]$^+$.

Step B: tert-Butyl 4-(6-(6-(1H-Pyrazol-4-yl)-1H-pyrazolo[4,3-c]pyridin-1-yl)pyridin-2-yl)-1,4-diazepane-1-carboxylate

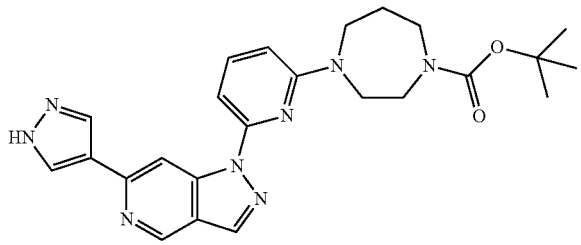 [SMILES: CC(C)(C)OC(=O)N1CCCN(c2cccc(-n3ncc4cnc(-c5cn[nH]c5)cc43)n2)CC1]

A suspension of tert-butyl 4-(6-(6-chloro-1H-pyrazolo[4,3-c]pyridin-1-yl)pyridin-2-yl)-1,4-diazepane-1-carboxylate (500 mg, 1.16 mmol), 4-(4,4,5,5-tetramethyl-1,3,2-dioxaborolan-2-yl)-1H-pyrazole (679 mg, 3.5 mmol), Pd(dppf)Cl$_2$ (47.5 mg, 0.058 mmol), and aqueous solution of Na$_2$CO$_3$ (2.0 M, 3 mL) in 1,4-dioxane (10 mL) under nitrogen was heated at 100° C. for 16 hours. The reaction mixture was filtered and the filtrate was concentrated under reduced pressure. The residue was purified by silica gel chromatography using petroleum ether/EtOAc (1/1) as eluting solvents to afford tert-butyl 4-(6-(6-(1H-pyrazol-4-yl)-1H-pyrazolo[4,3-c]pyridin-1-yl)pyridin-2-yl)-1,4-diazepane-1-carboxylate as a yellow solid (360 mg, 67%). MS (ESI) m/z: 461 [M+H]$^+$.

Step C

A solution of 4-(6-(6-(1H-pyrazol-4-yl)-1H-pyrazolo[4,3-c]pyridin-1-yl)pyridin-2-yl)-1,4-diazepane-1-carboxylate (440 mg, 0.93 mmol) in a solution of HCl/MeOH (2M, 10 mL) was stirred at room temperature for 3 hours. The reaction mixture was concentrated under reduced pressure. The crude was purified by reverse phase preparative HPLC to afford 224 as a yellow solid (180 mg, 51.8%). $^1$H NMR (500 MHz, DMSO-d$_6$) δ (ppm) 9.095-9.098 (d, J=1.5 Hz, 1H), 8.61 (s, 1H), 8.45 (s, 1H), 8.14 (s, 1H), 7.87 (s, 1H), 7.64-7.69 (t, J=13.5 Hz, 1H), 7.13-7.16 (d, J=12.5 Hz, 1H), 6.55-6.58 (d, J=14.5 Hz, 1H), 3.90-3.91 (d, J=8 Hz, 3H), 3.78-3.87 (m, 6H), 3.01-3.05 (t, J=13 Hz, 2H), 1.87-1.91 (m, 2H); MS (ESI) m/z: 375 [M+H]$^+$.

Example 125

(3S)-3-amino-1-[6-[6-(6-methylpyrazin-2-yl)pyrazolo[4,3-c]pyridin-1-yl]-2-pyridyl]piperidin-2-one 225

Step A: tert-butyl N-[(3S)-1-[6-(6-chloropyrazolo[4,3-c]pyridin-1-yl)-2-pyridyl]-2-oxo-3-piperidyl]carbamate

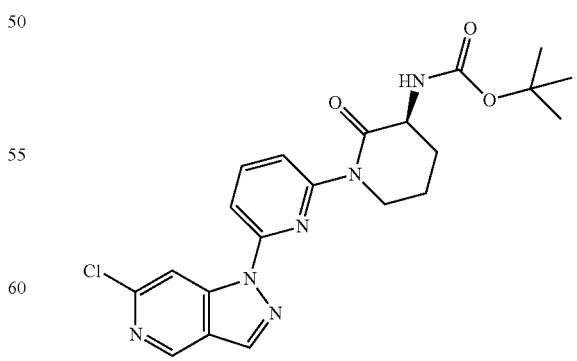

A solution containing 1-(6-bromo-2-pyridyl)-6-chloropyrazolo[4,3-c]pyridine (200 mg, 0.646 mmol), tert-butyl N-[(3S)-2-oxo-3-piperidyl]carbamate (166 mg, 0.775 mmol), Copper(I) iodide (123 mg, 0.646 mmol), Potassium carbonate (107 mg, 0.775 mmol) and N,N'-Dimethylethylenediamine (114 mg, 1.29 mmol) was stirred at 110° C. 4 h. The reaction was filtered through celite and concentrated. The crude product purified by isco column (EtOAc/Hep eluted at 70% EtOAc) to give the desired product 135 mg 47% yield. MS (ESI) m/z: 443.1.

Step B: tert-butyl N-[(3S)-1-[6-[6-(6-methylpyrazin-2-yl)pyrazolo[4,3-c]pyridin-1-yl]-2-pyridyl]-2-oxo-3-piperidyl]carbamate

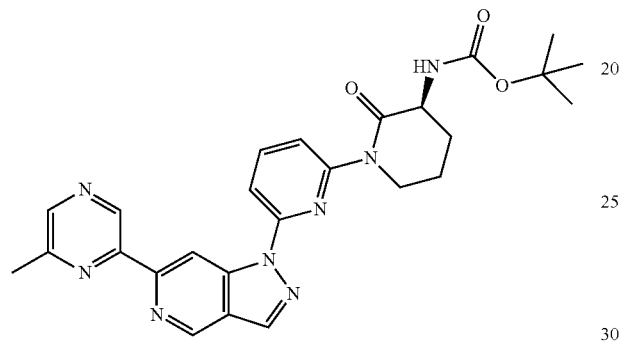

A solution of tert-butyl N-[(3S)-1-[6-(6-chloropyrazolo[4,3-c]pyridin-1-yl)-2-pyridyl]-2-oxo-3-piperidyl]carbamate (125 mg, 0.282 mmol) and palladium(0)tetrakis(triphenylphosphine) (32 mg, 0.028 mmol) in N,N-dimethylacetamide 5.0 mL was added trimethyl-(6-methylpyrazin-2-yl)stannane (145 mg, 0.565 mmol). The reaction mixture heated at 145° C. for 40 min in CEM microwave. The reaction mixture was filtered through celite and concentrated. The crude product was diluted with EtOAc then washed with water. The organic layers was dried with sodium sulfate, filtered, and concentrated in vacuum. The crude product was carried to next step. MS (ESI) m/z: 501.1.

Step C

A solution of tert-butyl N-[(3S)-1-[6-[6-(6-methylpyrazin-2-yl)pyrazolo[4,3-c]pyridin-1-yl]-2-pyridyl]-2-oxo-3-piperidyl]carbamate (140 mg, 0.280 mmol) in dichloromethane 4.0 ml and trifluoroacetic acid (0.80 ml, 10 mmol) was stirred at RT 3 h. The reaction was concentrated and diluted with water then extracted with EtOAc. The aqueous layer was basified with 1M NaOH to pH 10 then extracted with EtOAc. The organic layers was dried with sodium sulfate, filtered, and concentrated in vacuum. The crude product was submitted for reverse phase HPLC to give 225 (44 mg, 39% yield). MS (ESI) m/z: 401.1. 1H NMR (400 MHz, DMSO) δ 9.60 (s, 1H), 9.47 (s, 1H), 9.33 (s, 1H), 8.72 (s, 1H), 8.64 (s, 1H), 8.05 (t, J=8.1 Hz, 1H), 7.82 (d, J=8.0 Hz, 1H), 7.74 (d, J=8.1 Hz, 1H), 4.46-4.33 (m, 1H), 4.14-4.02 (m, 1H), 3.58 (dd, J=10.8, 6.4 Hz, 1H), 2.65 (s, 3H), 2.24 (dt, J=11.4, 5.3 Hz, 1H), 2.19-2.00 (m, 2H), 1.77 (ddd, J=23.0, 10.6, 5.1 Hz, 1H).

Example 126

(3S)-1-[3-chloro-6-[6-(6-methylpyrazin-2-yl)pyrazolo[4,3-c]pyridin-1-yl]pyrazin-2-yl]piperidin-3-amine 226

Step A: 3,5-dibromo-2-chloro-pyrazine

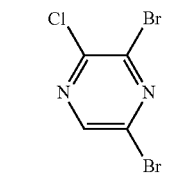

To a solution of 3,5-dibromopyrazin-2-amine (1.00 g, 3.95 mmol) in dichloromethane 6.0 ml at 0° C. was added titanium tetrachloride (1 mol/l) in dichloromethane (3.95 mL, 3.95 mmol) then tert-butyl nitrite (1.05 mL, 7.91 mmol) was added dropwise. The reaction was warmed to RT then 1 more equivalent of TiCL4 was added and stirred for 1 h. The reaction was quenched with water and extracted with DCM. The organic layers was dried with sodium sulfate, filtered, and concentrated in vacuum. The crude product was carried to next step. MS (ESI) m/z: 272.2.

Step B: tert-butyl N-[(3S)-1-(6-bromo-3-chloro-pyrazin-2-yl)-3-piperidyl]carbamate

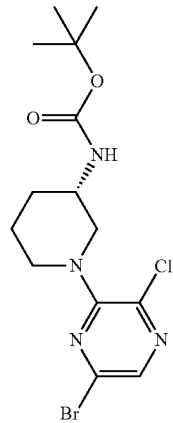 [SMILES: CC(C)(C)OC(=O)N[C@H]1CCCN(c2nc(Br)cnc2Cl)C1]

A solution containing 3,5-dibromo-2-chloropyrazine (1.03 g, 3.60 mmol) and tert-butyl n-[(3S)-3-piperidyl]carbamate (600 mg, 3.00 mmol) in methyl sulfoxide 5.0 mL was heated 85° C. The reaction was quenched with water then extract with EtOAc. The organic layers was dried with sodium sulfate, filtered, and concentrated in vacuum. The crude product was purified by flash chromatography (EtOAc/Heptane eluted at 35% EtOAc) to give the desired product 350 mg 30% yield. MS (ESI) m/z: 393.2.

Step C: tert-butyl N-[(3S)-1-[3-chloro-6-[6-(6-methylpyrazin-2-yl)pyrazolo[4,3-c]pyridin-1-yl]pyrazin-2-yl]-3-piperidyl]carbamate

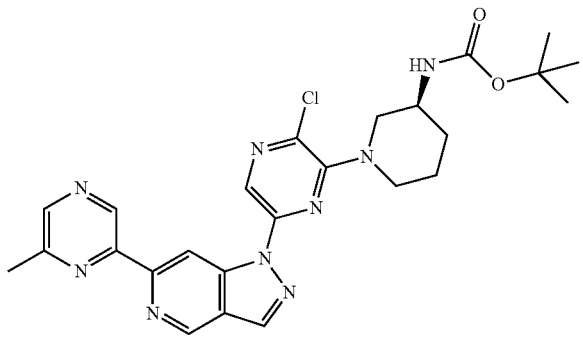

A mixture of 6-(6-methylpyrazin-2-yl)-1H-pyrazolo[4,3-c]pyridine (110 mg, 0.52 mmol), tert-butyl N-[(3S)-1-(6-bromo-3-chloro-pyrazin-2-yl)-3-piperidyl]carbamate (252 mg, 0.62 mmol), tris(dibenzylideneacetone)dipalladium(0) (47 mg, 0.052 mmol), xantphos (62 mg; 0.10 mmol), and sodium tert-butoxide (103 mg, 1.04 mmol) in toluene 5.0 mL was stirred at 110° C. 18 h. The reaction was filtered through celite. The crude product was purified by flash chromatography (EtOAc/Heptane eluted at 75% EtOAc) to give the desired product 112 mg 41% yield. MS (ESI) m/z: 523.2.

Step D

A solution of tert-butyl N-[(3S)-1-[3-chloro-6-[6-(6-methylpyrazin-2-yl)pyrazolo[4,3-c]pyridin-1-yl]pyrazin-2-yl]-3-piperidyl]carbamate (30 mg, 0.057 mmol) in dichloromethane 4.0 ml and trifluoroacetic acid (0.80 ml, 10 mmol) was stirred at RT 3 h. The reaction was concentrated and diluted with water then extracted with EtOAc. The aqueous layer was basified with 1M NaOH to pH 10 then extracted with EtOAc. The organic layers was dried with sodium sulfate, filtered, and concentrated in vacuum. The crude product was submitted for reverse phase HPLC to give 226 (12 mg, 49% yield). MS (ESI) m/z: 422.1.

Example 127

(S)-1-(3-(difluoromethyl)-6-(6-(6-methylpyrazin-2-yl)-1H-pyrazolo[4,3-c]pyridin-1-yl)pyridin-2-yl)piperidin-3-amine 227

Step A: [2-fluoro-6-[6-(6-methylpyrazin-2-yl)pyrazolo[4,3-c]pyridin-1-yl]-3-pyridyl]methanol

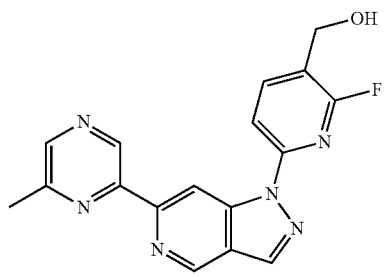 [SMILES: Cc1cncc(-c2cc3c(cn2)cnn3-c2ccc(CO)c(F)n2)n1]

A mixture of 6-(6-methylpyrazin-2-yl)-1H-pyrazolo[4,3-c]pyridine (2.000 mmol; 422.4 mg), (6-bromo-2-fluoro-3-pyridyl)methanol (2.400 mmol; 494.4 mg), potassium carbonate (4.000 mmol; 552.8 mg), copper(I) iodide (2.000 mmol; 380.9 mg), and N,N'-Dimethylethylenediamine (0.2000 mmol; 17.81 mg; 0.0217 mL) in 1,4-Dioxane (15 mL) was purged with Argon then sealed in a pressure tube and heated at 105° C. overnight. The mixture was cooled to room temperature and filtered through Celite. The filtrate was concentrated and the residue was purified on silica eluted with 0 to 100% EtOAc in Heptane to afford [2-fluoro-6-[6-(6-methylpyrazin-2-yl)pyrazolo[4,3-c]pyridin-1-yl]-3-pyridyl]methanol (79.5 mg, 12%).

Step B: 2-fluoro-6-[6-(6-methylpyrazin-2-yl)pyrazolo[4,3-c]pyridin-1-yl]pyridine-3-carbaldehyde

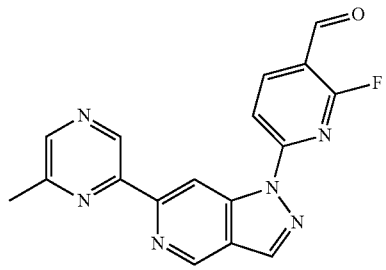 [SMILES: Cc1cncc(-c2cc3c(cn2)cnn3-c2ccc(C=O)c(F)n2)n1]

To [2-fluoro-6-[6-(6-methylpyrazin-2-yl)pyrazolo[4,3-c]pyridin-1-yl]-3-pyridyl]methanol (0.236 mmol; 79.5 mg) in dichloromethane (10 mL) was added DESS-MARTIN periodinane (0.355 mmol; 155 mg). The mixture as stirred at room temperature for 4 hours. The mixture was concentrated and the residue was purified on silica eluted with 0 to 100% EtOAc in DCM to afford 2-fluoro-6-[6-(6-methylpyrazin-2-yl)pyrazolo[4,3-c]pyridin-1-yl]pyridine-3-carbaldehyde as a pale yellow solid (69.7 mg, 88%).

Step C: 1-[5-(difluoromethyl)-6-fluoro-2-pyridyl]-6-(6-methylpyrazin-2-yl)pyrazolo[4,3-c]pyridine

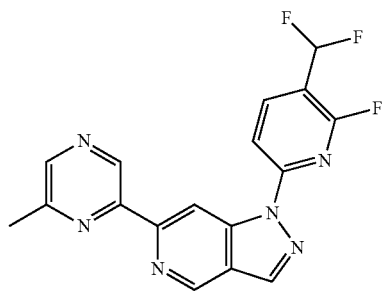 [SMILES: Cc1cncc(-c2cc3c(cn2)cnn3-c2ccc(C(F)F)c(F)n2)n1]

2-fluoro-6-[6-(6-methylpyrazin-2-yl)pyrazolo[4,3-c]pyridin-1-yl]pyridine-3-carbaldehyde (0.208 mmol; 69.7 mg)

was dissolved in dichloromethane (10 mL) and cooled to 0° C. DEOXO-FLUOR® (1.04 mmol; 231 mg; 0.19 mL) was added slowly and the mixture was stirred at room temperature overnight. The mixture was concentrated and the residue was purified on silica eluted with 0 to 100% EtOAc in DCM to afford 1-[5-(difluoromethyl)-6-fluoro-2-pyridyl]-6-(6-methylpyrazin-2-yl)pyrazolo[4,3-c]pyridine (34.8 mg, 47%).

Step D: tert-butyl N-[(3S)-1-[3-(difluoromethyl)-6-[6-(6-methylpyrazin-2-yl)pyrazolo[4,3-c]pyridin-1-yl]-2-pyridyl]-3-piperidyl]carbamate

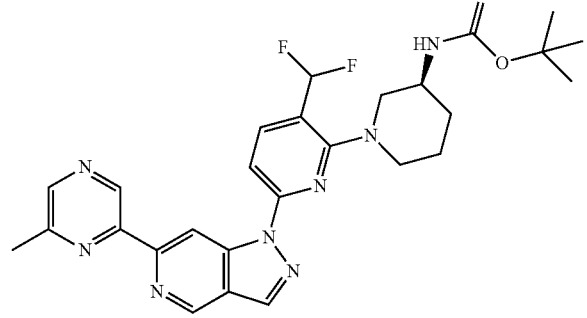

A mixture of 1-[5-(difluoromethyl)-6-fluoro-2-pyridyl]-6-(6-methylpyrazin-2-yl)pyrazolo[4,3-c]pyridine (0.0977 mmol; 34.8 mg), tert-butyl N-[(3S)-3-piperidyl]carbamate (0.147 mmol; 29.3 mg), and N-Methylmorpholine (0.244 mmol; 24.9 mg; 0.0271 mL) in 1-methyl-2-pyrrolidinone (3 mL) in a sealed pressure vial was heated at 100° C. overnight. The mixture was poured into water, and extracted with EtOAc. The organic layer was concentrated. The residue was purified on silica eluted with 0 to 100% EtOAc in DCM to afford tert-butyl N-[(3S)-1-[3-(difluoromethyl)-6-[6-(6-methylpyrazin-2-yl)pyrazolo[4,3-c]pyridin-1-yl]-2-pyridyl]-3-piperidyl]carbamate (~52.4 mg, 100%).

Step E

A mixture of tert-butyl N-[(3S)-1-[3-(difluoromethyl)-6-[6-(6-methylpyrazin-2-yl)pyrazolo[4,3-c]pyridin-1-yl]-2-pyridyl]-3-piperidyl]carbamate (0.0977 mmol; 52.4 mg) in TFA (1 mL) and dichloromethane (4 mL) was stirred at room temperature. The mixture was concentrated and the residue was purified by reverse phase HPLC to afford 228 as an off-white solid (17.5 mg, 40%). $^1$H NMR (400 MHz, DMSO) δ 9.73-9.66 (s, 1H), 9.48-9.42 (s, 1H), 9.36-9.29 (s, 1H), 8.76-8.72 (s, 1H), 8.65-8.61 (d, J=4.9 Hz, 1H), 8.20-8.15 (d, J=8.4 Hz, 1H), 7.74-7.70 (d, J=8.3 Hz, 1H), 7.34-7.05 (t, J=54.2 Hz, 1H), 3.60-3.47 (dd, J=17.4, 12.4 Hz, 2H), 3.06-2.97 (t, J=8.3 Hz, 1H), 2.94-2.86 (dd, J=11.9, 8.2 Hz, 1H), 2.68-2.61 (s, 3H), 1.98-1.86 (d, J=12.3 Hz, 2H), 1.86-1.67 (dd, J=16.0, 6.7 Hz, 2H), 1.41-1.31 (m, 1H); MS (ESI) m/z: 437.1 [M+H]$^+$ Example 128

(3S)-1-[3-methyl-6-[6-(6-methylpyrazin-2-yl)pyrazolo[4,3-c]pyridin-1-yl]pyrazin-2-yl]piperidin-3-amine 228

Step A: tert-butyl N-[(3S)-1-[3-methyl-6-[6-(6-methylpyrazin-2-yl)pyrazolo[4,3-c]pyridin-1-yl]pyrazin-2-yl]-3-piperidyl]carbamate

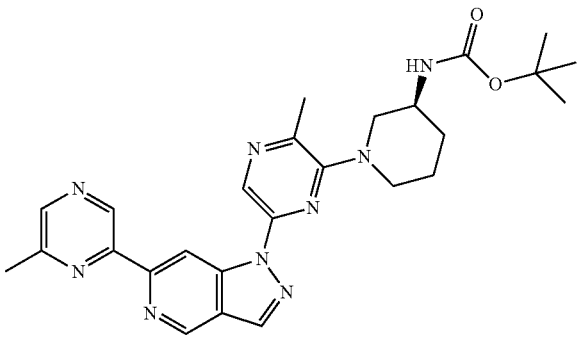 [SMILES: Cc1cncc(-c2cc3c(cn2)cnn3-c2cnc(C)c(N3CCC[C@H](NC(=O)OC(C)(C)C)C3)n2)n1]

To a solution of tert-butyl N-[(3S)-1-[3-chloro-6-[6-(6-methylpyrazin-2-yl)pyrazolo[4,3-c]pyridin-1-yl]pyrazin-2-yl]-3-piperidyl]carbamate (50 mg, 0.096 mmol), trimethylboroxine (36 mg, 0.29 mmol) and [1,1'-bis(diphenylphosphino)ferrocene]dichloropalladium(II) dichloromethane adduct (8.0 mg, 0.0095 mmol) in acetonitrile 2.0 mL was added 1.00M sodium carbonate in water (0.19 mL, 0.19 mmol) and 1.00M potassium acetate in Water (0.19 mL, 0.19 mmol). The reaction mixture was heated in microwave at 140° C. for 40 min. The reaction was filtered through celite. The crude product was purified by flash chromatography (EtOAc/Heptane eluted at 80% EtOAc) to give the desired product 34 mg 70% yield. MS (ESI) m/z: 502.2.

Step B

A solution of tert-butyl N-[(3S)-1-[3-methyl-6-[6-(6-methylpyrazin-2-yl)pyrazolo[4,3-c]pyridin-1-yl]pyrazin-2-yl]-3-piperidyl]carbamate (34 mg, 0.068 mmol) in hydrogen chloride (4 mol/l) in 1,4-dioxane (2.0 ml, 8.0 mmol) and 1,4-dioxane 2.0 mL was stirred at RT 18 h. The crude product was submitted for reverse phase HPLC to give 228 (15 mg, 56% yield). MS (ESI) m/z: 402.2. 1H NMR (400 MHz, DMSO) δ 9.58 (s, 1H), 9.44 (s, 1H), 9.32 (s, 1H), 8.71 (s, 1H), 8.66 (s, 1H), 8.63 (s, 1H), 3.67 (d, J=12.3 Hz, 2H), 3.19 (t, J=11.3 Hz, 1H), 2.93 (s, 1H), 2.73 (dd, J=12.1, 9.1 Hz, 1H), 2.64 (s, 3H), 2.54 (s, 3H), 1.94 (d, J=10.2 Hz, 2H), 1.74 (d, J=11.1 Hz, 1H), 1.39-1.26 (m, 1H).

Example 129

(R)-1-(6-(6-(1-Methyl-1H-pyrazol-4-yl)-1H-pyrazolo[4,3-c]pyridin-1-yl)pyridin-2-yl)-1,4-diazepan-6-ol 229

Following the procedures as described in Example 124 and starting with 1,4-diazepan-6-ol, 2-bromo-6-fluoropyridine, 6-chloro-1H-pyrazolo[4,3-c]pyridine, and 1-methyl-4-(4,4,5,5-tetramethyl-1,3,2-dioxaborolan-2-yl)-1H-pyrazole, 229 was obtained as a yellow solid (40 mg, 24.1%) over six steps. ¹H NMR (500 MHz, DMSO-d₆) δ (ppm) 9.09 (s, 1H), 8.65 (s, 1H), 8.44 (s, 1H), 8.25 (s, 1H), 7.98 (s, 1H), 7.63-7.68 (m, 1H), 7.14-7.16 (d, J=12.5 Hz, 1H), 6.61-6.64 (d, J=14 Hz, 1H), 4.10-4.14 (m, 1H), 3.86-3.91 (m, 6H), 3.55-3.66 (m, 2H), 2.98-3.04 (m, 3H), 2.84-2.90 (m, 1H), 2.69-2.71 (m, 1H); MS (ESI) m/z: 391 [M+H]⁺.

Example 130

4-(6-(6-(1-Methyl-1H-pyrazol-4-yl)-1H-pyrazolo[4,3-c]pyridin-1-yl)pyridin-2-yl)azepan-4-ol 230

A solution of tert-butyl 4-hydroxy-4-(6-(6-(1-methyl-1H-pyrazol-4-yl)-1H-pyrazolo[4,3-c]pyridin-1-yl)pyridin-2-yl)azepane-1-carboxylate (200 mg, 0.41 mmol) in a solution of HCl in MeOH (2.0 M, 10 mL) was stirred at room temperature for 1 hour, which was monitored by LCMS. After completion of the reaction, the reaction mixture was concentrated under reduced pressure. The crude was purified by reverse phase preparative HPLC to afford 230 as a light yellow solid (30 mg, 31%). ¹H NMR (500 MHz, CDCl₃) δ (ppm) 9.06 (s, 1H), 8.85 (s, 1H), 8.26 (s, 1H), 8.06 (s, 1H), 8.03 (s, 1H), 7.88-7.89 (d, J=4.5 Hz, 2H), 7.56-7.58 (t, J=9 Hz, 1H), 4.00 (s, 3H), 3.31-3.38 (m, 2H), 3.10-3.13 (t, J=13 Hz, 1H), 2.81-2.83 (t, J=12 Hz, 1H), 2.37-2.46 (m, 3H), 2.10-2.17 (m, 4H), 1.82-1.85 (t, J=14.5 Hz, 1H); MS (ESI) m/z: 390 [M+H]⁺.

Example 131

(S)-1-(6-(6-(1-Methyl-1H-pyrazol-4-yl)-1H-pyrazolo[4,3-c]pyridin-1-yl)pyridin-2-yl)-1,4-diazepan-6-ol 231

Following the procedures as described in Example 124 and starting with 1,4-diazepan-6-ol, 2-bromo-6-fluoropyridine, 6-chloro-1H-pyrazolo[4,3-c]pyridine, and 1-methyl-4-(4,4,5,5-tetramethyl-1,3,2-dioxaborolan-2-yl)-1H-pyrazole, 231 was obtained as a yellow solid (43 mg, 23.5%) over six steps. ¹H NMR (500 MHz, DMSO-d₆) δ (ppm) 9.09 (s, 1H), 8.65 (s, 1H), 8.44 (s, 1H), 8.25 (s, 1H), 7.98 (s, 1H), 7.63-7.68 (m, 1H), 7.14-7.16 (d, J=12.5 Hz, 1H), 6.61-6.64 (d, J=14 Hz, 1H), 4.10-4.14 (m, 1H), 3.86-3.91 (m, 6H), 3.55-3.66 (m, 2H), 2.98-3.04 (m, 3H), 2.84-2.90 (m, 1H), 2.69-2.71 (m, 1H); MS (ESI) m/z: 391 [M+H]⁺.

Example 132

1-[6-[6-(6-methylpyrazin-2-yl)pyrazolo[4,3-c]pyridin-1-yl]-2-pyridyl]pyrrolidine-3 4-diol 232

Following the procedures in preparation of EXAMPLE 23, 232 was obtained. MS (ESI) m/z: 390.1. 1H NMR (400 MHz, DMSO) δ 9.94 (s, 1H), 9.46 (s, 1H), 9.31 (s, 1H), 8.64 (d, J=8.1 Hz, 2H), 7.71 (t, J=8.0 Hz, 1H), 7.19 (d, J=7.7 Hz, 1H), 6.42 (d, J=8.3 Hz, 1H), 5.23 (d, J=3.1 Hz, 2H), 4.18 (s, 2H), 2.66 (s, 3H).

Example 133

(S)-3-(3-aminopiperidin-1-yl)-1-methyl-5-(6-(6-methylpyrazin-2-yl)-1H-pyrazolo[4,3-c]pyridin-1-yl)pyridin-2(1H)-one 233

Step A: tert-butyl N-[(3S)-1-(5-bromo-1-methyl-2-oxo-3-pyridyl)-3-piperidyl]carbamate

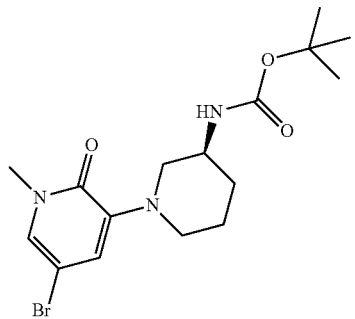 [SMILES: Cn1cc(Br)cc(N2CCC[C@H](NC(=O)OC(C)(C)C)C2)c1=O]

A mixture of 3,5-dibromo-1-methyl-pyridin-2-one (2.000 mmol; 533.8 mg), tert-butyl N-[(3S)-3-piperidyl]carbamate (2.00 mmol; 401 mg), cesium carbonate (4.0 mmol; 1303 mg), Xantphos (0.3400 mmol; 202.8 mg), and tris(dibenzylideneacetone)dipalladium(0) (0.2000 mmol; 185.0 mg) in 1,4-Dioxane (10 mL) was purged with Argon, then sealed and stirred at 110° C. overnight. The mixture was cooled to room temperature and filtered through Celite. The filtrate was concentrated and the residue was purified on silica eluted with 0 to 100% EtOAc in Heptane to afford tert-butyl N-[(3S)-1-(5-bromo-1-methyl-2-oxo-3-pyridyl)-3-piperidyl]carbamate as a yellow solid (458.6 mg, 59%).

Step B: tert-butyl N-[(3S)-1-[1-methyl-5-[6-(6-methylpyrazin-2-yl)pyrazolo[4,3-c]pyridin-1-yl]-2-oxo-3-pyridyl]-3-piperidyl]carbamate

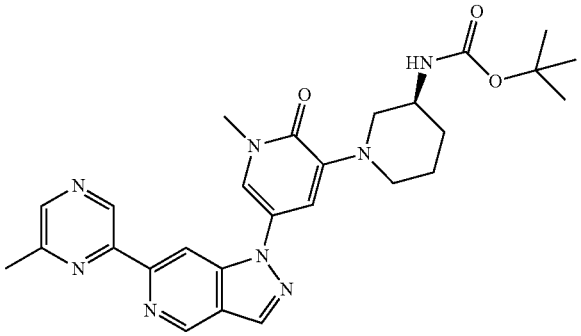 [SMILES: Cc1cncc(-c2cc3c(cn2)cnn3-c2cc(N3CCC[C@H](NC(=O)OC(C)(C)C)C3)c(=O)n(C)c2)n1]

A mixture of 6-(6-methylpyrazin-2-yl)-1H-pyrazolo[4,3-c]pyridine (0.49711 mmol; 105 mg), tert-butyl N-[(3S)-1-(5-bromo-1-methyl-2-oxo-3-pyridyl)-3-piperidyl]carbamate (0.59653 mmol; 230.4 mg), N,N'-Dimethylethylenediamine (0.049711 mmol; 4.382 mg; 0.00495 mL), copper iodide (0.49711 mmol; 95.629 mg), and potassium carbonate (0.99422 mmol; 138.79 mg) in 1,4-Dioxane (10 mL) was purged with Argon, then sealed and stirred at 100° C. overnight. The mixture was cooled to room temperature, and then filtered through Celite. The filtrate was concentrated; the residue was purified on silica eluted with 0 to 6% MeOH in DCM to afford tert-butyl N-[(3S)-1-[1-methyl-5-[6-(6-methylpyrazin-2-yl)pyrazolo[4,3-c]pyridin-1-yl]-2-oxo-3-pyridyl]-3-piperidyl]carbamate (116. mg, 45%).

Step C

A mixture of tert-butyl N-[(3S)-1-[1-methyl-5-[6-(6-methylpyrazin-2-yl)pyrazolo[4,3-c]pyridin-1-yl]-2-oxo-3-pyridyl]-3-piperidyl]carbamate (0.2245 mmol; 116.0 mg) in TFA (1 mL) and dichloromethane (4 mL) was stirred at room temperature overnight. The mixture was concentrated and the residue was purified by reverse phase HPLC to afford 233 as an off-white solid (51.6 mg, 54%). $^1$H NMR (400 MHz, DMSO) δ 9.47-9.40 (s, 1H), 9.36-9.30 (s, 1H), 8.66-8.57 (s, 2H), 8.48-8.40 (s, 1H), 7.96-7.90 (d, J=2.5 Hz, 1H), 6.96-6.90 (d, J=2.5 Hz, 1H), 3.69-3.61 (d, J=6.6 Hz, 2H), 3.58-3.52 (s, 3H), 2.83-2.72 (t, J=9.7 Hz, 1H), 2.63-2.58 (s, 3H), 2.30-2.23 (m, 1H), 1.88-1.81 (d, J=9.0 Hz, 1H), 1.74-1.68 (d, J=13.3 Hz, 1H), 1.63-1.53 (d, J=12.8 Hz, 1H), 1.18-1.06 (m, 1H); MS (ESI) m/z: 417.2 [M+H]$^+$ Example 134

(R)-1-(3-Methoxy-6-(6-(1-(2,2,2-trifluoroethyl)-1H-pyrazol-4-yl)-1H-pyrazolo-[4,3-c]pyridin-1-yl)pyridin-2-yl)-1,4-diazepan-6-ol 234

Following the procedures as described in Example 88 and starting with 6-bromo-2-fluoro-3-methoxypyridine and 1,4-diazepan-6-ol, 234 was obtained as a yellow solid (40 mg, 16.5%) over six steps. $^1$H NMR (500 MHz, DMSO-d$_6$) δ (ppm) 9.14 (s, 1H), 8.60 (s, 1H), 8.50 (s, 1H), 8.46 (s, 1H), 8.18 (s, 1H), 7.42 (d, J=8.5 Hz, 1H), 7.24 (d, J=8.5 Hz, 1H), 5.19-5.24 (m, 2H), 4.81 (s, 1H), 4.16-4.20 (m, 1H), 3.98-4.02 (m, 2H), 3.96 (s, 3H), 3.50-3.54 (m, 2H), 2.94-3.02 (m, 2H), 2.85-2.87 (m, 1H), 2.71-2.75 (m, 1H); MS (ESI) m/z: 489 [M+H]$^+$.

Example 135

1-(6-(azepan-4-yl)pyridin-2-yl)-6-(1-methyl-1H-pyrazol-4-yl)-1H-pyrazolo[4,3-c]pyridine 235

Step A: tert-Butyl 4-(6-Bromopyridin-2-yl)-4-hydroxyazepane-1-carboxylate

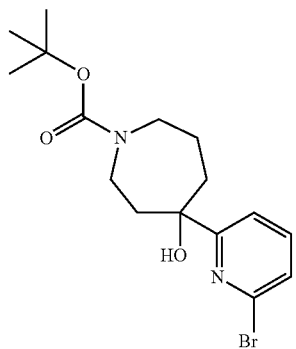 [SMILES: CC(C)(C)OC(=O)N1CCCC(O)(c2cccc(Br)n2)CC1]

To a solution of 2,6-dibromopyridine (0.2 g, 0.84 mmol) in Et$_2$O (20 mL) at −78° C. was added 2.5 M solution of n-BuLi in hexane (3.7 mL, 0.928 mmol) over 30 min. The mixture was stirred at −78° C. for 30 minutes. To it was dropped tert-butyl 4-oxoazepane-1-carboxylate (180 mg, 084 mmol) in Et$_2$O (20 mL) over 15 minutes. After the mixture was stirred for one hour, to it was added H$_2$O (100 mL). The aqueous layer was extracted with EtOAc (100 mL×2). The combined organic layers were washed with 10% solution of NaOH and brine, dried over MgSO$_4$, concentrated under reduced pressure. The crude product was purified by silica gel chromatography using petroleum ether/EtOAc (9:1) as eluting solvents to afford tert-butyl 4-(6-bromopyridin-2-yl)-4-hydroxyazepane-1-carboxylate as an oil (200 mg, 62.5%). MS (ESI) m/z: 371 [M+H]$^+$.

Step B: tert-Butyl 4-(6-(6-Chloro-1H-pyrazolo[4,3-c]pyridin-1-yl)pyridin-2-yl)-4-hydroxyazepane-1-carboxylate

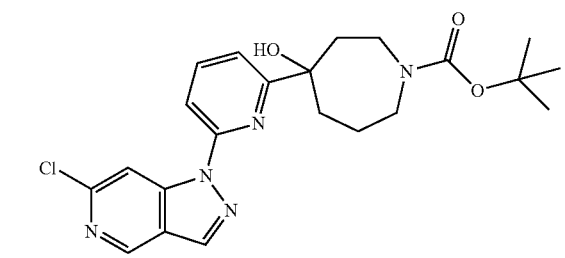 [SMILES: CC(C)(C)OC(=O)N1CCCC(O)(c2cccc(-n3ncc4cnc(Cl)cc43)n2)CC1]

To a mixture of tert-butyl 4-(6-bromopyridin-2-yl)-4-hydroxyazepane-1-carboxylate (792 mg, 2.4 mmol) and 6-chloro-1H-pyrazolo[4,3-c]pyridine (300 mg, 1.94 mmol) in 1,4-dioxane (20 mL) was added CuI (150 mg, 0.78 mmol), K$_2$CO$_3$ (1.08 g, 7.8 mmol), and N$^1$,N$^2$-dimethylethane-1,2-diamine (138 mg, 1.56 mmol). The mixture was heated at 100° C. for 3 hours, which was monitored by LCMS. After completion of the reaction, the reaction mixture was concentrated under reduced pressure. The crude was purified by silica gel chromatography using petroleum ether/EtOAc (4/1) to afford tert-butyl 4-(6-(6-chloro-1H-pyrazolo[4,3-c]pyridin-1-yl)pyridin-2-yl)-4-hydroxyazepane-1-carboxylate as a white solid (550 mg, 58%). MS (ESI) m/z: 444 [M+H]$^+$.

Step C: tert-Butyl 4-Hydroxy-4-(6-(6-(1-methyl-1H-pyrazol-4-yl)-1H-pyrazolo[4,3-c]-pyridin-1-yl)pyridin-2-yl)azepane-1-carboxylate

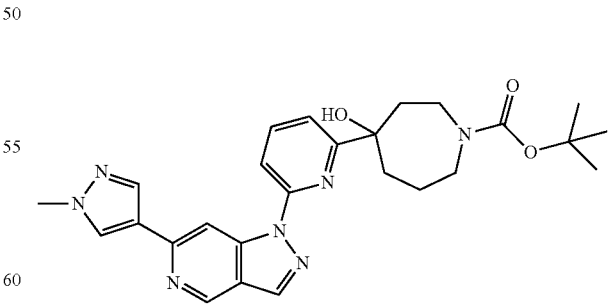

A suspension of tert-butyl 4-(6-(6-chloro-1H-pyrazolo[4,3-c]pyridin-1-yl)pyridin-2-yl)-4-hydroxyazepane-1-carboxylate (500 mg, 1.12 mmol), 4-(4,4,5,5-tetramethyl-1,3,2-dioxaborolan-2-yl)-1H-pyrazole (350 mg, 1.69 mmol), Pd(dppf)Cl$_2$ (50 mg, 0.06 mmol), and aqueous solution of Na₂CO₃ (2.0 M, 2.0 mL) in 1,4-dioxane (30 mL) under nitrogen was stirred at 100° C. for 18 hours. The reaction mixture was filtered and the filtrate was concentrated under reduced pressure. The residue was purified by silica gel chromatography using petroleum ether/EtOAc (2/1) as eluting solvents to afford tert-butyl 4-hydroxy-4-(6-(6-(1-methyl-1H-pyrazol-4-yl)-1H-pyrazolo[4,3-c]pyridin-1-yl)pyridin-2-yl)azepane-1-carboxylate as a yellow oil (500 mg, 91%). MS (ESI) m/z: 490 [M+H]⁺.

Step D

A mixture of tert-butyl 4-hydroxy-4-(6-(6-(1-methyl-1H-pyrazol-4-yl)-1H-pyrazolo[4,3-c]pyridin-1-yl)pyridin-2-yl)azepane-1-carboxylate (140 mg, 0.29 mmol) and SOCl₂ (10 mL) was stirred at room temperature for 24 hours. The reaction mixture was concentrated under reduced pressure. The residue was added MeOH (10 mL) and 10% Pd/C (0.1 g). The mixture was stirred under hydrogen (40 psi) at room temperature for 5 hours, which was monitored by LCMS. After completion of the reaction, the mixture was filtered with Celite and filtrate was concentrated under reduced pressure. The crude was purified by reverse phase preparative HPLC to afford the formate salt of 235 as a light yellow solid (8 mg, 7.4%). ¹H NMR (500 MHz, DMSO-d₆) δ (ppm) 9.15 (s, 1H), 8.75 (s, 1H), 8.58 (s, 1H), 8.416-8.421 (d, J=2.5 Hz, 1H), 8.31 (s, 1H), 8.01 (s, 1H), 7.96-7.99 (t, J=15.5 Hz, 1H), 7.82-7.83 (d, J=8 Hz, 1H), 7.26-7.28 (d, J=7 Hz, 1H), 4.08-4.22 (m, 3H), 3.13-3.31 (m, 6H), 2.24 (s, 1H), 2.17-2.19 (d, J=7.5 Hz, 2H), 1.96-2.03 (m, 3H); MS (ESI) m/z: 374 [M+H]⁺.

Example 136

1-(6-(4-Fluoroazepan-4-yl)pyridin-2-yl)-6-(1-methyl-1H-pyrazol-4-yl)-1H-pyrazolo[4,3-c]pyridine Format Salt 236

Step A: 1-(6-(4-Fluoroazepan-4-yl)pyridin-2-yl)-6-(1-methyl-1H-pyrazol-4-yl)-1H-pyrazolo[4,3-c]pyridine

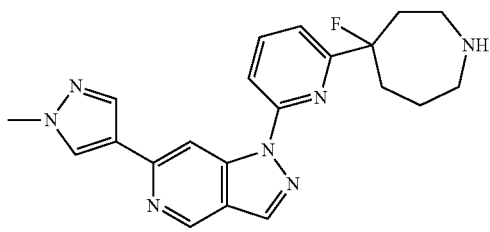 [SMILES: Cn1cc(-c2cc3c(cn2)cnn3-c2cccc(C3(F)CCCNCC3)n2)cn1]

To a solution of tert-butyl 4-hydroxy-4-(6-(6-(1-methyl-1H-pyrazol-4-yl)-1H-pyrazolo[4,3-c]pyridin-1-yl)pyridin-2-yl)azepane-1-carboxylate (150 mg, 0.3 mmol) in DCM (5 mL) was added diethylaminosulfur trifluoride (DAST, 0.12 mL, 0.9 mmol). The mixture was stirred at room temperature for 1 hour, which was monitored by LCMS. After completion of the reaction, it was concentrated under reduced pressure to afford 1-(6-(4-fluoroazepan-4-yl)pyridin-2-yl)-6-(1-methyl-1H-pyrazol-4-yl)-1H-pyrazolo[4,3-c]pyridine as a light yellow oil (130 mg, 87%). MS (ESI) m/z: 493 [M+H]⁺.

Step B

A solution of 1-(6-(4-fluoroazepan-4-yl)pyridin-2-yl)-6-(1-methyl-1H-pyrazol-4-yl)-1H-pyrazolo[4,3-c]pyridine (120 mg, 0.24 mmol) in a solution of HCl in MeOH (2.0 M, 10 mL) was stirred at room temperature for 1 hour. The reaction mixture was concentrated under reduced pressure. The crude was purified by reverse phase preparative HPLC to afford the formate salt of 236 as a light yellow solid (18 mg, 18.9%). ¹H NMR (500 MHz, DMSO-d₆) δ (ppm) 9.17 (s, 1H), 8.68 (s, 1H), 8.62 (s, 1H), 8.39 (s, 1H), 8.33 (s, 1H), 8.10-8.13 (t, J=16 Hz, 1H), 8.07 (s, 1H), 7.95-7.97 (d, J=8.5 Hz, 1H), 7.50-7.51 (d, J=8 Hz, 1H), 3.93 (s, 3H), 3.07-3.29 (m, 4H), 2.64-2.66 (t, J=10.5 Hz, 2H), 2.22-2.30 (m, 2H), 2.05-2.06 (t, J=6 Hz, 1H), 1.92 (s, 1H); MS (ESI) m/z: 392 [M+H]⁺.

Example 137

(S)-1-(3-Methoxy-6-(6-(1-(2,2,2-trifluoroethyl)-1H-pyrazol-4-yl)-1H-pyrazolo-[4,3-c]pyridin-1-yl)pyridin-2-yl)-1,4-diazepan-6-ol 237

Following the procedures as described in Example 88 and starting with 6-bromo-2-fluoro-3-methoxypyridine and 1,4-diazepan-6-ol, 237 was obtained as a yellow solid (40 mg, 16.3%) over six steps. ¹H NMR (500 MHz, DMSO-d₆) δ (ppm) 9.14 (s, 1H), 8.60 (s, 1H), 8.50 (s, 1H), 8.46 (s, 1H), 8.18 (s, 1H), 7.42 (d, J=8.5 Hz, 1H), 7.24 (d, J=8.5 Hz, 1H), 5.18-5.24 (m, 2H), 4.80 (s, 1H), 4.16-4.20 (m, 1H), 3.98-4.02 (m, 2H), 3.96 (s, 3H), 3.50-3.54 (m, 2H), 2.94-3.02 (m, 2H), 2.84-2.87 (m, 1H), 2.71-2.75 (m, 1H); MS (ESI) m/z: 489 [M+H]⁺.

Example 138

(3S)-1-[3-cyclopropyl-6-[6-(6-methylpyrazin-2-yl)pyrazolo[4,3-c]pyridin-1-yl]pyrazin-2-yl]piperidin-3-amine 238

Following the procedures in preparation of EXAMPLE 128, 238 was obtained. MS (ESI) m/z: 428.2. 1H NMR (400 MHz, DMSO) δ 9.61 (s, 1H), 9.45 (s, 1H), 9.33 (s, 1H), 8.71 (s, 1H), 8.63 (s, 1H), 8.62 (s, 1H), 3.86 (d, J=9.5 Hz, 1H), 3.74 (d, J=11.9 Hz, 1H), 2.98 (d, J=9.0 Hz, 1H), 2.86-2.76 (m, 1H), 2.65 (s, 3H), 2.25 (t, J=8.9 Hz, 1H), 1.96 (d, J=10.1 Hz, 2H), 1.83-1.64 (m, 2H), 1.34 (d, J=9.9 Hz, 1H), 1.09 (ddd, J=24.4, 12.6, 5.7 Hz, 4H).

Example 140

6-(6-methylpyrazin-2-yl)-1-(6-(4-(oxetan-3-yl)-1,4-diazepan-1-yl)pyridin-2-yl)-1H-pyrazolo[4,3-c]pyridine 240

Step A: 6-chloro-1-[6-[4-(oxetan-3-yl)-1,4-diazepan-1-yl]-2-pyridyl]pyrazolo[4,3-c]pyridine

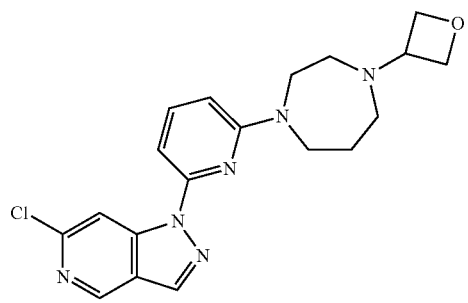 [SMILES: Clc1cc2c(cn1)cnn2-c1cccc(N2CCCN(C3COC3)CC2)n1]

A mixture of 6-chloro-1-[6-(1,4-diazepan-1-yl)-2-pyridyl]pyrazolo[4,3-c]pyridine (0.4094 mmol; 134.6 mg), oxetan-3-one (0.4912 mmol; 35.40 mg), and Molecular sieve (4A) in 1,2-dichloroethane (12 ml) was stirred at room temperature for 4 hours. STAB (0.6141 mmol; 137.0 mg) was added. The reaction was stirred for 3 days. The mixture was filtered through Celite. The filtrate was concentrated and the residue was purified on silica eluted with 0 to 5% MeOH in DCM to afford 6-chloro-1-[6-[4-(oxetan-3-yl)-1,4-diazepan-1-yl]-2-pyridyl]pyrazolo[4,3-c]pyridine (99.2 mg, 63%).

Step B

A mixture of trimethyl-(6-methylpyrazin-2-yl)stannane (0.387 mmol; 99.3 mg), 6-chloro-1-[6-[4-(oxetan-3-yl)-1,4-diazepan-1-yl]-2-pyridyl]pyrazolo[4,3-c]pyridine (0.258 mmol; 99.2 mg), and Palladium(0)tetrakis(triphenylphosphine) (0.0258 mmol; 29.8 mg) in N,N-Dimethylacetamide (3 ml) was purged with argon. The reaction mixture was sealed in a Biotage pressure vial and heated at 150° C. under microwave for 45 min. The mixture filtered through Celite. The filtrate was concentrated and the residue was purified on silica eluted with 0 to 10% MeOH in DCM. The material was further purified by reverse phase HPLC to afford 240 as an off-white solid (23.3 mg, 20%). $^1$H NMR (400 MHz, DMSO) δ 9.66-9.61 (s, 1H), 9.47-9.44 (s, 1H), 9.33-9.30 (s, 1H), 9.06-9.03 (s, OH), 8.67-8.60 (m, 2H), 8.52-8.50 (s, 1H), 7.76-7.68 (td, J=8.1, 3.4 Hz, 2H), 7.25-7.20 (d, J=7.7 Hz, 1H), 7.17-7.13 (d, J=7.7 Hz, 1H), 6.66-6.59 (dd, J=8.3, 6.0 Hz, 2H), 4.55-4.46 (m, 3H), 4.41-4.33 (dt, J=15.0, 6.0 Hz, 3H), 3.98-3.86 (d, J=5.5 Hz, 4H), 3.81-3.73 (m, 2H), 3.67-3.60 (dt, J=11.7, 5.8 Hz, 2H), 2.67-2.63 (s, 2H), 2.62-2.59 (s, 3H), 2.41-2.36 (dd, J=11.3, 6.0 Hz, 3H), 2.05-1.93 (dt, J=18.5, 6.1 Hz, 3H); MS (ESI) m/z: 443.2 [M+H]$^+$ Example 141

(S)-3-(3-aminopiperidin-1-yl)-1-methyl-5-(6-(6-methylpyrazin-2-yl)-1H-pyrazolo[4,3-c]pyridin-1-yl)pyrazin-2(1H)-one 241

Step A: tert-butyl N-[(3S)-1-(6-bromo-4-methyl-3-oxo-pyrazin-2-yl)-3-piperidyl]carbamate

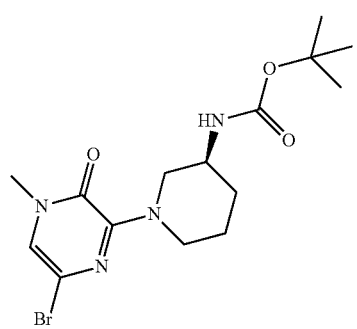 [SMILES: Cn1cc(Br)nc(N2CCC[C@H](NC(=O)OC(C)(C)C)C2)c1=O]

A mixture of 3,5-dibromo-1-methyl-pyrazin-2-one (2.025 mmol; 542.4 mg), tert-butyl N-[(3S)-3-piperidyl]carbamate (2.025 mmol; 405.5 mg), cesium carbonate (4.049 mmol; 1319 mg), Xantphos (0.1721 mmol; 102.7 mg), and tris(dibenzylideneacetone)dipalladium(0) (0.1012 mmol; 93.63 mg) in 1,4-dioxane (10 mL) was purged with Argon, then sealed and stirred at 110° C. overnight. The mixture was cooled to room temperature and filtered through Celite. The filtrate was concentrated and the residue was purified on silica eluted with 0 to 20% EtOAc in DCM to afford tert-butyl N-[(3S)-1-(6-bromo-4-methyl-3-oxo-pyrazin-2-yl)-3-piperidyl]carbamate as a yellow solid (451.0 mg, 58%).

Step B: tert-butyl N-[(3S)-1-[4-methyl-6-[6-(6-methylpyrazin-2-yl)pyrazolo[4,3-c]pyridin-1-yl]-3-oxo-pyrazin-2-yl]-3-piperidyl]carbamate

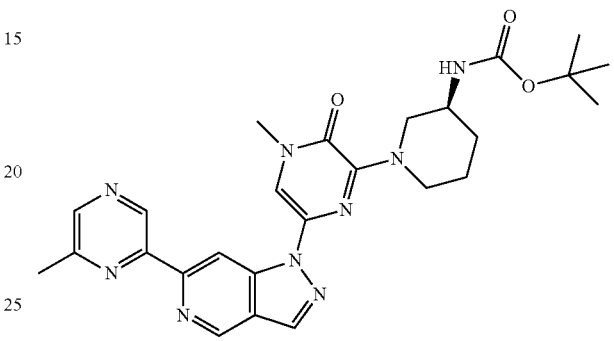

A mixture of 6-(6-methylpyrazin-2-yl)-1H-pyrazolo[4,3-c]pyridine (0.49711 mmol; 105 mg), tert-butyl N-[(3S)-1-(6-bromo-4-methyl-3-oxo-pyrazin-2-yl)-3-piperidyl]carbamate (0.6016 mmol; 233 mg), N,N'-Dimethylethylenediamine (0.049711 mmol; 4.382 mg; 0.00495 mL), copper iodide (0.49711 mmol; 95.629 mg), and potassium carbonate (0.99422 mmol; 138.79 mg) in 1,4-dioxane (10 ml) was purged with argon, then sealed and stirred at 100° C. overnight. The mixture was cooled to room temperature, and then filtered through Celite. The filtrate was concentrated; the residue was purified on silica eluted with 0 to % MeOH in DCM to afford tert-butyl N-[(3S)-1-[4-methyl-6-[6-(6-methylpyrazin-2-yl)pyrazolo[4,3-c]pyridin-1-yl]-3-oxo-pyrazin-2-yl]-3-piperidyl]carbamate (181.4 mg, 70%).

Step C

A mixture of tert-butyl N-[(3S)-1-[4-methyl-6-[6-(6-methylpyrazin-2-yl)pyrazolo[4,3-c]pyridin-1-yl]-3-oxo-pyrazin-2-yl]-3-piperidyl]carbamate (0.3505 mmol; 181.4 mg) in TFA (1 mL) and dichloromethane (4 ml) was stirred at room temperature overnight. The mixture was concentrated and the residue was purified by reverse phase HPLC to afford 241 as an off-white solid (28.1 mg, 18%). $^1$H NMR (400 MHz, DMSO) δ 9.47-9.40 (s, 1H), 9.36-9.30 (s, 1H), 8.66-8.57 (s, 2H), 8.48-8.40 (s, 1H), 7.96-7.90 (d, J=2.5 Hz, 1H), 6.96-6.90 (d, J=2.5 Hz, 1H), 3.69-3.61 (d, J=6.6 Hz, 2H), 3.58-3.52 (s, 3H), 2.83-2.72 (t, J=9.7 Hz, 1H), 2.63-2.58 (s, 3H), 2.30-2.23 (m, 1H), 1.88-1.81 (d, J=9.0 Hz, 1H), 1.74-1.68 (d, J=13.3 Hz, 1H), 1.63-1.53 (d, J=12.8 Hz, 1H), 1.18-1.06 (m, 1H); MS (ESI) m/z: 418.2 [M+H]$^+$ Example 142

(S)-3-(3-Aminopiperidin-1-yl)-1-methyl-5-(6-(1-methyl-1H-pyrazol-4-yl)-1H-pyrazolo[4,3-c]pyridin-1-yl)pyrazin-2(1H)-one 242

Following the procedures as described in Example 124 and starting with (5)-tert-butyl piperidin-3-ylcarbamate, 3,5- dibromo-1-methylpyrazin-2(1H)-one, 6-chloro-1H-pyrazolo[4,3-c]pyridine, and 1-methyl-4-(4,4,5,5-tetramethyl-1,3,2-dioxaborolan-2-yl)-1H-pyrazole, 242 was obtained as a yellow solid (60 mg, 18.1%) over four steps. ¹H NMR (500 MHz, DMSO-d₆) δ (ppm) 9.09 (s, 1H), 8.45 (s, 1H), 8.37 (s, 1H), 8.32 (s, 1H), 8.00 (s, 1H), 7.64 (s, 1H), 4.59-4.72 (m, 2H), 3.91 (s, 3H), 3.51 (s, 3H), 2.98-3.04 (m, 1H), 2.83-2.92 (m, 1H), 2.80-2.81 (m, 1H), 1.92-1.94 (m, 1H), 1.78-1.79 (m, 1H), 1.61-1.62 (m, 1H), 1.28-1.34 (m, 1H); MS (ESI) m/z: 406 (M+H)⁺.

Example 143

(R)-3-(3-aminopiperidin-1-yl)-1-methyl-5-(6-(1-methyl-1H-pyrazol-4-yl)-1H-pyrazolo[4,3-c]pyridin-1-yl)pyrazin-2(1H)-one 243

Following the procedures as described in Example 124 and starting with (R)-tert-butyl piperidin-3-ylcarbamate, 3,5-dibromo-1-methylpyrazin-2(1H)-one, 6-chloro-1H-pyrazolo[4,3-c]pyridine, and 1-methyl-4-(4,4,5,5-tetramethyl-1,3,2-dioxaborolan-2-yl)-1H-pyrazole, 243 was obtained as a yellow solid (58 mg, 17.9%) over four steps. ¹H NMR (500 MHz, DMSO-d₆) δ9.09 (s, 1H), 8.45 (s, 1H), 8.37 (s, 1H), 8.32 (s, 1H), 8.05 (s, 1H), 7.64 (s, 1H), 4.59-4.72 (m, 2H), 3.92 (s, 3H), 3.51 (s, 3H), 2.98-3.06 (m, 1H), 2.80-2.92 (m, 1H), 2.80-2.81 (m, 1H), 1.92-1.94 (m, 1H), 1.78-1.79 (m, 1H), 1.60-1.62 (m, 1H), 1.29-1.34 (m, 1H); MS (ESI) m/z: 406 (M+H)⁺.

Example 145

(3S)-3-amino-1-[3-methyl-6-[6-(6-methylpyrazin-2-yl)pyrazolo[4,3-c]pyridin-1-yl]-2-pyridyl]piperidin-2-one 245

Following the procedures in preparation of EXAMPLE 121, 245 was obtained. MS (ESI) m/z: 415.1. 1H NMR (400 MHz, DMSO) δ 9.63 (s, 1H), 9.48 (s, 1H), 9.35 (s, 1H), 8.72 (s, 1H), 8.65 (s, 1H), 7.97 (d, J=8.4 Hz, 1H), 7.91 (d, J=8.2 Hz, 1H), 4.41 (s, 1H), 3.69 (s, 1H), 3.54 (s, 1H), 2.66 (s, 3H), 2.17 (s, 4H), 1.87 (s, 2H).

Example 147

6-(1-(6-(1,4-diazepan-1-yl)pyridin-2-yl)-1H-pyrazolo[4,3-c]pyridin-6-yl)pyrazin-2-amine 247

Step A: tributyl-[1-(6-fluoro-2-pyridyl)pyrazolo[4,3-c]pyridin-6-yl]stannane

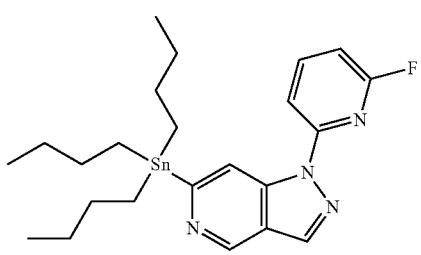 [SMILES: CCC[CH2][Sn]([CH2]CCC)([CH2]CCC)[c]1cc2c(cn1)cnn2-c1cccc(F)n1]

To a mixture of 6-chloro-1-(6-fluoro-2-pyridyl)pyrazolo[4,3-c]pyridine 6 (3.1411 mmol; 781 mg) in 1,4-Dioxane (40 mL) under Argon was added lithium chloride (18.847 mmol; 798.98 mg), Bis(tributyltin) (3.7693 mmol; 2301.7 mg; 2.005 mL), Tris(dibenzylideneacetone)dipalladium (0) (0.15705 mmol; 143.82 mg) and Tricyclohexylphosphine (0.37693 mmol; 105.70 mg). The resulting mixture was sealed in a pressure tube and heated at 120° C. overnight. The mixture was filtered through Celite. The filter cake was washed with DCM. The filtrate was concentrated, and the residue was purified on silica eluted with 0 to 30% EtOAc in Heptane to afford tributyl-[1-(6-fluoro-2-pyridyl)pyrazolo[4,3-c]pyridin-6-yl]stannane (1.0933 g, 69%).

Step B:
6-bromo-N-[(4-methoxyphenyl)methyl]pyrazin-2-amine

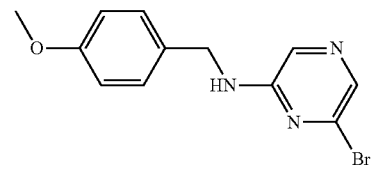 [SMILES: COc1ccc(CNc2cncc(Br)n2)cc1]

A mixture of 2,6-dibromopyrazine (3.431 mmol; 816.1 mg), (4-methoxyphenyl)methanamine (3.431 mmol; 470.6 mg; 0.4452 mL), and N-Methylmorpholine (8.577 mmol; 876 mg; 0.952 mL) in 1-methyl-2-pyrrolidinone (10 mL) in a sealed pressure vial was heated at 100° C. overnight. The mixture was poured into water, and extracted with EtOAc. The organic layer was concentrated. The residue was purified on silica eluted with 0 to 100% EtOAc in DCM to afford 6-bromo-N-[(4-methoxyphenyl)methyl]pyrazin-2-amine (768.8 mg, 29%).

Step C: 6-[1-(6-fluoro-2-pyridyl)pyrazolo[4,3-c]pyridin-6-yl]-N-[(4-methoxyphenyl)methyl]pyrazin-2-amine

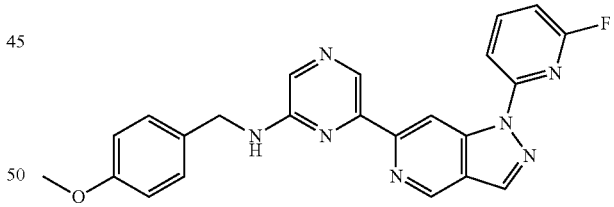

A mixture of 6-bromo-N-[(4-methoxyphenyl)methyl]pyrazin-2-amine (0.9932 mmol; 768.8 mg), tributyl-[1-(6-fluoro-2-pyridyl)pyrazolo[4,3-c]pyridin-6-yl]stannane (2.173 mmol; 1093 mg), tricyclohexylphosphine (0.1192 mmol; 33.42 mg) and Tris(dibenzylideneacetone)dipalladium (0) (0.04966 mmol; 45.47 mg) in N,N-Dimethylacetamide (15 mL) was purged with Argon for 1 min. The reaction mixture was sealed and heated at 150° C. under microwave for 45 min. The mixture was partitioned between EtOAc and water. The organic layer was concentrated and the residue was purified on silica eluted with 0 to 100% EtOAc in Heptane to afford 6-[1-(6-fluoro-2-pyridyl)pyrazolo[4,3-c]pyridin-6-yl]-N-[(4-methoxyphenyl)methyl]pyrazin-2-amine (316.3 mg, 48%).

Step D: tert-butyl 4-[6-[6-[6-[(4-methoxyphenyl)methylamino]pyrazin-2-yl]pyrazolo[4,3-c]pyridin-1-yl]-2-pyridyl]-1,4-diazepane-1-carboxylate

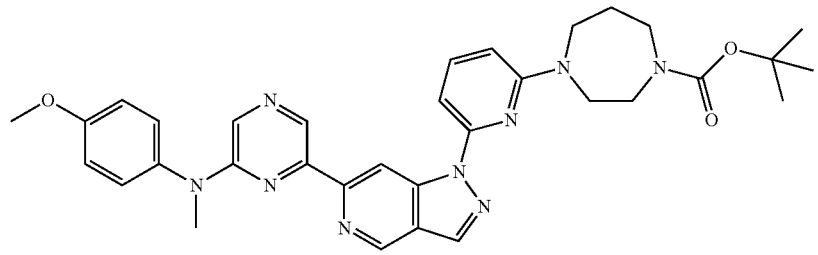 [SMILES: COc1ccc(N(C)c2cncc(-c3cc4c(cn3)cnn4-c3cccc(N4CCCN(C(=O)OC(C)(C)C)CC4)n3)n2)cc1]

A mixture of 6-[1-(6-fluoro-2-pyridyl)pyrazolo[4,3-c]pyridin-6-yl]-N-[(4-methoxyphenyl)methyl]pyrazin-2-amine (0.479 mmol; 316.3 mg), tert-butyl 1,4-diazepane-1-carboxylate (0.958 mmol; 192 mg), and N-Methylmorpholine (1.20 mmol; 122 mg; 0.133 mL) in 1-methyl-2-pyrrolidinone (5 mL) in a sealed pressure vial was heated at 110° C. overnight. The mixture was poured into water, and extracted with EtOAc. The organic layer was concentrated. The residue was purified on silica eluted with 0 to 100% EtOAc in DCM to afford tert-butyl 4-[6-[6-[6-[(4-methoxyphenyl)methylamino]pyrazin-2-yl]pyrazolo[4,3-c]pyridin-1-yl]-2-pyridyl]-1,4-diazepane-1-carboxylate (~291 mg, 100%).

Step E

To a mixture of tert-butyl 4-[6-[6-[6-[(4-methoxyphenyl)methylamino]pyrazin-2-yl]pyrazolo[4,3-c]pyridin-1-yl]-2-pyridyl]-1,4-diazepane-1-carboxylate (0.4789 mmol; 291 mg) in Dichloromethane (5 mL) was added Hydrogen Chloride, 4.0 M in 1,4-Dioxane (5 mL), and TRIFLIC ACID (4.789 mmol; 733.3 mg; 0.4293 mL). The reaction mixture was stirred at room temperature for 3 days. The mixture was concentrated and the residue was purified by reverse phase HPLC to afford 247 as an off-white solid (50.3 mg, 27%). $^1$H NMR (400 MHz, DMSO) δ 9.45-9.41 (s, 1H), 9.26-9.22 (s, 1H), 8.76-8.73 (s, 1H), 8.64-8.58 (s, 1H), 7.99-7.96 (s, 1H), 7.73-7.67 (t, J=8.1 Hz, 1H), 7.16-7.12 (d, J=7.7 Hz, 1H), 6.63-6.58 (d, J=8.5 Hz, 1H), 6.33-6.25 (s, 2H), 3.89-3.82 (dd, J=11.0, 5.2 Hz, 4H), 3.03-2.98 (m, 2H), 2.73-2.66 (m, 2H), 1.91-1.84 (dd, J=11.5, 5.8 Hz, 2H); MS (ESI) m/z: 388.2 [M+H]$^+$ Example 148

(S)-6-Methyl-1-(6-(6-(1-(2,2,2-trifluoroethyl)-1H-pyrazol-4-yl)-1H-pyrazolo[4,3-c]-pyridin-1-yl)pyridin-2-yl)-1,4-diazepan-6-ol 248

Step A: 1-(6-Bromopyridin-2-yl)-1,4-diazepan-6-ol

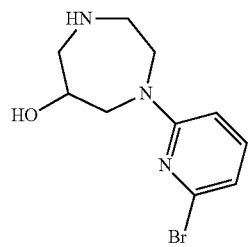 [SMILES: OC1CNCCN(c2cccc(Br)n2)C1]

To a mixture of 2-bromo-6-fluoropyridine (845 mg, 4.83 mmol) and 1,4-diazepan-6-ol (560 mg, 4.83 mmol) in EtOH (20 mL) was added DIPEA (5 mL). The reaction mixture was heated at 100° C. for 15 hours, which was monitored by LCMS. After completion of the reaction, it was concentrated under reduced pressure. The crude material was used in the next step without further purification. MS (ESI) m/z: 272 [M+H]$^+$.

Step B: tert-Butyl 4-(6-Bromopyridin-2-yl)-6-hydroxy-1,4-diazepane-1-carboxylate

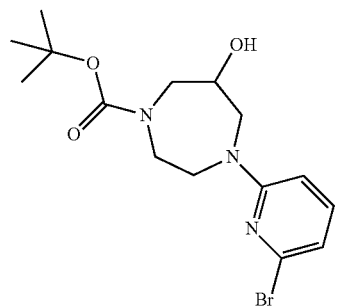 [SMILES: CC(C)(C)OC(=O)N1CCN(c2cccc(Br)n2)CC(O)C1]

To a mixture of 1-(6-bromopyridin-2-yl)-1,4-diazepan-6-ol (900 mg, 3.32 mmol) in MeOH (20 mL) was added TEA (5 mL), followed by Boc$_2$O (1.81 g, 8.30 mmol). The mixture was stirred at room temperature for 2 hours. The reaction mixture was purified by silica gel chromatography using DCM:MeOH (20:1~10:1) as eluting solvents to afford tert-butyl 4-(6-bromopyridin-2-yl)-6-hydroxy-1,4-diazepane-1-carboxylate as a white solid, (1.11 g, 90%). MS (ESI) m/z: 372 [M+H]$^+$.

Step C: tert-Butyl 4-(6-(6-Chloro-1H-pyrazolo[4,3-c]pyridin-1-yl)pyridin-2-yl)-6-hydroxy-1,4-diazepane-1-carboxylate

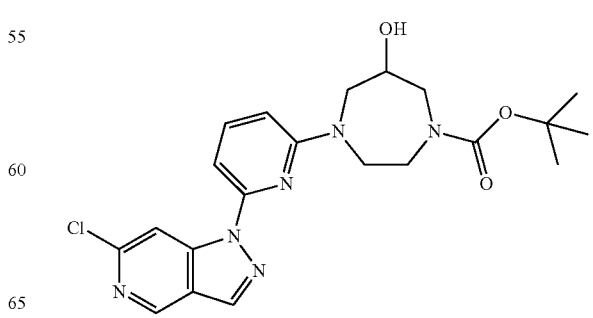

To a mixture of tert-butyl 4-(6-bromopyridin-2-yl)-6-hydroxy-1,4-diazepane-1-carboxylate (800 mg, 2.16 mmol) and 6-chloro-1H-pyrazolo[4,3-c]pyridine (330 mg, 2.16 mmol) in 1,4-dioxane (25 mL) was added CuI (164 mg, 0.86 mmol), $N^1,N^2$-dimethylethane-1,2-diamine (240 mg, 2.7 mmol), and $K_2CO_3$ (894 mg, 6.48 mmol). The mixture was heated at 100° C., which was monitored by LCMS. After completion of the reaction, it was concentrated under reduced pressure. The crude material was purified by silica gel chromatography using DCM:MeOH (20:1~10:1) as eluting solvents to afford tert-butyl 4-(6-(6-chloro-1H-pyrazolo[4,3-c]pyridin-1-yl)pyridin-2-yl)-6-hydroxy-1,4-diazepane-1-carboxylate as yellow solid (671 mg, 70%). MS (ESI) m/z: 445 [M+H]$^+$.

Step D: tert-Butyl 4-(6-(6-Chloro-1H-pyrazolo[4,3-c]pyridin-1-yl)pyridin-2-yl)-6-oxo-1,4-diazepane-1-carboxylate

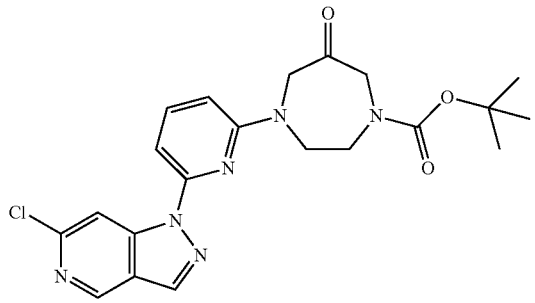 [SMILES: CC(C)(C)OC(=O)N1CCN(c2cccc(-n3ncc4cnc(Cl)cc43)n2)CC(=O)C1]

To a mixture of 4-(6-(6-chloro-1H-pyrazolo[4,3-c]pyridin-1-yl)pyridin-2-yl)-6-hydroxy-1,4-diazepane-1-carboxylate (650 mg, 1.46 mmol) in DCM (20 mL) at 0° C. was added (1,1,1-triacetoxy)-1,1-dihydro-1,2-benziodoxol-3(1H)-one (1.24 g, 2.92 mmol) and stirred overnight. The reaction mixture was quenched with brine (40 mL) and extracted with DCM (100 mL×3). The combined extracts was concentrated under reduced pressure. The residue was purified by silica gel chromatography using petroleum ether/ethyl acetate (5% to 50%) as eluting solvents to afford 4-(6-(6-chloro-1H-pyrazolo[4,3-c]pyridin-1-yl)pyridin-2-yl)-6-oxo-1,4-diazepane-1-carboxylate as a yellow oil (516 mg, 80%). MS (ESI) m/z: 443 [M+H]$^+$.

Step E: tert-Butyl 4-(6-(6-Chloro-1H-pyrazolo[4,3-c]pyridin-1-yl)pyridin-2-yl)-6-hydroxy-6-methyl-1,4-diazepane-1-carboxylate

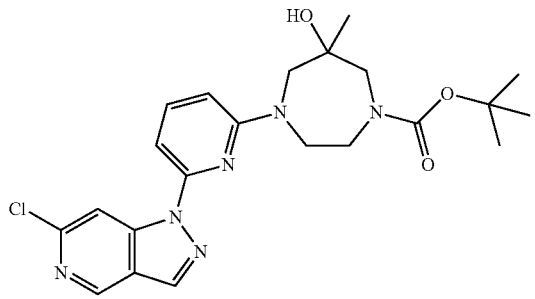 [SMILES: CC1(O)CN(C(=O)OC(C)(C)C)CCN(c2cccc(-n3ncc4cnc(Cl)cc43)n2)C1]

To a mixture of 4-(6-(6-chloro-1H-pyrazolo[4,3-c]pyridin-1-yl)pyridin-2-yl)-6-oxo-1,4-diazepane-1-carboxylate (460 mg, 1.04 mmol) in THF (25 mL) at −78° C. was added Grignard reagent $CH_3MgBr$ (147 mg, 1.25 mmol) and stirred at −78° C. for 2 hours. The reaction mixture was quenched with 10% $NH_4Cl$ solution (25 mL) and extracted with DCM (80 mL×3). The combined extracts was concentrated under reduced pressure. The residue was purified by silica gel chromatography using DCM:MeOH (20:1-10:1) as eluting solvents to afford tert-butyl 4-(6-(6-chloro-1H-pyrazolo[4,3-c]pyridin-1-yl)pyridin-2-yl)-6-hydroxy-6-methyl-1,4-diazepane-1-carboxylate as a yellow solid (357 mg, 75%). MS (ESI) m/z: 459 [M+H]$^+$.

Step F: tert-Butyl 4-(6-(6-(1H-Pyrazol-4-yl)-1H-pyrazolo[4,3-c]pyridin-1-yl)pyridin-2-yl)-6-hydroxy-6-methyl-1,4-diazepane-1-carboxylate

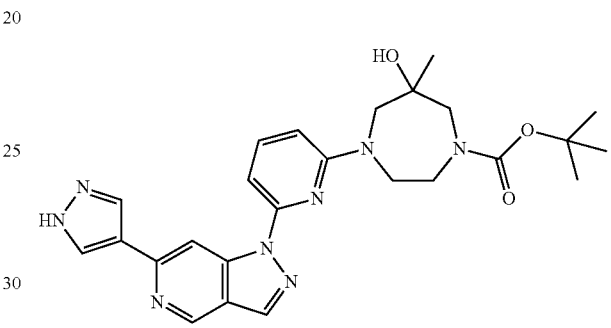

A suspension of tert-butyl 4-(6-(6-chloro-1H-pyrazolo[4,3-c]pyridin-1-yl)pyridin-2-yl)-6-hydroxy-6-methyl-1,4-diazepane-1-carboxylate (330 mg, 0.72 mmol), 4-(4,4,5,5-tetramethyl-1,3,2-dioxaborolan-2-yl)-1H-pyrazole (140 mg, 0.72 mmol), Pd(dppf)Cl2 (53 mg, 0.072 mmol), and a solution of $Na_2CO_3$ (2.0 M, 0.72 mL) in 1,4-dioxane (10 mL) under argon in a sealed vial was heated in a microwave oven at 120° C. for an hour. The reaction mixture was filtered and the filtrate was concentrated under reduced pressure. The residue was purified by silica gel chromatography using DCM:MeOH (20:1~10:1) as eluting solvents to afford tert-butyl 4-(6-(6-(1H-pyrazol-4-yl)-1H-pyrazolo[4,3-c]pyridin-1-yl)pyridin-2-yl)-6-hydroxy-6-methyl-1,4-diazepane-1-carboxylate as a yellow solid (212 mg, 60%). MS (ESI) m/z: 491 [M+H]$^+$.

Step G: (R)-tert-Butyl 6-Hydroxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate

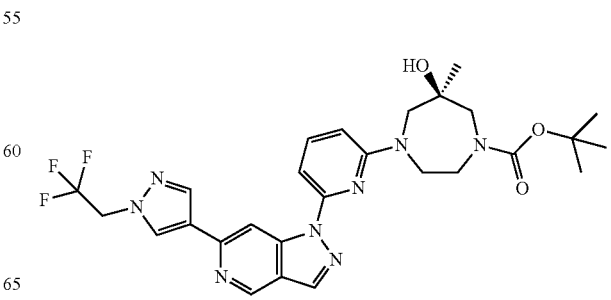

and (S)-tert-Butyl 6-Hydroxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate

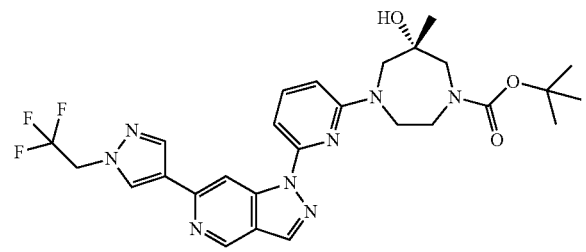 [SMILES: CC(C)(C)OC(=O)N1CCN(c2cccc(-n3ncc4cnc(-c5cnn(CC(F)(F)F)c5)cc43)n2)C[C@](C)(O)C1]

To a solution of tert-butyl 4-(6-(6-(1H-pyrazol-4-yl)-1H-pyrazolo[4,3-c]pyridin-1-yl)pyridin-2-yl)-6-hydroxy-6-methyl-1,4-diazepane-1-carboxylate (200 mg, 0.41 mmol) in DMF (15 mL) was added 2,2,2-trifluoroethyl trifluoromethanesulfonate (473 mg, 2.04 mmol). The reaction mixture was stirred at room temperature for 18 hours, quenched with brine, and extracted with DCM (100 mL×3), and concentrated under reduced pressure. The residue was purified by preparative HPLC to afford tert-butyl(±)-6-hydroxy-6-methyl-4-(6-(6-(1-(2,2,2-trifluoroethyl)-1H-pyrazol-4-yl)-1H-pyrazolo[4,3-c]-pyridin-1-yl)pyridin-2-yl)-1,4-diazepane-1-carboxylate as a white solid (183 mg, 78%). MS (ESI) m/z=573 [M+H]$^+$, which was separated by chiral preparative HPLC to afford (R)-tert-butyl 6-hydroxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (51 mg) and (S)-tert-butyl 6-hydroxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (48 mg).

Step H

To a solution of (R)-tert-butyl 6-hydroxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (46 mg, 0.08 mmol) in MeOH (3 mL) was added HCl solution (conc. 3.0 mL) and stirred at room temperature for 4 hours. The mixture was concentrated under reduced pressure. The crude was purified by reverse phase preparative HPLC to afford 248 as a white solid (36 mg, 94%). $^1$H NMR (500 MHz, DMSO-d$_6$) δ (ppm) 9.16 (s, 1H), 8.77 (s, 1H), 8.54 (s, 1H), 8.50 (s, 1H), 8.25 (s, 1H), 7.67 (t, 1H), 7.12 (d, 1H), 6.72 (d, 1H), 5.25-5.20 (t, 2H), 4.68 (s, 1H), 4.03-4.00 (m, 2H), 3.57-3.48 (m, 2H), 3.08-3.06 (m, 2H), 2.72 (d, 1H), 2.60 (d, 1H), 1.14 (s, 3H); MS (ESI) m/z: 473 [M+H]$^+$.

Example 149

(R)-6-Methyl-1-(6-(6-(1-(2,2,2-trifluoroethyl)-1H-pyrazol-4-yl)-1H-pyrazolo[4,3-c]-pyridin-1-yl)pyridin-2-yl)-1,4-diazepan-6-ol 249

Following the procedures as described in Example 148 and starting with (S)-tert-butyl 6-hydroxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate, 249 was obtained as white solid (34 mg, 90%). $^1$H NMR (500 MHz, DMSO-d$_6$) δ (ppm) 9.16 (s, 1H), 8.77 (s, 1H), 8.54 (s, 1H), 8.50 (s, 1H), 8.25 (s, 1H), 7.67 (t, 1H), 7.12 (d, 1H), 6.72 (d, 1H), 5.25-5.20 (t, 2H), 4.68 (s, 1H), 4.03-4.00 (m, 2H), 3.57-3.48 (m, 2H), 3.08-3.06 (m, 2H), 2.72 (d, 1H), 2.60 (d, 1H), 1.14 (s, 3H); MS (ESI) m/z: 473 [M+H]$^+$.

Example 150

(S)-1-(6-(6-(6-methylpyrazin-2-yl)-1H-pyrazolo[4,3-c]pyridin-1-yl)-4-(oxetan-3-yl)pyridin-2-yl)piperidin-3-amine 250

Step A: 2,6-difluoro-4-(oxetan-3-yl)pyridine

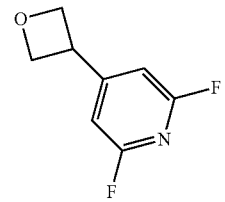 [SMILES: Fc1cc(C2COC2)cc(F)n1]

(2,6-difluoro-4-pyridyl)boronic acid (4.0004 mmol; 635.67 mg), Nickel(II) iodide (0.12001 mmol; 37.503 mg), Trans-2-aminocyclohexanol hydrochloride (0.12001 mmol; 18.382 mg), and Sodium hexamethyldisilazane (4.0004 mmol; 748.56 mg) were weighed into a CEM microwave vial. The mixture was capped then placed under a nitrogen atmosphere. Isopropanol (15 mL) was added and the mixture was stirred under nitrogen for 5 minutes. 3-Iodooxetane (2.0002 mmol; 368 mg) in Isopropanol (1.5 mL) was then added. The vial was heated at 100° C. under microwave for 20 minutes. The mixture was diluted with EtOH (15 mL) and filtered through Celite. The filter cake was washed with EtOH (2×10 mL). The mixture was concentrated and the residue was purified on silica eluted with 0 to 50% EtOAc in DCM to afford 2,6-difluoro-4-(oxetan-3-yl)pyridine (80.1 mg, 23%).

Step B

1-[6-fluoro-4-(oxetan-3-yl)-2-pyridyl]-6-(6-methylpyrazin-2-yl)pyrazolo[4,3-c]pyridine

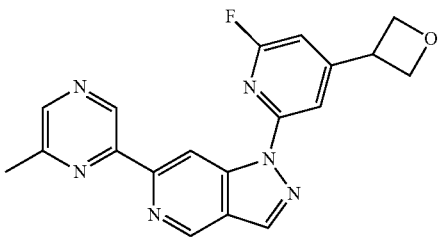 [SMILES: Cc1cncc(-c2cc3c(cn2)cnn3-c2cc(C3COC3)cc(F)n2)n1]

To a mixture of 6-(6-methylpyrazin-2-yl)-1H-pyrazolo[4,3-c]pyridine (0.468 mmol; 98.9 mg) and 2,6-difluoro-4-(oxetan-3-yl)pyridine (0.468 mmol; 80.1 mg) in DMF (5 mL) was added Cesium carbonate (0.562 mmol; 183 mg). The resulting mixture was stirred at room temperature. The mixture was filtered. The filtrate was partitioned between EtOAc and water. The organic layer was concentrated. The residue was purified on silica eluted with 0 to 6% MeOH in DCM to afford 1-[6-fluoro-4-(oxetan-3-yl)-2-pyridyl]-6-(6-methylpyrazin-2-yl)pyrazolo[4,3-c]pyridine as a white solid (63.2 mg, 31%).

Step C

A mixture of 1-[6-fluoro-4-(oxetan-3-yl)-2-pyridyl]-6-(6-methylpyrazin-2-yl)pyrazolo[4,3-c]pyridine (0.1443 mmol; 63 mg), tert-butyl N-[(3S)-3-piperidyl]carbamate (0.4329 mmol, 80.7 mg), and N-Methylmorpholine (0.3607 mmol; 36.9 mg; 0.0401 mL) in 1-Methyl-2-pyrrolidinone (3 mL) in a sealed pressure vial was heated at 100° C. overnight. The mixture was cooled to room temperature. The solvents were removed. The residue was treated with 20% TFA in DCM at room temperature for 2 h. The mixture was concentrated and the residue was purified by reverse phase HPLC to afford 250 as an off-white solid (17.5 mg, 26%). $^1$H NMR (400 MHz, DMSO) δ 9.61-9.57 (s, 1H), 9.49-9.43 (s, 1H), 9.36-9.29 (s, 1H), 8.69-8.66 (s, 1H), 8.65-8.61 (s, 1H), 7.33-7.30 (s, 1H), 6.82-6.76 (s, 1H), 5.02-4.95 (m, 2H), 4.73-4.66 (t, J=6.3 Hz, 2H), 4.42-4.35 (d, J=13.2 Hz, 1H), 4.35-4.27 (dd, J=15.0, 7.2 Hz, 1H), 4.20-4.13 (d, J=10.7 Hz, 1H), 3.29-3.21 (m, 2H), 3.08-3.01 (m, 1H), 2.98-2.91 (s, 1H), 2.66-2.61 (s, 3H), 2.01-1.83 (m, 3H), 1.71-1.58 (d, J=13.4 Hz, 1H), 1.51-1.40 (d, J=10.8 Hz, 1H), 0.99-0.92 (t, J=7.3 Hz, 1H); MS (ESI) m/z: 443.2 [M+H]$^+$ Example 151

1-[3-methoxy-6-[6-(6-methylpyrazin-2-yl)pyrazolo[4,3-c]pyridin-1-yl]-2-pyridyl]hexahydropyrimidin-2-one 251

Step A: 1-(6-bromo-2-pyridyl)-6-(6-methylpyrazin-2-yl)pyrazolo[4,3-c]pyridine

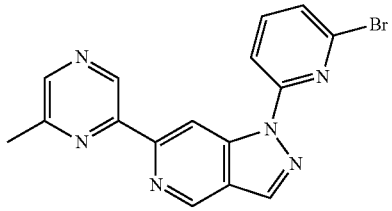 [SMILES: Cc1cncc(-c2cc3c(cn2)cnn3-c2cccc(Br)n2)n1]

A solution containing 6-(6-methylpyrazin-2-yl)-1H-pyrazolo[4,3-c]pyridine (250 mg, 1.18 mmol), 2-bromo-6-iodo-3-methoxypyridine (570 mg, 1.78 mmol), Copper(I) iodide (225 mg, 1.18 mmol), Potassium carbonate (196 mg, 1.42 mmol) and N,N'-Dimethylethylenediamine (0.25 mL, 2.37 mmol) was stirred at 85° C. 4 h. The reaction was filtered through celite and concentrated. The crude product purified by isco column (EtOAc/Hep eluted at 100% EtOAc) to give the desired product 280 mg 59% yield. MS (ESI) m/z: 397.1.

Step B

A solution containing 1-(6-bromo-5-methoxy-2-pyridyl)-6-(6-methylpyrazin-2-yl)pyrazolo[4,3-c]pyridine (50 mg, 0.126 mmol), tetrahydro-2-pyrimidinone (40 mg, 0.38 mmol), Copper(I) iodide (126 mg, 0.126 mmol), Potassium carbonate (21 mg, 0.15 mmol) and N,N'-Dimethylethylenediamine (0.028 mL, 0.252 mmol) was stirred at 110° C. 18 h. The reaction was filtered through celite and concentrated. The crude product was submitted for reverse phase HPLC to give 251 (8 mg, 14%). MS (ESI) m/z: 417.1. 1H NMR (400 MHz, DMSO) δ 9.61 (s, 1H), 9.47 (s, 1H), 9.33 (s, 1H), 8.68 (s, 1H), 8.63 (s, 1H), 7.89 (d, J=8.7 Hz, 1H), 7.77 (d, J=8.8 Hz, 1H), 6.74 (s, 1H), 3.86 (s, 3H), 3.35 (d, J=5.4 Hz, 2H), 2.63 (s, 3H), 2.16-2.08 (m, 2H).

Example 152

1-[6-[6-(6-methylpyrazin-2-yl)pyrazolo[4,3-c]pyridin-1-yl]-2-pyridyl]hexahydropyrimidin-2-one 252

Following the procedures in preparation of EXAMPLE 151, 252 was obtained. MS (ESI) m/z: 387.2. 1H NMR (400 MHz, DMSO) δ 9.65 (s, 1H), 9.47 (s, 1H), 9.33 (s, 1H), 8.70 (s, 1H), 8.63 (s, 1H), 7.96-7.86 (m, 2H), 7.67 (d, J=7.5 Hz, 1H), 7.12 (s, 1H), 4.28-4.21 (m, 2H), 2.62 (s, 3H), 2.17-2.08 (m, 2H).

Example 153

1-(6-(6-(1-Methyl-1H-pyrazol-4-yl)-1H-pyrazolo[4,3-c]pyridin-1-yl)pyridin-2-yl)azetidin-3-ol 253

Following the procedures as described in Example 124 and starting with azetidin-3-ol hydrochloride and 2-bromo-6-fluoropyridine and 6-chloro-1H-pyrazolo[4,3-c]pyridine, 253 was obtained as a white solid (70 mg, 30.4%) over three steps. $^1$H NMR (500 MHz, DMSO-d$_6$) δ (ppm) 9.12 (s, 1H), 8.77 (s, 1H), 8.53 (s, 1H), 8.27 (s, 1H), 7.93 (s, 1H), 7.70-7.73 (t, J=15.5 Hz, 1H), 7.21-7.22 (d, J=7.5 Hz, 1H), 6.32-6.33 (d, J=8.5 Hz, 1H), 5.79-5.80 (d, J=6 Hz, 1H), 4.70-4.72 (m, 1H), 4.39-4.42 (t, J=15 Hz, 2H), 3.93 (s, 3H), 3.88-3.91 (m, 2H); MS (ESI) m/z: 348 [M+H]$^+$.

Example 154

3-(6-Hydroxy-1,4-diazepan-1-yl)-1-methyl-5-(6-(1-methyl-1H-pyrazol-4-yl)-1H-pyrazolo[4,3-c]pyridin-1-yl)pyrazin-2(1H)-one 254

Following the procedures as described in Example 124 and starting with 1,4-diazepan-6-ol, 3,5-dibromo-1-methylpyrazin-2(1H)-one, 6-chloro-1H-pyrazolo[4,3-c]pyridine, and 1-methyl-4-(4,4,5,5-tetramethyl-1,3,2-dioxaborolan-2-yl)-1H-pyrazole, 254 was obtained as a yellow solid (80 mg, 7.2%) over five steps. $^1$H NMR (500 MHz, DMSO-d$_6$) δ (ppm) 9.09 (s, 1H), 8.43 (s, 1H), 8.30 (s, 1H), 8.29 (s, 1H), 8.05 (s, 1H), 8.00 (s, 1H), 4.91 (s, 1H), 4.49 (m, 1H), 3.92 (m, 1H), 3.89 (s, 3H), 3.70-3.71 (m, 2H), 3.51 (s, 3H), 2.99-3.02 (m, 1H), 2.90-2.91 (m, 1H), 2.74-2.86 (m, 2H); MS (ESI) m/z: 422 [M+H]$^+$.

Example 155

1-(6-(6-(1-(2,2,2-Trifluoroethyl)-1H-pyrazol-4-yl)-1H-pyrazolo[4,3-c]pyridin-1-yl)pyridin-2-yl)azetidin-3-ol 255

Following the procedures as described in Example 88 and starting with azetidin-3-ol hydrochloride, 2-bromo-6-fluoropyridine, and 6-chloro-1H-pyrazolo[4,3-c]pyridine, 255 was obtained as a white solid (30 mg, 9.6%) over four steps. $^{1}$H NMR (500 MHz, DMSO-$d_6$) δ (ppm) 9.16 (s, 1H), 8.83 (s, 1H), 8.555 (s, 1H), 8.44 (s, 1H), 8.09 (s, 1H), 7.70-7.73 (t, J=16 Hz, 1H), 7.21-7.23 (d, J=7.5 Hz, 1H), 6.32-6.34 (d, J=8 Hz, 1H), 5.78-5.80 (d, J=6.5 Hz, 1H), 5.23-5.28 (m, 2H), 4.71-4.72 (d, J=6 Hz, 1H), 4.39-4.42 (t, J=14.5 Hz, 2H), 3.89-3.91 (m, 2H); MS (ESI) m/z: 416 [M+H]$^+$.

Example 156

(1-(6-(6-(1-Methyl-1H-pyrazol-4-yl)-1H-pyrazolo[4,3-c]pyridin-1-yl)pyridin-2-yl)azetidin-3-yl)methanamine 256

Following the procedures as described in Example 124 and starting with tert-butyl azetidin-3-ylmethylcarbamate and 2-bromo-6-fluoropyridine and 6-chloro-1H-pyrazolo[4,3-c]pyridine, 256 was obtained as a yellow solid (31 mg, 26.4%) over four steps. $^{1}$H NMR (500 MHz, DMSO-$d_6$) δ (ppm) 9.12 (d, 1H), 8.78 (s, 1H), 8.52 (s, 1H), 8.23-8.26 (d, J=16.5 Hz, 1H), 7.957-7.963 (d, J=3 Hz, 1H), 7.70-7.73 (t, J=16 Hz, 1H), 7.19-7.21 (d, J=7.5 Hz, 1H), 6.28-6.30 (d, J=8 Hz, 1H), 4.17-4.22 (m, 2H), 3.87-3.93 (m, 5H), 2.95-2.96 (d, J=6.5 Hz, 2H), 2.87-2.89 (m, 1H); MS (ESI) m/z: 361 [M+H]$^+$.

Example 157

1-(6-(6-(1-Methyl-1H-pyrazol-4-yl)-1H-pyrazolo[4,3-c]pyridin-1-yl)pyridin-2-yl)azetidin-3-amine 257

Following the procedures as described in Example 124 and starting with tert-butyl azetidin-3-ylcarbamate, 2-bromo-6-fluoropyridine, and 6-chloro-1H-pyrazolo[4,3-c]pyridine, 257 was obtained as a yellow solid (128 mg, 23%) over four steps. $^{1}$H NMR (500 MHz, DMSO-$d_6$) δ (ppm) 9.11 (s, 1H), 8.79 (s, 1H), 8.51 (s, 1H), 8.25 (s, 1H), 7.92 (s, 1H), 7.69-7.71 (t, J=9 Hz, 1H), 7.18-7.20 (d, J=9 Hz, 1H), 6.29-6.30 (d, J=9 Hz, 1H), 4.33-4.36 (m, 2H), 3.92-3.93 (m, 1H), 3.92 (s, 3H), 3.74-3.77 (m, 2H), 2.68-2.70 (br, 2H); MS (ESI) m/z: 347 [M+H]$^+$.

Example 158

1-(6-(6-(1-(2,2,2-Trifluoroethyl)-1H-pyrazol-4-yl)-1H-pyrazolo[4,3-c]pyridin-1-yl)pyridin-2-yl)azetidin-3-amine 258

Following the procedures as described in Example 88 and starting with tert-butyl azetidin-3-ylcarbamate, 2-bromo-6-fluoropyridine and 6-chloro-1H-pyrazolo[4,3-c]pyridine, 258 was obtained as a yellow solid (80 mg, 15%) over five steps. $^{1}$H NMR (500 MHz, DMSO-$d_6$) δ (ppm) 9.16 (s, 1H), 8.84 (s, 1H), 8.55 (s, 1H), 8.45 (s, 1H), 8.09 (s, 1H), 7.70-7.74 (t, J=10 Hz, 1H), 7.21-7.23 (d, J=10 Hz, 1H), 6.33-6.35 (d, J=10 Hz, 1H), 5.25-5.27 (m, 2H), 4.36-4.39 (m, 4H), 4.00-4.01 (m, 1H), 3.85-3.87 (m, 2H); MS (ESI) m/z: 415 [M+H]$^+$.

Example 159

1-[6-(4,4-difluoro-3-piperidyl)-2-pyridyl]-6-(6-methylpyrazin-2-yl)pyrazolo[4,3-c]pyridine 259

Step A: tert-butyl 3-[6-[6-(6-methylpyrazin-2-yl)pyrazolo[4,3-c]pyridin-1-yl]-2-pyridyl]-4-oxo-piperidine-1-carboxylate

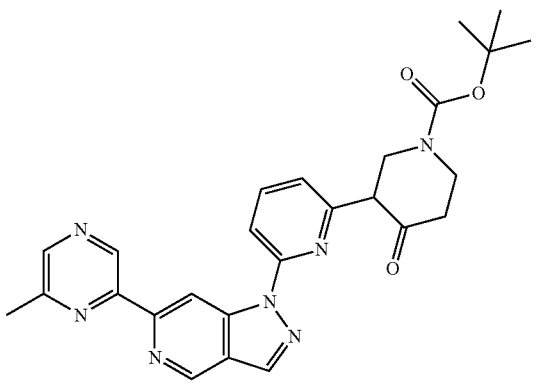 [SMILES: Cc1cncc(-c2cc3c(cn2)cnn3-c2cccc(C3CN(C(=O)OC(C)(C)C)CCC3=O)n2)n1]

To a solution of 1-(6-bromo-2-pyridyl)-6-(6-methylpyrazin-2-yl)pyrazolo[4,3-c]pyridine (125 mg, 0.340 mmol), tert-butyl 4-oxopiperidine-1-carboxylate (100 mg, 0.51 mmol), palladium acetate (8.0 mg, 0.034 mmol) and sodium tert-butoxide (74 mg, 0.75 mmol) in tetrahydrofuran (8.0 ml, 99 mmol) was added tri-t-butylphosphine (0.020 mL, 0.068 mmol). The mixture was degassed and heat at 48° C. 2 h. The reaction was quenched with water then extract with EtOAc. The organic layers was dried with sodium sulfate, filtered, and concentrated in vacuum. The crude product was purified by flash chromatography (EtOAc/Heptane eluted @75% EtOAc) to give the desired product 100 mg 60% yield. MS (ESI) m/z: 486.1.

Step B: tert-butyl 4,4-difluoro-3-[6-[6-(6-methylpyrazin-2-yl)pyrazolo[4,3-c]pyridin-1-yl]-2-pyridyl]piperidine-1-carboxylate

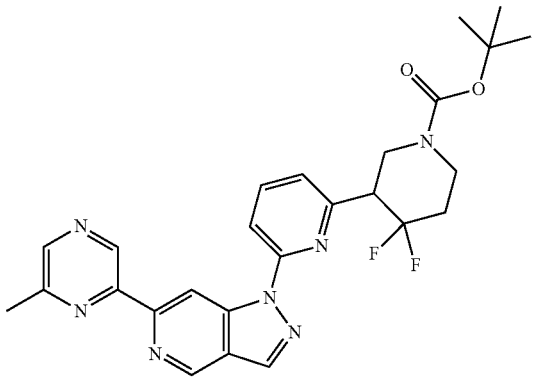 [SMILES: Cc1cncc(-c2cc3c(cn2)cnn3-c2cccc(C3CN(C(=O)OC(C)(C)C)CCC3(F)F)n2)n1]

To a solution of bis(2-methoxyethyl)aminosulfur trifluoride (White, A. R. et al (2004) J. Org. Chem., 69:2573-2576, Deoxo-fluor®, Sigma-Aldrich, 0.054 mL 0.295 mmol) in dichloromethane (1.0 mL, 16 mmol) at −78° C. was added tert-butyl 3-[6-[6-(6-methylpyrazin-2-yl)pyrazolo[4,3-c]

pyridin-1-yl]-2-pyridyl]-4-oxo-piperidine-1-carboxylate (65 mg, 0.13 mmol) in 1.0 mL DCM dropwise. The reaction mixture was warmed to RT overnight. The reaction was quenched with water and extracted with DCM. The organic layers was dried with sodium sulfate, filtered, and concentrated in vacuum. The crude product was purified by flash chromatography (EtOAc/Heptane eluted at 60% EtOAc) to give the desired product 38 mg 55% yield. MS (ESI) m/z: 508.1.

Step C

To a solution of tert-butyl 4,4-difluoro-3-[6-[6-(6-methylpyrazin-2-yl)pyrazolo[4,3-c]pyridin-1-yl]-2-pyridyl]piperidine-1-carboxylate (50 mg, 0.099 mmol) in 1,4-DIOXANE (2.00 mL, 23.4 mmol) was added hydrogen chloride (4 mol/l) in 1,4-dioxane (1.00 mL, 4.00 mmol). The reaction was stirred at RT 18 h. The reaction was concentrated and submitted for reverse phase HPLC to give 259 17 mg 42% yield. MS (ESI) m/z: 408.1. 1H NMR (400 MHz, DMSO) δ 9.72 (s, 1H), 9.46 (s, 1H), 9.36 (s, 1H), 8.74 (s, 1H), 8.63 (s, 1H), 8.04 (t, J=7.8 Hz, 1H), 7.98 (d, J=8.2 Hz, 1H), 7.40 (d, J=7.4 Hz, 1H), 3.60-3.42 (m, 2H), 3.18 (d, J=12.8 Hz, 1H), 2.87 (t, J=12.6 Hz, 1H), 2.67 (s, 3H), 2.36 (d, J=18.3 Hz, 1H), 2.21-2.09 (m, 1H), 1.99 (d, J=34.4 Hz, 1H).

Example 160 and 163

(R)-1-(3-methyl-6-(6-(1-(2,2,2-trifluoroethyl)-1H-pyrazol-4-yl)-1H-pyrazolo[4,3-c]pyridin-1-yl)pyridin-2-yl)-1,4-diazepan-6-ol 260 and (S)-1-(3-methyl-6-(6-(1-(2,2,2-trifluoroethyl)-1H-pyrazol-4-yl)-1H-pyrazolo[4,3-c]pyridin-1-yl)pyridin-2-yl)-1,4-diazepan-6-ol 263

Step A: 1-(3-Bromo-6-iodopyridin-2-yl)-1,4-diazepan-6-ol

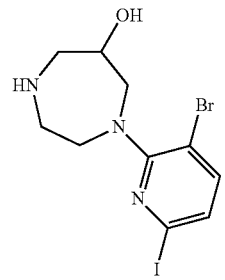 [SMILES: OC1CNCCN(c2nc(I)ccc2Br)C1]

A solution of 3-bromo-2-fluoro-6-iodopyridine (1.00 g, 3.4 mmol), 1,4-diazepan-6-ol (510 mg, 4.4 mmol), and DIPEA (2 mL) in EtOH (6 mL) in a sealed tube was stirred at 100° C. for 20 hours. The reaction mixture was concentrated under reduced pressure to give a residue (1.18 g), which was used for the next step without further purification. MS (ESI) m/z: 398 [M+H]+.

Step B: tert-Butyl 4-(3-Bromo-6-iodopyridin-2-yl)-6-hydroxy-1,4-diazepane-1-carboxylate

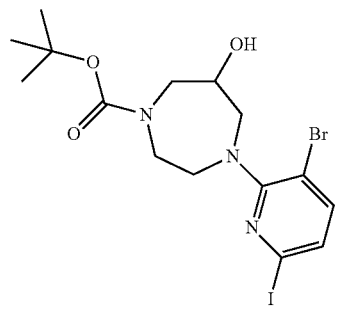 [SMILES: CC(C)(C)OC(=O)N1CCN(c2nc(I)ccc2Br)CC(O)C1]

A solution of 1-(3-bromo-6-iodopyridin-2-yl)-1,4-diazepan-6-ol (1.18 g, 3 mmol), Boc2O (980 mg, 4.5 mmol), and TEA (2 mL) in MeOH (15 mL) was stirred at room temperature for 20 hours. The reaction mixture was concentrated under reduced pressure. The residue was purified by silica gel chromatography using EtOAc:Petroleum Ether (10%~25%) as eluting solvents to afford tert-butyl 4-(3-bromo-6-iodopyridin-2-yl)-6-hydroxy-1,4-diazepane-1-carboxylate as white solid (980 mg, 60% in two steps). MS (ESI) m/z: 498 [M+H]+.

Step C: 6-Chloro-1-((2-(trimethylsilyl)ethoxy)methyl)-1H-pyrazolo[4,3-c]pyridine

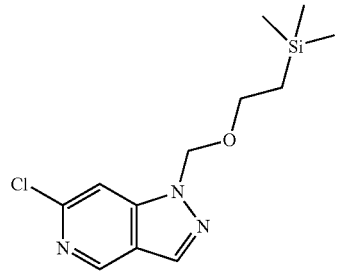 [SMILES: C[Si](C)(C)CCOCn1ncc2cnc(Cl)cc21]

To a solution of 6-chloro-1H-pyrazolo[4,3-c]pyridine (2.00 g, 13.1 mmol) and DIPEA (3 mL) in DCM (10 mL) was added SEMCl (3 mL). The mixture was stirred at 30° C. for 20 hours. The reaction mixture was concentrated under reduced pressure. The residue was purified by silica gel chromatography using EtOAc/Petroleum Ether (10%~60%) as eluting solvents to afford 6-chloro-1-((2-(trimethylsilyl)ethoxy)methyl)-1H-pyrazolo[4,3-c]pyridine as colorless oil (3.44 g, 93%). MS (ESI) m/z: 284 [M+H]+.

Step D: 6-(1H-Pyrazol-4-yl)-1-((2-(trimethylsilyl)ethoxy)methyl)-1H-pyrazolo[4,3-c]-pyridine

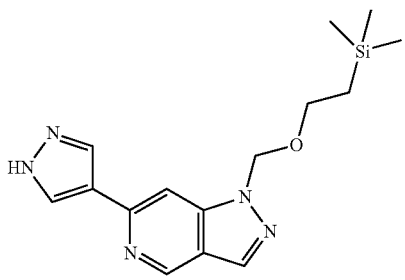 [SMILES: C[Si](C)(C)CCOCn1ncc2cnc(-c3cn[nH]c3)cc21]

A suspension of 6-chloro-1-((2-(trimethylsilyl)ethoxy)methyl)-1H-pyrazolo[4,3-c]pyridine (1.30 g, 4.6 mmol), 4-(4,4,5,5-tetramethyl-1,3,2-dioxaborolan-2-yl)-1H-pyrazole (1.16 g, 6 mmol), and Pd(dppf)Cl$_2$ (437 mg, 0.6 mmol) in aq. Na$_2$CO$_3$ (2.0 M, 12 mL) and 1,4-dioxane (20 mL) was heated at 110° C. for 20 hours. The reaction mixture was concentrated under reduced pressure. The residue was purified by silica gel chromatography using ethyl acetate/heptanes 50% to 100% as eluting solvents to afford 6-(1H-pyrazol-4-yl)-1-((2-(trimethylsilyl)ethoxy)methyl)-1H-pyrazolo[4,3-c]pyridine as a yellow oil (670 mg, 46%), and recovered 1 g of the starting material. MS (ESI) m/z: 316 [M+H]$^+$.

Step E: 6-(1-(2,2,2-Trifluoroethyl)-1H-pyrazol-4-yl)-1-((2-(trimethylsilyl)ethoxy)methyl)-1H-pyrazolo[4,3-c]pyridine

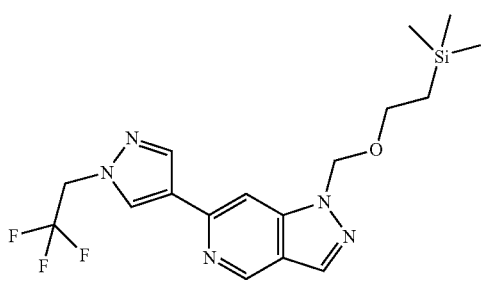 [SMILES: C[Si](C)(C)CCOCn1ncc2cnc(-c3cnn(CC(F)(F)F)c3)cc21]

A mixture of 6-(1H-pyrazol-4-yl)-1-(2-(trimethylsilyl)ethoxy)methyl)-1H-pyrazolo[4,3-c]pyridine (670 mg, 2.12 mmol), K$_2$CO$_3$ (587 mg, 4.24 mmol), and 2,2,2-trifluoroethyl trifluoromethanesulfonate (4 mL) in DMF (4 mL) was stirred at ambient temperature for 20 hours. The reaction mixture was quenched with EtOAc (10 mL) and H$_2$O (10 mL), and extracted with EtOAc (10 mL×3). The extracts were concentrated under reduced pressure. The residue was purified by silica gel chromatography using ethyl acetate/heptane (10% to 70%) as eluting solvents to afford 6-(1-(2,2,2-trifluoroethyl)-1H-pyrazol-4-yl)-1-((2-(trimethylsilyl)ethoxy)methyl)-1H-pyrazolo[4,3-c]pyridine as a white solid (800 mg, 95%). MS (ESI) m/z: 398 [M+H]$^+$.

Step F: 6-(1-(2,2,2-Trifluoroethyl)-1H-pyrazol-4-yl)-1H-pyrazolo[4,3-c]pyridine

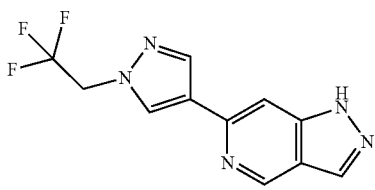 [SMILES: FC(F)(F)Cn1cc(-c2cc3[nH]ncc3cn2)cn1]

A mixture of 6-(1-(2,2,2-trifluoroethyl)-1H-pyrazol-4-yl)-1-((2-(trimethylsilyl)ethoxy)-methyl)-1H-pyrazolo[4,3-c]pyridine (800 mg, 2.02 mmol) and TFA (5 mL) in DCM (10 mL) was stirred at ambient temperature for 20 hours. The reaction mixture was concentrated under reduced pressure to afford 6-(1-(2,2,2-trifluoroethyl)-1H-pyrazol-4-yl)-1H-pyrazolo[4,3-c]-pyridine as a yellow oil (539 mg, 100%). MS (ESI) m/z: 268 [M+H]$^+$.

Step G: tert-Butyl 4-(3-Bromo-6-(6-(1-(2,2,2-trifluoroethyl)-1H-pyrazol-4-yl)-1H-pyrazolo-[4,3-c]pyridin-1-yl)pyridin-2-yl)-6-hydroxy-1,4-diazepane-1-carboxylate

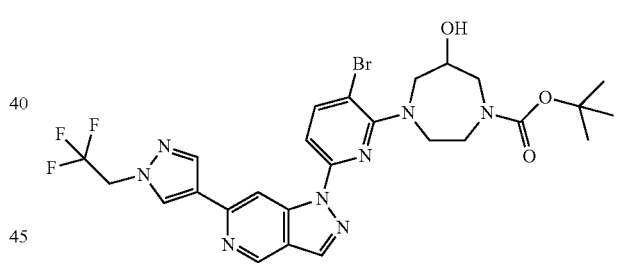

A mixture of 6-(1-(2,2,2-trifluoroethyl)-1H-pyrazol-4-yl)-1H-pyrazolo[4,3-c]pyridine (539 mg, 2.02 mmol), tert-butyl 4-(3-bromo-6-iodopyridin-2-yl)-6-hydroxy-1,4-diazepane-1-carboxylate (1.00 g, 2.02 mmol), N$^1$,N$^2$-dimethylethane-1,2-diamine (535 mg, 6.06 mmol), CuI (768 mg, 4.04 mmol), and K$_2$CO$_3$ (1.12 g, 8.08 mmol) in 1,4-dioxane (10 mL) under N$_2$ was heated at 100° C. for 20 hours. The reaction mixture was concentrated under reduced pressure. The residue was purified by silica gel chromatography using EtOAc/petroleum Ether (20%40%) as eluting solvents to afford tert-butyl 4-(3-bromo-6-(6-(1-(2,2,2-trifluoroethyl)-1H-pyrazol-4-yl)-1H-pyrazolo[4,3-c]pyridin-1-yl)pyridin-2-yl)-6-hydroxy-1,4-diazepane-1-carboxylate as a white solid (244 mg, 19%). MS (ESI) m/z: 637 [M+H]$^+$.

Step H: tert-Butyl(±)-6-Hydroxy-4-(3-methyl-6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate

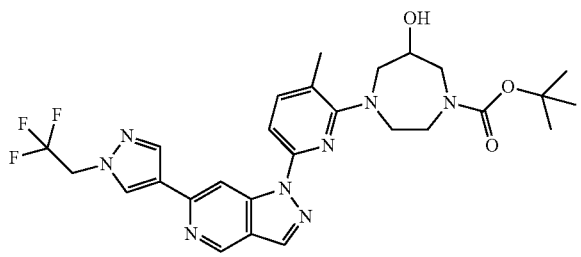 [SMILES: Cc1ccc(-n2ncc3cnc(-c4cnn(CC(F)(F)F)c4)cc32)nc1N1CCN(C(=O)OC(C)(C)C)CC(O)C1]

A mixture of tert-butyl 4-(3-bromo-6-(6-(1-(2,2,2-trifluoroethyl)-1H-pyrazol-4-yl)-1H-pyrazolo[4,3-c]pyridin-1-yl)pyridin-2-yl)-6-hydroxy-1,4-diazepane-1-carboxylate (244 mg, 0.38 mmol), 2,4,6-trimethyl-1,3,5,2,4,6-trioxatriborinane (194 mg, 1.53 mmol), Pd$_2$dba$_3$ (174 mg, 0.19 mmol), Pcy$_3$ (107 mg, 0.38 mmol), and Cs$_2$CO$_3$ (500 mg, 1.53 mmol) in 1,4-dioxane (10 mL) was heated in a microwave oven at 110° C. for 1.5 hour. The reaction mixture was concentrated under reduced pressure. The residue was purified by silica gel chromatography using EtOAc/petroleum Ether (20%~80%) as eluting solvents to afford tert-butyl(±)-6-hydroxy-4-(3-methyl-6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate as a white solid (120 mg, 55%). MS (ESI) m/z: 573 [M+H]$^+$.

Step I: (S)-tert-Butyl 6-Hydroxy-4-(3-methyl-6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate

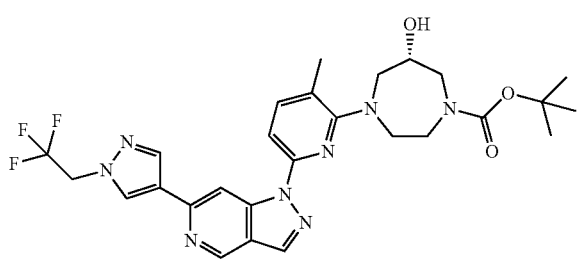 [SMILES: Cc1ccc(-n2ncc3cnc(-c4cnn(CC(F)(F)F)c4)cc32)nc1N1CCN(C(=O)OC(C)(C)C)C[C@@H](O)C1]

and (R)-tert-Butyl 6-Hydroxy-4-(3-methyl-6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate

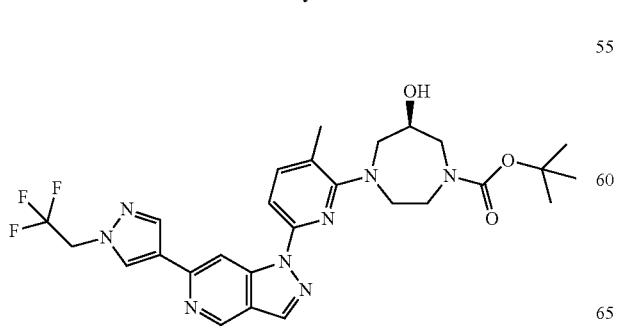

(±)-tert-Butyl 6-hydroxy-4-(3-methyl-6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (160 mg) was separated by chiral preparative HPLC to afford (S)-tert-butyl 6-hydroxy-4-(3-methyl-6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (60 mg) and (R)-tert-butyl 6-hydroxy-4-(3-methyl-6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (60 mg).

Step J

A mixture of (S)-tert-butyl 6-hydroxy-4-(3-methyl-6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (60 mg, 0.10 mmol) in HCl/MeOH (4 M, 10 mL) was stirred at ambient temperature for 20 hours. The reaction mixture was concentrated under reduced pressure. The residue was diluted with MeOH (10 mL), neutralized with 28% ammonia solution, concentrated under reduced pressure, and purified by preparative HPLC to afford 260 as a white solid (40 mg, 82%). $^1$H-NMR (500 MHz, CD$_3$OD) δ (ppm) 9.03 (s, 1H), 8.76 (s, 1H), 8.35 (d, J=10.5 Hz, 2H), 8.16 (s, 1H), 7.62 (d, J=8 Hz, 1H), 7.45 (d, J=7.5 Hz, 1H), 5.03-5.08 (m, 2H), 4.14-4.21 (m, 1H), 3.96-3.99 (m, 1H), 3.51-3.68 (m, 3H), 3.18-3.33 (m, 3H), 2.99-3.08 (m, 1H), 2.38 (s, 3H); MS (ESI) m/z: 473 [M+H]$^+$.

Step K

A mixture of (R)-tert-butyl 6-hydroxy-4-(3-methyl-6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (60 mg, 0.10 mmol) in HCl/MeOH (4 M, 10 mL) was stirred at ambient temperature for 20 hours. The reaction mixture was concentrated under reduced pressure. The residue was diluted with MeOH (10 mL), neutralized with 28% ammonia solution, concentrated under reduced pressure, and purified by preparative HPLC to afford 263 as a white solid (40 mg, 82%). $^1$H-NMR (500 MHz, CD$_3$OD) δ ppm 8.97 (s, 1H), 8.66 (s, 1H), 8.31 (d, J=10.5 Hz, 2H), 8.11 (s, 1H), 7.62 (d, J=8 Hz, 1H), 7.45 (d, J=7.5 Hz, 1H), 5.07-5.02 (m, 2H), 4.21-4.14 (m, 1H), 3.99-3.96 (m, 1H), 3.68-3.51 (m, 3H), 3.33-3.18 (m, 3H), 3.08-2.99 (m, 1H), 2.38 (s, 3H); MS (ESI) m/z: 473 [M+H]$^+$.

Example 161

(S)-1-(6-(6-Methoxy-6-methyl-1,4-diazepan-1-yl)pyridin-2-yl)-6-(1-(2,2,2-trifluoroethyl)-1H-pyrazol-4-yl)-1H-pyrazolo[4,3-c]pyridine 261

Step A: tert-Butyl 4-(6-Bromopyridin-2-yl)-6-oxo-1,4-diazepane-1-carboxylate

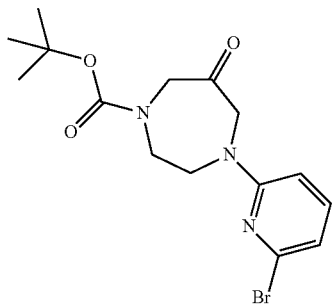 [SMILES: CC(C)(C)OC(=O)N1CCN(c2cccc(Br)n2)CC(=O)C1]

To a mixture of tert-butyl 4-(6-bromopyridin-2-yl)-6-hydroxy-1,4-diazepane-1-carboxylate (1.05 g, 2.83 mmol) from Examples 88, 89, 148 in DCM (35 mL) at 0° C. was added (1,1,1-triacetoxy)-1,1-dihydro-1,2-benziodoxol-3(1H)-one (2.40 g, 5.66 mmol). The mixture was stirred overnight, quenched with brine (40 mL) and DCM (30 mL), and extracted with DCM (100 mL×3), and concentrated under reduced pressure. The residue was purified by silica gel chromatography using petroleum ether/ethyl acetate (5% to 50%) as eluting solvents to afford tert-butyl 4-(6-bromopyridin-2-yl)-6-oxo-1,4-diazepane-1-carboxylate as a yellow oil (846 mg, 81%). MS (ESI) m/z: 370 [M+H]+.

Step B: tert-Butyl 4-(6-Bromopyridin-2-yl)-6-hydroxy-6-methyl-1,4-diazepane-1-carboxylate

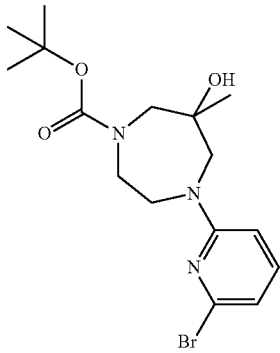 [SMILES: CC1(O)CN(C(=O)OC(C)(C)C)CCN(c2cccc(Br)n2)C1]

To a mixture of tert-butyl 4-(6-bromopyridin-2-yl)-6-oxo-1,4-diazepane-1-carboxylate (800 mg, 2.17 mmol) in THF (40 mL) at −78° C. was added CH$_3$MgBr (169 mg, 1.44 mmol). The mixture was stirred at −78° C. for 2 hours, quenched with 10% NH$_4$Cl solution (35 mL), extracted with DCM (100 mL×3), and concentrated under reduced pressure. The residue was purified by silica gel chromatography using DCM:MeOH (20:1~10:1) as eluting solvents to afford tert-butyl 4-(6-bromopyridin-2-yl)-6-hydroxy-6-methyl-1,4-diazepane-1-carboxylate as a yellow solid (636 mg, 76%). MS (ESI) m/z: 386 [M+H]+.

Step C: tert-Butyl 4-(6-Bromopyridin-2-yl)-6-methoxy-6-methyl-1,4-diazepane-1-carboxylate

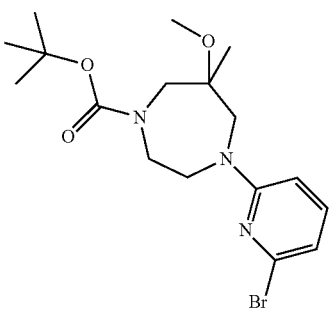 [SMILES: COC1(C)CN(C(=O)OC(C)(C)C)CCN(c2cccc(Br)n2)C1]

To a mixture of 4-(6-bromopyridin-2-yl)-6-hydroxy-6-methyl-1,4-diazepane-1-carboxylate (600 mg, 1.56 mmol) in DMF (20 mL) at 0° C. was added NaH (94 mg, 3.90 mmol) and stirred for 30 minutes. To the mixture was added dimethyl sulfate (295 mg, 2.34 mmol) and stirred at room temperature for 15 hours. It was quenched with brine (20 mL), extracted with EtOAc (100 mL×3), concentrated under reduced pressure. The residue was purified by silica gel chromatography using petroleum ether:EtOAc (4:1~1:1) as eluting solvents to afford tert-butyl 4-(6-bromopyridin-2-yl)-6-methoxy-6-methyl-1,4-diazepane-1-carboxylate as a yellow oil (554 mg, 89%). MS (ESI) m/z: 400 [M+H]+.

Step D: tert-Butyl 4-(6-(6-Chloro-1H-pyrazolo[4,3-c]pyridin-1-yl)pyridin-2-yl)-6-methoxy-6-methyl-1,4-diazepane-1-carboxylate

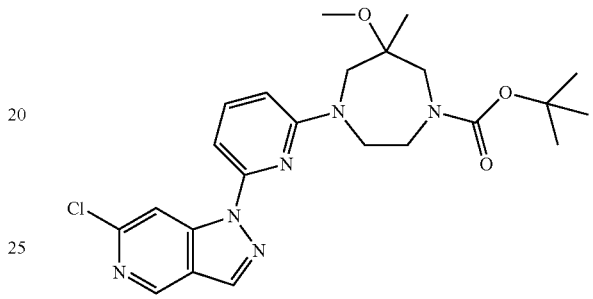

To a mixture of tert-butyl 4-(6-bromopyridin-2-yl)-6-methoxy-6-methyl-1,4-diazepane-1-carboxylate (530 mg, 1.33 mmol) and 6-chloro-1H-pyrazolo[4,3-c]pyridine (203 mg, 1.33 mmol) in 1,4-dioxane (30 mL) was added CuI (101 mg, 0.53 mmol), N$^1$,N$^2$-dimethylethane-1,2-diamine (94 mg, 1.06 mmol), and K$_2$CO$_3$ (734 mg, 5.32 mmol). The mixture was heated at 100° C., which was monitored by LCMS. After completion of the reaction, it was concentrated under reduced pressure. The crude material was purified by silica gel chromatography using petroleum ether:EtOAc (3:1~1:1) as eluting solvents to afford tert-butyl 4-(6-(6-chloro-1H-pyrazolo[4,3-c]pyridin-1-yl)pyridin-2-yl)-6-methoxy-6-methyl-1,4-diazepane-1-carboxylate as yellow solid (446 mg, 71%). MS (ESI) m/z: 473 [M+H]+.

Step E: tert-Butyl 4-(6-(6-(1H-Pyrazol-4-yl)-1H-pyrazolo[4,3-c]pyridin-1-yl)pyridin-2-yl)-6-methoxy-6-methyl-1,4-diazepane-1-carboxylate

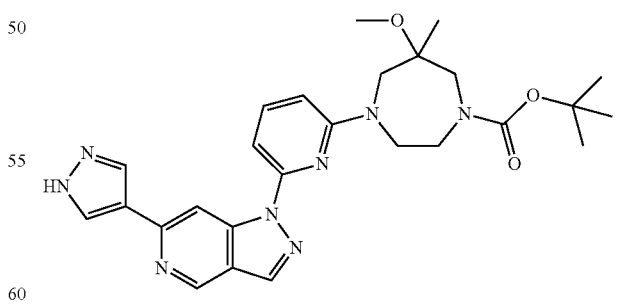

A suspension of tert-butyl 4-(6-(6-chloro-1H-pyrazolo[4,3-c]pyridin-1-yl)pyridin-2-yl)-6-methoxy-6-methyl-1,4-diazepane-1-carboxylate (420 mg, 0.89 mmol), 4-(4,4,5,5-tetramethyl-1,3,2-dioxaborolan-2-yl)-1H-pyrazole (173 mg, 0.89 mmol), Pd(dppf)Cl$_2$ (65 mg, 0.089 mmol), and a solution of Na$_2$CO$_3$ (2.0 M, 0.9 mL) in 1,4-dioxane (15 mL)

under argon in a sealed vial was heated in a microwave oven at 120° C. for 1 hour. The reaction mixture was filtered and the filtrate was concentrated under reduced pressure. The residue was purified by silica gel chromatography petroleum ether:EtOAc (3:1~1:1) as eluting solvents to afford tert-butyl 4-(6-(6-(1H-pyrazol-4-yl)-1H-pyrazolo[4,3-c]pyridin-1-yl)pyridin-2-yl)-6-methoxy-6-methyl-1,4-diazepane-1-carboxylate as a yellow solid (283 mg, 63%). MS (ESI) m/z: 505 [M+H]+.

Step F: (R)-tert-Butyl 6-Methoxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate

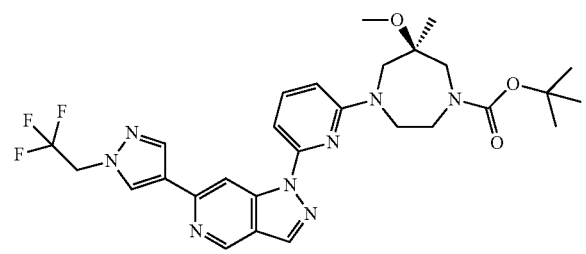 [SMILES: CO[C@@]1(C)CN(C(=O)OC(C)(C)C)CCN(c2cccc(-n3ncc4cnc(-c5cnn(CC(F)(F)F)c5)cc43)n2)C1]

and (S)-tert-Butyl 6-Methoxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate

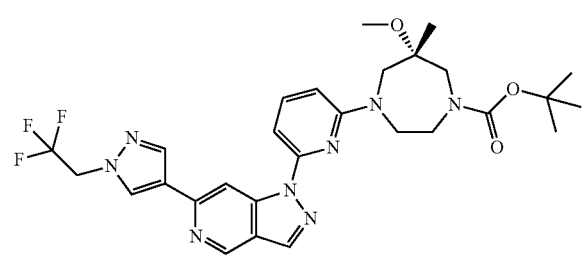 [SMILES: CO[C@]1(C)CN(C(=O)OC(C)(C)C)CCN(c2cccc(-n3ncc4cnc(-c5cnn(CC(F)(F)F)c5)cc43)n2)C1]

To a solution of tert-butyl 4-(6-(6-(1H-pyrazol-4-yl)-1H-pyrazolo[4,3-c]pyridin-1-yl)pyridin-2-yl)-6-methoxy-6-methyl-1,4-diazepane-1-carboxylate (265 mg, 0.53 mmol) in DMF (15 mL) was added 2,2,2-trifluoroethyl trifluoromethanesulfonate (610 mg, 2.63 mmol). The mixture was stirred at room temperature for 18 hours. The reaction mixture was quenched with brine, extracted with DCM (100 mL×3), and concentrated under reduced pressure. The residue was purified by preparative HPLC to afford tert-butyl (±)-6-methoxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate as a white solid (264 mg, 85%). MS (ESI) m/z: 587 [M+H]+.

tert-Butyl(±)-6-methoxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate was separated by chiral preparative HPLC to afford (R)-tert-butyl 6-methoxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (100 mg) and (S)-tert-butyl 6-methoxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (95 mg).

Step G

To a solution of (R)-tert-butyl 6-methoxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate (100 mg, 0.17 mmol) in MeOH (5 mL) was added HCl (conc., 5 mL). The mixture was stirred at room temperature for 4 hours. It was concentrated under reduced pressure. The crude was purified by reverse phase preparative HPLC to afford 261 as a white solid (75 mg, 91%). $^1$H NMR (500 MHz, DMSO-d$_6$) δ (ppm) 9.16 (s, 1H), 8.70 (s, 1H), 8.55 (s, 1H), 8.41 (s, 1H), 8.14 (s, 1H), 7.68 (t, 1H), 7.16 (d, 1H), 6.69 (d, 1H), 5.27-5.22 (m, 2H), 4.06-4.03 (m, 2H), 3.67-3.54 (m, 2H), 3.12 (s, 3H), 3.02 (s, 2H), 2.72 (s, 2H), 1.14 (s, 3H); MS (ESI) m/z: 487 [M+H]+.

Example 162

(1-(6-(6-(1-(2,2,2-Trifluoroethyl)-1H-pyrazol-4-yl)-1H-pyrazolo[4,3-c]pyridin-1-yl)pyridin-2-yl)azetidin-3-yl)methanamine 262

Following the procedures as described in Example 88 and starting with tert-butyl azetidin-3-ylmethylcarbamate, 2-bromo-6-fluoropyridine, and 6-chloro-1H-pyrazolo[4,3-c]pyridine, 262 was obtained as a yellow solid (35 mg, 30.9%) over five steps. $^1$H NMR (500 MHz, DMSO-d$_6$) δ (ppm) 9.15 (s, 1H), 8.83-8.86 (d, J=12 Hz, 1H), 8.55 (s, 1H), 8.43 (s, 1H), 8.10-8.12 (d, J=7 Hz, 1H), 7.69-7.72 (t, J=16 Hz, 1H), 7.19-7.20 (d, J=8 Hz, 1H), 6.28-6.29 (d, J=8 Hz, 1H), 5.23-5.25 (d, J=9.5 Hz, 2H), 4.17-4.20 (m, 2H), 3.87-3.89 (t, J=12 Hz, 2H), 2.84-2.86 (d, J=6.5 Hz, 3H); MS (ESI) m/z: 429 [M+H]+.

Example 164

(R)-1-(6-(6-Methoxy-6-methyl-1,4-diazepan-1-yl)pyridin-2-yl)-6-(1-(2,2,2-trifluoroethyl)-1H-pyrazol-4-yl)-1H-pyrazolo[4,3-c]pyridine 264

Following the procedures as described in Example 161 and starting with (S)-tert-butyl 6-methoxy-6-methyl-4-(6-(6-(1-(2,2,2-trifluoroethyl)-1H-pyrazol-4-yl)-1H-pyrazolo[4,3-c]pyridin-1-yl)pyridin-2-yl)-1,4-diazepane-1-carboxylate, 264 was obtained as white solid (133 mg, 92%). $^1$H NMR (500 MHz, DMSO-d$_6$) δ (ppm) 9.16 (s, 1H), 8.70 (s, 1H), 8.55 (s, 1H), 8.41 (s, 1H), 8.14 (s, 1H), 7.68 (t, 1H), 7.16 (d, 1H), 6.69 (d, 1H), 5.27-5.22 (m, 2H), 4.06-4.03 (m, 2H), 3.67-3.54 (m, 2H), 3.12 (s, 3H), 3.02 (s, 2H), 2.72 (s, 2H), 1.14 (s, 3H); MS (ESI) m/z: 487 [M+H]+.

Example 165

3-[6-[6-(6-methylpyrazin-2-yl)pyrazolo[4,3-c]pyridin-1-yl]-2-pyridyl]piperidin-4-ol 265

Step A: tert-butyl 4-hydroxy-3-[6-[6-(6-methylpyrazin-2-yl)pyrazolo[4,3-c]pyridin-1-yl]-2-pyridyl]piperidine-1-carboxylate

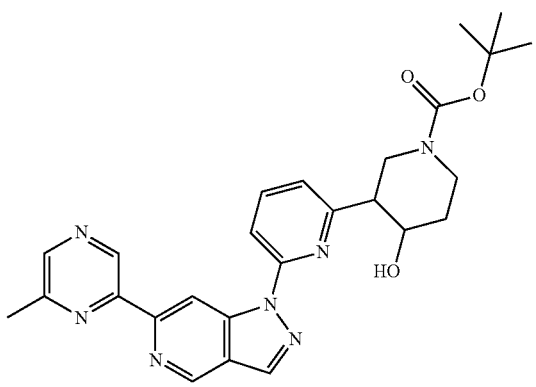 [SMILES: Cc1cncc(-c2cc3c(cn2)cnn3-c2cccc(C3CN(C(=O)OC(C)(C)C)CCC3O)n2)n1]

To a solution of tert-butyl 3-[6-[6-(6-methylpyrazin-2-yl)pyrazolo[4,3-c]pyridin-1-yl]-2-pyridyl]-4-oxo-piperidine-1-carboxylate (90 mg, 0.18 mmol) in tetrahydrofuran (8.0 ml) at 0° C. was added sodium borohydride (8.0 mg, 0.20 mmol). The reaction mixture was stirred at 0° C. for 30 min. The reaction was quenched with water and extracted with EtOAc. The organic layers was dried with sodium sulfate, filtered, and concentrated in vacuum. The crude product was purified by flash chromatography (EtOAc/Heptane eluted at 100% EtOAc) to give the desired product 40 mg 44% yield. MS (ESI) m/z: 488.1.

Step B

To a solution of tert-butyl 4-hydroxy-3-[6-[6-(6-methylpyrazin-2-yl)pyrazolo[4,3-c]pyridin-1-yl]-2-pyridyl]piperidine-1-carboxylate (35 mg, 0.072 mmol) in 1,4-dioxane (2.00 mL, 23.4 mmol) was added hydrogen chloride (4 mol/L) in 1,4-dioxane (1.00 mL, 4.00 mmol). The reaction was stirred at RT 18 h. The reaction was concentrated and purified by reverse phase HPLC to yield 265. MS (ESI) m/z: 388.1.

Example 166

1-(6-(2,5-Diazaspiro[3.5]nonan-2-yl)pyridin-2-yl)-6-(1-methyl-1H-pyrazol-4-yl)-1H-pyrazolo[4,3-c]pyridine 266

Following the procedures as described in Example 124 and starting with tert-butyl 2,5-diazaspiro[3.5]nonane-5-carboxylate, 2-bromo-6-fluoropyridine, and 6-chloro-1H-pyrazolo[4,3-c]pyridine, 266 was obtained as a yellow solid (10 mg, 5%) over four steps. $^1$H NMR (500 MHz, DMSO-d$_6$) δ (ppm) 9.12 (s, 1H), 8.85 (s, 1H), 8.52 (s, 1H), 8.26 (s, 1H), 7.92 (s, 1H), 7.69-7.72 (t, J=16 Hz, 1H), 7.18-7.19 (d, J=7.5 Hz, 1H), 6.33-6.34 (d, J=8 Hz, 1H), 4.00-4.01 (d, J=7 Hz, 2H), 3.92 (s, 3H), 3.87-3.88 (d, J=7 Hz, 2H), 2.715-2.724 (d, J=4.5 Hz, 2H), 1.76-1.78 (t, J=11 Hz, 2H), 1.59-1.60 (d, J=3.5 Hz, 2H), 1.45 (s, 2H); MS (ESI) m/z: 401 [M+H]$^+$.

Example 167

1-(6-(2,6-Diazaspiro[3.3]heptan-2-yl)pyridin-2-yl)-6-(1-(2,2,2-trifluoroethyl)-1H-pyrazol-4-yl)-1H-pyrazolo[4,3-c]pyridine 267

Following the procedures as described in Example 88 and starting with tert-butyl 2,6-diazaspiro[3.3]heptane-2-carboxylate, 2-bromo-6-fluoropyridine, and 6-chloro-1H-pyrazolo[4,3-c]pyridine, 267 was obtained as a yellow solid (58 mg, 11%) over five steps. $^1$H NMR (500 MHz, DMSO-d$_6$) δ (ppm) 9.15 (s, 1H), 8.81 (s, 1H), 8.54 (s, 1H), 8.47 (s, 1H), 8.14 (s, 1H), 7.70-7.73 (t, J=10 Hz, 1H), 7.21-7.22 (d, J=10 Hz, 1H), 6.31-6.32 (d, J=9 Hz, 1H), 5.23-5.27 (m, 2H), 4.24 (s, 4H), 4.07-4.08 (m, 1H), 3.76-3.82 (m, 3H), 3.42-3.43 (br, 1H); MS (ESI) m/z: 441 [M+H]$^+$.

Example 168

1-(6-(2,6-Diazaspiro[3.3]heptan-2-yl)pyridin-2-yl)-6-(1-methyl-1H-pyrazol-4-yl)-1H-pyrazolo[4,3-c]pyridine 268

Following the procedures as described in Example 124 and starting with tert-butyl 2,6-diazaspiro[3.3]heptane-2-carboxylate, 2-bromo-6-fluoropyridine, 6-chloro-1H-pyrazolo[4,3-c]pyridine, and 1-methyl-4-(4,4,5,5-tetramethyl-1,3,2-dioxaborolan-2-yl)-1H-pyrazole, 268 was obtained as a yellow solid (87 mg, 26%) over four steps. $^1$H NMR (500 MHz, DMSO-d6) δ (ppm) 9.10 (s, 1H), 8.74 (s, 1H), 8.51 (s, 1H), 8.28 (s, 1H), 7.98 (s, 1H), 7.69-7.71 (t, J=9 Hz, 1H), 7.20-7.21 (d, J=9 Hz, 1H), 6.30-6.31 (d, J=9 Hz, 1H), 4.24 (s, 3H), 4.08 (s, 1H), 3.86-3.93 (m, 3H), 3.79-3.83 (m, 2H), 3.35-3.42 (m, 3H); MS (ESI) m/z: 373 [M+H]$^+$.

Example 169

1-(6-(2,5-Diazaspiro[3.5]nonan-2-yl)pyridin-2-yl)-6-(1-(2,2,2-trifluoroethyl)-1H-pyrazol-4-yl)-1H-pyrazolo[4,3-c]pyridine 269

Following the procedures as described in Example 88 and starting with tert-butyl 2,5-diazaspiro[3.5]nonane-5-carboxylate, 2-bromo-6-fluoropyridine, and 6-chloro-1H-pyrazolo[4,3-c]pyridine, 269 was obtained as a yellow solid (8 mg, 5%) over five steps. $^1$H NMR (500 MHz, DMSO-d6) δ (ppm) 9.15-9.16 (d, J=5 Hz, 1H), 8.84 (s, 1H), 8.53-8.55 (d, J=9.5 Hz, 1H), 8.48 (s, 1H), 8.28-8.29 (d, J=7.5 Hz, 1H), 7.56-7.59 (t, J=15.5 Hz, 1H), 7.05-7.09 (m, 2H), 6.55-6.57 (d, J=8 Hz, 1H), 5.21-5.26 (m, 2H), 3.44-3.45 (d, J=4.5 Hz, 2H), 3.33 (s, 1H), 2.61-2.64 (t, J=13 Hz, 1H), 1.90-1.97 (m, 2H), 1.76 (s, 1H), 1.57 (s, 1H), 1.28-1.37 (m, 4H); MS (ESI) m/z: 469 [M+H]$^+$.

Example 170

3-(Aminomethyl)-1-(6-(6-(1-methyl-1H-pyrazol-4-yl)-1H-pyrazolo[4,3-c]pyridin-1-yl)pyridin-2-yl)azetidin-3-ol 270

Step A: 1-(6-(6-(1-Methyl-1H-pyrazol-4-yl)-1H-pyrazolo[4,3-c]pyridin-1-yl)pyridin-2-yl)azetidin-3-one

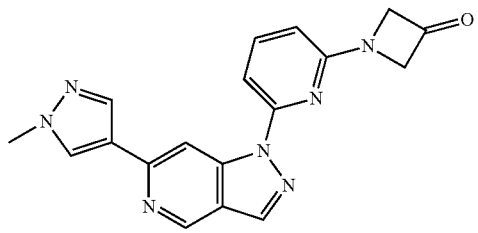 [SMILES: Cn1cc(-c2cc3c(cn2)cnn3-c2cccc(N3CC(=O)C3)n2)cn1]

To a solution of dimethyl sulfoxide (225 mg, 2.88 mmol) in DCM (10 mL) at −60° C. was added oxalyl chloride (366 mg, 2.88 mmol). After the mixture was stirred at −60° C. for 0.5 hour, to it was dropped a solution of 1-(6-(6-(1-Methyl-1H-pyrazol-4-yl)-1H-pyrazolo[4,3-c]pyridin-1-yl)pyridin-2-yl)azetidin-3-ol (200 mg, 0.58 mmol) in DCM (10 mL) at −60° C. The reaction mixture was stirred at −60° C. for 2 hours, and to it was added triethylamine (583 mg, 5.76 mmol) dropwise. The reaction mixture was stirred at −60° C. for another hour. It was concentrated under reduced pressure to afford a white solid. The crude product (1.1 g), 1-(6-(6-(1-methyl-1H-pyrazol-4-yl)-1H-pyrazolo[4,3-c]pyridin-1-yl)pyridin-2-yl)azetidin-3-one, was used for next reaction without further purification. MS (ESI) m/z: 346 [M+H]$^+$.

Step B: 1-(6-(6-(1-Methyl-1H-pyrazol-4-yl)-1H-pyrazolo[4,3-c]pyridin-1-yl)pyridin-2-yl)-3-(nitromethyl)azetidin-3-ol

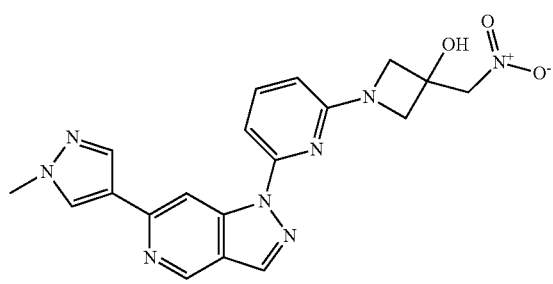 [SMILES: Cn1cc(-c2cc3c(cn2)cnn3-c2cccc(N3CC(O)(C[N+](=O)[O-])C3)n2)cn1]

To a solution of 1-(6-(6-(1-methyl-1H-pyrazol-4-yl)-1H-pyrazolo[4,3-c]pyridin-1-yl)pyridin-2-yl)azetidin-3-one (1.1 g) in DCM (10 mL) at 20° C. was added nitromethane (1 mL) and triethylamine (0.5 mL). The mixture was stirred at ambient temperature for 2 hours. It was concentrated under reduced pressure to afford a white solid. The crude product (1.3 g), 1-(6-(6-(1-methyl-1H-pyrazol-4-yl)-1H-pyrazolo[4,3-c]pyridin-1-yl)pyridin-2-yl)-3-(nitromethyl)azetidin-3-ol, was used for next step without further purification. MS (ESI) m/z: 407 [M+H]$^+$.

Step C: 3-(Aminomethyl)-1-(6-(6-(1-methyl-1H-pyrazol-4-yl)-1H-pyrazolo[4,3-c]pyridin-1-yl)pyridin-2-yl)azetidin-3-ol

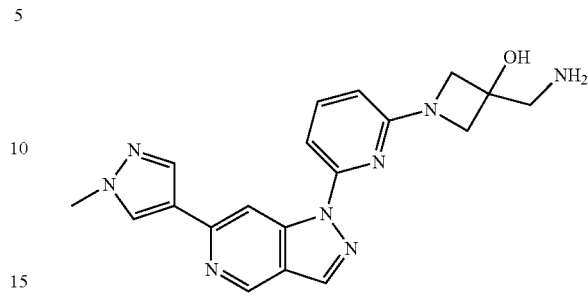

To a solution of 1-(6-(6-(1-methyl-1H-pyrazol-4-yl)-1H-pyrazolo[4,3-c]pyridin-1-yl)pyridin-2-yl)-3-(nitromethyl)azetidin-3-ol (100 mg, 0.25 mmol) in MeOH (5 mL) and H$_2$O (0.5 mL) was added Zn powder (129 mg, 2 mmol) and NH$_4$Cl (132 mg, 2.5 mmol). The reaction mixture was stirred at ambient temperature for 2 hours and filtered through Celite. The filtrate was concentrated under reduced pressure. The residue was purified by reverse phase preparative HPLC to afford 270 as red solid (60 mg, 64.8%). $^1$H NMR (500 MHz, DMSO-d6) δ (ppm) 9.13 (s, 1H), 8.75 (s, 1H), 8.53 (s, 1H), 8.34-8.40 (m, 2H), 7.98 (s, 1H), 7.72-7.75 (m, 1H), 7.24-7.25 (m, 1H), 6.34-6.36 (d, J=8.5 Hz, 1H), 4.23-4.25 (d, J=8.5 Hz, 2H), 3.89-3.97 (m, 5H), 3.06-3.10 (m, 2H); MS (ESI) m/z: 377 [M+H]$^+$.

Example 171 and 172

(R)-1-[6-(4 4-difluoro-3-piperidyl)-2-pyridyl]-6-(6-methylpyrazin-2-yl)pyrazolo[4,3-c]pyridine 271 and (S)-1-[6-(4 4-difluoro-3-piperidyl)-2-pyridyl]-6-(6-methylpyrazin-2-yl)pyrazolo[4,3-c]pyridine 272

Enantiomer compounds 271 and 272 were separated by chiral SFC separation according to EXAMPLE 159. 1H NMR (400 MHz, DMSO) δ 9.72 (s, 1H), 9.46 (s, 1H), 9.36 (s, 1H), 8.74 (s, 1H), 8.63 (s, 1H), 8.04 (t, J=7.8 Hz, 1H), 7.98 (d, J=8.2 Hz, 1H), 7.40 (d, J=7.4 Hz, 1H), 3.60-3.42 (m, 2H), 3.18 (d, J=12.8 Hz, 1H), 2.87 (t, J=12.6 Hz, 1H), 2.67 (s, 3H), 2.36 (d, J=18.3 Hz, 1H), 2.21-2.09 (m, 1H), 1.99 (d, J=34.4 Hz, 1H). MS (ESI) m/z: 408.1.

Example 173

(6-(1-(6-(piperazin-1-yl)pyridin-2-yl)-1H-pyrazolo[4,3-c]pyridin-6-yl)pyrazin-2-yl)methanol dihydrochloride 273

Step A: tert-butyl 4-(6-(6-(6-formylpyrazin-2-yl)-1H-pyrazolo[4,3-c]pyridin-1-yl)pyridin-2-yl)piperazine-1-carboxylate

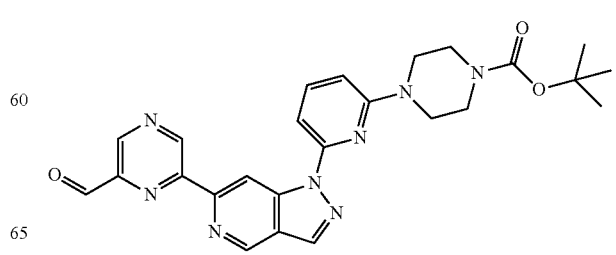

A solution of sodium periodate (260 mg 1.22 mmol) in 5 ml of water was added to a solution of tert-butyl 4-[6-[6-[6-(1,2-dihydroxyethyl)pyrazin-2-yl]pyrazolo[4,3-c]pyridin-1-yl]-2-pyridyl]piperazine-1-carboxylate (315 mg, 0.61 mmol) in 25 ml of tetrahydrofuran and 5 ml of water. The mixture was stirred for 24 hours, concentrated, the residue partitioned between ethyl acetate and water, the organic extracts were washed with water, brine, dried over sodium sulfate and concentrated. The residue was purified on 12 g silica gel column eluting with ethyl acetate gradient in heptane to afford 245 mg (83%). MS (ESI) m/z: 505.2 [M+H$_2$O+H]$^+$.

Step B: tert-butyl 4-(6-(6-(6-(hydroxymethyl)pyrazin-2-yl)-1H-pyrazolo[4,3-c]pyridin-1-yl)pyridin-2-yl)piperazine-1-carboxylate

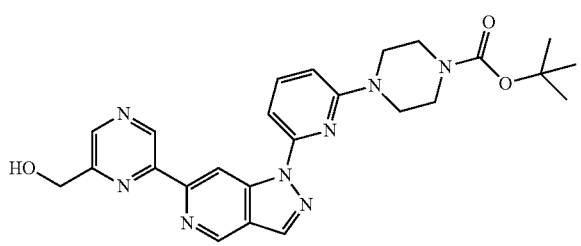 [SMILES: CC(C)(C)OC(=O)N1CCN(c2cccc(-n3ncc4cnc(-c5cncc(CO)n5)cc43)n2)CC1]

Sodium borohydride (25 mg, 0.66 mmol) was added portionwise to a solution of tert-butyl 4-[6-[6-(6-formylpyrazin-2-yl)pyrazolo[4,3-c]pyridin-1-yl]-2-pyridyl]piperazine-1-carboxylate (162 mg, 0.33 mmol) in 6 ml of methanol. The mixture was stirred for 1 hour, concentrated in vacuum, the residue partitioned between ethyl acetate and water. The organic extracts were washed with water, 1% aq. citric acid, water, and brine, dried over sodium sulfate and concentrated. The residue was purified on a 12 g silica gel column eluting with 0-7% gradient of methanol in DCM to afford 125 mg (77%). MS (ESI) m/z: 489.2 [M+H]$^+$ Step C Compound 273w as obtained by treatment with 4 M HCl in dioxane in methanol for 1-2 hours, collected by filtration from the reaction mixture, dissolved in water and lyophilized. $^1$H NMR (400 MHz, DMSO-d6) δ 9.57 (s, 1H), 9.52 (s, 1H), 9.28 (s, 2H), 8.81 (s, 1H), 8.71 (s, 1H), 7.88 (t, J=8.0 Hz, 1H), 7.39 (d, J=7.8 Hz, 1H), 6.95 (d, J=8.4 Hz, 1H), 4.78 (s, 2H), 3.96 (d, J=5.5 Hz, 4H), 3.33 (d, J=5.1 Hz, 4H). MS (ESI) m/z: 389.2 [M+H]$^+$.

Example 174

1-(6-(piperazin-1-yl)pyridin-2-yl)-6-(6-vinylpyrazin-2-yl)-1H-pyrazolo[4,3-c]pyridine dihydrochloride 274

Step A: tert-butyl 4-(6-(6-(6-vinylpyrazin-2-yl)-1H-pyrazolo[4,3-c]pyridin-1-yl)pyridin-2-yl)piperazine-1-carboxylate

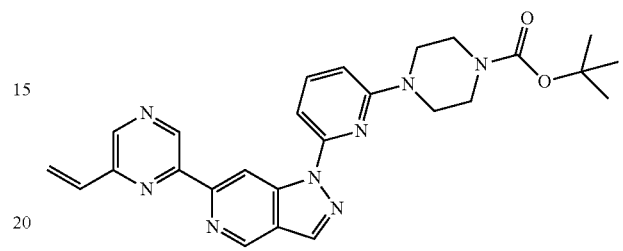

A mixture of tert-butyl 4-[6-[6-(6-chloropyrazin-2-yl)pyrazolo[4,3-c]pyridin-1-yl]-2-pyridyl]piperazine-1-carboxylate (493 mg, 1 mmol), potassium vinyltrifluoroborate (335 mg, 2.500 mmol), 1,1'-bis(diphenylphosphino)ferrocene-palladium(II)dichloride, DCM complex (55 mg, 0.07500 mmol) and triethylamine (0.63 ml, 4.500 mmol) in ethanol (9 mL) was degassed and heated in a sealed vial for 2 hours at 105° C. The mixture was left at room temperature for 20 hours. The precipitate was collected and washed with ethanol to give the crude material, 605 mg (99.8%). MS (ESI) m/z: 485.4 [M+H]$^+$ Step B Compound 274 was obtained by treatment with 4 M HCl in dioxane in methanol for 1-2 hours, collected by filtration from a reaction mixture, dissolved in water and lyophilized. 1H NMR (400 MHz, DMSO-d6) δ 9.54 (s, 1H), 9.46 (s, 1H), 9.37 (s, 1H), 9.09 (s, 2H), 8.95 (s, 1H), 8.72 (s, 1H), 7.89 (t, J=8.1 Hz, 1H), 7.39 (d, J=7.8 Hz, 1H), 7.03 (dd, J=17.6, 11.0 Hz, 1H), 6.96 (d, J=8.4 Hz, 1H), 6.50 (d, J=17.3 Hz, 1H), 5.80 (d, J=11.2 Hz, 1H), 3.96 (t, J=5.3 Hz, 4H), 3.27 (s, 4H). MS (ESI) m/z: 385.2 [M+H]$^+$ Example 175

6-(6-Chloropyrazin-2-yl)-1-(6-(piperazin-1-yl)pyridin-2-yl)-1H-pyrazolo[4,3-c]pyridine dihydrochloride 275

Step A: tert-butyl 4-(6-(6-(tributylstannyl)-1H-pyrazolo[4,3-c]pyridin-1-yl)pyridin-2-yl)piperazine-1-carboxylate

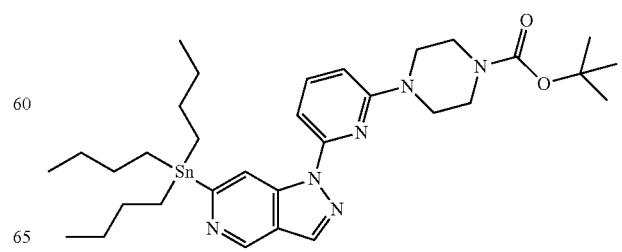

To a mixture of tert-butyl 4-(6-(6-chloro-1H-pyrazolo[4,3-c]pyridin-1-yl)pyridin-2-yl)piperazine-1-carboxylate (10 g, 0.024 mol) in DMF (100 mL) under N₂ was added LiCl (6.14 g, 0.145 mol), nBu₆Sn₂ (15.3 g 0.0264 mol), Pd₂(dba)₃ (0.44 g, 0.48 mmol) and Pcy₃ (0.27 g, 0.96 mmol). The resulting mixture was heated at 130° C. overnight. The mixture was filtered through Celite. The filter was extracted with petroleum ether (300 mL×6). The combined organic layers were dried over Na₂SO₄, filtered and concentrated. The crude product was purified by column chromatography on silica gel (PE:EA=50:1) to afford 8 (4.5 g, yield 28%) as a clear oil. $^1$H NMR (400 MHz, CDCl₃) δ 9.26 (d, J=1.2 Hz, 1H), 8.67-8.60 (m, 1H), 8.25 (d, J=0.6 Hz, 1H), 7.68 (t, J=8.1 Hz, 1H), 7.38 (d, J=7.8 Hz, 1H), 6.56 (d, J=8.3 Hz, 1H), 3.66 (s, 9H), 1.66-1.57 (m, 6H), 1.52 (s, 8H), 1.36 (dd, J=14.6, 7.1 Hz, 6H), 1.23-1.15 (m, 6H), 0.88 (t, J=7.3 Hz, 9H). MS (ESI) m/z: 671 [M+H]⁺

Step B: tert-butyl 4-(6-(6-(6-chloropyrazin-2-yl)-1H-pyrazolo[4,3-c]pyridin-1-yl)pyridin-2-yl)piperazine-1-carboxylate

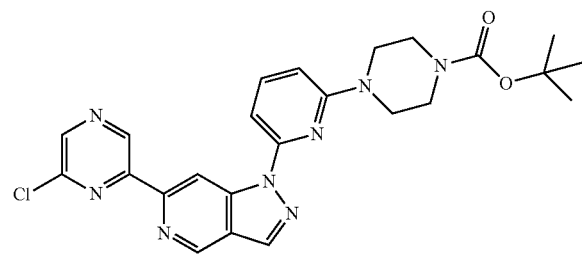 [SMILES: CC(C)(C)OC(=O)N1CCN(c2cccc(-n3ncc4cnc(-c5cncc(Cl)n5)cc43)n2)CC1]

A mixture of tert-butyl 4-(6-(6-(tributylstannyl)-1H-pyrazolo[4,3-c]pyridin-1-yl)pyridin-2-yl)piperazine-1-carboxylate (27 g, 0.04 mol), 2,6-dichloropyrazine (8.9 g, 0.06 mol), Pd₂(dba)₃ (0.37 g, 0.4 mmol) and Pcy₃ (0.23 g, 0.8 mmol) in DMA (150 mL) was purged with N₂ for 1 min. The reaction mixture was heated at 130° C. overnight. The mixture was cooled to room temperature, added water and a little EA, Stirred for 10 minutes and filtered washed with MTBE. The crude product was purified by column chromatography on silica gel (PE:EA=1:1) to afford 9 (6.1 g, 30%) as a yellow solid. 1H NMR (400 MHz, DMSO) δ 9.58 (d, J=18.5 Hz, 2H), 9.33 (s, 1H), 8.90 (s, 1H), 8.69 (s, 1H), 7.80 (t, J=8.1 Hz, 1H), 7.32 (d, J=7.8 Hz, 1H), 6.85 (d, J=8.4 Hz, 1H), 3.64 (s, 8H), 1.55-1.38 (m, 9H). MS (ESI) m/z: 493 [M+H]⁺

Step C

Compound 275 was obtained by deprotection of the Boc group with 4 M HCl in dioxane in methanol. Corresponding hydrochloride was collected by filtration from a reaction mixture, dissolved in water and lyophilized. 1H NMR (400 MHz, DMSO-d6) δ 9.63 (s, 1H), 9.51 (s, 1H), 9.38 (s, 1H), 9.12 (s, 2H), 8.91 (s, 1H), 8.73 (s, 1H), 7.89 (t, J=8.1 Hz, 1H), 7.40 (d, J=7.8 Hz, 1H), 6.95 (d, J=8.4 Hz, 1H), 3.97 (t, J=5.3 Hz, 4H), 3.37 (s, 4H). MS (ESI) m/z: 393.0 [M+H]⁺

Example 176

6-(6-(benzyloxy)pyrazin-2-yl)-1-(6-(piperazin-1-yl)pyridin-2-yl)-1H-pyrazolo[4,3-c]pyridine 276

Step A: tert-butyl 4-(6-(6-(6-(benzyloxy)pyrazin-2-yl)-1H-pyrazolo[4,3-c]pyridin-1-yl)pyridin-2-yl)piperazine-1-carboxylate

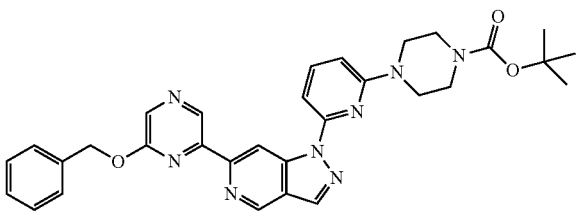 [SMILES: CC(C)(C)OC(=O)N1CCN(c2cccc(-n3ncc4cnc(-c5cncc(OCc6ccccc6)n5)cc43)n2)CC1]

A mixture of 3-5 eq. of benzyl alcohol, 1 eq. of tert-butyl 4-(6-(6-(6-chloropyrazin-2-yl)-1H-pyrazolo[4,3-c]pyridin-1-yl)pyridin-2-yl)piperazine-1-carboxylate, 6-10 eq of potassium tert-butoxide in dioxane was heated at 90° C. for 2-4 hours. The mixture was mixed with water and extracted with ethyl acetate. The organic extracts were washed with water, brine, dried over sodium sulfate and concentrated in vacuum. The crude products were purified on a silica gel column eluting with gradient of ethyl acetate in heptane or methanol in DCM to give tert-butyl 4-(6-(6-(6-(benzyloxy)pyrazin-2-yl)-1H-pyrazolo[4,3-c]pyridin-1-yl)pyridin-2-yl)piperazine-1-carboxylate as the dihydrochloride salt. MS (ESI) m/z: 603.4 [M+H]⁺

Step B

Compound 276 as the dihydrochloride salt was obtained by deprotection of the Boc group with 4 M HCl in dioxane in methanol for 1-2 hours. Corresponding hydrochlorides were collected by filtration from a reaction mixture, dissolved in water and lyophilized. MS (ESI) m/z: 465.3 [M+H]⁺

Example 177

1-(6-(1-(6-(piperazin-1-yl)pyridin-2-yl)-1H-pyrazolo[4,3-c]pyridin-6-yl)pyrazin-2-yl)ethane-1,2-diol 277

Step A: tert-butyl 4-(6-(6-(6-(1,2-dihydroxyethyl)pyrazin-2-yl)-1H-pyrazolo[4,3-c]pyridin-1-yl)pyridin-2-yl)piperazine-1-carboxylate

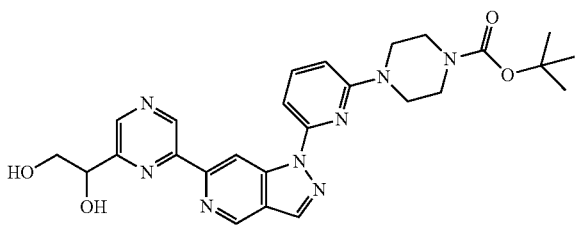 [SMILES: CC(C)(C)OC(=O)N1CCN(c2cccc(-n3ncc4cnc(-c5cncc(C(O)CO)n5)cc43)n2)CC1]

A mixture of tert-butyl 4-[6-[6-(6-vinylpyrazin-2-yl)pyrazolo[4,3-c]pyridin-1-yl]-2-pyridyl]piperazine-1-carboxylate (513 mg; 1.06 mmol), N-methylmorpholine-N-oxide monohydrate (744 mg, 6.35 mmol) and 2.5% solution of osmium tetroxide in tert-butanol (0.6 ml, 0.04764 mmol) in 20 ml of acetone and 2.5 ml of water was stirred at room temperature for 24 hours. The mixture was filtered, mixed with water and extracted with EtOAc. The organic extracts were washed with water, 5% aq. citric acid, sat. aq. NaHCO$_3$, brine, dried over Na$_2$SO$_4$ and concentrated. The residue was triturated with ethyl ether, the precipitate was collected by filtration and washed with ethyl ether affording tert-butyl 4-(6-(6-(6-(1,2-dihydroxyethyl)pyrazin-2-yl)-1H-pyrazolo[4,3-c]pyridin-1-yl)pyridin-2-yl)piperazine-1-carboxylate (424 mg, 67%). MS (ESI) m/z: 519.3 [M+H]$^+$ Step B:

Compound 277 was obtained as the hydrochloride salt by treatment with 4 M HCl in dioxane in methanol for 1-2 hours, collected by filtration from a reaction mixture, dissolved in water and lyophilized. 1H NMR (400 MHz, DMSO-d6) δ 9.57 (s, 1H), 9.46 (s, 1H), 9.37 (d, J=1.0 Hz, 1H), 9.17 (s, 2H), 8.81 (s, 1H), 8.72 (s, 1H), 7.88 (t, J=8.1 Hz, 1H), 7.40 (d, J=7.8 Hz, 1H), 6.96 (d, J=8.4 Hz, 1H), 4.80 (t, J=5.5 Hz, 1H), 3.98 (t, J=5.3 Hz, 4H), 3.83 (dd, J=11.1, 5.0 Hz, 1H), 3.75 (dd, J=11.1, 6.0 Hz, 1H), 3.33 (s, 4H). MS (ESI) m/z: 419.2 [M+H]$^+$ Example 178

2-((6-(1-(6-(piperazin-1-yl)pyridin-2-yl)-1H-pyrazolo[4,3-c]pyridin-6-yl)pyrazin-2-yl)oxy)ethanol dihydrochloride 278

Following the procedures as described in Example 176 and with 3-5 eq. of 2-((tetrahydro-2H-pyran-2-yl)oxy)ethanol, 278 was obtained. 1H NMR (400 MHz, DMSO-d6) δ 9.35 (s, 1H), 9.24 (m, 3H), 8.71 (s, 1H), 8.42 (s, 1H), 7.88 (t, J=8.1 Hz, 1H), 7.36 (d, J=7.8 Hz, 1H), 6.96 (d, J=8.4 Hz, 1H), 4.49 (t, J=5.0 Hz, 2H), 3.97 (t, J=5.3 Hz, 4H), 3.89 (t, J=5.0 Hz, 2H), 3.27 (s, 4H). MS (ESI) m/z: 419.2 [M+H]$^+$ Example 179

6-(6-(difluoromethyl)pyrazin-2-yl)-1-(6-(piperazin-1-yl)pyridin-2-yl)-1H-pyrazolo[4,3-c]pyridine trifluoroacetate 279

Step A: tert-butyl 4-(6-(6-(6-(difluoromethyl)pyrazin-2-yl)-1H-pyrazolo[4,3-c]pyridin-1-yl)pyridin-2-yl)piperazine-1-carboxylate

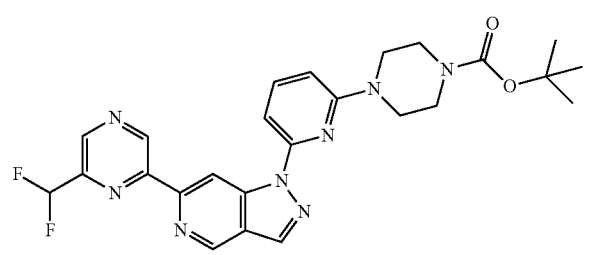 [SMILES: CC(C)(C)OC(=O)N1CCN(c2cccc(-n3ncc4cnc(-c5cncc(C(F)F)n5)cc43)n2)CC1]

A mixture of tert-butyl 4-[6-[6-(6-formylpyrazin-2-yl)pyrazolo[4,3-c]pyridin-1-yl]-2-pyridyl]piperazine-1-carboxylate (49 mg, 0.10 mmol) and Deoxo-fluor® (50 mass %) in toluene (0.175 ml 0.40 mmol) in 4 ml of DCM was stirred for 24 hours. The mixture was concentrated in vacuum, the residue partitioned between ethyl acetate and saturated aqueous sodium bicarbonate. The organic extracts were washed with water, 5% aqueous citric acid, water, brine, dried over sodium sulfate and concentrated. The crude residue was purified on a 4 g silica gel column eluting with 0-70% gradient of ethyl acetate in heptane affording 38 mg of tert-butyl 4-(6-(6-(6-(difluoromethyl)pyrazin-2-yl)-1H-pyrazolo[4,3-c]pyridin-1-yl)pyridin-2-yl)piperazine-1-carboxylate (74%). MS (ESI) m/z: 509.3 [M+H]$^+$ Step B A solution of tert-butyl 4-[6-[6-[6-(difluoromethyl)pyrazin-2-yl]pyrazolo[4,3-c]pyridin-1-yl]-2-pyridyl]piperazine-1-carboxylate (16) (38 mg, 0.075 mmol) in 3 ml of trifluoroacetic acid was stirred for 2 hours. The mixture was concentrated in vacuum, the residue triturated with ethyl ether collecting the precipitate by filtration. The solid material was washed with ethyl ether, dried on air, re-dissolved in water and lyophilized affording 279 as the trifluoroacetate salt (16 mg, 42%). 1H NMR (400 MHz, DMSO-d6) δ 9.86 (s, 1H), 9.51 (s, 1H), 9.41 (s, 1H), 9.07 (s, 1H), 8.89 (d, J=30.2 Hz, 2H), 8.74 (s, 1H), 7.89 (t, J=8.1 Hz, 1H), 7.41 (d, J=7.8 Hz, 1H), 7.25 (t, J=54.2 Hz, 1H), 6.96 (d, J=8.4 Hz, 1H), 3.94 (t, J=5.3 Hz, 4H), 3.36-3.31 (m, 4H). MS (ESI) m/z: 409.2 [M+H]$^+$ Example 180

(S)-(1-(6-(1-(6-(piperazin-1-yl)pyridin-2-yl)-1H-pyrazolo[4,3-c]pyridin-6-yl)pyrazin-2-yl)pyrrolidin-2-yl)methanol dihydrochloride 280

A mixture of 3-5 eq. of (S)-pyrrolidin-2-ylmethanol, 1 eq. of tert-butyl 4-(6-(6-(6-chloropyrazin-2-yl)-1H-pyrazolo[4,3-c]pyridin-1-yl)pyridin-2-yl)piperazine-1-carboxylate, 6-10 eq of cesium fluoride in DMSO was heated at 105° C. for 12-24 hours. The mixture was mixed with water and extracted with ethyl acetate. The organic extracts were washed with water, brine, dried over sodium sulfate and concentrated in vacuum. The crude products were purified on a silica gel column eluting with gradient of ethyl acetate in heptane or DCM. The Boc group was deprotected with 4 M HCl in dioxane in methanol. The crude product was collected by filtration, dissolved in water and lyophilized to give 280. 1H NMR (400 MHz, DMSO-d6) δ 9.37 (s, 1H), 9.31-9.19 (m, 2H), 9.10 (s, 1H), 8.80 (s, 1H), 8.73 (s, 1H), 8.19 (s, 1H), 7.89 (t, J=8.1 Hz, 1H), 7.35 (d, J=7.8 Hz, 1H), 6.97 (d, J=8.5 Hz, 1H), 4.21 (d, J=6.0 Hz, 1H), 3.93 (t, J=5.3 Hz, 4H), 3.58 (m, 1H), 3.49 (m, 2H), 3.22 (d, J=5.4 Hz, 4H), 2.06 (m, 4H). MS (ESI) m/z: 458.3.

Example 181

1-(6-(1-(6-(piperazin-1-yl)pyridin-2-yl)-1H-pyrazolo[4,3-c]pyridin-6-yl)pyrazin-2-yl)azetidin-3-ol 281

Following the procedures as described in Example 180, 281 was obtained. 1H NMR (400 MHz, DMSO-d6) δ 9.28 (s, 1H), 9.22 (s, 1H), 8.91 (s, 1H), 8.64 (s, 1H), 8.27 (s, 1H), 7.96 (s, 1H), 7.77 (t, J=8.1 Hz, 1H), 7.24 (d, J=7.7 Hz, 1H), 6.83 (d, J=8.4 Hz, 1H), 4.72-4.62 (m, 1H), 4.37 (dd, J=8.7, 6.7 Hz, 2H), 3.89 (dd, J=8.9, 4.6 Hz, 2H), 3.63 (t, J=5.1 Hz, 4H), 2.86 (dd, J=6.3, 3.9 Hz, 4H). MS (ESI) m/z: 430.3.

Example 182

2-[[6-[1-(6-piperazin-1-yl-2-pyridyl)pyrazolo[4,3-c]pyridin-6-yl]pyrazin-2-yl]amino]ethanol 282

Following the procedures as described in Example 180, 282 was obtained. 1H NMR (400 MHz, DMSO-d6) δ 9.41 (d, J=7.8 Hz, 3H), 9.21 (s, 1H), 8.78 (s, 1H), 8.70 (s, 1H), 8.13 (s, 1H), 7.89 (t, J=8.1 Hz, 1H), 7.35 (d, J=7.8 Hz, 1H), 6.98 (d, J=8.5 Hz, 1H), 3.97 (t, J=5.2 Hz, 4H), 3.68 (t, J=5.9 Hz, 2H), 3.60-3.51 (m, 2H), 3.25 (s, 4H). MS (ESI) m/z: 418.2

Example 183

(1S,2S)-2-(6-(1-(6-(piperazin-1-yl)pyridin-2-yl)-1H-pyrazolo[4,3-c]pyridin-6-yl)pyrazin-2-yl)amino)cyclopentanol 283

Following the procedures as described in Example 180, 283 was obtained. 1H NMR (400 MHz, DMSO-d6) δ 9.38 (s, 1H), 9.22 (s, 2H), 9.19 (s, 1H), 8.74 (s, 1H), 8.69 (s, 1H), 8.09 (s, 1H), 7.89 (t, J=8.1 Hz, 1H), 7.35 (d, J=7.8 Hz, 1H), 7.18 (s, 1H), 6.98 (d, J=8.4 Hz, 1H), 4.01 (t, J=5.1 Hz, 2H), 3.94 (t, J=5.2 Hz, 4H), 3.25 (s, 4H), 2.19 (dq, J=13.7, 6.8 Hz, 1H), 1.90 (ddt, J=14.6, 8.9, 4.2 Hz, 1H), 1.73 (tp, J=10.3, 5.3 Hz, 2H), 1.56 (ddq, J=26.2, 13.5, 6.9, 6.0 Hz, 2H). MS (ESI) m/z: 458.3.

Example 184

6-(6-(azetidin-1-yl)pyrazin-2-yl)-1-(6-(piperazin-1-yl)pyridin-2-yl)-1H-pyrazolo[4,3-c]pyridine 284

Following the procedures as described in Example 180, 284 was obtained. 1H NMR (400 MHz, DMSO-d6) δ 9.25 (d, J=18.9 Hz, 2H), 8.89 (s, 1H), 8.64 (s, 1H), 7.93 (s, 1H), 7.77 (t, J=8.1 Hz, 1H), 7.22 (d, J=7.7 Hz, 1H), 6.82 (d, J=8.5 Hz, 1H), 4.16 (t, J=7.5 Hz, 4H), 3.60 (dd, J=6.3, 3.8 Hz, 4H), 2.84 (dd, J=6.1, 4.0 Hz, 4H), 2.44 (q, J=7.5 Hz, 2H). MS (ESI) m/z: 414.2.

Example 185

N-ethyl-6-(1-(6-(piperazin-1-yl)pyridin-2-yl)-1H-pyrazolo[4,3-c]pyridin-6-yl)pyrazin-2-amine 285

Following the procedures as described in Example 180, 285 was obtained as the dihydrochloride salt. 1H NMR (400 MHz, DMSO-d6) δ 9.32 (s, 1H), 9.24 (s, 2H), 9.17 (s, 1H), 8.73 (s, 1H), 8.70 (s, 1H), 8.03 (s, 1H), 7.88 (t, J=8.1 Hz, 1H), 7.35 (d, J=7.7 Hz, 1H), 7.20 (s, 1H), 6.97 (d, J=8.4 Hz, 1H), 3.95 (t, J=4.2 Hz, 4H), 3.44 (q, J=7.2 Hz, 2H), 3.23 (t, J=4.2 Hz, 4H), 1.27 (t, J=7.2 Hz, 3H). MS (ESI) m/z: 402.2.

Example 186

2-((6-(1-(6-(piperazin-1-yl)pyridin-2-yl)-1H-pyrazolo[4,3-c]pyridin-6-yl)pyrazin-2-yl)oxy)ethanamine 286

Following the procedures as described in Example 176, 286 was obtained as the trihydrochloride salt. MS (ESI) m/z: 418.3 [M+H]+

Example 901

Pim Kinase Binding Activity

PIM-1, -2, and -3 enzymes were generated as fusion proteins expressed in bacteria and purified by IMAC column chromatography (Sun, X., Chiu, J. F., and He, Q. Y. (2005) Expert Rev. Proteomics, 2:649-657). A fluorescent-labeled Pim-specific peptide substrate, was custom synthesized by American Peptide Company (Sunnyvale, Calif.). Reaction Buffer contained 10 mM HEPES, pH 7.2, 10 mM MgCl$_2$, 0.01% Tween 20, 2 mM DTT. Termination Buffer contained 190 mM HEPES, pH 7.2, 0.015% Brij-35, 0.2% Coating Reagent 3 (Caliper Life Sciences, Hopkinton, Mass.), 20 mM EDTA. Separation Buffer contained 100 mM HEPES, pH 7.2, 0.015% Brij-35, 0.1% Coating Reagent 3, 1:200 Coating Reagent 8 (Caliper Life Sciences, Hopkinton, Mass.), 10 mM EDTA and 5% DMSO.

PIM reactions were carried out in a final volume of 10 μL per well in a 384-well plate. A standard enzymatic reaction, initiated by the addition of 5 μL 2×ATP and test compound to 5 μL of 2× enzyme and FAM-peptide, contained 20 μM PIM1, 50 μM PIM2, or 55 μM PIM3, 1 μM FAM-peptide, and 10 μM ATP, in Reaction Buffer. After 90 minutes of incubation at room temperature, the phosphorylation reaction was stopped by the addition of 10 μL Termination Buffer. The product and substrate in each independent reaction were separated on a 12-sipper microfluidic chip (Caliper Life Sciences, Hopkinton, Mass.) run on a Caliper LC3000® (Caliper Life Sciences, Hopkinton, Mass.). The separation of product and substrate was optimized by choosing voltages and pressure using Caliper's Optimizer software (Hopkinton, Mass.). The separation conditions used a downstream voltage of −500V, an upstream voltage of −2150V, and a screening pressure of −1.2 psi. The product and substrate fluorophore were excited at 488 nm and detected at 530 nm. Substrate conversion was calculated from the electropherogram using HTS Well Analyzer software (Caliper Life Sciences, Hopkinton, Mass.). Ki values for the test compound were calculated. See Tables 3 and 4 for representative PIM1, PIM2, PIM3 LC3K Ki in micromolar values of exemplary compounds.

Example 902

In Vitro Cell Proliferation Potency Assays

BaF3 parental line was obtained from the DSMZ repository. BaF3 lines transfected with PIM1 or PIM2 were generated. Mouse IL-3 was purchased from R&D Systems. G418 was purchased from Clontech. Media for BaF3 parental line contained RPMI, 10% FBS, 2 mM L-Glutamine, 2 ng/mL mIL-3. Media for BaF3 PIM1 & 2 lines contained RPMI, 10% FBS, 2 mM L-Glutamine, 250 μg/mL. Media for MM1.S (multiple myeloma cells) line contained RPMI, 10% FBS, 2 mM L-Glutamine.

BaF3, a murine interleukin-3 dependent pro-B cell line, parental cells, BaF3 PIM1 cells, BaF3 PIM2 cells, and MM1.S (multiple myeloma) cells were seeded at 2 k/well, 5 k/well, 5 k/well, and 10 k/well respectively, in a 384-well plate, at 45 μL/well. Test compound was added at 5 μL/well. BaF3 cells (parental and transfected) were incubated overnight, while MM1.S cells were incubated for 72 hours at 37° C., 5% CO$_2$. CELL TITER GLO® Reagent (Promega) was added at 50 μL/well, the plates were incubated for 30 minutes, and their luminescence read on an HT Analyst. IC$_{50}$/EC$_{50}$ values for the test compound were calculated.

Representative compounds of the present invention were tested as described above and found to exhibit a Ki/IC$_{50}$/EC$_{50}$ as shown below in Tables 3 and 4.

TABLE 3

| No. | PIM1 LC3K (KI) | PIM2 LC3K (KI) | PIM3 LC3K (KI) | Prolif BaF3_PIM 1 (IC50) | Prolif MM1S ATP (EC50) |
|---|---|---|---|---|---|
| 101 | 0.000817 | 0.0146 | 0.000676 | 1.7 | |
| 102 | 0.000623 | 0.0121 | 0.000291 | | |
| 103 | 0.000032 | 0.00276 | 0.000065 | 1.2 | |
| 104 | 0.000119 | 0.00386 | 0.000077 | 1.5 | |
| 105 | 0.000124 | 0.00714 | 0.000183 | 1.6 | |
| 106 | 0.000104 | 0.00726 | 0.000159 | 1.2 | |
| 107 | 0.00013 | 0.00958 | 0.000203 | 2.4 | |
| 108 | 0.0001 | 0.00193 | 0.000049 | 4.5 | |
| 109 | 0.000476 | 0.00403 | 0.000285 | 1.5 | |
| 110 | 0.000504 | 0.0045 | 0.00037 | 1.7 | |
| 111 | 0.000165 | 0.00911 | 0.000181 | | |
| 112 | 0.000038 | 0.00387 | 0.000093 | 0.49 | |
| 113 | 0.000107 | 0.0101 | 0.000186 | | |
| 114 | 0.000479 | 0.0169 | 0.000652 | | |
| 115 | 0.000155 | 0.0149 | 0.000306 | | |
| 116 | 0.000294 | 0.0276 | 0.000405 | | |
| 117 | 0.000141 | 0.00103 | 0.000098 | 2.9 | |
| 118 | 0.00008 | 0.00904 | 0.000117 | | |
| 119 | 0.000426 | 0.00849 | 0.000307 | | |
| 120 | 0.000225 | 0.00466 | 0.000168 | 1.4 | |
| 121 | 0.00016 | 0.0105 | 0.000301 | | |
| 122 | 0.000056 | 0.00459 | 0.000083 | 0.0715 | 2.7 |
| 123 | 0.000095 | 0.000893 | 0.0000498 | 0.284 | 3.9 |
| 124 | 0.00071 | 0.00348 | 0.00014 | 0.804 | |
| 125 | 0.00029 | 0.00427 | 0.000226 | 1.4 | |
| 126 | 0.000349 | 0.00736 | 0.000349 | | |
| 127 | 0.00304 | 0.0307 | 0.00131 | | |
| 128 | 0.00722 | 0.0567 | 0.00439 | | |
| 129 | 0.00347 | 0.0283 | 0.00246 | | |
| 130 | 0.000113 | 0.00187 | 0.000068 | 1.5 | |
| 131 | 0.00058 | 0.0159 | 0.000385 | | |
| 132 | 0.00156 | 0.0193 | 0.00087 | | |
| 133 | 0.000867 | 0.00456 | 0.000155 | 3 | |
| 134 | 0.000951 | 0.0108 | 0.000473 | | |
| 135 | 0.00212 | 0.0111 | 0.00084 | | |
| 136 | 0.00205 | 0.0173 | 0.000615 | | |
| 137 | 0.000159 | 0.000499 | 0.000038 | 2.1 | |
| 138 | 0.0000204 | 0.00044 | 0.0000199 | 0.574 | 4.6 |
| 139 | 0.000033 | 0.000187 | 0.000035 | 2.3 | |
| 140 | 0.00104 | 0.0134 | 0.000454 | | |
| 141 | 0.000085 | 0.00337 | 0.000078 | 1 | 5 |
| 142 | 0.000802 | 0.015 | 0.000458 | | |
| 143 | 0.00246 | 0.0311 | 0.00162 | | |
| 144 | 0.000177 | 0.00116 | 0.00005 | 0.385 | 2.6 |
| 145 | 0.000362 | 0.0105 | 0.000636 | 2.5 | |
| 146 | 0.000532 | 0.00781 | 0.000656 | 0.797 | 4.3 |
| 147 | 0.000213 | 0.00392 | 0.000259 | 0.869 | 2.7 |
| 148 | 0.128 | 4.1+ | 0.0452 | | |
| 149 | 0.000058 | 0.000678 | 0.000048 | 0.24 | 4.7 |
| 150 | 0.000021 | 0.000333 | 0.000019 | 0.196 | 1.9 |
| 151 | 0.000181 | 0.00332 | 0.000081 | 0.544 | 8.6 |
| 152 | 0.000215 | 0.00538 | 0.000134 | 1.5 | |
| 153 | 0.000095 | 0.00137 | 0.000085 | 0.291 | 2.5 |
| 154 | 0.000081 | 0.00101 | 0.000175 | 0.344 | 2.3 |
| 155 | 0.000144 | 0.00149 | 0.000109 | 0.518 | 3.5 |
| 156 | 0.000047 | 0.00037 | 0.000014 | 1.4 | |
| 157 | 0.000087 | 0.0062 | 0.000055 | 2.8 | 4 |
| 158 | 0.287 | 2.9+ | 0.284 | | |
| 159 | 0.000283 | 0.00833 | 0.000185 | | |
| 160 | 0.00117 | 0.00831 | 0.00106 | | |
| 161 | 0.00186 | 0.0188 | 0.00219 | | |
| 162 | 0.000416 | 0.00226 | 0.000814 | 0.175 | |
| 163 | 0.00163 | 0.0266 | 0.00296 | | |
| 164 | 0.0502 | 0.527+ | 0.0148 | | |
| 165 | 0.000063 | 0.00114 | 0.000174 | 0.139 | |
| 166 | 0.000517 | 0.00462 | 0.000447 | 0.27 | |
| 167 | 0.000773 | 0.00227 | 0.00034 | 0.546 | |
| 168 | 0.000977 | 0.00474 | 0.000806 | 0.0755 | 5 |
| 169 | 0.000228 | 0.00179 | 0.000164 | 0.457 | |
| 170 | 0.0205 | 0.0912 | 0.00802 | | |
| 171 | 0.000032 | 0.000204 | 0.00003 | 0.219 | |
| 172 | 0.000034 | 0.00147 | 0.000048 | 0.111 | |
| 173 | 0.00121 | 0.00954 | 0.00109 | | |
| 174 | 0.000069 | 0.000978 | 0.000079 | 0.271 | 3.1 |
| 175 | 0.0113 | 0.196 | 0.00672 | | |
| 176 | 0.000073 | 0.000317 | 0.000047 | 0.533 | |
| 177 | 0.00104 | 0.0161 | 0.000363 | | |
| 178 | 0.000386 | 0.00668 | 0.00135 | 0.549 | |
| 179 | 0.000402 | 0.0051 | 0.00176 | 0.376 | |
| 180 | 0.000122 | 0.0016 | 0.000086 | 0.745 | |
| 181 | 0.000014 | 0.000077 | 0.000019 | 0.214 | |
| 182 | 0.000028 | 0.000761 | 0.000035 | 0.336 | 1.9 |
| 183 | 0.00003 | 0.000109 | 0.000016 | 0.663 | |
| 184 | 0.000164 | 0.00242 | 0.000076 | 1.1 | |
| 185 | 0.00006 | 0.00054 | 0.000022 | 0.4 | 4.8 |
| 186 | 0.0000212 | 0.000134 | 0.000013 | 0.22 | 0.508 |
| 187 | 0.00007 | 0.00106 | 0.000067 | 0.963 | |
| 188 | 0.000173 | 0.00464 | 0.000611 | 0.418 | |
| 189 | 0.000038 | 0.000373 | 0.000089 | 0.181 | |
| 190 | 0.00006 | 0.00128 | 0.000023 | 0.235 | |
| 191 | 0.000156 | 0.000659 | 0.000033 | 0.919 | |
| 192 | 0.000428 | 0.00335 | 0.00021 | 1.7 | |
| 193 | 0.000046 | 0.000596 | 0.000035 | 1.2 | |
| 194 | 0.000243 | 0.00312 | 0.000125 | 1.5 | |
| 195 | 0.000065 | 0.00103 | 0.000057 | 1 | |
| 196 | 0.000072 | 0.000864 | 0.000074 | 0.572 | |
| 197 | 0.000055 | 0.00122 | 0.000046 | 2.2 | |
| 198 | 0.000117 | 0.00255 | 0.000089 | 1.1 | |
| 199 | 0.000716 | 0.0137 | 0.000655 | | |
| 200 | 0.00121 | 0.017 | 0.000451 | | |
| 201 | 0.000068 | 0.000286 | 0.00002 | 0.49 | 1.1 |
| 202 | 0.0564 | 0.421+ | 0.0364 | | |
| 203 | 0.000375 | 0.00483 | 0.000331 | 2 | |
| 204 | 0.000034 | 0.000477 | 0.000025 | 0.693 | |
| 205 | 0.000018 | 0.000142 | 0.000014 | 0.278 | 1.2 |
| 206 | 0.00374 | 0.0404 | 0.0023 | | |
| 207 | 0.000182 | 0.00367 | 0.000093 | 1.5 | |
| 208 | 0.000012 | 0.000748 | 0.000014 | 0.173 | |
| 209 | 0.000045 | 0.000575 | 0.000011 | 0.682 | |
| 210 | 0.000609 | 0.00939 | 0.00036 | | |
| 211 | 0.000086 | 0.000936 | 0.000074 | 0.459 | |
| 212 | 0.000483 | 0.00299 | 0.000169 | 1.6 | |
| 213 | 0.000048 | 0.000672 | 0.000035 | 0.317 | |
| 214 | 0.000385 | 0.00265 | 0.000199 | 1 | |
| 215 | 0.000048 | 0.000314 | 0.000011 | 1.2 | |
| 216 | 0.000223 | 0.00295 | 0.000094 | 0.715 | |
| 217 | 0.00117 | 0.0151 | 0.000258 | | |
| 218 | 0.00006 | 0.000394 | 0.000054 | 0.212 | 0.574 |
| 219 | 0.000433 | 0.0125 | 0.000265 | | |
| 220 | 0.000034 | 0.000115 | 0.000009 | 1.2 | |
| 221 | 0.0262 | 0.744+ | 0.0232 | | |
| 222 | 0.000125 | 0.000979 | 0.000073 | | |
| 223 | 0.00237 | 0.00711 | 0.00184 | | |
| 224 | 0.000154 | 0.00501 | 0.000097 | 1.5 | |
| 225 | 0.000817 | 0.00429 | 0.000267 | 0.84 | |
| 226 | 0.00165 | 0.0104 | 0.00089 | | |
| 227 | 0.000036 | 0.000233 | 0.000019 | 0.869 | |
| 228 | 0.000074 | 0.000724 | 0.000047 | 0.778 | |
| 229 | 0.000316 | 0.00939 | 0.000131 | | |
| 230 | 0.00505 | 0.0633 | 0.00432 | | |
| 231 | 0.000078 | 0.00139 | 0.000032 | | 2.2 |
| 232 | 0.00119 | 0.0211 | 0.00083 | | |
| 233 | 0.528+ | 2.3++ | 0.903+ | | |
| 234 | 0.000107 | 0.00225 | 0.000236 | | |
| 235 | 0.00155 | 0.0165 | 0.000806 | | |
| 236 | 0.000715 | 0.0086 | 0.00037 | | |
| 237 | 0.00031 | 0.0101 | 0.000587 | | |
| 238 | 0.000026 | 0.000257 | 0.000032 | | |
| 239 | | | | | |
| 240 | 0.00151 | 0.0317 | 0.00203 | | |
| 241 | 0.00353 | 0.0455 | 0.000762 | | |
| 242 | 0.128 | 1.6+ | 0.0422 | | |
| 243 | 0.0571 | 0.528+ | 0.00864 | | |
| 244 | | | | | |

TABLE 3-continued

| No. | PIM1 LC3K (KI) | PIM2 LC3K (KI) | PIM3 LC3K (KI) | Prolif BaF3_PIM 1 (IC50) | Prolif MM1S ATP (EC50) |
|---|---|---|---|---|---|
| s245 | 0.00561 | 0.0525 | 0.00213 | | |
| 246 | | | | | |
| 247 | 0.000023 | 0.000664 | 0.000026 | | 2.5 |
| 248 | 0.00164 | 0.0221 | 0.00336 | | |
| 249 | 0.00216 | 0.0168 | 0.00309 | | |
| 250 | 0.00389 | 0.0248 | 0.000743 | | |
| 251 | 0.0488 | 0.181+ | 0.0316 | | |
| 252 | 0.00567 | 0.035 | 0.00316 | | |
| 253 | 0.00252 | 0.0451 | 0.00178 | | |
| 254 | 0.0306 | 0.718+ | 0.00624 | | |
| 255 | 0.000876 | 0.00962 | 0.00158 | | |
| 256 | 0.00558 | 0.0832 | 0.00202 | | |
| 257 | 0.000784 | 0.0233 | 0.000507 | | |
| 258 | 0.000514 | 0.00818 | 0.00114 | | |
| 259 | 0.000053 | 0.000242 | 0.000025 | | |
| 260 | 0.000047 | 0.00154 | 0.000127 | 0.38 | 0.852 |
| 261 | 0.000763 | 0.0165 | 0.00274 | | |
| 262 | 0.00123 | 0.0125 | 0.00184 | | |
| 263 | 0.000253 | 0.00651 | 0.000536 | | |
| 264 | 0.00294 | 0.0582 | 0.00637 | | |
| 265 | 0.000941 | 0.00879 | 0.000206 | | |
| 266 | 0.0011 | 0.0293 | 0.00121 | | |
| 267 | 0.00381 | 0.0303 | 0.00601 | | |
| 268 | 0.0115 | 0.149 | 0.00565 | | |
| 269 | 0.0157 | 0.194 | 0.027 | | |
| 270 | 0.00108 | 0.0204 | 0.000361 | | |
| 271 | 0.000189 | 0.00245 | 0.00021 | 1.4 | 4.9 |
| 272 | 0.000067 | 0.000235 | 0.0000235 | 0.194 | 1.2 |
| 273 | 0.000117 | 0.00263 | 0.000036 | 0.629 | 5.5 |
| 274 | 0.000133 | 0.00426 | 0.000098 | 0.749 | 5.1 |
| 275 | 0.000725 | 0.00574 | 0.000267 | | |
| 276 | 0.000494 | 0.0348 | 0.000337 | | |
| 277 | 0.000224 | 0.00467 | 0.000142 | 0.912 | 4.2 |
| 278 | 0.000163 | 0.00262 | 0.000105 | 0.261 | >6.2 |
| 279 | 0.000229 | 0.00399 | 0.000132 | 0.622 | 2.3 |
| 280 | 0.000051 | 0.018 | 0.000101 | | |
| 281 | 0.000048 | 0.00337 | 0.000064 | 0.695 | 16 |
| 282 | 0.000026 | 0.000357 | 0.000021 | 0.17 | 9.7 |
| 283 | 0.000148 | 0.00805 | 0.000182 | 1 | 8.9 |
| 284 | 0.00002 | 0.00183 | 0.000025 | 0.385 | 4.6 |
| 285 | 0.000044 | 0.00228 | 0.00009 | 0.112 | 6.4 |
| 286 | 0.000105 | 0.000806 | 0.000092 | 4.2 | 8.2 |
| 287 | 0.000698 | 0.0175 | 0.00037 | | |
| 288 | 0.000918 | 0.00556 | 0.000564 | | |
| 289 | 0.0313 | 1 | 0.03 | | |
| 290 | 0.0163 | 0.0432 | 0.00631 | | |
| 291 | 0.00441 | 0.0409 | 0.00342 | | >25 |
| 292 | 0.0016 | 0.0194 | 0.000796 | | 11.7 |
| 293 | 0.000061 | 0.00148 | 0.000112 | 0.976 | 7.2 |
| 294 | 0.000514 | 0.00237 | 0.000209 | 0.772 | 9.3 |
| 295 | 0.000256 | 0.00143 | 0.000144 | 0.425 | 10.9 |
| 296 | 0.000727 | 0.00969 | 0.000562 | 3.8 | |
| 297 | 0.00043 | 0.00343 | 0.000235 | 1.2 | |
| 298 | 0.000854 | 0.00268 | 0.000396 | 1.6 | |
| 299 | 0.000419 | 0.00417 | 0.000248 | 1.6 | |
| 300 | 0.000089 | 0.000228 | 0.000032 | 1.3 | 2.4 |
| 301 | 0.000034 | 0.000446 | 0.000018 | 0.781 | 4 |

TABLE 4

| No. | PIM1 LC3K (KI) | PIM2 LC3K (KI) | PIM3 LC3K (KI) | Prolif BaF3_PIM 1 (IC50) | Prolif MM1S ATP (EC50) |
|---|---|---|---|---|---|
| 302 | 0.0103 | 0.183 | 0.0201 | 6.1 | |
| 303 | 0.0118 | 0.193 | 0.0156 | 6.6 | |
| 304 | 0.000094 | 0.000744 | 0.000070 | 0.255 | 1.2 |
| 305 | 0.000094 | 0.000986 | 0.000079 | 0.554 | 2.2 |
| 306 | 0.000040 | 0.00056 | 0.000125 | 0.129 | 1.7 |
| 307 | 0.00012 | 0.00297 | 0.000098 | 0.64 | 2.9 |
| 308 | 0.000279 | 0.00431 | 0.00040 | 1.3 | |

TABLE 4-continued

| No. | PIM1 LC3K (KI) | PIM2 LC3K (KI) | PIM3 LC3K (KI) | Prolif BaF3_PIM 1 (IC50) | Prolif MM1S ATP (EC50) |
|---|---|---|---|---|---|
| 309 | 0.487 | 2.2 | 0.944 | | |
| 310 | 0.00164 | 0.0333 | 0.00163 | | |
| 311 | 0.000069 | 0.000779 | 0.000036 | 1 | 5.5 |
| 312 | 0.000644 | 0.00358 | 0.000481 | | |
| 313 | 0.000073 | 0.00071 | 0.000050 | 0.236 | 7.1 |
| 314 | 0.13 | 1.1 | 0.166 | | |
| 315 | 0.000136 | 0.00172 | 0.000057 | 2 | 0.696 |
| 316 | 0.0155 | 0.336 | 0.0475 | >25 | >25 |
| 317 | 0.000068 | 0.00171 | 0.000026 | 1 | 2.7 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

We claim:

1. A compound selected from Formula I:

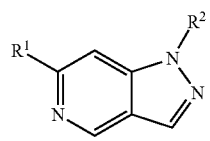

I and stereoisomers, geometric isomers, tautomers, and pharmaceutically acceptable salts thereof, wherein:
$R^1$ is a five-membered or six-membered heteroaryl selected from the group consisting of:

where the wavy line indicates the point of attachment
$R^3$ is selected from H, —$CH_3$, —$CH_2CH_3$, —$CH(CH_3)_2$, —$C(CH_3)_3$, —$CH_2CH(CH_3)_2$, —$CH_2NH_2$, —$CH_2NHCH_3$, —$CH_2CH_2NH_2$, —$CH_2CH_2CH_2NH_2$, —$CH_2CH(CH_3)NH_2$, —$CH_2OH$, —$CH_2CH_2OH$, —$C(CH_3)_2OH$, —$CH(OH)CH(CH_3)_2$, —$C(CH_3)_2$ CH₂OH, —CH₂CH₂SO₂CH₃, —CN, —CF₃, —CO₂H, —COCH₃, —CO₂CH₃, —CO₂C(CH₃)₃, —COCH(OH)CH₃, —CONH₂, —CONHCH₃, —CON(CH₃)₂, —C(CH₃)₂CONH₂, —S(O)₂N(CH₃)₂, —SCH₃, —CH₂OCH₃, —S(O)₂CH₃, cyclopropyl, cyclobutyl, cyclopentyl, cyclohexyl, cycloheptyl, and oxetanyl;

R⁴ is independently selected from F, Cl, Br, I, —CH₃, —CH₂CH₃, —CH(CH₃)₂, —C(CH₃)₃, —CH₂CH(CH₃)₂, —CH₂NH₂, —CH₂NHCH₃, —CH₂CH₂NH₂, —CH₂CH₂CH₂NH₂, —CH₂CH(CH₃)NH₂, —CH₂OH, —CH₂CH₂OH, —C(CH₃)₂OH, —CH(OH)CH(CH₃)₂, —C(CH₃)₂CH₂OH, —CH₂CH₂SO₂CH₃, —CN, —CHF₂, —CF₃, —CO₂H, —COCH₃, —CO₂CH₃, —CO₂C(CH₃)₃, —COCH(OH)CH₃, —CONH₂, —CONHCH₃, —CON(CH₃)₂, —C(CH₃)₂CONH₂, —NO₂, —NH₂, —NHCH₃, —N(CH₃)₂, —NHCH₂CHF₂, —NHCH₂CF₃, —NHCOCH₃, —N(CH₃)COCH₃, —NHC(O)OCH₂CH₃, —NHC(O)OCH₂Cl₃, —NHC(O)OC₆H₅, —NHS(O)₂CH₃, —N(CH₃)C(CH₃)₂CONH₂, —N(CH₃)CH₂CH₂S(O)₂CH₃, =O, —OH, —OCH₃, —OCH₂CH₃, —S(O)₂N(CH₃)₂, —SCH₃, —CH₂OCH₃, —S(O)₂CH₃, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholino; and n is 0, 1, 2, or 3;

R² is a six-membered heteroaryl, having the structure:

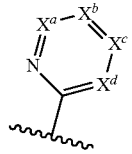

where the wavy line indicates the point of attachment;
Xᵃ is N or CRᵃ;
Xᵇ is N or CRᵇ;
Xᶜ is N or CRᶜ;
Xᵈ is N or CRᵈ;
where 0 or 1 of Xᵃ, Xᵇ, Xᶜ, and Xᵈ is N;
Rᵃ, Rᵇ, Rᶜ and Rᵈ are independently selected from H, F, Cl, Br, I, —CH₃, —CH₂CH₃, —CH(CH₃)₂, —C(CH₃)₃, —CH₂CH(CH₃)₂, —CH₂NH₂, —CH₂NHCH₃, —CH₂CH₂NH₂, —CH₂CH₂CH₂NH₂, —CH₂CH(CH₃)NH₂, —CH₂OH, —CH₂CH₂OH, —C(CH₃)₂OH, —CH(OH)CH(CH₃)₂, —C(CH₃)₂CH₂OH, —CH₂CH₂SO₂CH₃, —CN, —CHF₂, —CF₃, —CO₂H, —COCH₃, —CO₂CH₃, —CO₂C(CH₃)₃, —COCH(OH)CH₃, —CONH₂, —CONHCH₃, —CON(CH₃)₂, —C(CH₃)₂CONH₂, —NO₂, —NH₂, —NHCH₃, —N(CH₃)₂, —NHCH₂CHF₂, —NHCH₂F₃, —NHCOCH₃, —N(CH₃)COCH₃, —NHCH(O)OCH₂CH₃, —NHC(O)OCH₂Cl₃, —NHC(O)(OC₆H₅, —NHS(O)₂CH₃, —N(CH₃)C(CH₃)₂CONH₂, —N(CH₃)CH₂CH₂S(O)₂CH₃, =O, —OH, —OCH₃, —OCH₂CH₃, —S(O)₂N(CH₃)₂, —SCH₃, —CH₂OCH₃, —S(O)₂CH₃, cyclopropyl, cyclobutyl, cyclopentyl, cyclohexyl, cycloheptyl, azetidinyl, azepanyl, pyrrolidinyl, piperazinyl, piperidinyl, (piperidin-4-yl)ethyl), pyranyl, (piperidin-4-ylmethyl), morpholinomethyl, and morpholine;

and, wherein at least one of Rᵃ, Rᵇ, Rᶜ and Rᵈ is independently selected from a 3-7 member monocyclic heterocyclyl, having 1 or 2 N, and a 7-10 member bicyclic heterocyclyl, having 1 or 2 N, the other of Rᵃ, Rᵇ, Rᶜ and Rᵈ are as described above, wherein said heterocyclyl is optionally substituted with one or more groups independently selected from F, Cl, Br, I, —CH³, —CH₂CH₃, —CH(CH₃)₂, —C(CH₃)₃, —CH₂CH(CH₃)₂, —CH₂NH₂, —CH₂NHCH₃, —CH₂CH₂NH₂, —CH₂CH₂CH₂NH₂, —CH₂CH(CH₃)NH₂, —CH₂OH, —CH₂CH₂OH, —C(CH₃)₂₀H, —CH(OH)CH(CH₃)₂, —C(CH₃)₂CH₂OH, —CH₂CH₂SO₂CH₃, —CN, —CHF₂, —CF₃, —CO₂H, —COCH₃, —CO₂CH₃, —CO₂C(CH₃)₃, —COCH(OH)CH₃, —CONH₂, —CONHCH₃, —CON(CH₃)₂, —C(CH₃)₂CONH₂, —NO₂, —NH₂, —NHCH₃, —N(CH₃)₂, —NHCH₂CHF₂, —NHCH₂F₃, —NHCOCH₃, —N(CH₃)COCH₃, —NHCH(O)OCH₂CH₃, —NHC(O)OCH₂Cl₃, —NHC(O)OC₆H₅, —NHS(O)₂CH₃, —N(CH₃)C(CH₃)₂CONH₂, —N(CH₃)CH₂CH₂S(O)₂CH₃, =O, —OH, —OCH₃, —OCH₂CH₃, —S(O)₂N(CH₃)₂, —SCH₃, —CH₂OCH₃, —S(O)₂CH₃, cyclopropyl, cyclobutyl, cyclopentyl, cyclohexyl, cycloheptyl, azetidinyl, azepanyl, oxetanyl, pyrrolidinyl, piperazinyl, piperidinyl, (piperidin-4-yl)ethyl), pyranyl, (piperidin-4-ylmethyl), morpholinomethyl, and morpholine.

2. The compound of claim 1 wherein R² is selected from the structures:

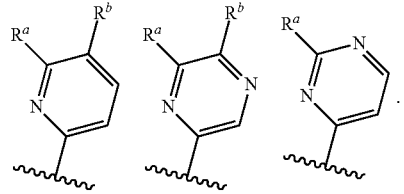

3. The compound of claim 1 wherein R² is selected from the structures:

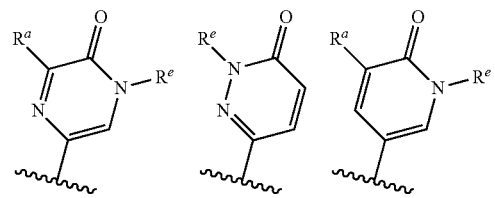

where Rᵉ is selected from H, —CH₃, —CH₂CH₃, —CH(CH₃)₂, —C(CH₃)₃, —CH₂CH(CH₃)₂, —CH₂NH₂, —CH₂NHCH₃, —CH₂CH₂NH₂, —CH₂CH₂CH₂NH₂, —CH₂CH(CH₃)NH₂, —CH₂OH, —CH₂CH₂OH, —C(CH₃)₂OH, —CH(OH)CH(CH₃)₂, —C(CH₃)₂CH₂OH, —CH₂CH₂SO₂CH₃, —CN, —CF₃, —CO₂H, —COCH₃, —CO₂CH₃, —CO₂C(CH₃)₃, —COCH(OH)CH₃, —CONH₂, —CONHCH₃, —CON(CH₃)₂, —C(CH₃)₂CONH₂, —S(O)₂N(CH₃)₂, —SCH₃, —CH₂OCH₃, —S(O)₂CH₃, cyclopropyl, cyclobutyl, cyclopentyl, cyclohexyl, cycloheptyl, and oxetanyl.

4. The compound of claim 1 wherein Rᵃ is a heterocyclyl selected from the structures:

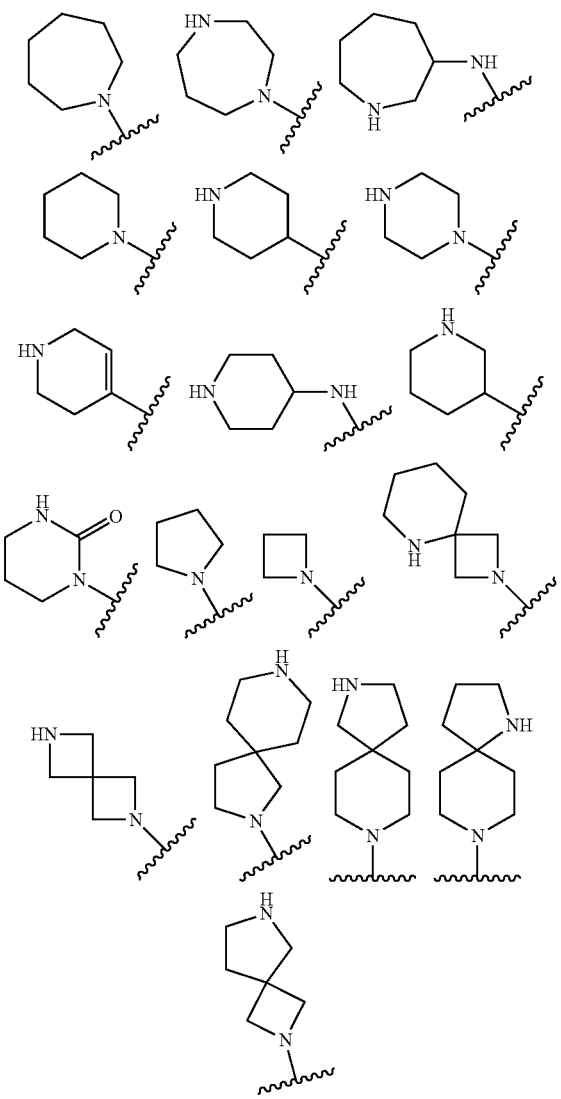

wherein the heterocyclyl is optionally substituted with one or more groups independently selected from F, —OH, —OCH₃, =O, —NH₂, —CH₃, —CH₂CH₃, and oxetan-3-yl.

5. The compound of claim 1 having the structure of Formula Ia:

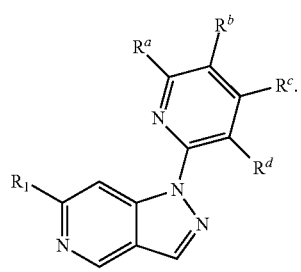

Ia

6. The compound of claim 1 having the structure of Formula Ib:

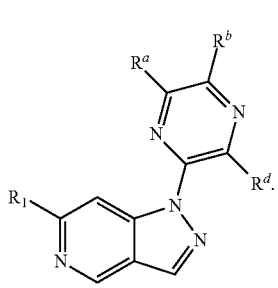

Ib

7. The compound of claim 1 having the structure of Formula Ic:

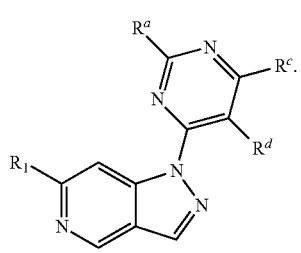

Ic

8. The compound of claim 1 having the structure of Formula Id:

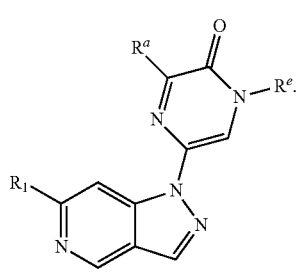

Id

9. A compound selected from Table 1, excluding:
(S)-2-((6-(1-(2-fluorophenyl)-1H-pyrazolo[4,3-c]pyridin-6-yl)pyrazin-2-yl)oxy)-1-phenylethanamine; and
(R)-2-((6-(1-(2-fluorophenyl)-1H-pyrazolo[4,3-c]pyridin-6-yl)pyrazin-2-yl)oxy)-1-phenylethanamine.

10. A compound selected from Table 2, excluding:
6-(5-chloro-1-methyl-1H-pyrazol-4-yl)-1-(2-fluorophenyl)-1H-pyrazolo[4,3-c]pyridine;
1-(2-fluorophenyl)-6-(1-methyl-5-(1,2,3,6-tetrahydropyridin-4-yl)-1H-pyrazol-4-yl)-1H-pyrazolo[4,3-c]pyridine; and
1-(4-(1-(2-fluorophenyl)-1H-pyrazolo[4,3-c]pyridin-6-yl)-1-methyl-1H-pyrazol-5-yl)piperidin-4-amine.

11. A pharmaceutical composition comprised of a compound of claim 1, 9 or 10 and a pharmaceutically acceptable carrier, glidant, diluent, or excipient.

12. The pharmaceutical composition according to claim 11, further comprising a chemotherapeutic agent.

13. A method of treating a disease or disorder which method comprises administering a therapeutically effective amount of a pharmaceutical composition of claim 11 to a patient with a disease or disorder selected from a hematopoietic cancer and prostate cancer.

14. The method of claim 13 wherein the hematopoietic cancer is selected from the group consisting of multiple myeloma, myeloid disorders, Hodgkin's, leukemia, acute myelogenous leukemia, chronic myelogenous leukemia, lymphocytic leukemia, myeloid leukemia, and non-Hodgkin lymphoma.

15. The method of claim 13 further comprising administering an additional therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

16. A kit for treating a condition mediated by Pim kinase, comprising:
   a) a pharmaceutical composition of claim 11; and
   b) instructions for use.

17. A method of inhibiting a PIM kinase comprising contacting a PIM kinase with a compound of claim 1, 9 or 10.

* * * * *